US010316104B2

(12) United States Patent
Ast et al.

(10) Patent No.: US 10,316,104 B2

(45) **Date of Patent: *Jun. 11, 2019**

(54) IMMUNOCONJUGATES

(71) Applicant: Roche Glycart AG, Schlieren (CH)

(72) Inventors: Oliver Ast, Bassersdorf (CH); Peter Bruenker, Hittnau (CH); Thomas U. Hofer, Zurich (CH); Ralf Hosse, Cham (CH); Christian Klein, Bonstetten (CH); Ekkehard Moessner, Kreuzlingen (CH); Pablo Umana, Wollerau (CH)

(73) Assignee: ROCHE GLYCART AG, Schlieren (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/996,893

(22) Filed: Jan. 15, 2016

(65) Prior Publication Data

US 2016/0263240 A1 Sep. 15, 2016

Related U.S. Application Data

(63) Continuation of application No. 13/457,039, filed on Apr. 26, 2012, now Pat. No. 9,447,159.

(30) Foreign Application Priority Data

Apr. 29, 2011 (EP) .................................... 11164237

(51) Int. Cl.

| | |
|---|---|
| ***C07K 14/55*** | (2006.01) |
| ***C07K 16/28*** | (2006.01) |
| ***C07K 16/40*** | (2006.01) |
| ***C07K 14/54*** | (2006.01) |
| ***C07K 16/18*** | (2006.01) |
| ***C07K 16/30*** | (2006.01) |
| ***A61K 38/20*** | (2006.01) |
| ***C07K 16/46*** | (2006.01) |
| ***A61K 47/68*** | (2017.01) |
| *A61K 39/00* | (2006.01) |
| *A61K 39/395* | (2006.01) |
| *C07K 14/52* | (2006.01) |

(52) U.S. Cl.

CPC .......... *C07K 16/40* (2013.01); *A61K 38/2013* (2013.01); *A61K 47/6813* (2017.08); *A61K 47/6843* (2017.08); *A61K 47/6849* (2017.08); *A61K 47/6851* (2017.08); *A61K 47/6853* (2017.08); *C07K 14/5434* (2013.01); *C07K 14/55* (2013.01); *C07K 16/18* (2013.01); *C07K 16/283* (2013.01); *C07K 16/2866* (2013.01); *C07K 16/30* (2013.01); *C07K 16/3007* (2013.01); *C07K 16/46* (2013.01); *A61K 39/395* (2013.01); *A61K 2039/505* (2013.01); *C07K 14/52* (2013.01); *C07K 2317/21* (2013.01); *C07K 2317/41* (2013.01); *C07K 2317/52* (2013.01); *C07K 2317/524* (2013.01); *C07K 2317/55* (2013.01); *C07K 2317/56* (2013.01); *C07K 2317/71* (2013.01); *C07K 2317/732* (2013.01); *C07K 2317/92* (2013.01); *C07K 2319/00* (2013.01); *C07K 2319/30* (2013.01); *C07K 2319/33* (2013.01); *C07K 2319/74* (2013.01)

(58) Field of Classification Search

CPC ............ A61K 2300/00; A61K 39/3955; A61K 39/395; A61K 47/6849; A61K 47/48569; A61K 47/6801; C07K 16/30; C07K 2317/21; C07K 16/2866; C07K 16/2839; C12N 15/1037; C12N 15/86; C12N 2740/16122; C12P 21/005; G01N 2333/54; G01N 2333/70546; G01N 33/6854

See application file for complete search history.

(56) References Cited

U.S. PATENT DOCUMENTS

| | | | |
|---|---|---|---|
| 5,731,168 | A | 3/1998 | Carter et al. |
| 5,965,710 | A | 10/1999 | Bodmer et al. |
| 6,602,684 | B1 | 8/2003 | Umana et al. |
| 7,371,371 | B2 | 5/2008 | Epstein et al. |
| 7,396,917 | B2 | 7/2008 | Bowdish et al. |
| 7,404,956 | B2 | 7/2008 | Peters et al. |
| 7,767,405 | B2 | 8/2010 | Gillies et al. |
| 8,642,742 | B2 | 2/2014 | Hofer et al. |
| 8,945,571 | B2 | 2/2015 | Mossner et al. |

(Continued)

FOREIGN PATENT DOCUMENTS

| | | | |
|---|---|---|---|
| EP | 0 721 470 | B1 | 10/2002 |
| EP | 1071700 | B1 | 2/2010 |

(Continued)

OTHER PUBLICATIONS

U.S. Appl. No. 60/495,142, filed Aug. 15, 2003, Umana et al.

Buchli et al., "Structural and Biologic Properties of a Human Aspartic Acid-126 Interleukin-2 Analog" Archives of Biochemistry and Biophysics 307(2):411-415 (Dec. 1993).

(Continued)

*Primary Examiner* — Bridget E Bunner

(57) ABSTRACT

The present invention generally relates to antigen-specific immunoconjugates for selectively delivering effector moieties that influence cellular activity. More specifically, the invention provides novel immunoconjugates comprising a first antigen binding moiety, an Fc domain and a single effector moiety. In addition, the present invention relates to polynucleotides encoding such immunoconjugates, and vectors and host cells comprising such polynucleotides. The invention further relates to methods for producing the immunoconjugates of the invention, and to methods of using these immunoconjugates in the treatment of disease.

23 Claims, 42 Drawing Sheets

Specification includes a Sequence Listing.

(56) References Cited

U.S. PATENT DOCUMENTS

| | | | |
|---|---|---|---|
| 8,969,526 | B2 | 3/2015 | Baehner et al. |
| 9,068,008 | B2 | 6/2015 | Mossner et al. |
| 9,206,243 | B2 | 12/2015 | Leóon Monzón et al. |
| 9,206,260 | B2 | 12/2015 | Hofer et al. |
| 9,266,938 | B2 | 2/2016 | Ast et al. |
| 9,447,159 | B2 | 9/2016 | Ast et al. |
| 9,526,797 | B2 | 12/2016 | Gerdes et al. |
| 2003/0027994 | A1 | 2/2003 | Anderson et al. |
| 2003/0124678 | A1 | 7/2003 | Epstein et al. |
| 2003/0166163 | A1 | 9/2003 | Gillies |
| 2003/0175884 | A1 | 9/2003 | Umana et al. |
| 2004/0132066 | A1 | 7/2004 | Balint et al. |
| 2004/0175357 | A1 | 9/2004 | Shanafelt et al. |
| 2004/0241817 | A1 | 12/2004 | Umana et al. |
| 2006/0269515 | A1 | 11/2006 | Denis-Mize et al. |
| 2008/0025947 | A1 | 1/2008 | Gillies et al. |
| 2008/0138860 | A1 | 6/2008 | Torikai et al. |
| 2009/0238789 | A1 | 9/2009 | Guyon et al. |
| 2009/0304718 | A1 | 12/2009 | Adolf et al. |
| 2010/0021477 | A1 | 1/2010 | Tsui et al. |
| 2010/0260765 | A1 | 10/2010 | Barry et al. |
| 2011/0064751 | A1 | 3/2011 | Mössner et al. |
| 2011/0110987 | A1 | 5/2011 | Kanemaru |
| 2012/0244112 | A1 | 9/2012 | Ast et al. |
| 2012/0251529 | A1 | 10/2012 | Hofer et al. |
| 2013/0058936 | A1 | 3/2013 | Bruenker et al. |
| 2013/0058937 | A1 | 3/2013 | Auer et al. |
| 2013/0060011 | A1 | 3/2013 | Bruenker et al. |
| 2013/0078249 | A1 | 3/2013 | Ast et al. |
| 2015/0239981 | A1 | 8/2015 | Baehner et al. |
| 2015/0274845 | A1 | 10/2015 | Bruenker et al. |
| 2016/0075795 | A1 | 3/2016 | Mossner et al. |
| 2016/0130347 | A1 | 5/2016 | Bruenker et al. |
| 2016/0175397 | A1 | 6/2016 | Umana et al. |
| 2016/0208017 | A1 | 7/2016 | Ast et al. |
| 2016/0229923 | A1 | 8/2016 | Hofer et al. |
| 2017/0056522 | A1 | 3/2017 | Gerdes et al. |
| 2017/0088631 | A1 | 3/2017 | Ast et al. |
| 2017/0198043 | A1 | 7/2017 | Auer et al. |
| 2017/0209573 | A1 | 7/2017 | Bacac et al. |

FOREIGN PATENT DOCUMENTS

| | | | |
|---|---|---|---|
| EP | 1587921 | B1 | 7/2010 |
| EP | 11160251.2 | | 3/2012 |
| WO | 1988/007089 | A1 | 9/1988 |
| WO | 95/06067 | A1 | 3/1995 |
| WO | WO 95/06067 | A1 | 3/1995 |
| WO | 96/11013 | A1 | 4/1996 |
| WO | WO 96/11013 | A1 | 4/1996 |
| WO | 1998/017797 | A1 | 4/1998 |
| WO | 99/43817 | A1 | 9/1999 |
| WO | WO 99/43817 | A1 | 9/1999 |
| WO | 1999/051642 | A1 | 10/1999 |
| WO | 1999/054342 | A1 | 10/1999 |
| WO | 1999/060128 | A1 | 11/1999 |
| WO | 2000/047228 | A1 | 8/2000 |
| WO | 2003/011878 | A2 | 2/2003 |
| WO | 2003/048334 | A2 | 6/2003 |
| WO | 2004/065540 | A2 | 8/2004 |
| WO | 2004/101790 | A1 | 11/2004 |
| WO | WO 2004/101790 | A1 | 11/2004 |
| WO | 2005/062929 | A2 | 7/2005 |
| WO | 2005/086751 | A2 | 9/2005 |
| WO | 2005/086798 | A3 | 9/2005 |
| WO | 2006/019447 | A1 | 2/2006 |
| WO | WO 2006/019447 | A1 | 2/2006 |
| WO | 2006/119897 | A2 | 11/2006 |
| WO | 2007/128563 | A1 | 11/2007 |
| WO | 2008/003473 | A2 | 1/2008 |
| WO | 2008/017963 | A2 | 2/2008 |
| WO | 2008/143954 | A2 | 11/2008 |
| WO | 2085095 | A1 | 8/2009 |
| WO | 2010/085495 | A1 | 7/2010 |
| WO | 2010/088444 | A1 | 8/2010 |
| WO | 2010/111282 | A1 | 9/2010 |
| WO | 2010/117448 | A2 | 10/2010 |
| WO | 2011/001276 | A1 | 1/2011 |
| WO | 2011/020783 | A2 | 2/2011 |
| WO | 2011/023787 | A1 | 3/2011 |
| WO | WO 2011/023787 | A1 | 3/2011 |
| WO | 2011/039126 | A1 | 4/2011 |
| WO | WO 2011/039126 | A1 | 4/2011 |
| WO | 2012/020006 | A2 | 2/2012 |
| WO | 2012/117002 | A1 | 9/2012 |
| WO | 2012/130831 | A1 | 10/2012 |
| WO | 2012/146628 | A1 | 11/2012 |
| WO | 2014/023752 | A1 | 2/2014 |

OTHER PUBLICATIONS de Jong et al., "Interaction of IL-15 with the Shared IL-2 Receptor β and $\gamma_c$ Subunits" Journal of Immunology 156(4):1339-1348 (1996).

Ferrara et al., "Modulation of Therapeutic Antibody Effector Functions by Glycosylation Engineering: Influence of Golgi Enzyme Localization Domain and Co-Expression of Heterologous β1, 4-N-Acetylglucosaminyltransferase III and Golgi α-Mannosidase II" Biotechnology and Bioengineering 93(5):851-861 (Apr. 5, 2006).

Fingl et al. Basis of Therapeutics, "Ch.1—General Principles" Fifth edition, New York: Macmillan Publishing Co., Inc.:1-46 (1975).

Heaton et al., "Characterization of Lymphokine-Activated Killing by Human Peripheral Blood Mononuclear Cells Stimulated with Interleukin 2 (IL-2) Analogs Specific for the Intermediate Affinity IL-2 Receptor" Cellular Immunology 147:167-179 (1993).

Hezareh et al., "Effector Function Activities of a Panel of Mutants of a Broadly Neutralizing Antibody against Human Immunodeficiency Virus Type 1" Journal of Virology 75(24):12161-12168 (Dec. 2001).

Mott et al., "The Solution Structure of the F42A Mutant of Human Interleukin 2" Journal of Molecular Biology 247:979-994 (1995).

Ortiz-Sanchez et al., "Antibody-Cytokine Fusion Proteins: Applications in Cancer Therapy" Expert Opin. Biol. Ther. 8(5):609-632 (2008).

PCT ISR and Written Opinion for PCT/EP2012/051990 dated Aug. 20, 2012.

Rao et al., "Interleukin-2 Mutants with Enhanced α-Receptor Subunit Binding Affinity" Protein Engineering 16(12):1081-1087 (2003).

Remington. Remington's Pharmaceutical Sciences. 18th edition, Mack Publishing:1289-1329 (1990).

Ricart et al., "Technology Insight: Cytotoxic Drug Immunoconjugates for Cancer Therapy" Nature Clinical Practice Oncology 4(4):245-255 (Apr. 2007).

Sauve et al., "Localization in Human Interleukin 2 of the Binding Site to the α chain (p55) of the Interleukin 2 Receptor" Proc Natl Acad Sci USA. 88(11):4636-40 (Jun. 1991).

Schliemann et al., "Complete Eradication of Human B-Cell Lymphoma Xenografts Using Rituximab in Combination with the Immunocytokine L19-IL2" Blood 113 (10):2275-2283 (Mar. 5, 2009).

Shanafelt et al., "A T-Cell-Selective Interleukin 2 Mutein Exhibits Potent Antitumor Activity and is Well Tolerated in Vivo" Nature Biotechnology 18(11):1197-1202 (Nov. 2000).

Shields et al., "High Resolution Mapping of the Binding Site on Human IgG1 for FcγRI, FcγRII, FcγRIII, and FcRn and Design of IgG1 Variants with Improved Binding to the FcγR" Journal of Biological Chemistry 276(9):6591-6604 (Mar. 2, 2001).

Umana et al., "Engineered Glycoforms of an Antineuroblastoma IgG1 with Optimized Antibody-Dependent Cellular Cytotoxic Activity" Nature Biotechnology 17:176-180 (Feb. 1999).

Ashraf et al. (2009). "Humanised IgG1 antibody variants targeting membrane-bound carcinoembryonic antigen by antibody-dependent cellular cytotoxicity and phagocytosis," *British Journal of Cancer* 101(10):1758-68.

Barbas et al. (1994). "In Vitro Evolution of a Neutralizing Human Antibody to Human Immunodeficiency Virus Type 1 to Enhance Affinity and Broaden Strain Cross-Reactivity," *Proc. Natl. Acad Sci. USA* 91(9):3809-3813.

(56) References Cited

OTHER PUBLICATIONS

Brown et al. (1996). "Tolerance of single, but not multiple, amino acid replacements in antibody VH CDR 2: A Means of Minimizing B cell Wastage from Somatic Hypermutation?," *The Journal of Immunology* 156(9):3285-3291.
Conaghan et al. (2008). "Targeted killing of colorectal cancer cell lines by a humanised IgG1 monoclonal antibody that binds to membrane-bound carcinoembryonic antigen," *British Journal of Cancer* 98(7):1217-25.
Dall'Acqua et al. (2005). "Antibody humanization by framework shuffling," *Methods* 36:43-60.
Davies et al. (1996). "Affinity improvement of single antibody VH domains: residues in all three hypervariable regions affect antigen binding," *Immunotechnology* 2(3):169-179.
Durbin et al. (1994). "An epitope on carcinoembryonic antigen defined by the clinically relevant antibody PR1A3," *Proc Natl Acad Sci USA* 91(10):4313-7.
Garambois et al. (2004). "Fully human IgG and IgM antibodies directed against the carcinoembryonic antigen (CEA) Gold 4 epitope and designed for radioimmunotherapy (RIT) of colorectal cancers," *BMC Cancer* 4:75.
Giusti, A.M. et al. (1987). "Somatic diversification of S107 from an antiphosphocholine to an anti-DNA autoantibody is due to a single base change in its heavy chain variable region," *Proc. Nati. Acad. Sci. USA* 84:2926-2930.
Hawkins et al. (1992). "Selection of phage antibodies by binding affinity mimicking affinity maturation," *J. Mol. Biol.* 226:889-896.
Holt et al. (2003). "Domain antibodies: proteins for therapy," *TRENDS in Biotechnology* 21(11):484-490.
Jackson et al. (1995). "In Vitro antibody maturation. Improvement of a high affinity, neutralizing antibody against IL-1β," *The Journal Immunology* 154(7):3310-3319.
Kashmiri et al. (2005). "SDR grafting—a new approach to antibody humanization," *Methods* 36:25-34.
Kaufman et al. (1992). "Effect of Bivalent Interaction upon Apparent Antibody Affinity: Experimental Confirmation of Theory Using Fluorescence Photobleaching and Implications for Antibody Binding Assays1," *Cancer Research* 52:4157-4167.
Kim et al. (2002). "Enhancement of colorectal tumor targeting using a novel biparatopic monoclonal antibody against carcinoembryonic antigen in experimental radioimmunoguided surgery," *Int. J. Cancer* 97(4):542-7.
Marks et al., "By-passing immunization: building high affinity human antibodies by chain shuffling" Bio/Technology 10(7):779-783 (Jul. 1992).
Rudikoff et al. (1982). "Single amino acid substitution altering antigen-binding specificity" *Proc. Natl. Acad. Sci. USA* 79:1979-1983.
Schier et al. (1996). "Identification of Functional and Structural Amino-Acid Residues by Parsimonious Mutagenesis," *GENE* 169:147-155.
Schildbach et al. (1994). "Contribution of a single heavy chain residue to specificity of an anti-digoxin monoclonal antibody," *Protein Science* 3:737-749.
Shiba et al. (2010). "Polydispersity as a Parameter for Indicating the Thermal Stability of Proteins by Dynamic Light Scattering," *Analytical Sciences* 26:659-663.
Silacci et al. (2005). "Design, construction, and characterization of a large synthetic human antibody phage display library," *Proteomics* 5(9):2340-50.
Steidl et al. (2008). "In vitro affinity maturation of human GM-CSF antibodies by targeted CDR-diversification," *Molecular Immunology* 46(1):135-44.
Stewart et al. (1999). "Humanisation and characterisation of PR1A3, a monoclonal antibody specific for cell-bound carcinoembryonic antigen," *Cancer Immunol Immunother* 47(6):299-306.
Tsurushita et al. (2005). "Design of humanized antibodies: From anti-Tac to Zenapax," *Methods* 36(1):69-83.
Wilkinson et al. (2002). "Evaluation of a transgenic mouse model for anti-human CEA radioimmunotherapeutics," *The Journal of Nuclear Medicine* 43(10):1368-76.
Xiang et al. (2000). "Study of B72.3 combining sites by molecular modeling and site-directed mutagenesis," *Protein Science* 13(5):339-344.
Yang, et al. et al., "CDR walking mutagenesis for the affinity maturation of a potent human anti-hiv-1 antibody into the picomolar range" J Mol Biol 254:392-403 ( 1995).
Yelton et al. (1995). "Affinity Maturation of the BR96 Anti-Carcinoma Antibody by Codon-Based Mutagenesis," *The Journal Immunology* 155:1994-2004.
Zbar et al. (2005). "Immune responses in advanced colorectal cancer following repeated intradermal vaccination with the anti-CEA murine monoclonal antibody, PR1A3: results of a phase I study," *International Journal of Colorectal Disease* 20(5):403-14.
Ashraf et al., "Humanised IgG1 antibody variants targeting membrane-bound carcinoembryonic antigen by antibody-dependent cellular cytotoxicity and phagocytosis" Br J Cancer 101(10):1758-68 (2009).
Barbas et al., "In Vitro Evolution of a Neutralizing Human Antibody to Human Immunodeficiency Virus Type 1 to Enhance Affinity and Broaden Strain Cross-Reactivity" P Natl Acad Sci USA 91(9):3809-3813 (1994).
Brown et al., "Tolerance of single, but not multiple, amino acid replacements in antibody VHCDR 2: a means of minimizing B cell wastage from somatic hypermutation?" The Journal of Immunology 156(9):3285-3291 (1996).
Conaghan et al., "Targeted kiling of colorectal cancer cell lines by a humanised IgG1 monoclonal antibody that binds to membrane-bound carcinoembryonic antigen" Br J Cancer 98(7):1217-25 (2008).
Dall'Acqua et al., "Antibody humanization by framework shuffling" Methods 36:43-60 (2005).
Davies and Reichmann, "Affinity improvement of single antibody VH domains: residues in all three hypervariable regions affect antigen binding" Immunotechnology 2(3):169-179 (1996).
Durbin et al., "An epitope on carcinoembryonic antigen defined by the clinically relevant antibody PR1A3" Proc Natl Acad Sci U S A. 91(10):4313-7 (1994).
Garambois et al., "Fully human IgG and IgM antibodies directed against the carcinoembryonic antigen (CEA) Gold 4 epitope and designed for radioimmunotherapy (RIT) of colorectal cancers" BMC Cancer 4:75 (2004).
Giusti, A.M. et al., "Somatic diversification of S107 from an antiphosphocholine to an anti-DNA autoantibody is due to a single base change in its heavy chain variable region" Proc. Nati. Acad. Sci. USA 84:2926-2930 (1987).
Hawkins et al., "Selection of phage antibodies by binding affinity mimicking affinity maturation" J. Mol. Biol. 226:889-896 (1992).
Holt et al., "Domain antibodies: proteins for therapy" TRENDS in Biotechnology 21(11):484-490 (2003).
Jackson et al., "In vitro antibody maturation. Improvement of a high affinity, neutralizing antibody against IL-1β" J Immunol 154(7):3310-3319 (1995).
Kashmiri et al., "SDR grafting—a new approach to antibody humanization" Methods 36:25-34(2005).
Kaufman, E.N. et al., "Effect of Bivalent Interaction upon Apparent Antibody Affinity: Experimental Confirmation of Theory Using Fluorescence Photobleaching and Implications for Antibody Binding Assays1" Cancer Research 52:4157-4167 (1992).
Kim et al., "Enhancement of colorectal tumor targeting using a novel biparatopic monoclonal antibody against carcinoembryonic antigen in experimental radioimmunoguided surgery" Int J Cancer 97(4):542-7 (2002).
Marks et al., "By-passing immunization: building high affinity human antibodies by chain shuffling" Bio/Technology 10(7):779-783 (1992).
Pakula et al., "Genetic analysis of protein stability and function" Annu. Rev. Genet. 23:289-310 (1989).
Paul et al. Fundamental Immunology 3rd edition, Raven Press,:292-295 ( 1993).
Roitt et al., Immunology, Moscow: Mir, pp. 110-111 (2000), with English Translation, total in 6 pages.

(56) References Cited

OTHER PUBLICATIONS

Rudikoff et al., "Single amino acid substitution altering antigen-binding specificity" P Natl Acad Sci USA 79:1979-1983 (1982).
Schier et al., "Identification of Functional and Structural Amino-Acid Residues by Parsimonious Mutagenesis." GENE 169:147-155 (1996).
Schildbach, J.F. et al., "Contribution of a single heavy chain residue to specificity of an anti-digoxin monoclonal antibody" Protein Science 3:737-749 (1994).
Shiba, K. et al., "Polydispersity as a Parameter for Indicating the Thermal Stability of Proteins by Dynamic Light Scattering" Analytical Sciences 26:659-663 (2010).
Silacci et al., "Design, construction, and characterization of a large synthetic human antibody phage display library" Proteomics 5(9):2340-50 (2005).
Steidl et al., "In vitro affinity maturation of human GM-CSF antibodies by targeted CDR-diversification" Mol Immunol. 46(1):135-44 (2008).
Stewart et al., "Humanisation and characterisation of PR1A3, a monoclonal antibody specific for cell-bound carcinoembryonic antigen" Cancer Immunol Immunother.47(6):299-306. (1999).
Tsurushita et al., "Design of humanized antibodies: From anti-Tac to Zenapax" Methods 36(1):69-83 (2005).
Wei-Ping Yang, et al. et al., "CDR walking mutagenesis for the affinity maturation of a potent human anti-hiv-1 antibody into the picomolar range" J Mol Biol 254:392-403 (1995).
Wilkinson et al., "Evaluation of a transgenic mouse model for anti-human CEA radioimmunotherapeutics" J Nucl Med. 43(10):1368-76 (2002).
Xiang, J. et al., "Study of B72.3 combining sites by molecular modeling and site-directed mutagenesis" Protein Science 13(5):339-344 (2000).
Yelton et al., "Affinity maturation of the BR96 anti-carcinoma antibody by codon-based mutagenesis" J Immunol. 155:1994-2004 (1995).
Zbar et al., "Immune responses in advanced colorectal cancer following repeated intradermal vaccination with the anti-CEA murine monoclonal antibody, PR1A3: results of a phase I study" International Journal of Colorectal Disease 20(5): 403-414 (2005).

FIG. 5A
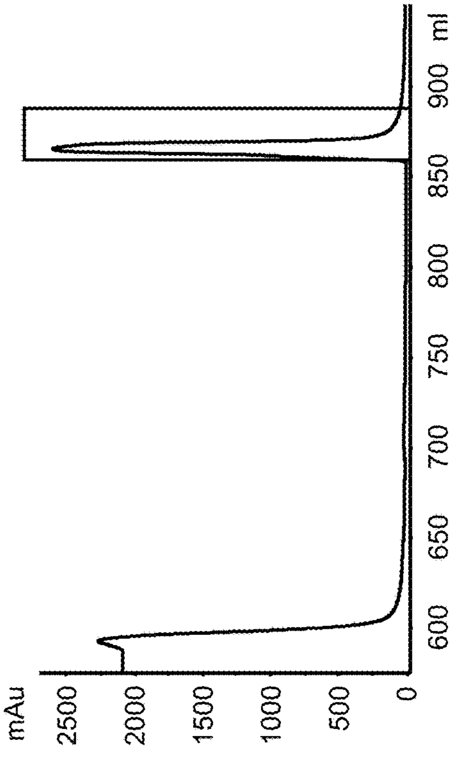
FIG. 5B
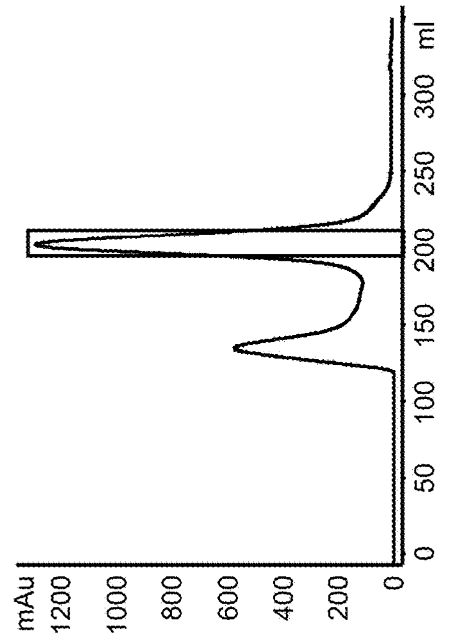
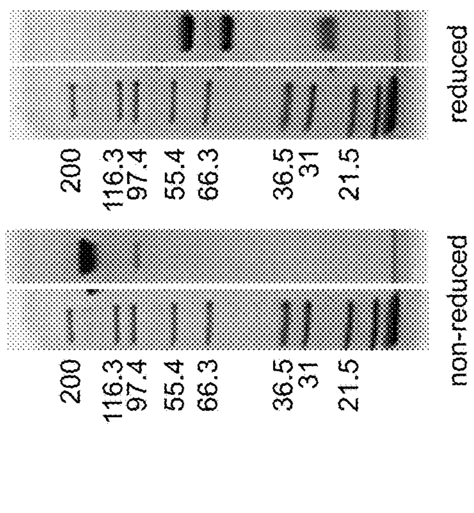
FIG. 5C
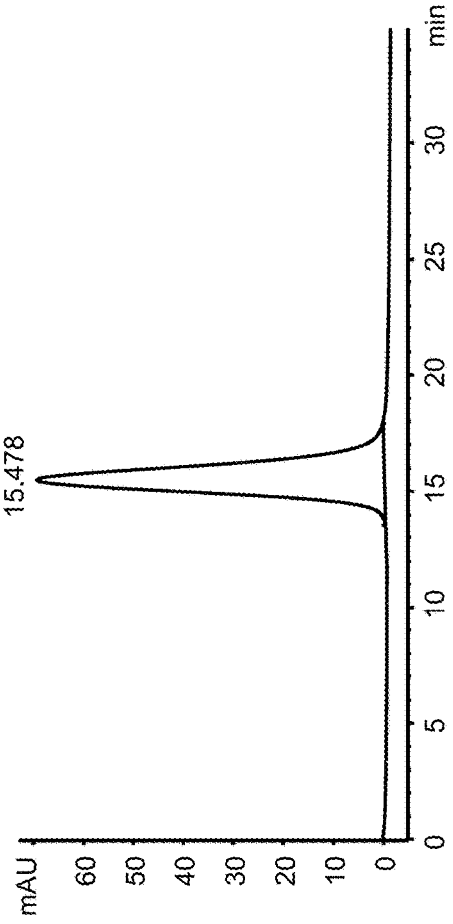
FIG. 5D

FIG. 7A
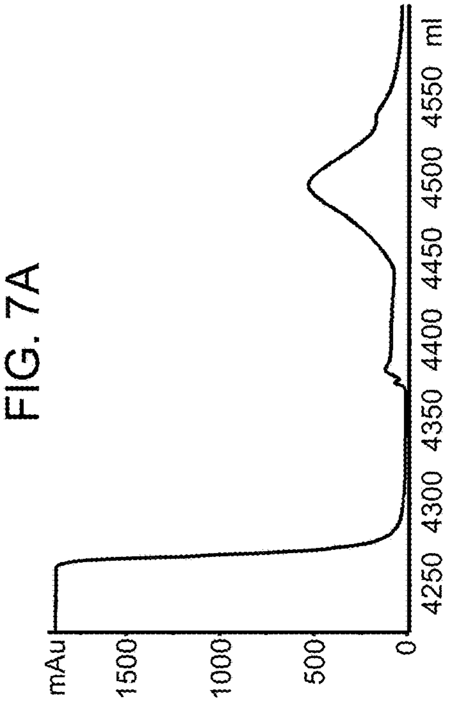
FIG. 7B
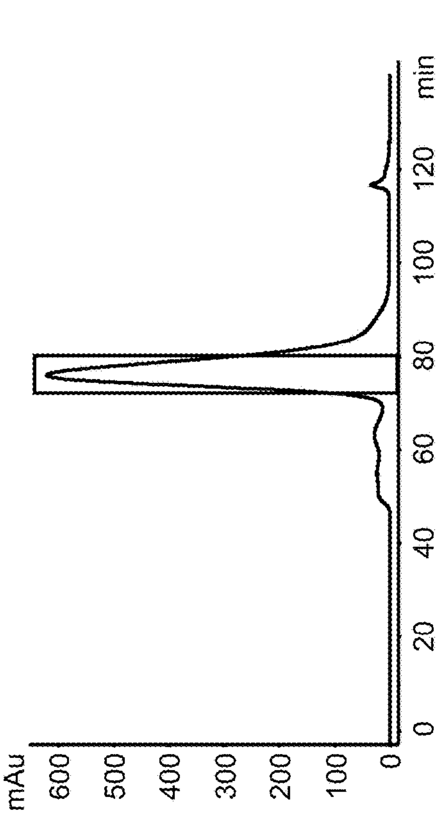
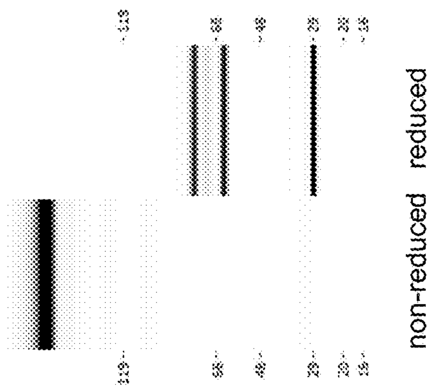
FIG. 7C
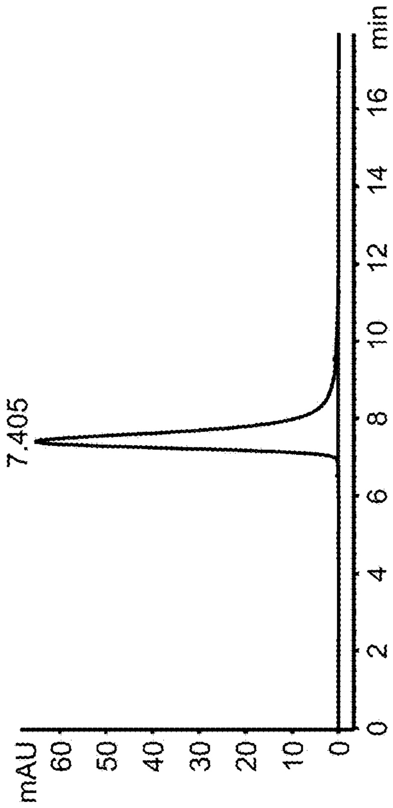
FIG. 7D

FIG. 18A
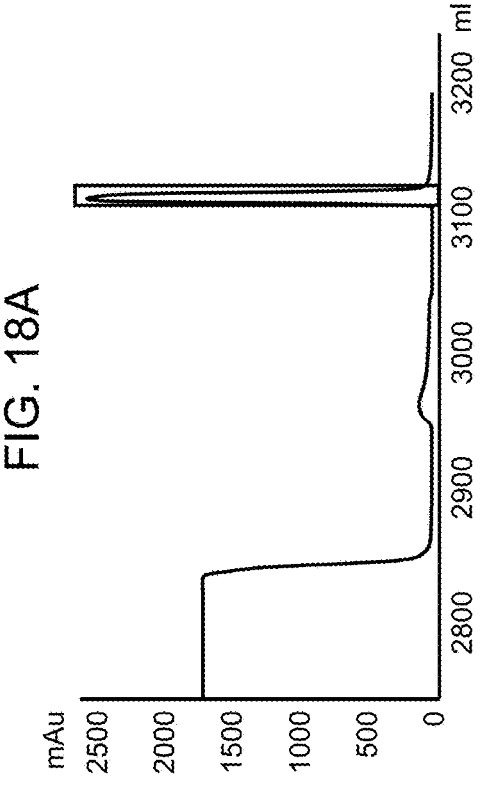
FIG. 18B
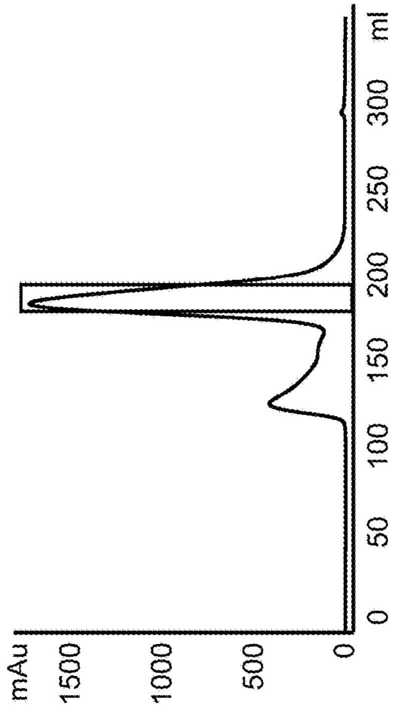
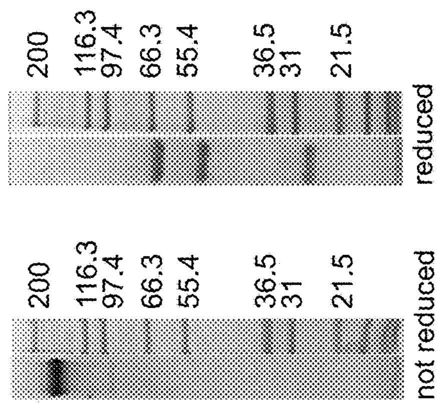
FIG. 18C
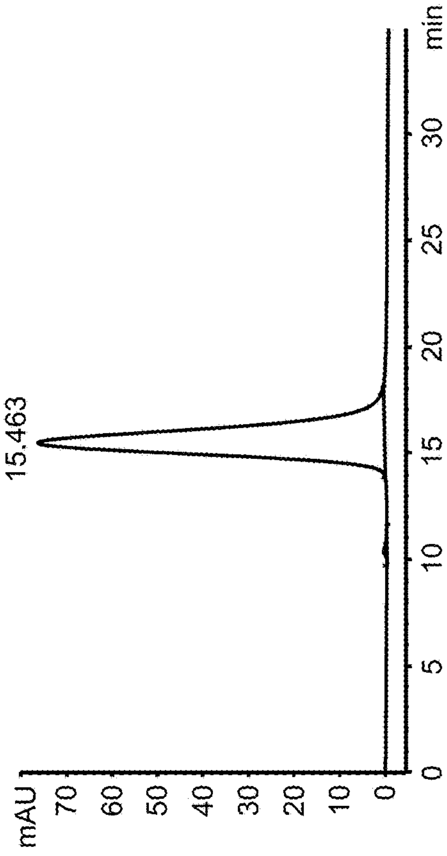
FIG. 18D

FIG. 22A
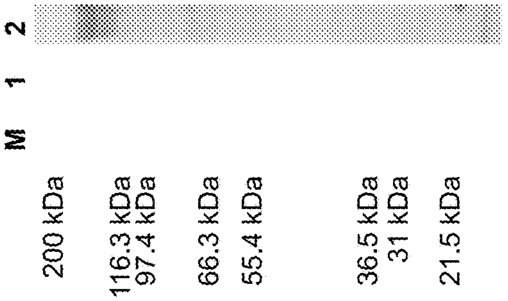
FIG. 22B
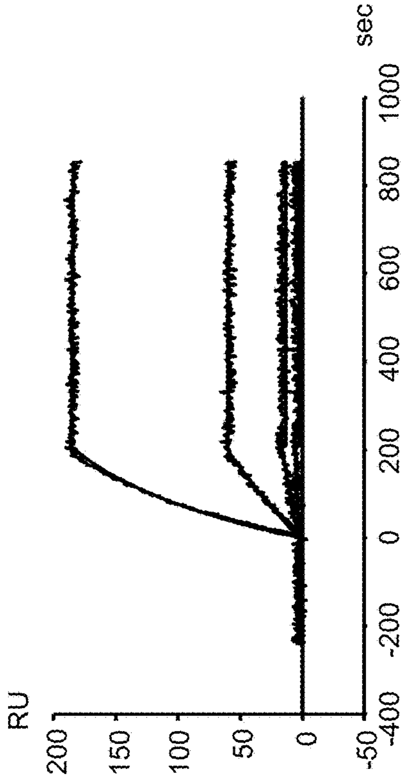
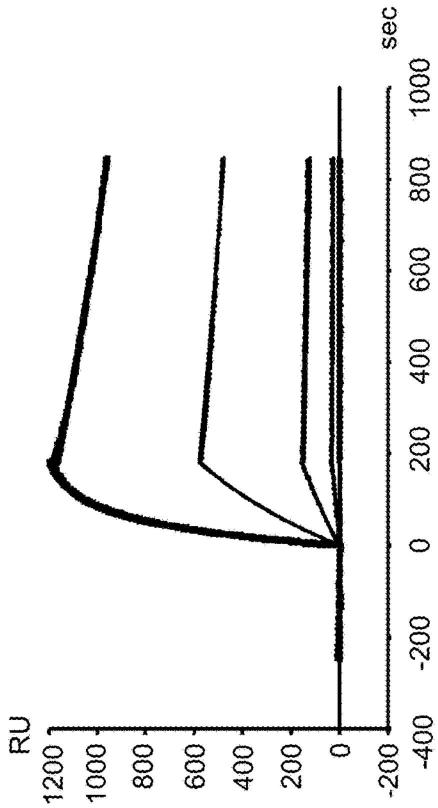
FIG. 22C

FIG. 23A
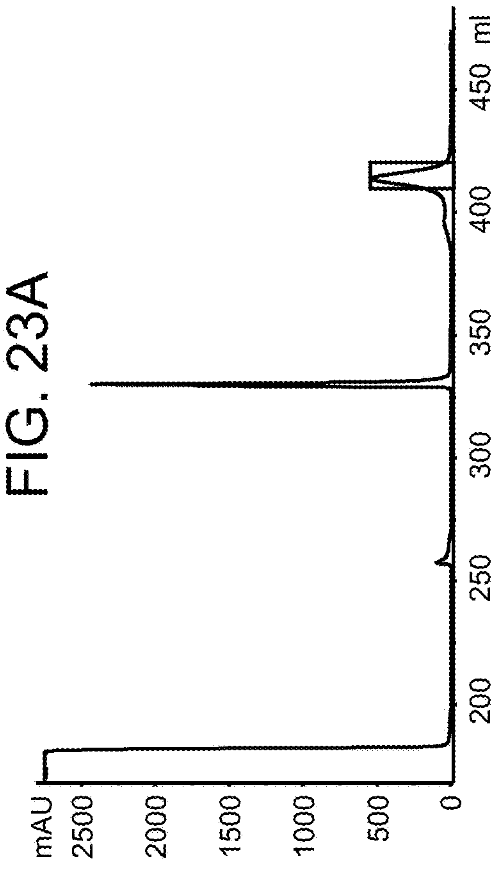
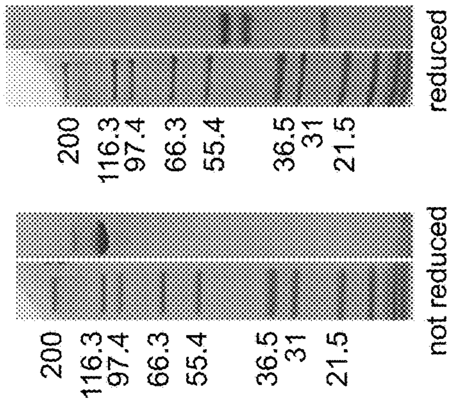
FIG. 23B
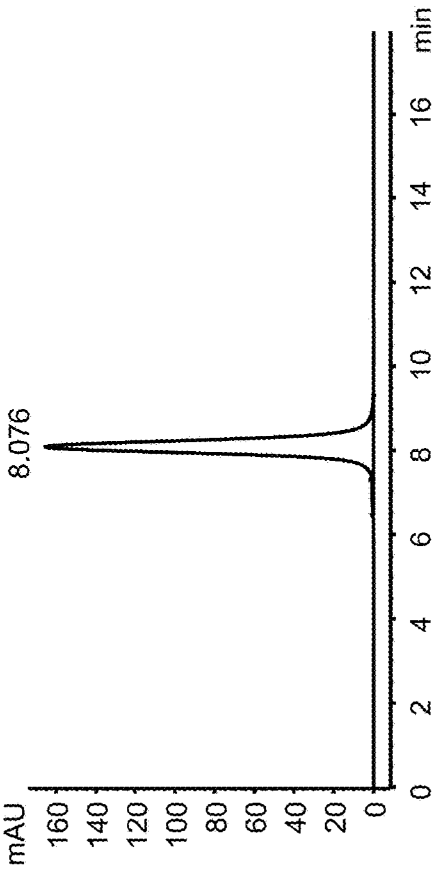
FIG. 23C

FIG. 26A
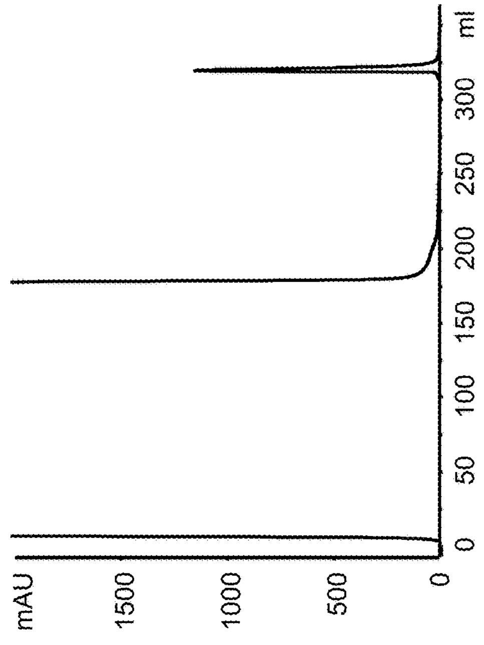
FIG. 26B
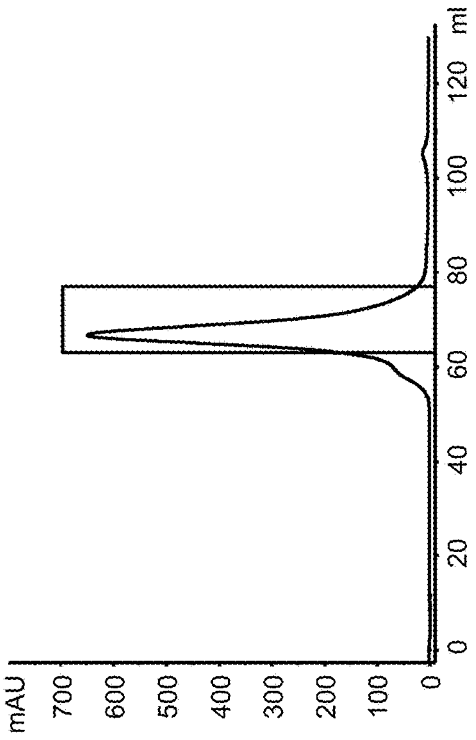
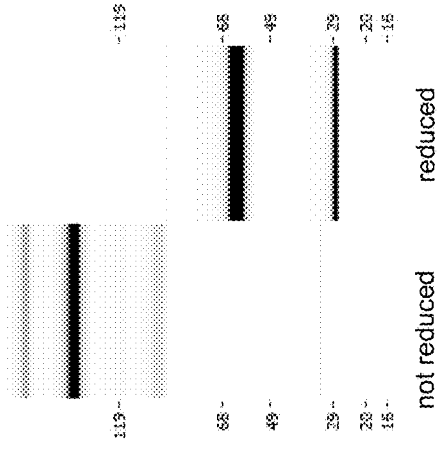
FIG. 26C
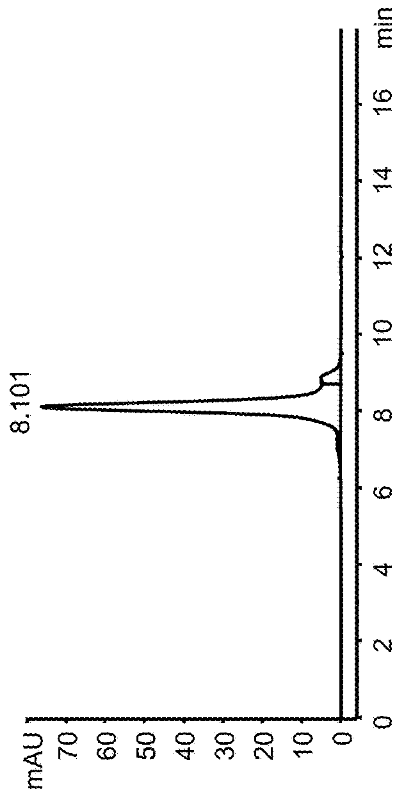
FIG. 26D

FIG. 33A
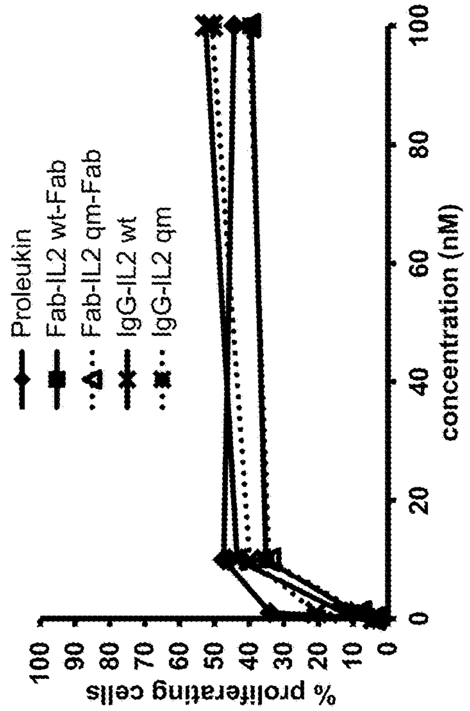
FIG. 33B
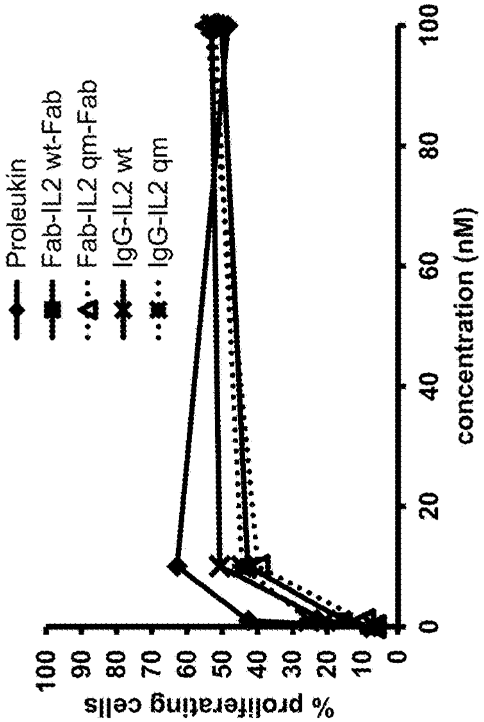
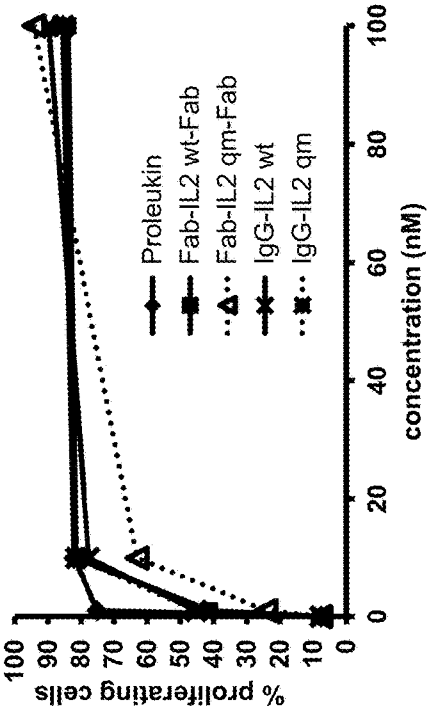
FIG. 33C

Fig. 34A
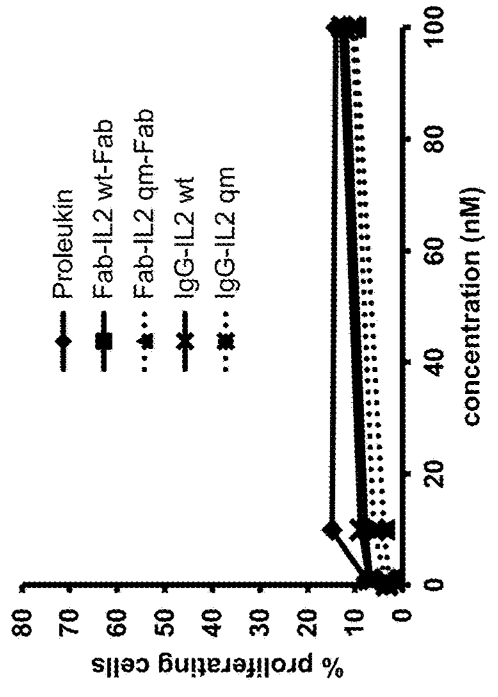
Fig. 34B
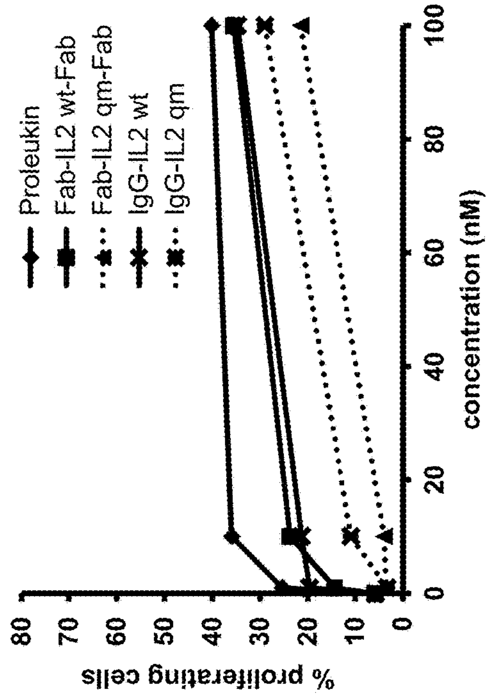
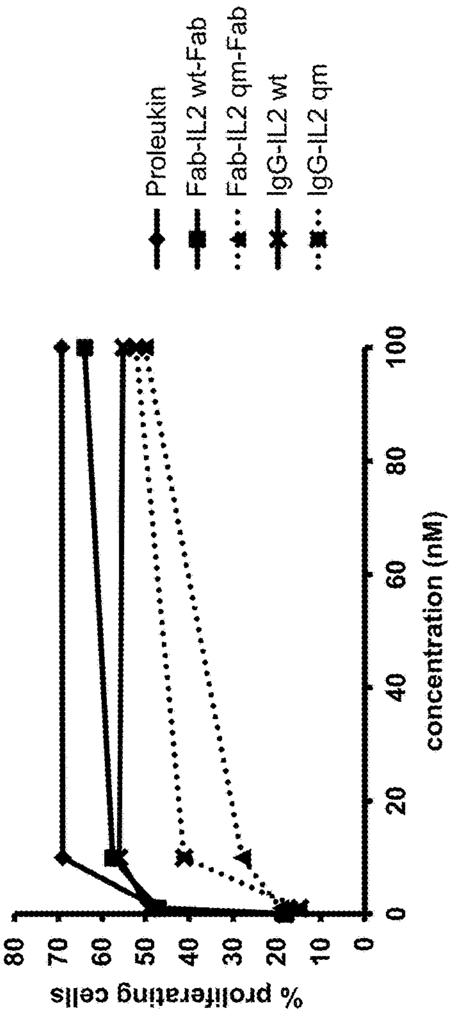
Fig. 34C

FIG. 35B
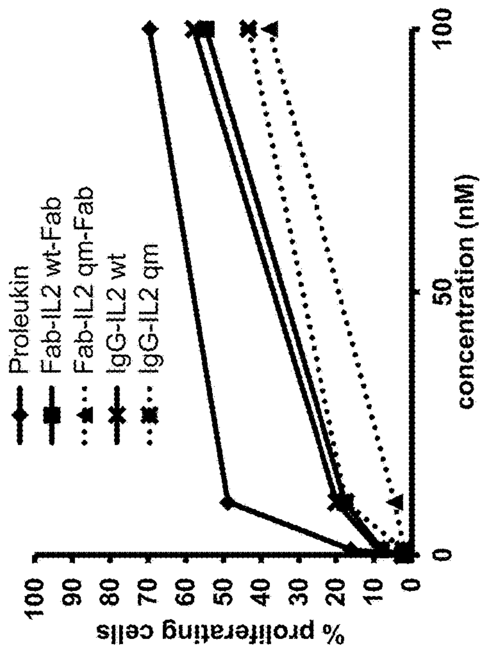
FIG. 35A
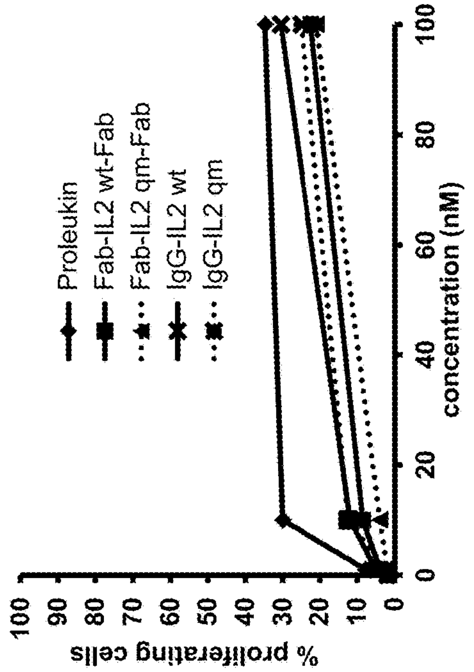
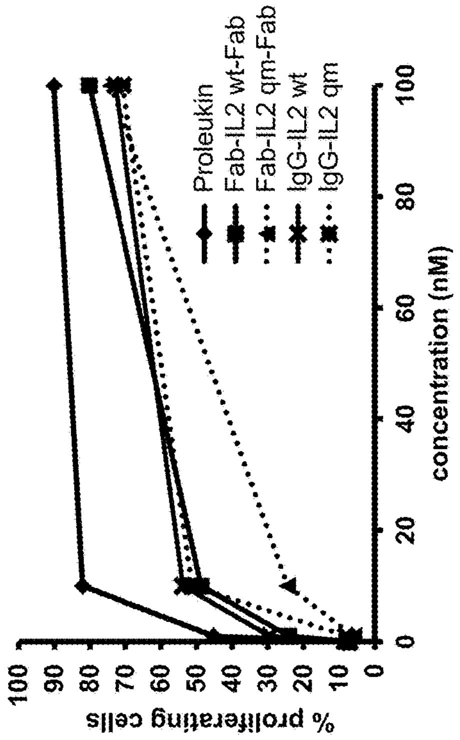
FIG. 35C

FIG. 36A
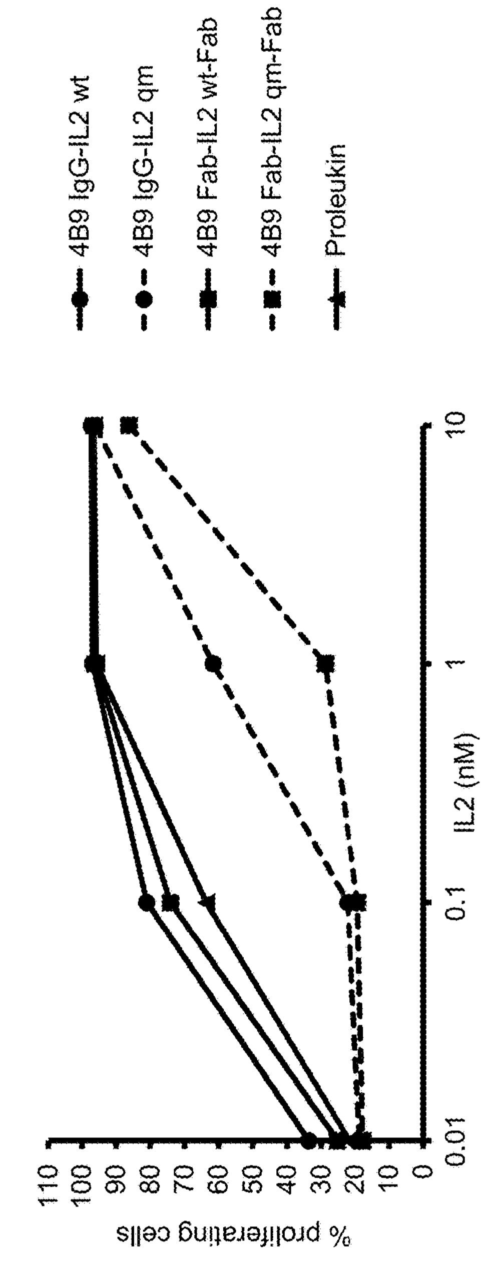
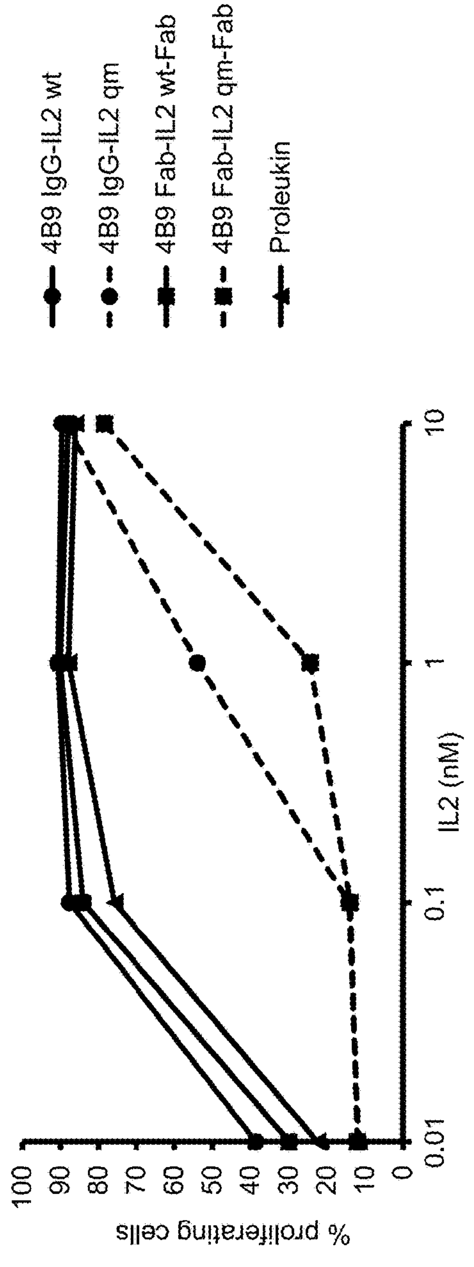
FIG. 36B

FIG. 38A
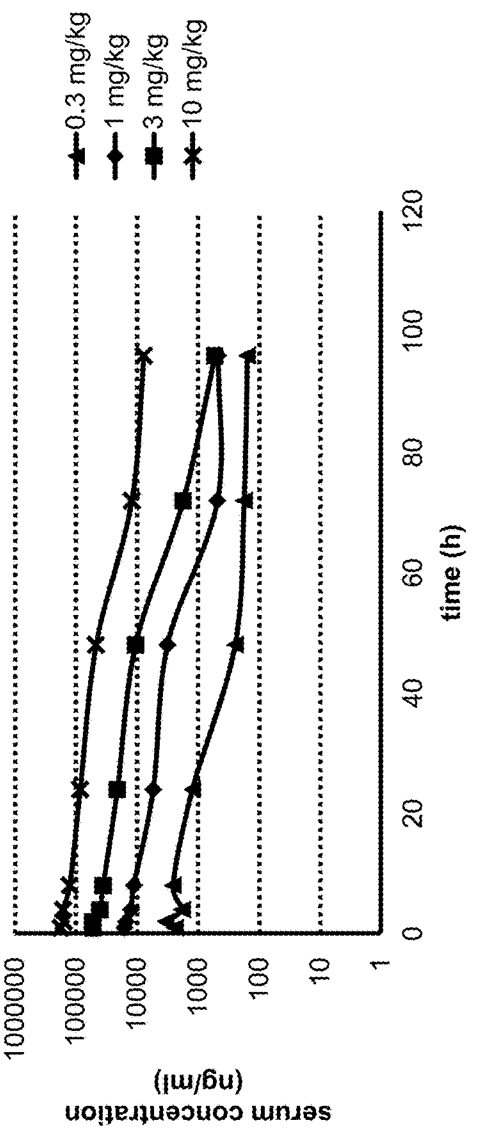
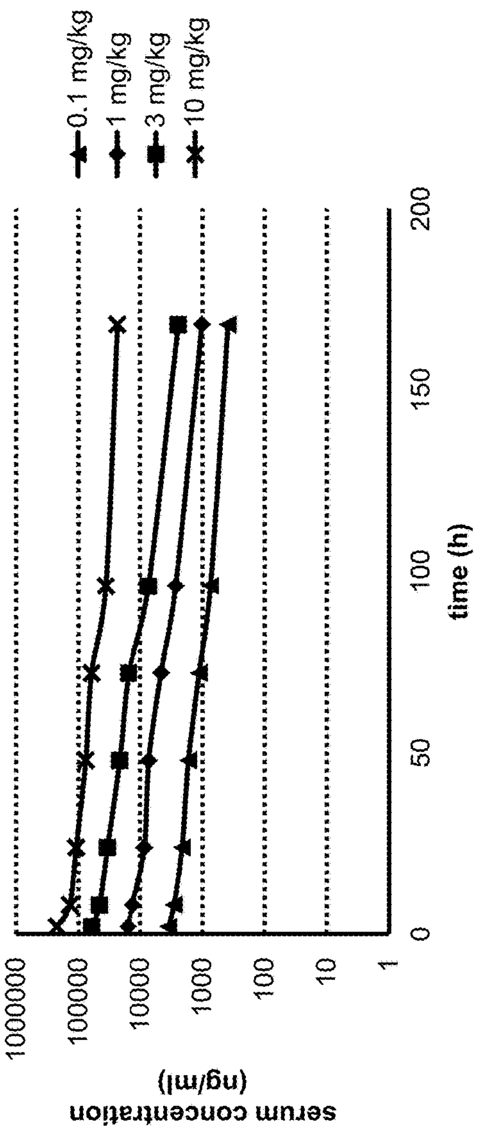
FIG. 38B

SEQUENCE LISTING

<160> NUMBER OF SEQ ID NOS: 300

<210> SEQ ID NO 1
<211> LENGTH: 227
<212> TYPE: PRT
<213> ORGANISM: Homo sapiens

<400> SEQUENCE: 1

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 2
<211> LENGTH: 133
<212> TYPE: PRT
<213> ORGANISM: Artificial Sequence
<220> FEATURE:
<223> OTHER INFORMATION: Human IL-2 (C125A)

<400> SEQUENCE: 2

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45
```

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130

<210> SEQ ID NO 3
<211> LENGTH: 133
<212> TYPE: PRT
<213> ORGANISM: Artificial Sequence
<220> FEATURE:
<223> OTHER INFORMATION: Quadruple mutant human IL-2 (IL-2 qm)

<400> SEQUENCE: 3

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Ala Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Gly Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130

<210> SEQ ID NO 4
<211> LENGTH: 518
<212> TYPE: PRT
<213> ORGANISM: Artificial Sequence
<220> FEATURE:
<223> OTHER INFORMATION: Single chain IL-12 (p40-linker-p35)

<400> SEQUENCE: 4

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

-continued

```
Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495
```

```
Leu Leu His Ala Phe Arg Ile Arg Ala Val Thr Ile Asp Arg Val Met
            500                 505                 510

Ser Tyr Leu Asn Ala Ser
        515


<210> SEQ ID NO 5
<211> LENGTH: 340
<212> TYPE: PRT
<213> ORGANISM: Artificial Sequence
<220> FEATURE:
<223> OTHER INFORMATION: Single chain human IL-10

<400> SEQUENCE: 5

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Gly Gly Ser Gly Gly Gly Gly Ser Gly Gly Gly Gly Ser Gly
                165                 170                 175

Gly Gly Gly Ser Ser Pro Gly Gln Gly Thr Gln Ser Glu Asn Ser Cys
            180                 185                 190

Thr His Phe Pro Gly Asn Leu Pro Asn Met Leu Arg Asp Leu Arg Asp
        195                 200                 205

Ala Phe Ser Arg Val Lys Thr Phe Phe Gln Met Lys Asp Gln Leu Asp
    210                 215                 220

Asn Leu Leu Leu Lys Glu Ser Leu Leu Glu Asp Phe Lys Gly Tyr Leu
225                 230                 235                 240

Gly Cys Gln Ala Leu Ser Glu Met Ile Gln Phe Tyr Leu Glu Glu Val
                245                 250                 255

Met Pro Gln Ala Glu Asn Gln Asp Pro Asp Ile Lys Ala His Val Asn
            260                 265                 270

Ser Leu Gly Glu Asn Leu Lys Thr Leu Arg Leu Arg Leu Arg Arg Cys
        275                 280                 285

His Arg Phe Leu Pro Cys Glu Asn Lys Ser Lys Ala Val Glu Gln Val
    290                 295                 300

Lys Asn Ala Phe Asn Lys Leu Gln Glu Lys Gly Ile Tyr Lys Ala Met
305                 310                 315                 320

Ser Glu Phe Asp Ile Phe Ile Asn Tyr Ile Glu Ala Tyr Met Thr Met
                325                 330                 335
```

```
Lys Ile Arg Asn
            340


<210> SEQ ID NO 6
<211> LENGTH: 166
<212> TYPE: PRT
<213> ORGANISM: Artificial Sequence
<220> FEATURE:
<223> OTHER INFORMATION: Human IL-10 monomer (IL-10M1)

<400> SEQUENCE: 6

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Gly Gly Gly Ser Gly Gly Lys Ser Lys Ala Val Glu
        115                 120                 125

Gln Val Lys Asn Ala Phe Asn Lys Leu Gln Glu Lys Gly Ile Tyr Lys
    130                 135                 140

Ala Met Ser Glu Phe Asp Ile Phe Ile Asn Tyr Ile Glu Ala Tyr Met
145                 150                 155                 160

Thr Met Lys Ile Arg Asn
                165


<210> SEQ ID NO 7
<211> LENGTH: 114
<212> TYPE: PRT
<213> ORGANISM: Artificial Sequence
<220> FEATURE:
<223> OTHER INFORMATION: Mutant human IL-15 (E53A, N79A)

<400> SEQUENCE: 7

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Ala Ser Gly Asp Ala Ser Ile His Asp Thr Val Glu
    50                  55                  60

Asn Leu Ile Ile Leu Ala Asn Asn Ser Leu Ser Ser Asn Gly Ala Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 8
<211> LENGTH: 19
<212> TYPE: PRT
<213> ORGANISM: Artificial Sequence
<220> FEATURE:
<223> OTHER INFORMATION: leader sequence

<400> SEQUENCE: 8

Met Asp Trp Thr Trp Arg Ile Leu Phe Leu Val Ala Ala Ala Thr Gly
1 5 10 15

Ala His Ser

<210> SEQ ID NO 9
<211> LENGTH: 57
<212> TYPE: DNA
<213> ORGANISM: Artificial Sequence
<220> FEATURE:
<223> OTHER INFORMATION: leader sequence

<400> SEQUENCE: 9
atggactgga cctggagaat cctcttcttg gtggcagcag ccacaggagc ccactcc 57

<210> SEQ ID NO 10
<211> LENGTH: 57
<212> TYPE: DNA
<213> ORGANISM: Artificial Sequence
<220> FEATURE:
<223> OTHER INFORMATION: leader sequence

<400> SEQUENCE: 10
atggactgga cctggaggat cctcttcttg gtggcagcag ccacaggagc ccactcc 57

<210> SEQ ID NO 11
<211> LENGTH: 22
<212> TYPE: PRT
<213> ORGANISM: Artificial Sequence
<220> FEATURE:
<223> OTHER INFORMATION: leader sequence

<400> SEQUENCE: 11

Met Asp Met Arg Val Pro Ala Gln Leu Leu Gly Leu Leu Leu Leu Trp
1 5 10 15

Phe Pro Gly Ala Arg Cys
20

<210> SEQ ID NO 12
<211> LENGTH: 66
<212> TYPE: DNA
<213> ORGANISM: Artificial Sequence
<220> FEATURE:
<223> OTHER INFORMATION: leader sequence

<400> SEQUENCE: 12
atggacatga gggtccccgc tcagctcctg ggcctcctgc tgctctggtt cccaggtgcc 60
aggtgt 66

<210> SEQ ID NO 13
<211> LENGTH: 19
<212> TYPE: PRT
<213> ORGANISM: Artificial Sequence
<220> FEATURE:
<223> OTHER INFORMATION: leader sequence

<400> SEQUENCE: 13

-continued

Met Gly Trp Ser Cys Ile Ile Leu Phe Leu Val Ala Thr Ala Thr Gly
1               5                   10                  15

Val His Ser

<210> SEQ ID NO 14
<211> LENGTH: 57
<212> TYPE: DNA
<213> ORGANISM: Artificial Sequence
<220> FEATURE:
<223> OTHER INFORMATION: leader sequence

<400> SEQUENCE: 14
atgggatgga gctgtatcat cctcttcttg gtagcaacag ctaccggtgt gcattcc        57

<210> SEQ ID NO 15
<211> LENGTH: 57
<212> TYPE: DNA
<213> ORGANISM: Artificial Sequence
<220> FEATURE:
<223> OTHER INFORMATION: leader sequence

<400> SEQUENCE: 15
atgggctggt cctgcatcat cctgtttctg gtggctaccg ccactggagt gcattcc        57

<210> SEQ ID NO 16
<211> LENGTH: 57
<212> TYPE: DNA
<213> ORGANISM: Artificial Sequence
<220> FEATURE:
<223> OTHER INFORMATION: leader sequence

<400> SEQUENCE: 16
atgggctggt cctgcatcat cctgtttctg gtcgccacag ccaccggcgt gcactct        57

<210> SEQ ID NO 17
<211> LENGTH: 466
<212> TYPE: PRT
<213> ORGANISM: Artificial Sequence
<220> FEATURE:
<223> OTHER INFORMATION: Human IL-2R-beta-Fc(hole) fusion protein

<400> SEQUENCE: 17

Met Asp Met Arg Val Pro Ala Gln Leu Leu Gly Leu Leu Leu Leu Trp
1               5                   10                  15

Phe Pro Gly Ala Arg Cys Ala Val Asn Gly Thr Ser Gln Phe Thr Cys
            20                  25                  30

Phe Tyr Asn Ser Arg Ala Asn Ile Ser Cys Val Trp Ser Gln Asp Gly
        35                  40                  45

Ala Leu Gln Asp Thr Ser Cys Gln Val His Ala Trp Pro Asp Arg Arg
    50                  55                  60

Arg Trp Asn Gln Thr Cys Glu Leu Leu Pro Val Ser Gln Ala Ser Trp
65                  70                  75                  80

Ala Cys Asn Leu Ile Leu Gly Ala Pro Asp Ser Gln Lys Leu Thr Thr
                85                  90                  95

Val Asp Ile Val Thr Leu Arg Val Leu Cys Arg Glu Gly Val Arg Trp
            100                 105                 110

Arg Val Met Ala Ile Gln Asp Phe Lys Pro Phe Glu Asn Leu Arg Leu
        115                 120                 125

Met Ala Pro Ile Ser Leu Gln Val Val His Val Glu Thr His Arg Cys
    130                 135                 140

Asn Ile Ser Trp Glu Ile Ser Gln Ala Ser His Tyr Phe Glu Arg His

-continued

```
145                 150                 155                 160

Leu Glu Phe Glu Ala Arg Thr Leu Ser Pro Gly His Thr Trp Glu Glu
                165                 170                 175

Ala Pro Leu Leu Thr Leu Lys Gln Lys Gln Glu Trp Ile Cys Leu Glu
            180                 185                 190

Thr Leu Thr Pro Asp Thr Gln Tyr Glu Phe Gln Val Arg Val Lys Pro
        195                 200                 205

Leu Gln Gly Glu Phe Thr Thr Trp Ser Pro Trp Ser Gln Pro Leu Ala
    210                 215                 220

Phe Arg Thr Lys Pro Ala Ala Leu Gly Lys Asp Thr Gly Ala Gln Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Cys
        355                 360                 365

Thr Leu Pro Pro Ser Arg Asp Glu Leu Thr Lys Asn Gln Val Ser Leu
    370                 375                 380

Ser Cys Ala Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Val Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465
```

```
<210> SEQ ID NO 18
<211> LENGTH: 1401
<212> TYPE: DNA
<213> ORGANISM: Artificial Sequence
<220> FEATURE:
<223> OTHER INFORMATION: Human IL-2R-beta-Fc(hole) fusion protein

<400> SEQUENCE: 18

atggacatga gggtccccgc tcagctcctg ggcctcctgc tgctctggtt cccaggtgcc      60

aggtgtgcgg tgaatggcac ttcccagttc acatgcttct acaactcgag agccaacatc     120

tcctgtgtct ggagccaaga tggggctctg caggacactt cctgccaagt ccatgcctgg     180

ccggacagac ggcggtggaa ccaaacctgt gagctgctcc ccgtgagtca agcatcctgg     240
```

gcctgcaacc tgatcctcgg agccccagat tctcagaaac tgaccacagt tgacatcgtc 300
accctgaggg tgctgtgccg tgagggggtg cgatggaggg tgatggccat ccaggacttc 360
aagccctttg agaaccttcg cctgatggcc cccatctccc tccaagttgt ccacgtggag 420
acccacagat gcaacataag ctgggaaatc tcccaagcct cccactactt tgaaagacac 480
ctggagttcg aggcccggac gctgtcccca ggccacacct gggaggaggc ccccctgctg 540
actctcaagc agaagcagga atggatctgc ctggagacgc tcaccccaga cacccagtat 600
gagtttcagg tgcgggtcaa gcctctgcaa ggcgagttca cgacctggag cccctggagc 660
cagcccctgg ccttcagaac aaagcctgca gcccttggga aggacaccgg agctcaggac 720
aaaactcaca catgcccacc gtgcccagca cctgaactcc tggggggacc gtcagtcttc 780
ctcttccccc caaaacccaa ggacaccctc atgatctccc ggacccctga ggtcacatgc 840
gtggtggtgg acgtgagcca cgaagaccct gaggtcaagt tcaactggta cgtggacggc 900
gtggaggtgc ataatgccaa gacaaagccg cgggaggagc agtacaacag cacgtaccgt 960
gtggtcagcg tcctcaccgt cctgcaccag gactggctga atggcaagga gtacaagtgc 1020
aaggtctcca acaaagccct cccagccccc atcgagaaaa ccatctccaa agccaaaggg 1080
cagccccgag aaccacaggt gtgcaccctg cccccatccc gggatgagct gaccaagaac 1140
caggtcagcc tctcgtgcgc agtcaaaggc ttctatccca gcgacatcgc cgtggagtgg 1200
gagagcaatg ggcagccgga gaacaactac aagaccacgc ctcccgtgct ggactccgac 1260
ggctccttct tcctcgtgag caagctcacc gtggacaaga gcaggtggca gcaggggaac 1320
gtcttctcat gctccgtgat gcatgaggct ctgcacaacc actacacgca gaagagcctc 1380
tccctgtctc cgggtaaatg a 1401

<210> SEQ ID NO 19
<211> LENGTH: 492
<212> TYPE: PRT
<213> ORGANISM: Artificial Sequence
<220> FEATURE:
<223> OTHER INFORMATION: Human IL-2R-gamma-Fc(knob) fusion protein

<400> SEQUENCE: 19

Met Leu Lys Pro Ser Leu Pro Phe Thr Ser Leu Leu Phe Leu Gln Leu
1 5 10 15

Pro Leu Leu Gly Val Gly Leu Asn Thr Thr Ile Leu Thr Pro Asn Gly
20 25 30

Asn Glu Asp Thr Thr Ala Asp Phe Phe Leu Thr Thr Met Pro Thr Asp
35 40 45

Ser Leu Ser Val Ser Thr Leu Pro Leu Pro Glu Val Gln Cys Phe Val
50 55 60

Phe Asn Val Glu Tyr Met Asn Cys Thr Trp Asn Ser Ser Ser Glu Pro
65 70 75 80

Gln Pro Thr Asn Leu Thr Leu His Tyr Trp Tyr Lys Asn Ser Asp Asn
85 90 95

Asp Lys Val Gln Lys Cys Ser His Tyr Leu Phe Ser Glu Glu Ile Thr
100 105 110

Ser Gly Cys Gln Leu Gln Lys Lys Glu Ile His Leu Tyr Gln Thr Phe
115 120 125

Val Val Gln Leu Gln Asp Pro Arg Glu Pro Arg Arg Gln Ala Thr Gln
130 135 140

Met Leu Lys Leu Gln Asn Leu Val Ile Pro Trp Ala Pro Glu Asn Leu

-continued

```
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

Leu Phe Ala Leu Glu Ala Gly Ala Gln Asp Lys Thr His Thr Cys Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Cys Arg
385                 390                 395                 400

Asp Glu Leu Thr Lys Asn Gln Val Ser Leu Trp Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490
```

<210> SEQ ID NO 20
<211> LENGTH: 1479
<212> TYPE: DNA
<213> ORGANISM: Artificial Sequence
<220> FEATURE:
<223> OTHER INFORMATION: Human IL-2R-gamma-Fc(knob) fusion protein

<400> SEQUENCE: 20

```
atgttgaagc catcattacc attcacatcc ctcttattcc tgcagctgcc cctgctggga     60

gtggggctga acacgacaat tctgacgccc aatgggaatg aagacaccac agctgatttc    120
```

```
ttcctgacca ctatgcccac tgactccctc agtgtttcca ctctgcccct cccagaggtt    180

cagtgttttg tgttcaatgt cgagtacatg aattgcactt ggaacagcag ctctgagccc    240

cagcctacca acctcactct gcattattgg tacaagaact cggataatga taaagtccag    300

aagtgcagcc actatctatt ctctgaagaa atcacttctg gctgtcagtt gcaaaaaaag    360

gagatccacc tctaccaaac atttgttgtt cagctccagg acccacggga acccaggaga    420

caggccacac agatgctaaa actgcagaat ctggtgatcc cctgggctcc agagaaccta    480

acacttcaca aactgagtga atcccagcta gaactgaact ggaacaacag attcttgaac    540

cactgtttgg agcacttggt gcagtaccgg actgactggg accacagctg gactgaacaa    600

tcagtggatt atagacataa gttctccttg cctagtgtgg atgggcagaa acgctacacg    660

tttcgtgttc ggagccgctt taacccactc tgtggaagtg ctcagcattg gagtgaatgg    720

agccacccaa tccactgggg gagcaatact tcaaaagaga atcctttcct gtttgcattg    780

gaagccggag ctcaggacaa aactcacaca tgcccaccgt gcccagcacc tgaactcctg    840

gggggaccgt cagtcttcct cttcccccca aaacccaagg acaccctcat gatctcccgg    900

acccctgagg tcacatgcgt ggtggtggac gtgagccacg aagaccctga ggtcaagttc    960

aactggtacg tggacggcgt ggaggtgcat aatgccaaga caaagccgcg ggaggagcag   1020

tacaacagca cgtaccgtgt ggtcagcgtc ctcaccgtcc tgcaccagga ctggctgaat   1080

ggcaaggagt acaagtgcaa ggtctccaac aaagccctcc cagcccccat cgagaaaacc   1140

atctccaaag ccaaagggca gccccgagaa ccacaggtgt acaccctgcc cccatgccgg   1200

gatgagctga ccaagaacca ggtcagcctg tggtgcctgg tcaaaggctt ctatcccagc   1260

gacatcgccg tggagtggga gagcaatggg cagccggaga acaactacaa gaccacgcct   1320

cccgtgctgg actccgacgg ctccttcttc ctctacagca agctcaccgt ggacaagagc   1380

aggtggcagc aggggaacgt cttctcatgc tccgtgatgc atgaggctct gcacaaccac   1440

tacacgcaga agagcctctc cctgtctccg ggtaaatga                          1479
```

```
<210> SEQ ID NO 21
<211> LENGTH: 219
<212> TYPE: PRT
<213> ORGANISM: Artificial Sequence
<220> FEATURE:
<223> OTHER INFORMATION: Human IL-2R alpha subunit + Avi-tag + His-tag

<400> SEQUENCE: 21

Met Gly Trp Ser Cys Ile Ile Leu Phe Leu Val Ala Thr Ala Thr Gly
1               5                   10                  15

Val His Ser Glu Leu Cys Asp Asp Asp Pro Pro Glu Ile Pro His Ala
            20                  25                  30

Thr Phe Lys Ala Met Ala Tyr Lys Glu Gly Thr Met Leu Asn Cys Glu
        35                  40                  45

Cys Lys Arg Gly Phe Arg Arg Ile Lys Ser Gly Ser Leu Tyr Met Leu
    50                  55                  60

Cys Thr Gly Asn Ser Ser His Ser Ser Trp Asp Asn Gln Cys Gln Cys
65                  70                  75                  80

Thr Ser Ser Ala Thr Arg Asn Thr Thr Lys Gln Val Thr Pro Gln Pro
                85                  90                  95

Glu Glu Gln Lys Glu Arg Lys Thr Thr Glu Met Gln Ser Pro Met Gln
            100                 105                 110

Pro Val Asp Gln Ala Ser Leu Pro Gly His Cys Arg Glu Pro Pro Pro
        115                 120                 125
```

```
Trp Glu Asn Glu Ala Thr Glu Arg Ile Tyr His Phe Val Val Gly Gln
    130                 135                 140

Met Val Tyr Tyr Gln Cys Val Gln Gly Tyr Arg Ala Leu His Arg Gly
145                 150                 155                 160

Pro Ala Glu Ser Val Cys Lys Met Thr His Gly Lys Thr Arg Trp Thr
                165                 170                 175

Gln Pro Gln Leu Ile Cys Thr Gly Val Asp Glu Gln Leu Tyr Phe Gln
            180                 185                 190

Gly Gly Ser Gly Leu Asn Asp Ile Phe Glu Ala Gln Lys Ile Glu Trp
        195                 200                 205

His Glu Ala Arg Ala His His His His His His
    210                 215


<210> SEQ ID NO 22
<211> LENGTH: 660
<212> TYPE: DNA
<213> ORGANISM: Artificial Sequence
<220> FEATURE:
<223> OTHER INFORMATION: Human IL-2R alpha subunit + Avi-tag + His-tag

<400> SEQUENCE: 22

atgggatgga gctgtatcat cctcttcttg gtagcaacag ctaccggtgt gcattccgag      60

ctctgtgacg atgacccgcc agagatccca cacgccacat tcaaagccat ggcctacaag     120

gaaggaacca tgttgaactg tgaatgcaag agaggtttcc gcagaataaa aagcgggtca     180

ctctatatgc tctgtacagg aaactctagc cactcgtcct gggacaacca atgtcaatgc     240

acaagctctg ccactcggaa cacaacgaaa caagtgacac ctcaacctga agaacagaaa     300

gaaaggaaaa ccacagaaat gcaaagtcca atgcagccag tggaccaagc gagccttcca     360

ggtcactgca gggaacctcc accatgggaa aatgaagcca cagagagaat ttatcatttc     420

gtggtggggc agatggttta ttatcagtgc gtccagggat acagggctct acacagaggt     480

cctgctgaga gcgtctgcaa aatgacccac gggaagacaa ggtggaccca gccccagctc     540

atatgcacag gtgtcgacga acagttatat tttcagggcg gctcaggcct gaacgacatc     600

ttcgaggccc agaagatcga gtggcacgag gctcgagctc accaccatca ccatcactga     660


<210> SEQ ID NO 23
<211> LENGTH: 107
<212> TYPE: PRT
<213> ORGANISM: Artificial Sequence
<220> FEATURE:
<223> OTHER INFORMATION: 2B10; VL

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95
```

Thr Phe Gly Gln Gly Thr Lys Val Glu Ile Lys
100 105

<210> SEQ ID NO 24
<211> LENGTH: 321
<212> TYPE: DNA
<213> ORGANISM: Artificial Sequence
<220> FEATURE:
<223> OTHER INFORMATION: 2B10; VL

<400> SEQUENCE: 24
gatatccaga tgacccagtc tccatcctcc ctgtctgcat ctgtcggaga ccgggtcacc 60
atcacctgcc gggcaagtca gggcattaga aatgatttag gctggtacca gcagaagcca 120
gggaaagccc ctaagcgcct gatctatgct gcatccagtt tgcagagtgg cgtcccatca 180
aggttcagcg gcggtggatc cgggacagag ttcactctca ccatcagcag cttgcagcct 240
gaagattttg ccacctatta ctgcttgcag aatggtctgc agcccgcgac gtttggccag 300
ggcaccaaag tcgagatcaa g 321

<210> SEQ ID NO 25
<211> LENGTH: 107
<212> TYPE: PRT
<213> ORGANISM: Artificial Sequence
<220> FEATURE:
<223> OTHER INFORMATION: 2B10(GS); VL

<400> SEQUENCE: 25

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Asn Asp
20 25 30

Leu Gly Trp Tyr Gln Gln Lys Pro Gly Lys Ala Pro Lys Arg Leu Ile
35 40 45

Tyr Ala Ala Ser Ser Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Leu Gln Asn Gly Leu Gln Pro Ala
85 90 95

Thr Phe Gly Gln Gly Thr Lys Val Glu Ile Lys
100 105

<210> SEQ ID NO 26
<211> LENGTH: 321
<212> TYPE: DNA
<213> ORGANISM: Artificial Sequence
<220> FEATURE:
<223> OTHER INFORMATION: 2B10(GS); VL

<400> SEQUENCE: 26
gatatccaga tgacccagtc tccatcctcc ctgtctgcat ctgtcggaga ccgggtcacc 60
atcacctgcc gggcaagtca gggcattaga aatgatttag gctggtacca gcagaagcca 120
gggaaagccc ctaagcgcct gatctatgct gcatccagtt tgcagagtgg cgtcccatca 180
aggttcagcg gcagtggatc cgggacagag ttcactctca ccatcagcag cttgcagcct 240
gaagattttg ccacctatta ctgcttgcag aatggtctgc agcccgcgac gtttggccag 300
ggcaccaaag tcgagatcaa g 321

<210> SEQ ID NO 27
<211> LENGTH: 121
<212> TYPE: PRT
<213> ORGANISM: Artificial Sequence
<220> FEATURE:
<223> OTHER INFORMATION: 2B10; VH

<400> SEQUENCE: 27

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120
```

<210> SEQ ID NO 28
<211> LENGTH: 363
<212> TYPE: DNA
<213> ORGANISM: Artificial Sequence
<220> FEATURE:
<223> OTHER INFORMATION: 2B10; VH

<400> SEQUENCE: 28

```
caggtgcaat tggtgcagtc tggggctgag gtgaagaagc ctgggtcctc ggtgaaggtc      60

tcctgcaagg cctccggagg cacattcagc agctacgcta taagctgggt gcgacaggcc     120

cctggacaag ggctcgagtg gatgggaggg atcatcccta tctttggtac agcaaactac     180

gcacagaagt tccagggcag ggtcaccatt actgcagaca aatccacgag cacagcctac     240

atggagctga gcagcctgag atctgaggac accgccgtgt attactgtgc gagactgtac     300

ggttacgctt actacggtgc ttttgactac tggggccaag ggaccaccgt gaccgtctcc     360

tca                                                                   363
```

<210> SEQ ID NO 29
<211> LENGTH: 108
<212> TYPE: PRT
<213> ORGANISM: Artificial Sequence
<220> FEATURE:
<223> OTHER INFORMATION: 2F11; VL

<400> SEQUENCE: 29

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60
```

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Gly Gln Tyr Thr Pro
85 90 95

Pro Thr Phe Gly Gln Gly Thr Lys Val Glu Ile Lys
100 105

<210> SEQ ID NO 30
<211> LENGTH: 324
<212> TYPE: DNA
<213> ORGANISM: Artificial Sequence
<220> FEATURE:
<223> OTHER INFORMATION: 2F11; VL

<400> SEQUENCE: 30
gaaatcgtgt taacgcagtc tccaggcacc ctgtctttgt ctccagggga aagagccacc 60
ctctcttgca gggccagtca gagtgttagc agcagctact tagcctggta ccagcagaaa 120
cctggccagg ctcccaggct cctcatctat ggagcatcca gcagggccac tggcgtccca 180
gacaggttca gtggcagtgg atccgggaca gacttcactc tcaccatcag cagactggag 240
cctgaagatt ttgcagtgta ttactgtcag cagggtcagt atactccccc cacgttcggc 300
caggggacca aagtggaaat caaa 324

<210> SEQ ID NO 31
<211> LENGTH: 108
<212> TYPE: PRT
<213> ORGANISM: Artificial Sequence
<220> FEATURE:
<223> OTHER INFORMATION: 2F11(VI); VL

<400> SEQUENCE: 31

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Gly Gln Tyr Thr Pro
85 90 95

Pro Thr Phe Gly Gln Gly Thr Lys Val Glu Ile Lys
100 105

<210> SEQ ID NO 32
<211> LENGTH: 324
<212> TYPE: DNA
<213> ORGANISM: Artificial Sequence
<220> FEATURE:
<223> OTHER INFORMATION: 2F11(VI); VL

<400> SEQUENCE: 32
gaaatcgtgt taacgcagtc tccaggcacc ctgtctttgt ctccagggga aagagccacc 60
ctctcttgca gggccagtca gagtgttagc agcagctact tagcctggta ccagcagaaa 120
cctggccagg ctcccaggct cctcatctat ggagcatcca gcagggccac tggcatccca 180
gacaggttca gtggcagtgg atccgggaca gacttcactc tcaccatcag cagactggag 240
cctgaagatt ttgcagtgta ttactgtcag cagggtcagt atactccccc cacgttcggc 300
caggggacca aagtggaaat caaa 324

<210> SEQ ID NO 33
<211> LENGTH: 117
<212> TYPE: PRT
<213> ORGANISM: Artificial Sequence
<220> FEATURE:
<223> OTHER INFORMATION: 2F11; VH

<400> SEQUENCE: 33

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Met Ala Val Tyr Tyr Cys
85 90 95

Ala Lys Trp Arg Trp Met Met Phe Asp Tyr Trp Gly Gln Gly Thr Leu
100 105 110

Val Thr Val Ser Ser
115

<210> SEQ ID NO 34
<211> LENGTH: 351
<212> TYPE: DNA
<213> ORGANISM: Artificial Sequence
<220> FEATURE:
<223> OTHER INFORMATION: 2F11; VH

<400> SEQUENCE: 34
gaggtgcaat tgttggagtc tgggggaggc ttggtacagc ctggggggtc cctgagactc 60
tcctgtgcag cctccggatt cacctttagc agttatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcagatga acagcctgag agccgaggac atggccgtat attactgtgc gaaatggaga 300
tggatgatgt ttgactactg gggccaagga accctggtca ccgtctcgag t 351

<210> SEQ ID NO 35
<211> LENGTH: 117
<212> TYPE: PRT
<213> ORGANISM: Artificial Sequence
<220> FEATURE:
<223> OTHER INFORMATION: 2F11(MT); VH

<400> SEQUENCE: 35

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

```
Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Arg Trp Met Met Phe Asp Tyr Trp Gly Gln Gly Thr Leu
            100                 105                 110

Val Thr Val Ser Ser
        115


<210> SEQ ID NO 36
<211> LENGTH: 351
<212> TYPE: DNA
<213> ORGANISM: Artificial Sequence
<220> FEATURE:
<223> OTHER INFORMATION: 2F11(MT); VH

<400> SEQUENCE: 36

gaggtgcaat tgttggagtc tgggggaggc ttggtacagc ctggggggtc cctgagactc      60

tcctgtgcag cctccggatt cacctttagc agttatgcca tgagctgggt ccgccaggct     120

ccagggaagg ggctggagtg ggtctcagct attagtggta gtggtggtag cacatactac     180

gcagactccg tgaagggccg gttcaccatc tccagagaca attccaagaa cacgctgtat     240

ctgcagatga acagcctgag agccgaggac accgccgtat attactgtgc gaaatggaga     300

tggatgatgt ttgactactg gggccaagga accctggtca ccgtctcgag t              351


<210> SEQ ID NO 37
<211> LENGTH: 108
<212> TYPE: PRT
<213> ORGANISM: Artificial Sequence
<220> FEATURE:
<223> OTHER INFORMATION: 3F2; VL

<400> SEQUENCE: 37

Glu Ile Val Leu Thr Gln Ser Pro Gly Thr Leu Ser Leu Tyr Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105


<210> SEQ ID NO 38
<211> LENGTH: 324
<212> TYPE: DNA
<213> ORGANISM: Artificial Sequence
<220> FEATURE:
<223> OTHER INFORMATION: 3F2; VL

<400> SEQUENCE: 38
```

gaaatcgtgt taacgcagtc tccaggcacc ctgtctttgt atccagggga aagagccacc 60
ctctcttgca gggccagtca gagtgttacc agtagctact tagcctggta ccagcagaaa 120
cctggccagg ctcccaggct cctcatcaat gtgggctccc gtagggccac tggcatccca 180
gacaggttca gtggcagtgg atccgggaca gacttcactc tcaccatcag cagactggag 240
cctgaagatt ttgcagtgta ttactgtcag cagggtatta tgcttccccc gacgttcggc 300
caggggacca aagtggaaat caaa 324

<210> SEQ ID NO 39
<211> LENGTH: 108
<212> TYPE: PRT
<213> ORGANISM: Artificial Sequence
<220> FEATURE:
<223> OTHER INFORMATION: 3F2(YS); VL

<400> SEQUENCE: 39

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Thr Ser Ser
20 25 30

Tyr Leu Ala Trp Tyr Gln Gln Lys Pro Gly Gln Ala Pro Arg Leu Leu
35 40 45

Ile Asn Val Gly Ser Arg Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Gly Ile Met Leu Pro
85 90 95

Pro Thr Phe Gly Gln Gly Thr Lys Val Glu Ile Lys
100 105

<210> SEQ ID NO 40
<211> LENGTH: 324
<212> TYPE: DNA
<213> ORGANISM: Artificial Sequence
<220> FEATURE:
<223> OTHER INFORMATION: 3F2(YS); VL

<400> SEQUENCE: 40
gaaatcgtgt taacgcagtc tccaggcacc ctgtctttgt ctccagggga aagagccacc 60
ctctcttgca gggccagtca gagtgttacc agtagctact tagcctggta ccagcagaaa 120
cctggccagg ctcccaggct cctcatcaat gtgggctccc gtagggccac tggcatccca 180
gacaggttca gtggcagtgg atccgggaca gacttcactc tcaccatcag cagactggag 240
cctgaagatt ttgcagtgta ttactgtcag cagggtatta tgcttccccc gacgttcggc 300
caggggacca aagtggaaat caaa 324

<210> SEQ ID NO 41
<211> LENGTH: 117
<212> TYPE: PRT
<213> ORGANISM: Artificial Sequence
<220> FEATURE:
<223> OTHER INFORMATION: 3F2; VH

<400> SEQUENCE: 41

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr

```
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115


<210> SEQ ID NO 42
<211> LENGTH: 351
<212> TYPE: DNA
<213> ORGANISM: Artificial Sequence
<220> FEATURE:
<223> OTHER INFORMATION: 3F2; VH

<400> SEQUENCE: 42

gaggtgcaat tgttggagtc tgggggaggc ttggtacagc ctggggggtc cctgagactc      60

tcctgtgcag cctccggatt cacctttagc agttatgcca tgagctgggt ccgccaggct     120

ccagggaagg ggctggagtg ggtctcagct attagtggta gtggtggtag cacatactac     180

gcagactccg tgaagggccg gttcaccatc tccagagaca attccaagaa cacgctgtat     240

ctgcagatga acagcctgag agccgaggac acggccgtat attactgtgc gaaagggtgg     300

tttggtggtt ttaactactg gggccaagga accctggtca ccgtctcgag t              351


<210> SEQ ID NO 43
<211> LENGTH: 108
<212> TYPE: PRT
<213> ORGANISM: Artificial Sequence
<220> FEATURE:
<223> OTHER INFORMATION: 3D9, VL

<400> SEQUENCE: 43

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Leu Ile Pro
                85                  90                  95

Pro Thr Phe Gly Gln Gly Thr Lys Val Glu Ile Lys
            100                 105


<210> SEQ ID NO 44
<211> LENGTH: 324
<212> TYPE: DNA
<213> ORGANISM: Artificial Sequence
<220> FEATURE:
```

<223> OTHER INFORMATION: 3D9, VL

<400> SEQUENCE: 44

```
gaaatcgtgt taacgcagtc tccaggcacc ctgtctttgt ctccagggga aagagccacc     60

ctctcttgca gggccagtca gagtgttagc agcagctact tagcctggta ccagcagaaa    120

cctggccagg ctcccaggct cctcatctat ggagcatcca gcagggccac tggcatccca    180

gacaggttca gtggcagtgg atccgggaca gacttcactc tcaccatcag cagactggag    240

cctgaagatt ttgcagtgta ttactgtcag cagggtcagc ttattccccc tacgttcggc    300

caggggacca aagtggaaat caaa                                           324
```

<210> SEQ ID NO 45
<211> LENGTH: 117
<212> TYPE: PRT
<213> ORGANISM: Artificial Sequence
<220> FEATURE:
<223> OTHER INFORMATION: 3D9, VH

<400> SEQUENCE: 45

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Thr Pro Gly Lys Gly Leu Glu Trp Val
        35                  40                  45

Ser Ala Ile Gly Val Ser Thr Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Pro Phe Asp Tyr Trp Gly Gln Gly Thr Leu
            100                 105                 110

Val Thr Val Ser Ser
        115
```

<210> SEQ ID NO 46
<211> LENGTH: 351
<212> TYPE: DNA
<213> ORGANISM: Artificial Sequence
<220> FEATURE:
<223> OTHER INFORMATION: 3D9, VH

<400> SEQUENCE: 46

```
gaggtgcaat tgttggagtc tgggggaggc ttggtacagc ctggggggtc cctgagactc     60

tcctgtgcag cctccggatt cacctttagc agttatgcta tgagctgggt ccgccagact    120

ccagggaagg ggctggagtg ggtctcagct attggtgtta gtactggtag cacatactac    180

gcagactccg tgaagggccg gttcaccatc tccagagaca attccaagaa cacgctgtat    240

ctgcagatga acagcctgag agccgaggac acggccgtat attactgtgc gaaaggttgg    300

ctgggtcctt ttgactactg gggccaagga accctggtca ccgtctcgag t             351
```

<210> SEQ ID NO 47
<211> LENGTH: 117
<212> TYPE: PRT
<213> ORGANISM: Artificial Sequence
<220> FEATURE:
<223> OTHER INFORMATION: 3D9(TA); VH

<400> SEQUENCE: 47

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Gly Val Ser Thr Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Trp Leu Gly Pro Phe Asp Tyr Trp Gly Gln Gly Thr Leu
100 105 110

Val Thr Val Ser Ser
115

<210> SEQ ID NO 48
<211> LENGTH: 351
<212> TYPE: DNA
<213> ORGANISM: Artificial Sequence
<220> FEATURE:
<223> OTHER INFORMATION: 3D9(TA); VH

<400> SEQUENCE: 48
gaggtgcaat tgttggagtc tgggggaggc ttggtacagc ctggggggtc cctgagactc 60
tcctgtgcag cctccggatt cacctttagc agttatgcta tgagctgggt ccgccaggct 120
ccagggaagg ggctggagtg ggtctcagct attggtgtta gtactggtag cacatactac 180
gcagactccg tgaagggccg gttcaccatc tccagagaca attccaagaa cacgctgtat 240
ctgcagatga acagcctgag agccgaggac acggccgtat attactgtgc gaaaggttgg 300
ctgggtcctt ttgactactg gggccaagga accctggtca ccgtctcgag t 351

<210> SEQ ID NO 49
<211> LENGTH: 108
<212> TYPE: PRT
<213> ORGANISM: Artificial Sequence
<220> FEATURE:
<223> OTHER INFORMATION: 4G8; VL

<400> SEQUENCE: 49

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Arg Ser
20 25 30

Tyr Leu Ala Trp Tyr Gln Gln Lys Pro Gly Gln Ala Pro Arg Leu Leu
35 40 45

Ile Ile Gly Ala Ser Thr Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Gly Gln Val Ile Pro
85 90 95

Pro Thr Phe Gly Gln Gly Thr Lys Val Glu Ile Lys
100 105

<210> SEQ ID NO 50
<211> LENGTH: 324
<212> TYPE: DNA
<213> ORGANISM: Artificial Sequence
<220> FEATURE:
<223> OTHER INFORMATION: 4G8; VL

<400> SEQUENCE: 50
gaaatcgtgt taacgcagtc tccaggcacc ctgtctttgt ctccagggga aagagccacc 60
ctctcttgca gggccagtca gagtgttagc cgcagctact tagcctggta ccagcagaaa 120
cctggccagg ctcccaggct cctcatcatt ggggcctcca ccagggccac tggcatccca 180
gacaggttca gtggcagtgg atccgggacg gacttcactc tcaccatcag cagactggag 240
cctgaagatt ttgcagtgta ttactgtcag cagggtcagg ttattccccc tacgttcggc 300
caggggacca aagtggaaat caaa 324

<210> SEQ ID NO 51
<211> LENGTH: 117
<212> TYPE: PRT
<213> ORGANISM: Artificial Sequence
<220> FEATURE:
<223> OTHER INFORMATION: 4G8; VH

<400> SEQUENCE: 51

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Trp Leu Gly Asn Phe Asp Tyr Trp Gly Gln Gly Thr Leu
100 105 110

Val Thr Val Ser Ser
115

<210> SEQ ID NO 52
<211> LENGTH: 351
<212> TYPE: DNA
<213> ORGANISM: Artificial Sequence
<220> FEATURE:
<223> OTHER INFORMATION: 4G8; VH

<400> SEQUENCE: 52
gaggtgcaat tgttggagtc tgggggaggc ttggtacagc ctggggggtc cctgagactc 60
tcctgtgcag cctccggatt cacctttagc agttatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcagatga acagcctgag agccgaggac acggccgtat attactgtgc gaaagggtgg 300
ctgggtaatt ttgactactg gggccaagga accctggtca ccgtctcgag t 351

<210> SEQ ID NO 53
<211> LENGTH: 108
<212> TYPE: PRT
<213> ORGANISM: Artificial Sequence
<220> FEATURE:
<223> OTHER INFORMATION: 4B3; VL

<400> SEQUENCE: 53

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Tyr Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105
```

<210> SEQ ID NO 54
<211> LENGTH: 324
<212> TYPE: DNA
<213> ORGANISM: Artificial Sequence
<220> FEATURE:
<223> OTHER INFORMATION: 4B3; VL

<400> SEQUENCE: 54

```
gaaatcgtgt taacgcagtc tccaggcacc ctgtctttgt ctccagggga aagagccacc      60

ctctcttgca gggccagtca gagtgttagc agcaattact tagcctggta ccagcagaaa     120

cctggccagg ctcccaggct cctcatctat ggcgcctaca tcagggccac tggcatccca     180

gacaggttca gtggcagtgg atccgggaca gacttcactc tcaccatcag cagactggag     240

cctgaagatt ttgcagtgta ttactgtcag cagggtcagg ttattccccc tacgttcggc     300

caggggacca aagtggaaat caaa                                            324
```

<210> SEQ ID NO 55
<211> LENGTH: 117
<212> TYPE: PRT
<213> ORGANISM: Artificial Sequence
<220> FEATURE:
<223> OTHER INFORMATION: 4B3; VH

<400> SEQUENCE: 55

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                85                  90                  95

Ala Lys Gly Trp Leu Gly Asn Phe Asp Tyr Trp Gly Gln Gly Thr Leu
            100                 105                 110

Val Thr Val Ser Ser
        115


<210> SEQ ID NO 56
<211> LENGTH: 351
<212> TYPE: DNA
<213> ORGANISM: Artificial Sequence
<220> FEATURE:
<223> OTHER INFORMATION: 4B3; VH

<400> SEQUENCE: 56

gaggtgcaat tgttggagtc tgggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaagggtgg    300

ctgggtaatt ttgactactg gggccaagga accctggtca ccgtctcgag t             351


<210> SEQ ID NO 57
<211> LENGTH: 108
<212> TYPE: PRT
<213> ORGANISM: Artificial Sequence
<220> FEATURE:
<223> OTHER INFORMATION: 4D6; VL

<400> SEQUENCE: 57

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Gln Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105


<210> SEQ ID NO 58
<211> LENGTH: 324
<212> TYPE: DNA
<213> ORGANISM: Artificial Sequence
<220> FEATURE:
<223> OTHER INFORMATION: 4D6; VL

<400> SEQUENCE: 58

gaaatcgtgt taacgcagtc tccaggcacc ctgtctttgt ctccagggga aagagccacc     60

ctctcttgca gggccagtca gagtgttagc agcaactact tagcctggta ccagcagaaa    120

cctggccagg ctcccaggct cctcatccag ggcgcctcca gcagggccac tggcatccca    180

gacaggttca gtggcagtgg atccgggaca gacttcactc tcaccatcag cagactggag    240
```

```
cctgaagatt ttgcagtgta ttactgtcag cagggtcagg ttattccccc tacgttcggc    300

caggggacca aagtggaaat caaa                                           324


<210> SEQ ID NO 59
<211> LENGTH: 117
<212> TYPE: PRT
<213> ORGANISM: Artificial Sequence
<220> FEATURE:
<223> OTHER INFORMATION: 4D6; VH

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser
        115


<210> SEQ ID NO 60
<211> LENGTH: 351
<212> TYPE: DNA
<213> ORGANISM: Artificial Sequence
<220> FEATURE:
<223> OTHER INFORMATION: 4D6; VH

<400> SEQUENCE: 60

gaggtgcaat tgttggagtc tgggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaagggtgg    300

ctgggtaatt ttgactactg gggccaagga accctggtca ccgtctcgag t             351


<210> SEQ ID NO 61
<211> LENGTH: 108
<212> TYPE: PRT
<213> ORGANISM: Artificial Sequence
<220> FEATURE:
<223> OTHER INFORMATION: 2C6; VL

<400> SEQUENCE: 61

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45
```

-continued

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Gln Ile Pro
                85                  90                  95

Pro Thr Phe Gly Gln Gly Thr Lys Val Glu Ile Lys
            100                 105

<210> SEQ ID NO 62
<211> LENGTH: 324
<212> TYPE: DNA
<213> ORGANISM: Artificial Sequence
<220> FEATURE:
<223> OTHER INFORMATION: 2C6; VL

<400> SEQUENCE: 62
gaaatcgtgt taacgcagtc tccaggcacc ctgtctttgt ctccagggga aagagccacc 60
ctctcttgca gggccagtca gagtgttagc agcagctact tagcctggta ccagcagaaa 120
cctggccagg ctcccaggct cctcatctat ggagcatcca gcagggccac tggcatccca 180
gacaggttca gtggcagtgg atccgggaca gacttcactc tcaccatcag caggctggag 240
cctgaagatt ttgcagtgta ttactgtcag cagggtcagc agattccccc tacgttcggc 300
caggggacca aagtggaaat caaa 324

<210> SEQ ID NO 63
<211> LENGTH: 117
<212> TYPE: PRT
<213> ORGANISM: Artificial Sequence
<220> FEATURE:
<223> OTHER INFORMATION: 2C6; VH

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Ala Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Asn Phe Asp Tyr Trp Gly Gln Gly Thr Leu
            100                 105                 110

Val Thr Val Ser Ser
        115

<210> SEQ ID NO 64
<211> LENGTH: 351
<212> TYPE: DNA
<213> ORGANISM: Artificial Sequence
<220> FEATURE:
<223> OTHER INFORMATION: 2C6; VH

<400> SEQUENCE: 64
gaggtgcaat tgttggagtc tgggggaggc ttggtacagc ctggggggtc cctgagactc 60

```
tcctgtgcag cctccggatc cacctttagc agttatgcca tgagctgggt ccgccaggct    120

ccagggaagg ggctggagtg ggtctcagct attagtggga gtgctggtta tacatactac    180

gcagactccg tgaagggccg gttcaccatc tccagagaca attccaagaa cacgctgtat    240

ctgcagatga acagcctgag agccgaggac acggccgtat attactgtgc gaaaggttgg    300

tttgggaatt ttgactactg gggccaagga accctggtca ccgtctcgag t             351


<210> SEQ ID NO 65
<211> LENGTH: 108
<212> TYPE: PRT
<213> ORGANISM: Artificial Sequence
<220> FEATURE:
<223> OTHER INFORMATION: 5H5; VL

<400> SEQUENCE: 65

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Asn Gln Ile Pro
                85                  90                  95

Pro Thr Phe Gly Gln Gly Thr Lys Val Glu Ile Lys
            100                 105


<210> SEQ ID NO 66
<211> LENGTH: 324
<212> TYPE: DNA
<213> ORGANISM: Artificial Sequence
<220> FEATURE:
<223> OTHER INFORMATION: 5H5; VL

<400> SEQUENCE: 66

gaaatcgtgt taacgcagtc tccaggcacc ctgtctttgt ctccagggga aagagccacc     60

ctctcttgca gggccagtca gagtgttagc agcagctact tagcctggta ccagcagaaa    120

cctggccagg ctcccaggct cctcatctat ggagcatcca gcagggccac tggcatccca    180

gacaggttca gtggcagtgg atccgggaca gacttcactc tcaccatcag cagactggag    240

cctgaagatt ttgcagtgta ttactgtcag cagggtaatc agattccccc tacgttcggt    300

caggggacca aagtggaaat caaa                                           324


<210> SEQ ID NO 67
<211> LENGTH: 116
<212> TYPE: PRT
<213> ORGANISM: Artificial Sequence
<220> FEATURE:
<223> OTHER INFORMATION: 5H5; VH

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

-continued

```
Thr Met Ser Trp Val Arg Arg Ser Pro Gly Lys Gly Leu Glu Trp Val
        35                  40                  45

Ser Ala Ile Ser Gly Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Trp Phe Thr Pro Phe Asp Tyr Trp Gly Gln Gly Thr Leu Val
            100                 105                 110

Thr Val Ser Ser
        115
```

<210> SEQ ID NO 68
<211> LENGTH: 348
<212> TYPE: DNA
<213> ORGANISM: Artificial Sequence
<220> FEATURE:
<223> OTHER INFORMATION: 5H5; VH

<400> SEQUENCE: 68

```
gaggtgcaat tgttggagtc tgggggaggc ttggtacagc ctggggggtc cctgagactc      60

tcctgtgcag cctccggatt cacctttagc agttatacca tgagctgggt ccgccggtct     120

ccagggaagg ggctggagtg ggtctcagct attagtggtg gtggtaggac atactacgca     180

gactccgtga agggccggtt caccatctcc agagacaatt ccaagaacac gctgtatctg     240

cagatgaaca gcctgagagc cgaggacacg gccgtatatt actgtgcgaa aggttggttt     300

acgccttttg actactgggg ccaaggaacc ctggtcaccg tctcgagt                  348
```

<210> SEQ ID NO 69
<211> LENGTH: 108
<212> TYPE: PRT
<213> ORGANISM: Artificial Sequence
<220> FEATURE:
<223> OTHER INFORMATION: 2C4; VL

<400> SEQUENCE: 69

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Asn Gln Ile Pro
                85                  90                  95

Pro Thr Phe Gly Gln Gly Thr Lys Val Glu Ile Lys
            100                 105
```

<210> SEQ ID NO 70
<211> LENGTH: 324
<212> TYPE: DNA
<213> ORGANISM: Artificial Sequence
<220> FEATURE:
<223> OTHER INFORMATION: 2C4; VL

<400> SEQUENCE: 70
gaaatcgtgt taacgcagtc tccaggcacc ctgtctttgt ctccagggga aagagccacc 60
ctctcttgca gggccagtca gagtgttagc agtaactact tagcctggta ccagcagaaa 120
cctggccagg ctcccaggct cctcatctat ggtgcctcca ttagggccac tggcatccca 180
gacaggttca gtggcagtgg atccgggaca gacttcactc tcaccatcag cagactggag 240
cctgaagatt ttgcagtgta ttactgtcag cagggtaatc agattccccc tacgttcggt 300
caggggacca aagtggaaat caaa 324

<210> SEQ ID NO 71
<211> LENGTH: 117
<212> TYPE: PRT
<213> ORGANISM: Artificial Sequence
<220> FEATURE:
<223> OTHER INFORMATION: 2C4; VH

<400> SEQUENCE: 71

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Trp Phe Thr Pro Phe Asp Tyr Trp Gly Gln Gly Thr Leu
100 105 110

Val Thr Val Ser Ser
115

<210> SEQ ID NO 72
<211> LENGTH: 351
<212> TYPE: DNA
<213> ORGANISM: Artificial Sequence
<220> FEATURE:
<223> OTHER INFORMATION: 2C4; VH

<400> SEQUENCE: 72
gaggtgcaat tgttggagtc tgggggaggc ttggtacagc ctgggggtc cctgagactc 60 tcctgtgcag cctccggatt cacctttagc agttatgcca tgagctgggt ccgccaggct 120
ccagggaagg ggctggagtg ggtctcagct attagcggta gtggtggtag cacatactac 180
gcagactccg tgaagggccg gttcaccatc tccagagaca attccaagaa cacgctgtat 240
ctgcagatga acagcctgag agccgaggac acggccgtat attactgtgc gaaaggttgg 300
tttacgcctt ttgactactg gggccaagga accctggtca ccgtctcgag t 351

<210> SEQ ID NO 73
<211> LENGTH: 108
<212> TYPE: PRT
<213> ORGANISM: Artificial Sequence
<220> FEATURE:
<223> OTHER INFORMATION: 2D9; VL

<400> SEQUENCE: 73

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Gly Asn Gln Ile Pro
85 90 95

Pro Thr Phe Gly Gln Gly Thr Lys Val Glu Ile Lys
100 105

<210> SEQ ID NO 74
<211> LENGTH: 324
<212> TYPE: DNA
<213> ORGANISM: Artificial Sequence
<220> FEATURE:
<223> OTHER INFORMATION: 2D9; VL

<400> SEQUENCE: 74
gaaatcgtgt taacgcagtc tccaggcacc ctgtctttgt ctccagggga aagagccacc 60
ctctcttgca gggccagtca gagtgttagc agcagctact tagcctggta ccagcagaaa 120
cctggccagg ctcccaggct cctcatctat ggagcatcca gcagggccac tggcatccca 180
gacaggttca gtggcagtgg atccgggaca gacttcactc tcaccatcag cagactggag 240
cctgaagatt ttgcagtgta ttactgtcag cagggtaatc agattccccc tacgttcggt 300
caggggacca aagtggaaat caaa 324

<210> SEQ ID NO 75
<211> LENGTH: 117
<212> TYPE: PRT
<213> ORGANISM: Artificial Sequence
<220> FEATURE:
<223> OTHER INFORMATION: 2D9; VH

<400> SEQUENCE: 75

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Trp Phe Thr Pro Phe Asp Tyr Trp Gly Gln Gly Thr Leu
100 105 110

Val Thr Val Ser Ser
115

<210> SEQ ID NO 76
<211> LENGTH: 351
<212> TYPE: DNA
<213> ORGANISM: Artificial Sequence
<220> FEATURE:
<223> OTHER INFORMATION: 2D9; VH

<400> SEQUENCE: 76
gaggtgcaat tgttggagtc tgggggaggc ttggtacagc ctggggggtc cctgagactc 60
tcctgtgcag cctccggatt cacctttagc agttatgcca tgagctgggt ccgccaggct 120
ccagggaagg ggctggagtg ggtctcagct attagcggta gtggtggtag cacatactac 180
gcagactccg tgaagggccg gttcaccatc tccagagaca attccaagaa cacgctgtat 240
ctgcagatga acagcctgag agccgaggac acggccgtat attactgtgc gaaaggttgg 300
tttacgcctt ttgactactg gggccaagga accctggtca ccgtctcgag t 351

<210> SEQ ID NO 77
<211> LENGTH: 108
<212> TYPE: PRT
<213> ORGANISM: Artificial Sequence
<220> FEATURE:
<223> OTHER INFORMATION: 4B8; VL

<400> SEQUENCE: 77

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Gly Gln Val Ile Pro
85 90 95

Pro Thr Phe Gly Gln Gly Thr Lys Val Glu Ile Lys
100 105

<210> SEQ ID NO 78
<211> LENGTH: 324
<212> TYPE: DNA
<213> ORGANISM: Artificial Sequence
<220> FEATURE:
<223> OTHER INFORMATION: 4B8; VL

<400> SEQUENCE: 78
gaaatcgtgt taacgcagtc tccaggcacc ctgtctttgt ctccagggga aagagccacc 60
ctctcttgca gggccagtca gagtgttagc agcagctact tagcctggta ccagcagaaa 120
cctggccagg ctcccaggct cctcatctat ggagcatcca gcagggccac tggcatccca 180
gacaggttca gtggcagtgg atccgggaca gacttcactc tcaccatcag cagactggag 240
cctgaagatt ttgcagtgta ttactgtcag cagggtcagg ttattccccc tacgttcggc 300
caggggacca aagtggaaat caaa 324

<210> SEQ ID NO 79
<211> LENGTH: 117
<212> TYPE: PRT

<213> ORGANISM: Artificial Sequence
<220> FEATURE:
<223> OTHER INFORMATION: 4B8; VH

<400> SEQUENCE: 79

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser
        115
```

<210> SEQ ID NO 80
<211> LENGTH: 351
<212> TYPE: DNA
<213> ORGANISM: Artificial Sequence
<220> FEATURE:
<223> OTHER INFORMATION: 4B8; VH

<400> SEQUENCE: 80

```
gaggtgcaat tgttggagtc tgggggaggc ttggtacagc ctggggggtc cctgagactc      60

tcctgtgcag cctccggatt cacctttagc agttatgcca tgagctgggt ccgccaggct     120

ccagggaagg ggctggagtg ggtctcagct attagtggta gtggtggtag cacatactac     180

gcagactccg tgaagggccg gttcaccatc tccagagaca attccaagaa cacgctgtat     240

ctgcagatga acagcctgag agccgaggac acggccgtat attactgtgc gaaagggtgg     300

ctgggtaatt ttgactactg gggccaagga accctggtca ccgtctcgag t              351
```

<210> SEQ ID NO 81
<211> LENGTH: 108
<212> TYPE: PRT
<213> ORGANISM: Artificial Sequence
<220> FEATURE:
<223> OTHER INFORMATION: 7A1; VL

<400> SEQUENCE: 81

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Gln Ile Pro
                85                  90                  95
```

Pro Thr Phe Gly Gln Gly Thr Lys Val Glu Ile Lys
            100                 105

<210> SEQ ID NO 82
<211> LENGTH: 324
<212> TYPE: DNA
<213> ORGANISM: Artificial Sequence
<220> FEATURE:
<223> OTHER INFORMATION: 7A1; VL

<400> SEQUENCE: 82
gaaatcgtgt taacgcagtc tccaggcacc ctgtctttgt ctccagggga aagagccacc 60
ctctcttgca gggccagtca gagtgttagc agcagctact tagcctggta ccagcagaaa 120
cctggccagg ctcccaggct cctcatctat ggagcatcca gcagggccac tggcatccca 180
gacaggttca gtggcagtgg atccgggaca gacttcactc tcaccatcag cagactggag 240
cctgaagatt ttgcagtgta ttactgtcag cagggtcagc agattccccc tacgttcggc 300
caggggacca aagtggaaat caaa 324

<210> SEQ ID NO 83
<211> LENGTH: 117
<212> TYPE: PRT
<213> ORGANISM: Artificial Sequence
<220> FEATURE:
<223> OTHER INFORMATION: 7A1; VH

<400> SEQUENCE: 83

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Asn Phe Asp Tyr Trp Gly Gln Gly Thr Leu
            100                 105                 110

Val Thr Val Ser Ser
        115

<210> SEQ ID NO 84
<211> LENGTH: 351
<212> TYPE: DNA
<213> ORGANISM: Artificial Sequence
<220> FEATURE:
<223> OTHER INFORMATION: 7A1; VH

<400> SEQUENCE: 84
gaggtgcaat tgttggagtc tgggggaggc ttggtacagc ctggggggtc cctgagactc 60
tcctgtgcag cctccggatt cacctttagc agttatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcagatga acagcctgag agccgaggac acggccgtat attactgtgc gaaaggttgg 300
tttgggaatt ttgactactg gggccaagga accctggtca ccgtctcgag t 351

<210> SEQ ID NO 85
<211> LENGTH: 108
<212> TYPE: PRT
<213> ORGANISM: Artificial Sequence
<220> FEATURE:
<223> OTHER INFORMATION: 13C2; VL

<400> SEQUENCE: 85

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Gly Gln Leu Ile Pro
85 90 95

Pro Thr Phe Gly Gln Gly Thr Lys Val Glu Ile Lys
100 105

<210> SEQ ID NO 86
<211> LENGTH: 324
<212> TYPE: DNA
<213> ORGANISM: Artificial Sequence
<220> FEATURE:
<223> OTHER INFORMATION: 13C2; VL

<400> SEQUENCE: 86
gaaatcgtgt taacgcagtc tccaggcacc ctgtctttgt ctccagggga aagagccacc 60
ctctcttgca gggccagtca gagtgttagc agcagctact tagcctggta ccagcagaaa 120
cctggccagg ctcccaggct cctcatctat ggagcatcca gcagggccac tggcatccca 180
gacaggttca gtggcagtgg atccgggaca gacttcactc tcaccatcag cagactggag 240
cctgaagatt ttgcagtgta ttactgtcag cagggtcagc ttattccccc tacgttcggc 300
caggggacca aagtggaaat caaa 324

<210> SEQ ID NO 87
<211> LENGTH: 117
<212> TYPE: PRT
<213> ORGANISM: Artificial Sequence
<220> FEATURE:
<223> OTHER INFORMATION: 13C2; VH

<400> SEQUENCE: 87

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr

```
65                  70                  75                  80

Leu Gln Met Asn Ser Leu Arg Ala Glu Asp Thr Ala Val Tyr Tyr Cys
                85                  90                  95

Ala Lys Gly Trp Leu Gly Pro Phe Asp Tyr Trp Gly Gln Gly Thr Leu
            100                 105                 110

Val Thr Val Ser Ser
        115


<210> SEQ ID NO 88
<211> LENGTH: 351
<212> TYPE: DNA
<213> ORGANISM: Artificial Sequence
<220> FEATURE:
<223> OTHER INFORMATION: 13C2; VH

<400> SEQUENCE: 88

gaggtgcaat tgttggagtc tgggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaaggttgg    300

ctgggtcctt ttgactactg gggccaagga accctggtca ccgtctcgag t             351


<210> SEQ ID NO 89
<211> LENGTH: 108
<212> TYPE: PRT
<213> ORGANISM: Artificial Sequence
<220> FEATURE:
<223> OTHER INFORMATION: 13E8; VL

<400> SEQUENCE: 89

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Leu Asn Ile Pro
                85                  90                  95

Ser Thr Phe Gly Gln Gly Thr Lys Val Glu Ile Lys
            100                 105


<210> SEQ ID NO 90
<211> LENGTH: 324
<212> TYPE: DNA
<213> ORGANISM: Artificial Sequence
<220> FEATURE:
<223> OTHER INFORMATION: 13E8; VL

<400> SEQUENCE: 90

gaaatcgtgt taacgcagtc tccaggcacc ctgtctttgt ctccagggga aagagccacc     60

ctctcttgca gggccagtca gagtgttagc agcagctact tagcctggta ccagcagaaa    120

cctggccagg ctcccaggct cctcatctat ggagcatcca gcagggccac tggcatccca    180
```

gacaggttca gtggcagtgg atccgggaca gacttcactc tcaccatcag cagactggag 240
cctgaagatt ttgcagtgta ttactgtcag cagggtctga atattccctc gacgttcggc 300
caggggacca aagtggaaat caaa 324

<210> SEQ ID NO 91
<211> LENGTH: 117
<212> TYPE: PRT
<213> ORGANISM: Artificial Sequence
<220> FEATURE:
<223> OTHER INFORMATION: 13E8; VH

<400> SEQUENCE: 91

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Trp Leu Gly Pro Phe Asp Tyr Trp Gly Gln Gly Thr Leu
100 105 110

Val Thr Val Ser Ser
115

<210> SEQ ID NO 92
<211> LENGTH: 351
<212> TYPE: DNA
<213> ORGANISM: Artificial Sequence
<220> FEATURE:
<223> OTHER INFORMATION: 13E8; VH

<400> SEQUENCE: 92
gaggtgcaat tgttggagtc tgggggaggc ttggtacagc ctggggggtc cctgagactc 60
tcctgtgcag cctccggatt cacctttagc agttatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcagatga acagcctgag agccgaggac acggccgtat attactgtgc gaaaggttgg 300
ttgggtccgt ttgactactg gggccaagga accctggtca ccgtctcgag t 351

<210> SEQ ID NO 93
<211> LENGTH: 108
<212> TYPE: PRT
<213> ORGANISM: Artificial Sequence
<220> FEATURE:
<223> OTHER INFORMATION: 14C10; VL

<400> SEQUENCE: 93

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Gly His Ile Ile Pro
85 90 95

Pro Thr Phe Gly Gln Gly Thr Lys Val Glu Ile Lys
100 105

<210> SEQ ID NO 94
<211> LENGTH: 324
<212> TYPE: DNA
<213> ORGANISM: Artificial Sequence
<220> FEATURE:
<223> OTHER INFORMATION: 14C10; VL

<400> SEQUENCE: 94
gaaatcgtgt taacgcagtc tccaggcacc ctgtctttgt ctccagggga aagagccacc 60
ctctcttgca gggccagtca gagtgttagc agcagctact tagcctggta ccagcagaaa 120
cctggccagg ctcccaggct cctcatctat ggagcatcca gcagggccac tggcatccca 180
gacaggttca gtggcagtgg atccgggaca gacttcactc tcaccatcag cagactggag 240
cctgaagatt ttgcagtgta ttactgtcag cagggtcata ttattccccc gacgttcggc 300
caggggacca aagtggaaat caaa 324

<210> SEQ ID NO 95
<211> LENGTH: 117
<212> TYPE: PRT
<213> ORGANISM: Artificial Sequence
<220> FEATURE:
<223> OTHER INFORMATION: 14C10; VH

<400> SEQUENCE: 95

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Ala Trp Met Gly Pro Phe Asp Tyr Trp Gly Gln Gly Thr Leu
100 105 110

Val Thr Val Ser Ser
115

<210> SEQ ID NO 96
<211> LENGTH: 351
<212> TYPE: DNA
<213> ORGANISM: Artificial Sequence
<220> FEATURE:
<223> OTHER INFORMATION: 14C10; VH

<400> SEQUENCE: 96
gaggtgcaat tgttggagtc tgggggaggc ttggtacagc ctggggggtc cctgagactc 60
tcctgtgcag cctccggatt cacctttagc agttatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcagatga acagcctgag agccgaggac acggccgtat attactgtgc gaaagcttgg 300
atggggcctt ttgactactg gggccaagga accctggtca ccgtctcgag t 351

<210> SEQ ID NO 97
<211> LENGTH: 108
<212> TYPE: PRT
<213> ORGANISM: Artificial Sequence
<220> FEATURE:
<223> OTHER INFORMATION: 17A11; VL

<400> SEQUENCE: 97

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Gly Leu Asn Ile Pro
85 90 95

Ser Thr Phe Gly Gln Gly Thr Lys Val Glu Ile Lys
100 105

<210> SEQ ID NO 98
<211> LENGTH: 324
<212> TYPE: DNA
<213> ORGANISM: Artificial Sequence
<220> FEATURE:
<223> OTHER INFORMATION: 17A11; VL

<400> SEQUENCE: 98
gaaatcgtgt taacgcagtc tccaggcacc ctgtctttgt ctccagggga aagagccacc 60
ctctcttgca gggccagtca gagtgttagc agcagctact tagcctggta ccagcagaaa 120
cctggccagg ctcccaggct cctcatctat ggagcatcca gcagggccac tggcatccca 180
gacaggttca gtggcagtgg atccgggaca gacttcactc tcaccatcag cagactggag 240
cctgaagatt ttgcagtgta ttactgtcag cagggtctga atattccctc gacgttcggc 300
caggggacca aagtggaaat caaa 324

<210> SEQ ID NO 99
<211> LENGTH: 117
<212> TYPE: PRT
<213> ORGANISM: Artificial Sequence
<220> FEATURE:
<223> OTHER INFORMATION: 17A11; VH

<400> SEQUENCE: 99

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Trp Leu Gly Pro Phe Asp Tyr Trp Gly Gln Gly Thr Leu
100 105 110

Val Thr Val Ser Ser
115

<210> SEQ ID NO 100
<211> LENGTH: 351
<212> TYPE: DNA
<213> ORGANISM: Artificial Sequence
<220> FEATURE:
<223> OTHER INFORMATION: 17A11; VH

<400> SEQUENCE: 100
gaggtgcaat tgttggagtc tgggggaggc ttggtacagc ctggggggtc cctgagactc 60
tcctgtgcag cctccggatt cacctttagc agttatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcagatga acagcctgag agccgaggac acggccgtat attactgtgc gaaaggttgg 300
ttgggtccgt ttgactactg gggccaagga accctggtca ccgtctcgag t 351

<210> SEQ ID NO 101
<211> LENGTH: 108
<212> TYPE: PRT
<213> ORGANISM: Artificial Sequence
<220> FEATURE:
<223> OTHER INFORMATION: 19G1; VL

<400> SEQUENCE: 101

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Thr Ser Ser
20 25 30

Tyr Leu Ala Trp Tyr Gln Gln Lys Pro Gly Gln Ala Pro Arg Leu Leu
35 40 45

Ile Asn Val Gly Ser Arg Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Gly Ile Met Leu Pro
85 90 95

Pro Thr Phe Gly Gln Gly Thr Lys Val Glu Ile Lys
100 105

<210> SEQ ID NO 102
<211> LENGTH: 324
<212> TYPE: DNA

<213> ORGANISM: Artificial Sequence
<220> FEATURE:
<223> OTHER INFORMATION: 19G1; VL

<400> SEQUENCE: 102
gaaatcgtgt taacgcagtc tccaggcacc ctgtctttgt ctccagggga aagagccacc 60
ctctcttgca gggccagtca gagtgttacc agtagctact tagcctggta ccagcagaaa 120
cctggccagg ctcccaggct cctcatcaat gtgggctccc gtagggccac tggcatccca 180
gacaggttca gtggcagtgg atccgggaca gacttcactc tcaccatcag cagactggag 240
cctgaagatt ttgcagtgta ttactgtcag cagggtatta tgcttccccc gacgttcggc 300
caggggacca aagtggaaat caaa 324

<210> SEQ ID NO 103
<211> LENGTH: 117
<212> TYPE: PRT
<213> ORGANISM: Artificial Sequence
<220> FEATURE:
<223> OTHER INFORMATION: 19G1; VH

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Ser Ser Gly Gly Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115

<210> SEQ ID NO 104
<211> LENGTH: 351
<212> TYPE: DNA
<213> ORGANISM: Artificial Sequence
<220> FEATURE:
<223> OTHER INFORMATION: 19G1; VH

<400> SEQUENCE: 104
gaggtgcaat tgttggagtc tgggggaggc ttggtacagc ctggggggtc cctgagactc 60
tcctgtgcag cctccggatt cacctttagc agttatgcga tgagctgggt ccgccaggct 120
ccagggaagg ggctggagtg ggtctcagcg attattagta gtggtggtct cacatactac 180
gcagactccg tgaagggccg gttcaccatc tccagagaca attccaagaa cacgctgtat 240
ctgcagatga acagcctgag agccgaggac acggccgtat attactgtgc gaaagggtgg 300
tttggtggtt ttaactactg gggccaagga accctggtca ccgtctcgtc c 351

<210> SEQ ID NO 105
<211> LENGTH: 108
<212> TYPE: PRT
<213> ORGANISM: Artificial Sequence

<220> FEATURE:
<223> OTHER INFORMATION: 20G8; VL

<400> SEQUENCE: 105

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Thr Ser Ser
20 25 30

Tyr Leu Ala Trp Tyr Gln Gln Lys Pro Gly Gln Ala Pro Arg Leu Leu
35 40 45

Ile Asn Val Gly Ser Arg Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Gly Ile Met Leu Pro
85 90 95

Pro Thr Phe Gly Gln Gly Thr Lys Val Glu Ile Lys
100 105

<210> SEQ ID NO 106
<211> LENGTH: 324
<212> TYPE: DNA
<213> ORGANISM: Artificial Sequence
<220> FEATURE:
<223> OTHER INFORMATION: 20G8; VL

<400> SEQUENCE: 106
gaaatcgtgt taacgcagtc tccaggcacc ctgtctttgt ctccagggga aagagccacc 60
ctctcttgca gggccagtca gagtgttacc agtagctact tagcctggta ccagcagaaa 120
cctggccagg ctcccaggct cctcatcaat gtgggctccc gtagggccac tggcatccca 180
gacaggttca gtggcagtgg atccgggaca gacttcactc tcaccatcag cagactggag 240
cctgaagatt ttgcagtgta ttactgtcag cagggtatta tgcttccccc gacgttcggc 300
caggggacca aagtggaaat caaa 324

<210> SEQ ID NO 107
<211> LENGTH: 117
<212> TYPE: PRT
<213> ORGANISM: Artificial Sequence
<220> FEATURE:
<223> OTHER INFORMATION: 20G8; VH

<400> SEQUENCE: 107

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ile Gly Ser Gly Ser Arg Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Trp Phe Gly Gly Phe Asn Tyr Trp Gly Gln Gly Thr Leu
100 105 110

Val Thr Val Ser Ser
        115

<210> SEQ ID NO 108
<211> LENGTH: 351
<212> TYPE: DNA
<213> ORGANISM: Artificial Sequence
<220> FEATURE:
<223> OTHER INFORMATION: 20G8; VH

<400> SEQUENCE: 108
gaggtgcaat tgttggagtc tgggggaggc ttggtacagc ctgggggtc cctgagactc 60 tcctgtgcag cctccggatt cacctttagc agttatgcaa tgagctgggt ccgccaggct 120
ccagggaagg ggctggagtg ggtctcagct attattggga gtggtagtcg tacatactac 180
gcagactccg tgaagggccg gttcaccatc tccagagaca attccaagaa cacgctgtat 240
ctgcagatga acagcctgag agccgaggac acggccgtat attactgtgc gaaagggtgg 300
tttggtggtt ttaactactg gggccaagga accctggtca ccgtctcgtc c 351

<210> SEQ ID NO 109
<211> LENGTH: 108
<212> TYPE: PRT
<213> ORGANISM: Artificial Sequence
<220> FEATURE:
<223> OTHER INFORMATION: 4B9; VL

<400> SEQUENCE: 109

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 110
<211> LENGTH: 324
<212> TYPE: DNA
<213> ORGANISM: Artificial Sequence
<220> FEATURE:
<223> OTHER INFORMATION: 4B9; VL

<400> SEQUENCE: 110
gaaatcgtgt taacgcagtc tccaggcacc ctgtctttgt ctccagggga aagagccacc 60
ctctcttgca gggccagtca gagtgttacc agtagctact tagcctggta ccagcagaaa 120
cctggccagg ctcccaggct cctcatcaat gtgggctccc gtagggccac tggcatccca 180
gacaggttca gtggcagtgg atccgggaca gacttcactc tcaccatcag cagactggag 240
cctgaagatt ttgcagtgta ttactgtcag cagggtatta tgcttccccc gacgttcggc 300
caggggacca aagtggaaat caaa 324

-continued

<210> SEQ ID NO 111
<211> LENGTH: 117
<212> TYPE: PRT
<213> ORGANISM: Artificial Sequence
<220> FEATURE:
<223> OTHER INFORMATION: 4B9; VH

<400> SEQUENCE: 111

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115
```

<210> SEQ ID NO 112
<211> LENGTH: 351
<212> TYPE: DNA
<213> ORGANISM: Artificial Sequence
<220> FEATURE:
<223> OTHER INFORMATION: 4B9; VH

<400> SEQUENCE: 112

```
gaggtgcaat tgttggagtc tgggggaggc ttggtacagc ctggggggtc cctgagactc      60

tcctgtgcag cctccggatt cacctttagc agttatgcta tgagctgggt ccgccaggct     120

ccagggaagg ggctggagtg ggtctcagct attattggta gtggtgctag cacatactac     180

gcagactccg tgaagggccg gttcaccatc tccagagaca attccaagaa cacgctgtat     240

ctgcagatga acagcctgag agccgaggac acggccgtat attactgtgc gaaagggtgg     300

tttggtggtt ttaactactg gggccaagga accctggtca ccgtctcgtc c              351
```

<210> SEQ ID NO 113
<211> LENGTH: 108
<212> TYPE: PRT
<213> ORGANISM: Artificial Sequence
<220> FEATURE:
<223> OTHER INFORMATION: 5B8; VL

<400> SEQUENCE: 113

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

Pro Glu Asp Phe Ala Val Tyr Tyr Cys Gln Gln Gly Ile Met Leu Pro
85 90 95

Pro Thr Phe Gly Gln Gly Thr Lys Val Glu Ile Lys
100 105

<210> SEQ ID NO 114
<211> LENGTH: 324
<212> TYPE: DNA
<213> ORGANISM: Artificial Sequence
<220> FEATURE:
<223> OTHER INFORMATION: 5B8; VL

<400> SEQUENCE: 114
gaaatcgtgt taacgcagtc tccaggcacc ctgtctttgt ctccagggga aagagccacc 60
ctctcttgca gggccagtca gagtgttacc agtagctact tagcctggta ccagcagaaa 120
cctggccagg ctcccaggct cctcatcaat gtgggctccc gtagggccac tggcatccca 180
gacaggttca gtggcagtgg atccgggaca gacttcactc tcaccatcag cagactggag 240
cctgaagatt ttgcagtgta ttactgtcag cagggtatta tgcttccccc gacgttcggc 300
caggggacca aagtggaaat caaa 324

<210> SEQ ID NO 115
<211> LENGTH: 117
<212> TYPE: PRT
<213> ORGANISM: Artificial Sequence
<220> FEATURE:
<223> OTHER INFORMATION: 5B8; VH

<400> SEQUENCE: 115

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Trp Gly Gly Gly Arg Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Trp Phe Gly Gly Phe Asn Tyr Trp Gly Gln Gly Thr Leu
100 105 110

Val Thr Val Ser Ser
115

<210> SEQ ID NO 116
<211> LENGTH: 351
<212> TYPE: DNA
<213> ORGANISM: Artificial Sequence
<220> FEATURE:
<223> OTHER INFORMATION: 5B8; VH

<400> SEQUENCE: 116
gaggtgcaat tgttggagtc tgggggaggc ttggtacagc ctggggggtc cctgagactc 60
tcctgtgcag cctccggatt cacctttagc agttatgcta tgagctgggt ccgccaggct 120
ccagggaagg ggctggagtg ggtctcagct atttggggtg gtggtcgtag cacatactac 180
gcagactccg tgaagggccg gttcaccatc tccagagaca attccaagaa cacgctgtat 240
ctgcagatga acagcctgag agccgaggac acggccgtat attactgtgc gaaagggtgg 300
tttggtggtt ttaactactg gggccaagga accctggtca ccgtctcgtc c 351

<210> SEQ ID NO 117
<211> LENGTH: 108
<212> TYPE: PRT
<213> ORGANISM: Artificial Sequence
<220> FEATURE:
<223> OTHER INFORMATION: 5F1; VL

<400> SEQUENCE: 117

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Thr Ser Ser
20 25 30

Tyr Leu Ala Trp Tyr Gln Gln Lys Pro Gly Gln Ala Pro Arg Leu Leu
35 40 45

Ile Asn Val Gly Ser Arg Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Gly Ile Met Leu Pro
85 90 95

Pro Thr Phe Gly Gln Gly Thr Lys Val Glu Ile Lys
100 105

<210> SEQ ID NO 118
<211> LENGTH: 324
<212> TYPE: DNA
<213> ORGANISM: Artificial Sequence
<220> FEATURE:
<223> OTHER INFORMATION: 5F1; VL

<400> SEQUENCE: 118
gaaatcgtgt taacgcagtc tccaggcacc ctgtctttgt ctccagggga aagagccacc 60
ctctcttgca gggccagtca gagtgttacc agtagctact tagcctggta ccagcagaaa 120
cctggccagg ctcccaggct cctcatcaat gtgggctccc gtagggccac tggcatccca 180
gacaggttca gtggcagtgg atccgggaca gacttcactc tcaccatcag cagactggag 240
cctgaagatt ttgcagtgta ttactgtcag cagggtatta tgcttccccc gacgttcggc 300
caggggacca aagtggaaat caaa 324

<210> SEQ ID NO 119
<211> LENGTH: 117
<212> TYPE: PRT
<213> ORGANISM: Artificial Sequence
<220> FEATURE:
<223> OTHER INFORMATION: 5F1; VH

<400> SEQUENCE: 119

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ile Ser Ser Gly Ala Ser Thr Tyr Tyr Ala Asp Ser Val

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115


<210> SEQ ID NO 120
<211> LENGTH: 351
<212> TYPE: DNA
<213> ORGANISM: Artificial Sequence
<220> FEATURE:
<223> OTHER INFORMATION: 5F1; VH

<400> SEQUENCE: 120

gaggtgcaat tgttggagtc tgggggaggc ttggtacagc ctggggggtc cctgagactc      60

tcctgtgcag cctccggatt cacctttagc agttatgcta tgagctgggt ccgccaggct     120

ccagggaagg ggctggagtg ggtctcagct attattagta gtggggctag cacatactac     180

gcagactccg tgaagggccg gttcaccatc tccagagaca attccaagaa cacgctgtat     240

ctgcagatga acagcctgag agccgaggac acggccgtat attactgtgc gaaagggtgg     300

tttggtggtt ttaactactg gggccaagga accctggtca ccgtctcgtc c              351


<210> SEQ ID NO 121
<211> LENGTH: 108
<212> TYPE: PRT
<213> ORGANISM: Artificial Sequence
<220> FEATURE:
<223> OTHER INFORMATION: 14B3; VL

<400> SEQUENCE: 121

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105


<210> SEQ ID NO 122
<211> LENGTH: 324
<212> TYPE: DNA
<213> ORGANISM: Artificial Sequence
<220> FEATURE:
<223> OTHER INFORMATION: 14B3; VL

<400> SEQUENCE: 122

gaaatcgtgt taacgcagtc tccaggcacc ctgtctttgt ctccagggga aagagccacc      60
```

-continued

```
ctctcttgca gggccagtca gagtgttacc agtagctact tagcctggta ccagcagaaa    120

cctggccagg ctcccaggct cctcatcaat gtgggctccc gtagggccac tggcatccca    180

gacaggttca gtggcagtgg atccgggaca gacttcactc tcaccatcag cagactggag    240

cctgaagatt ttgcagtgta ttactgtcag cagggtatta tgcttccccc gacgttcggc    300

caggggacca aagtggaaat caaa                                           324


<210> SEQ ID NO 123
<211> LENGTH: 117
<212> TYPE: PRT
<213> ORGANISM: Artificial Sequence
<220> FEATURE:
<223> OTHER INFORMATION: 14B3; VH

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Leu Ala Ser Gly Ala Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115


<210> SEQ ID NO 124
<211> LENGTH: 351
<212> TYPE: DNA
<213> ORGANISM: Artificial Sequence
<220> FEATURE:
<223> OTHER INFORMATION: 14B3; VH

<400> SEQUENCE: 124

gaggtgcaat tgttggagtc tgggggaggc ttggtacagc ctggggggtc cctgagactc     60

tcctgtgcag cctccggatt cacctttagc agttatgcta tgagctgggt ccgccaggct    120

ccagggaagg ggctggagtg ggtctcagct attttggcta gtggtgcgat cacatactac    180

gcagactccg tgaagggccg gttcaccatc tccagagaca attccaagaa cacgctgtat    240

ctgcagatga acagcctgag agccgaggac acggccgtat attactgtgc gaaagggtgg    300

tttggtggtt ttaactactg gggccaagga accctggtca ccgtctcgtc c             351


<210> SEQ ID NO 125
<211> LENGTH: 108
<212> TYPE: PRT
<213> ORGANISM: Artificial Sequence
<220> FEATURE:
<223> OTHER INFORMATION: 16F1; VL

<400> SEQUENCE: 125

Glu Ile Val Leu Thr Gln Ser Pro Gly Thr Leu Ser Leu Ser Pro Gly
1               5                   10                  15
```

```
Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105
```

<210> SEQ ID NO 126
<211> LENGTH: 324
<212> TYPE: DNA
<213> ORGANISM: Artificial Sequence
<220> FEATURE:
<223> OTHER INFORMATION: 16F1; VL

<400> SEQUENCE: 126

```
gaaatcgtgt taacgcagtc tccaggcacc ctgtctttgt ctccagggga aagagccacc      60

ctctcttgca gggccagtca gagtgttacc agtagctact tagcctggta ccagcagaaa     120

cctggccagg ctcccaggct cctcatcaat gtgggctccc gtagggccac tggcatccca     180

gacaggttca gtggcagtgg atccgggaca gacttcactc tcaccatcag cagactggag     240

cctgaagatt ttgcagtgta ttactgtcag cagggtatta tgcttccccc gacgttcggc     300

caggggacca aagtggaaat caaa                                            324
```

<210> SEQ ID NO 127
<211> LENGTH: 117
<212> TYPE: PRT
<213> ORGANISM: Artificial Sequence
<220> FEATURE:
<223> OTHER INFORMATION: 16F1; VH

<400> SEQUENCE: 127

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ile Gly Ser Gly Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115
```

<210> SEQ ID NO 128
<211> LENGTH: 351
<212> TYPE: DNA
<213> ORGANISM: Artificial Sequence

<220> FEATURE:
<223> OTHER INFORMATION: 16F1; VH

<400> SEQUENCE: 128
gaggtgcaat tgttggagtc tgggggaggc ttggtacagc ctggggggtc cctgagactc 60
tcctgtgcag cctccggatt cacctttagc agttatgcta tgagctgggt ccgccaggct 120
ccagggaagg ggctggagtg ggtctcaggt attattggta gtggtggtat cacatactac 180
gcagactccg tgaagggccg gttcaccatc tccagagaca attccaagaa cacgctgtat 240
ctgcagatga acagcctgag agccgaggac acggccgtat attactgtgc gaaagggtgg 300
tttggtggtt ttaactactg gggccaagga accctggtca ccgtctcgtc c 351

<210> SEQ ID NO 129
<211> LENGTH: 108
<212> TYPE: PRT
<213> ORGANISM: Artificial Sequence
<220> FEATURE:
<223> OTHER INFORMATION: 16F8; VL

<400> SEQUENCE: 129

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Thr Ser Ser
20 25 30

Tyr Leu Ala Trp Tyr Gln Gln Lys Pro Gly Gln Ala Pro Arg Leu Leu
35 40 45

Ile Asn Val Gly Ser Arg Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Gly Ile Met Leu Pro
85 90 95

Pro Thr Phe Gly Gln Gly Thr Lys Val Glu Ile Lys
100 105

<210> SEQ ID NO 130
<211> LENGTH: 324
<212> TYPE: DNA
<213> ORGANISM: Artificial Sequence
<220> FEATURE:
<223> OTHER INFORMATION: 16F8; VL

<400> SEQUENCE: 130
gaaatcgtgt taacgcagtc tccaggcacc ctgtctttgt ctccagggga aagagccacc 60
ctctcttgca gggccagtca gagtgttacc agtagctact tagcctggta ccagcagaaa 120
cctggccagg ctcccaggct cctcatcaat gtgggctccc gtagggccac tggcatccca 180
gacaggttca gtggcagtgg atccgggaca gacttcactc tcaccatcag cagactggag 240
cctgaagatt ttgcagtgta ttactgtcag cagggtatta tgcttccccc gacgttcggc 300
caggggacca aagtggaaat caaa 324

<210> SEQ ID NO 131
<211> LENGTH: 117
<212> TYPE: PRT
<213> ORGANISM: Artificial Sequence
<220> FEATURE:
<223> OTHER INFORMATION: 16F8; VH

<400> SEQUENCE: 131

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Leu Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115


<210> SEQ ID NO 132
<211> LENGTH: 351
<212> TYPE: DNA
<213> ORGANISM: Artificial Sequence
<220> FEATURE:
<223> OTHER INFORMATION: 16F8; VH

<400> SEQUENCE: 132

gaggtgcaat tgttggagtc tgggggaggc ttggtacagc ctggggggtc cctgagactc      60

tcctgtgcag cctccggatt cacctttagc agttatgcca tgagctgggt ccgccaggct     120

ccagggaagg ggctggagtg ggtctcagct attcttggta gtggtggtag cacatactac     180

gcagactccg tgaagggccg gttcaccatc tccagagaca attccaagaa cacgctgtat     240

ctgcagatga acagcctgag agccgaggac acggccgtat attactgtgc gaaagggtgg     300

tttggtggtt ttaactactg gggccaagga accctggtca ccgtctcgtc c              351


<210> SEQ ID NO 133
<211> LENGTH: 108
<212> TYPE: PRT
<213> ORGANISM: Artificial Sequence
<220> FEATURE:
<223> OTHER INFORMATION: 03C9; VL

<400> SEQUENCE: 133

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105
```

-continued

<210> SEQ ID NO 134
<211> LENGTH: 324
<212> TYPE: DNA
<213> ORGANISM: Artificial Sequence
<220> FEATURE:
<223> OTHER INFORMATION: O3C9; VL

<400> SEQUENCE: 134
gaaatcgtgt taacgcagtc tccaggcacc ctgtctttgt ctccagggga aagagccacc 60
ctctcttgca gggccagtca gagtgttacc agtagctact tagcctggta ccagcagaaa 120
cctggccagg ctcccaggct cctcatcaat gtgggctccc gtagggccac tggcatccca 180
gacaggttca gtggcagtgg atccgggaca gacttcactc tcaccatcag cagactggag 240
cctgaagatt ttgcagtgta ttactgtcag cagggtatta tgcttccccc gacgttcggc 300
caggggacca aagtggaaat caaa 324

<210> SEQ ID NO 135
<211> LENGTH: 117
<212> TYPE: PRT
<213> ORGANISM: Artificial Sequence
<220> FEATURE:
<223> OTHER INFORMATION: O3C9; VH

<400> SEQUENCE: 135

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ser Pro Gly Lys Gly Leu Glu Trp Val
        35                  40                  45

Ser Ala Ile Ile Gly Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115

<210> SEQ ID NO 136
<211> LENGTH: 351
<212> TYPE: DNA
<213> ORGANISM: Artificial Sequence
<220> FEATURE:
<223> OTHER INFORMATION: O3C9; VH

<400> SEQUENCE: 136
gaggtgcaat tgttggagtc tggggggaggc ttggtacagc ctgggggggtc cctgagactc 60 tcctgtgcag cctccggatt cacctttagc agttttgcca tgagctgggt ccgtcagtct 120
ccagggaagg ggctggagtg ggtctcagct attattggta gtggtagtaa cacatactac 180
gcagactccg tgaagggccg gttcaccatc tccagagaca attccaagaa cacgctgtat 240
ctgcagatga acagcctgag agccgaggac acggccgtat attactgtgc gaaagggtgg 300
tttggtggtt ttaactactg gggccaagga accctggtca ccgtctcgtc c 351

<210> SEQ ID NO 137

<211> LENGTH: 108
<212> TYPE: PRT
<213> ORGANISM: Artificial Sequence
<220> FEATURE:
<223> OTHER INFORMATION: O2D7; VL

<400> SEQUENCE: 137

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Thr Ser Ser
20 25 30

Tyr Leu Ala Trp Tyr Gln Gln Lys Pro Gly Gln Ala Pro Arg Leu Leu
35 40 45

Ile Asn Val Gly Ser Arg Arg Ala Thr Gly Thr Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Ala Ile Met Leu Pro
85 90 95

Pro Thr Phe Gly Gln Gly Thr Lys Val Glu Ile Lys
100 105

<210> SEQ ID NO 138
<211> LENGTH: 324
<212> TYPE: DNA
<213> ORGANISM: Artificial Sequence
<220> FEATURE:
<223> OTHER INFORMATION: O2D7; VL

<400> SEQUENCE: 138
gaaatcgtgt taacgcagtc tccaggcacc ctgtctttgt ctccagggga aagagccacc 60
ctctcttgca gggccagtca gagtgttacc agtagctact tagcctggta ccagcagaaa 120
cctggccagg ctcccaggct cctcatcaat gtgggctccc gtagggccac tggcacccca 180
gacaggttca gtggcagtgg atccgggaca gacttcactc tcaccatcag cagactggag 240
cctgaagatt ttgcagtgta ttactgtcag caggctatta tgcttcctcc gacgttcggc 300
caggggacca aagtggaaat caaa 324

<210> SEQ ID NO 139
<211> LENGTH: 117
<212> TYPE: PRT
<213> ORGANISM: Artificial Sequence
<220> FEATURE:
<223> OTHER INFORMATION: O2D7; VH

<400> SEQUENCE: 139

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Trp Phe Gly Gly Phe Asn Tyr Trp Gly Gln Gly Thr Leu
            100                 105                 110

Val Thr Val Ser Ser
            115

<210> SEQ ID NO 140
<211> LENGTH: 351
<212> TYPE: DNA
<213> ORGANISM: Artificial Sequence
<220> FEATURE:
<223> OTHER INFORMATION: O2D7; VH

<400> SEQUENCE: 140
gaggtgcaat tgttggagtc tgggggaggc ttggtacagc ctggggggtc cctgagactc    60
tcctgtgcag cctccggatt cacctttagc agttatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcagatga acagcctgag agccgaggac acggccgtat attactgtgc gaaagggtgg   300
tttggtggtt ttaactactg gggccaagga accctggtca ccgtctcgtc c            351

<210> SEQ ID NO 141
<211> LENGTH: 108
<212> TYPE: PRT
<213> ORGANISM: Artificial Sequence
<220> FEATURE:
<223> OTHER INFORMATION: 28H1; VL

<400> SEQUENCE: 141

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105

<210> SEQ ID NO 142
<211> LENGTH: 324
<212> TYPE: DNA
<213> ORGANISM: Artificial Sequence
<220> FEATURE:
<223> OTHER INFORMATION: 28H1; VL

<400> SEQUENCE: 142
gaaatcgtgt taacgcagtc tccaggcacc ctgtctttgt ctccagggga aagagccacc    60
ctctcttgca gggccagtca gagtgttagc cgcagctact tagcctggta ccagcagaaa   120
cctggccagg ctcccaggct cctcatcatt ggggcctcca ccagggccac tggcatccca   180
gacaggttca gtggcagtgg atccgggaca gacttcactc tcaccatcag cagactggag   240
cctgaagatt ttgcagtgta ttactgtcag cagggtcagg ttattccccc tacgttcggc   300
caggggacca aagtggaaat caaa 324

<210> SEQ ID NO 143
<211> LENGTH: 116
<212> TYPE: PRT
<213> ORGANISM: Artificial Sequence
<220> FEATURE:
<223> OTHER INFORMATION: 28H1; VH

<400> SEQUENCE: 143

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser His
20 25 30

Ala Met Ser Trp Val Arg Gln Ala Pro Gly Lys Gly Leu Glu Trp Val
35 40 45

Ser Ala Ile Trp Ala Ser Gly Glu Gln Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Lys Gly Trp Leu Gly Asn Phe Asp Tyr Trp Gly Gln Gly Thr Leu Val
100 105 110

Thr Val Ser Ser
115

<210> SEQ ID NO 144
<211> LENGTH: 348
<212> TYPE: DNA
<213> ORGANISM: Artificial Sequence
<220> FEATURE:
<223> OTHER INFORMATION: 28H1; VH

<400> SEQUENCE: 144
gaggtgcaat tgttggagtc tgggggaggc ttggtacagc ctggggggtc cctgagactc 60
tcctgtgcag cctccggatt cacctttagc agtcatgcta tgagctgggt ccgccaggct 120
ccagggaagg ggctggagtg ggtctcagct atttgggcta gtggggagca atactacgca 180
gactccgtga agggccggtt caccatctcc agagacaatt ccaagaacac gctgtatctg 240
cagatgaaca gcctgagagc cgaggacacg gccgtatatt actgtgcgaa agggtggctg 300
ggtaattttg actactgggg ccaaggaacc ctggtcaccg tctcgagt 348

<210> SEQ ID NO 145
<211> LENGTH: 108
<212> TYPE: PRT
<213> ORGANISM: Artificial Sequence
<220> FEATURE:
<223> OTHER INFORMATION: 22A3; VL

<400> SEQUENCE: 145

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Thr Ser Ser
20 25 30

Tyr Leu Ala Trp Tyr Gln Gln Lys Pro Gly Gln Ala Pro Arg Leu Leu
35 40 45

Ile Asn Val Gly Ser Arg Arg Ala Thr Gly Ile Pro Asp Arg Phe Ser
50 55 60

```
Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105


<210> SEQ ID NO 146
<211> LENGTH: 324
<212> TYPE: DNA
<213> ORGANISM: Artificial Sequence
<220> FEATURE:
<223> OTHER INFORMATION: 22A3; VL

<400> SEQUENCE: 146

gaaatcgtgt taacgcagtc tccaggcacc ctgtctttgt ctccagggga aagagccacc     60

ctctcttgca gggccagtca gagtgttacc agtagctact tagcctggta ccagcagaaa    120

cctggccagg ctcccaggct cctcatcaat gtgggctccc gtagggccac tggcatccca    180

gacaggttca gtggcagtgg atccgggaca gacttcactc tcaccatcag cagactggag    240

cctgaagatt ttgcagtgta ttactgtcag cagggtatta tgcttccccc gacgttcggc    300

caggggacca aagtggaaat caaa                                           324


<210> SEQ ID NO 147
<211> LENGTH: 117
<212> TYPE: PRT
<213> ORGANISM: Artificial Sequence
<220> FEATURE:
<223> OTHER INFORMATION: 22A3; VH

<400> SEQUENCE: 147

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ser Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115


<210> SEQ ID NO 148
<211> LENGTH: 351
<212> TYPE: DNA
<213> ORGANISM: Artificial Sequence
<220> FEATURE:
<223> OTHER INFORMATION: 22A3; VH

<400> SEQUENCE: 148

gaggtgcaat tgttggagtc tgggggaggc ttggtacagc ctggggggtc cctgagactc     60

tcctgtgcag cctccggatt cacctttagc agttatgcca tgagctgggt ccgccaggct    120
```

```
ccagggaagg ggctggagtg ggtctcagct attattggta gtggtagtat cacatactac    180

gcagactccg tgaagggccg gttcaccatc tccagagaca attccaagaa cacgctgtat    240

ctgcagatga acagcctgag agccgaggac acggccgtat attactgtgc gaaagggtgg    300

tttggtggtt ttaactactg gggccaagga accctggtca ccgtctcgag t             351


<210> SEQ ID NO 149
<211> LENGTH: 108
<212> TYPE: PRT
<213> ORGANISM: Artificial Sequence
<220> FEATURE:
<223> OTHER INFORMATION: 29B11; VL

<400> SEQUENCE: 149

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105


<210> SEQ ID NO 150
<211> LENGTH: 324
<212> TYPE: DNA
<213> ORGANISM: Artificial Sequence
<220> FEATURE:
<223> OTHER INFORMATION: 29B11; VL

<400> SEQUENCE: 150

gaaatcgtgt taacgcagtc tccaggcacc ctgtctttgt ctccagggga aagagccacc     60

ctctcttgca gggccagtca gagtgttacc agtagctact tagcctggta ccagcagaaa    120

cctggccagg ctcccaggct cctcatcaat gtgggctccc gtagggccac tggcatccca    180

gacaggttca gtggcagtgg atccgggaca gacttcactc tcaccatcag cagactggag    240

cctgaagatt ttgcagtgta ttactgtcag cagggtatta tgcttccccc gacgttcggc    300

caggggacca aagtggaaat caaa                                           324


<210> SEQ ID NO 151
<211> LENGTH: 117
<212> TYPE: PRT
<213> ORGANISM: Artificial Sequence
<220> FEATURE:
<223> OTHER INFORMATION: 29B11; VH

<400> SEQUENCE: 151

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
```

```
        35                  40                  45

Ser Ala Ile Ile Gly Ser Gly Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115


<210> SEQ ID NO 152
<211> LENGTH: 351
<212> TYPE: DNA
<213> ORGANISM: Artificial Sequence
<220> FEATURE:
<223> OTHER INFORMATION: 29B11; VH

<400> SEQUENCE: 152

gaggtgcaat tgttggagtc tgggggaggc ttggtacagc ctggggggtc cctgagactc      60

tcctgtgcag cctccggatt cacctttagc agttatgcta tgagctgggt ccgccaggct     120

ccagggaagg ggctggagtg ggtctcagct attattggta gtggtggtat cacatactac     180

gcagactccg tgaagggccg gttcaccatc tccagagaca attccaagaa cacgctgtat     240

ctgcagatga acagcctgag agccgaggac acggccgtat attactgtgc gaaagggtgg     300

tttggtggtt ttaactactg gggccaagga accctggtca ccgtctcgag t              351


<210> SEQ ID NO 153
<211> LENGTH: 108
<212> TYPE: PRT
<213> ORGANISM: Artificial Sequence
<220> FEATURE:
<223> OTHER INFORMATION: 23C10; VL

<400> SEQUENCE: 153

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105


<210> SEQ ID NO 154
<211> LENGTH: 324
<212> TYPE: DNA
<213> ORGANISM: Artificial Sequence
<220> FEATURE:
<223> OTHER INFORMATION: 23C10; VL

<400> SEQUENCE: 154
```

gaaatcgtgt taacgcagtc tccaggcacc ctgtctttgt ctccagggga aagagccacc 60
ctctcttgca gggccagtca gagtgttagc cgcagctact tagcctggta ccagcagaaa 120
cctggccagg ctcccaggct cctcatcatt ggggcctcca ccagggccac tggcatccca 180
gacaggttca gtggcagtgg atccgggaca gacttcactc tcaccatcag cagactggag 240
cctgaagatt ttgcagtgta ttactgtcag cagggtcagg ttattccccc tacgttcggc 300
caggggacca aagtggaaat caaa 324

<210> SEQ ID NO 155
<211> LENGTH: 117
<212> TYPE: PRT
<213> ORGANISM: Artificial Sequence
<220> FEATURE:
<223> OTHER INFORMATION: 23C10; VH

<400> SEQUENCE: 155

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Ser
20 25 30

Ala Met Ser Trp Val Arg Gln Ala Pro Gly Lys Gly Leu Glu Trp Val
35 40 45

Ser Ala Ile Ser Thr Asn Gly Asn Tyr Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Trp Leu Gly Asn Phe Asp Tyr Trp Gly Gln Gly Thr Leu
100 105 110

Val Thr Val Ser Ser
115

<210> SEQ ID NO 156
<211> LENGTH: 351
<212> TYPE: DNA
<213> ORGANISM: Artificial Sequence
<220> FEATURE:
<223> OTHER INFORMATION: 23C10; VH

<400> SEQUENCE: 156
gaggtgcaat tgttggagtc tgggggaggc ttggtacagc ctggggggtc cctgagactc 60
tcctgtgcag cctccggatt cacctttagc agttctgcca tgagctgggt ccgccaggct 120
ccagggaagg ggctggagtg ggtctcagct attagtacta atggtaatta tacatactac 180
gcagactccg tgaagggccg gttcaccatc tccagagaca attccaagaa cacgctgtat 240
ctgcagatga acagcctgag agccgaggac acggccgtat attactgtgc gaaagggtgg 300
ctgggtaatt ttgactactg gggccaagga accctggtca ccgtctcgag t 351

<210> SEQ ID NO 157
<211> LENGTH: 107
<212> TYPE: PRT
<213> ORGANISM: Artificial Sequence
<220> FEATURE:
<223> OTHER INFORMATION: 2B10_C3B6; VL

<400> SEQUENCE: 157

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105
```

<210> SEQ ID NO 158
<211> LENGTH: 321
<212> TYPE: DNA
<213> ORGANISM: Artificial Sequence
<220> FEATURE:
<223> OTHER INFORMATION: 2B10_C3B6; VL

<400> SEQUENCE: 158

```
gatatccaga tgacccagtc tccatcctcc ctgtctgcat ctgtcggaga ccgggtcacc     60

atcacctgcc gggcaagtca gggcattaga aatgatttag gctggtacca gcagaagcca    120

gggaaagccc ctaagcgcct gatctatgct gcatccagtt tgcagagtgg cgtcccatca    180

aggttcagcg gcagtggatc cgggacagag ttcactctca ccatcagcag cttgcagcct    240

gaagattttg ccacctatta ctgcttgcag aatggtctgc agcccgcgac gtttggccag    300

ggcaccaaag tcgagatcaa g                                              321
```

<210> SEQ ID NO 159
<211> LENGTH: 121
<212> TYPE: PRT
<213> ORGANISM: Artificial Sequence
<220> FEATURE:
<223> OTHER INFORMATION: 2B10_C3B6; VH

<400> SEQUENCE: 159

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ala Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120
```

<210> SEQ ID NO 160

<211> LENGTH: 363
<212> TYPE: DNA
<213> ORGANISM: Artificial Sequence
<220> FEATURE:
<223> OTHER INFORMATION: 2B10_C3B6; VH

<400> SEQUENCE: 160

```
caggtgcaat tggtgcagtc tggggctgag gtgaagaagc ctgggtcctc ggtgaaggtc     60

tcctgcaagg cctccggagg cacattcagc agctacgcta taagctgggt gcgacaggcc    120

cctggacaag ggctcgagtg gatgggagct atcatcccga tccttggtat cgcaaactac    180

gcacagaagt tccagggcag ggtcaccatt actgcagaca aatccacgag cacagcctac    240

atggagctga gcagcctgag atctgaggac accgccgtgt attactgtgc gagactgtac    300

ggttacgctt actacggtgc ttttgactac tggggccaag ggaccaccgt gaccgtctcc    360

tca                                                                  363
```

<210> SEQ ID NO 161
<211> LENGTH: 107
<212> TYPE: PRT
<213> ORGANISM: Artificial Sequence
<220> FEATURE:
<223> OTHER INFORMATION: 2B10_6A12; VL

<400> SEQUENCE: 161

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105
```

<210> SEQ ID NO 162
<211> LENGTH: 321
<212> TYPE: DNA
<213> ORGANISM: Artificial Sequence
<220> FEATURE:
<223> OTHER INFORMATION: 2B10_6A12; VL

<400> SEQUENCE: 162

```
gatatccaga tgacccagtc tccatcctcc ctgtctgcat ctgtcggaga ccgggtcacc     60

atcacctgcc gggcaagtca gggcattaga aatgatttag gctggtacca gcagaagcca    120

gggaaagccc ctaagcgcct gatctatgct gcatccagtt tgcagagtgg cgtcccatca    180

aggttcagcg gcagtggatc cgggacagag ttcactctca ccatcagcag cttgcagcct    240

gaagattttg ccacctatta ctgcttgcag aatggtctgc agcccgcgac gtttggccag    300

ggcaccaaag tcgagatcaa g                                              321
```

<210> SEQ ID NO 163
<211> LENGTH: 121
<212> TYPE: PRT

<213> ORGANISM: Artificial Sequence
<220> FEATURE:
<223> OTHER INFORMATION: 2B10_6A12; VH

<400> SEQUENCE: 163

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Val Ile Ile Pro Ile Leu Gly Thr Ala Asn Tyr Ala Gln Lys Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Leu Tyr Gly Tyr Ala Tyr Tyr Gly Ala Phe Asp Tyr Trp Gly
100 105 110

Gln Gly Thr Thr Val Thr Val Ser Ser
115 120

<210> SEQ ID NO 164
<211> LENGTH: 363
<212> TYPE: DNA
<213> ORGANISM: Artificial Sequence
<220> FEATURE:
<223> OTHER INFORMATION: 2B10_6A12; VH

<400> SEQUENCE: 164
caggtgcaat tggtgcagtc tggggctgag gtgaagaagc ctgggtcctc ggtgaaggtc 60
tcctgcaagg cctccggagg cacattcagc agctatgcta taagctgggt gcgacaggcc 120
cctggacaag ggctcgagtg gatgggagtg atcatcccta tccttggtac cgcaaactac 180
gcacagaagt tccagggcag ggtcaccatt actgcagaca aatccacgag cacagcctac 240
atggagctga gcagcctgag atctgaggac accgccgtgt attactgtgc gagactgtac 300
ggttacgctt actacggtgc ttttgactac tggggccaag ggaccaccgt gaccgtctcc 360
tca 363

<210> SEQ ID NO 165
<211> LENGTH: 107
<212> TYPE: PRT
<213> ORGANISM: Artificial Sequence
<220> FEATURE:
<223> OTHER INFORMATION: 2B10_C3A6; VL

<400> SEQUENCE: 165

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Asn Val
20 25 30

Leu Gly Trp Tyr Gln Gln Lys Pro Gly Lys Ala Pro Lys Arg Leu Ile
35 40 45

Tyr Asp Ser Ser Ser Leu Gln Ser Gly Val Pro Ser Arg Phe Ser Gly
50 55 60

Gly Gly Ser Gly Thr Glu Phe Thr Leu Thr Ile Ser Ser Leu Gln Pro
65 70 75 80

```
Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105


<210> SEQ ID NO 166
<211> LENGTH: 321
<212> TYPE: DNA
<213> ORGANISM: Artificial Sequence
<220> FEATURE:
<223> OTHER INFORMATION: 2B10_C3A6; VL

<400> SEQUENCE: 166

gacatccaga tgacccagtc tccttcctcc ctgtctgcat ctgtcggaga ccgggtcacc     60

atcacctgcc gggcaagtca gggcattcgt aatgttttag gctggtacca gcagaagcca    120

gggaaagccc ctaagcgcct gatctatgat tcgtccagtt tgcagagtgg cgtcccatca    180

aggttcagcg gcggtggatc cgggacagag ttcactctca ccatcagcag cttgcagcct    240

gaagattttg ccacctatta ctgcttgcag aatggtctgc agcccgcgac gtttggccag    300

ggcaccaaag tcgagatcaa g                                              321


<210> SEQ ID NO 167
<211> LENGTH: 121
<212> TYPE: PRT
<213> ORGANISM: Artificial Sequence
<220> FEATURE:
<223> OTHER INFORMATION: 2B10_C3A6; VH

<400> SEQUENCE: 167

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120


<210> SEQ ID NO 168
<211> LENGTH: 363
<212> TYPE: DNA
<213> ORGANISM: Artificial Sequence
<220> FEATURE:
<223> OTHER INFORMATION: 2B10_C3A6; VH

<400> SEQUENCE: 168

caggtgcaat tggtgcagtc tggggctgag gtgaagaagc ctgggtcctc ggtgaaggtc     60

tcctgcaagg cctccggagg cacattcagc agctacgcta taagctgggt gcgacaggcc    120

cctggacaag ggctcgagtg gatgggaggg atcatcccta tctttggtac agcaaactac    180

gcacagaagt tccagggcag ggtcaccatt actgcagaca aatccacgag cacagcctac    240
```

atggagctga gcagcctgag atctgaggac accgccgtgt attactgtgc gagactgtac 300
ggttacgctt actacggtgc ttttgactac tggggccaag ggaccaccgt gaccgtctcc 360
tca 363

<210> SEQ ID NO 169
<211> LENGTH: 107
<212> TYPE: PRT
<213> ORGANISM: Artificial Sequence
<220> FEATURE:
<223> OTHER INFORMATION: 2B10_D1A2_wt; VL

<400> SEQUENCE: 169

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Asn Val
20 25 30

Leu Gly Trp Tyr Gln Gln Lys Pro Gly Lys Ala Pro Lys Arg Leu Ile
35 40 45

Tyr Asp Ala Tyr Ser Leu Gln Ser Gly Val Pro Ser Arg Phe Ser Gly
50 55 60

Gly Gly Ser Gly Thr Glu Phe Thr Leu Thr Ile Ser Ser Leu Gln Pro
65 70 75 80

Glu Asp Phe Ala Thr Tyr Tyr Cys Leu Gln Asn Gly Leu Gln Pro Ala
85 90 95

Thr Phe Gly Gln Gly Thr Lys Val Glu Ile Lys
100 105

<210> SEQ ID NO 170
<211> LENGTH: 321
<212> TYPE: DNA
<213> ORGANISM: Artificial Sequence
<220> FEATURE:
<223> OTHER INFORMATION: 2B10_D1A2_wt; VL

<400> SEQUENCE: 170
gatatccaga tgacccagtc tccatcctcc ctgtctgcat ctgtcggaga ccgggtcacc 60
atcacctgcc gggcaagtca ggggattcgt aatgttttag gctggtacca gcagaagcca 120
gggaaagccc ctaagcgcct gatctatgat gcttacagct tgcagagtgg cgtcccatca 180
aggttcagcg gcggtggatc cgggacagag ttcactctca ccatcagcag cttgcagcct 240
gaagattttg ccacctatta ctgcttgcag aatggtctgc agcccgcgac gtttggccag 300
ggcaccaaag tcgagatcaa g 321

<210> SEQ ID NO 171
<211> LENGTH: 121
<212> TYPE: PRT
<213> ORGANISM: Artificial Sequence
<220> FEATURE:
<223> OTHER INFORMATION: 2B10_D1A2_wt; VH

<400> SEQUENCE: 171

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120

<210> SEQ ID NO 172
<211> LENGTH: 363
<212> TYPE: DNA
<213> ORGANISM: Artificial Sequence
<220> FEATURE:
<223> OTHER INFORMATION: 2B10_D1A2_wt; VH

<400> SEQUENCE: 172
caggtgcaat tggtgcagtc tggggctgag gtgaagaagc ctgggtcctc ggtgaaggtc 60
tcctgcaagg cctccggagg cacattcagc agctacgcta taagctgggt gcgacaggcc 120
cctggacaag ggctcgagtg gatgggaggg atcatcccta tctttggtac agcaaactac 180
gcacagaagt tccagggcag ggtcaccatt actgcagaca aatccacgag cacagcctac 240
atggagctga gcagcctgag atctgaggac accgccgtgt attactgtgc gagactgtac 300
ggttacgctt actacggtgc ttttgactac tggggccaag ggaccaccgt gaccgtctcc 360
tca 363

<210> SEQ ID NO 173
<211> LENGTH: 107
<212> TYPE: PRT
<213> ORGANISM: Artificial Sequence
<220> FEATURE:
<223> OTHER INFORMATION: 2B10_D1A2_VD; VL

<400> SEQUENCE: 173

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Asp Ala Tyr Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105

<210> SEQ ID NO 174
<211> LENGTH: 321
<212> TYPE: DNA
<213> ORGANISM: Artificial Sequence
<220> FEATURE:
<223> OTHER INFORMATION: 2B10_D1A2_VD; VL

<400> SEQUENCE: 174

```
gacatccaga tgacccagtc tccatcctcc ctgtctgcat ctgtcggaga ccgggtcacc     60

atcacctgcc gggcaagtca ggggattcgt aatgatttag gctggtacca gcagaagcca    120

gggaaagccc ctaagcgcct gatctatgat gcttacagct tgcagagtgg cgtcccatca    180

aggttcagcg gcggtggatc cgggacagag ttcactctca ccatcagcag cttgcagcct    240

gaagattttg ccacctatta ctgcttgcag aatggtctgc agcccgcgac gtttggccag    300

ggcaccaaag tcgagatcaa g                                              321
```

<210> SEQ ID NO 175
<211> LENGTH: 121
<212> TYPE: PRT
<213> ORGANISM: Artificial Sequence
<220> FEATURE:
<223> OTHER INFORMATION: 2B10_D1A2_VD; VH

<400> SEQUENCE: 175

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120
```

<210> SEQ ID NO 176
<211> LENGTH: 363
<212> TYPE: DNA
<213> ORGANISM: Artificial Sequence
<220> FEATURE:
<223> OTHER INFORMATION: 2B10_D1A2_VD; VH

<400> SEQUENCE: 176

```
caggtgcaat tggtgcagtc tggggctgag gtgaagaagc ctgggtcctc ggtgaaggtc     60

tcctgcaagg cctccggagg cacattcagc agctacgcta taagctgggt gcgacaggcc    120

cctggacaag ggctcgagtg gatgggaggg atcatcccta tctttggtac agcaaactac    180

gcacagaagt tccagggcag ggtcaccatt actgcagaca aatccacgag cacagcctac    240

atggagctga gcagcctgag atctgaggac accgccgtgt attactgtgc gagactgtac    300

ggttacgctt actacggtgc ttttgactac tggggccaag ggaccaccgt gaccgtctcc    360

tca                                                                  363
```

<210> SEQ ID NO 177
<211> LENGTH: 107
<212> TYPE: PRT
<213> ORGANISM: Artificial Sequence
<220> FEATURE:
<223> OTHER INFORMATION: 2B10_O7D8; VL

<400> SEQUENCE: 177

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Asn Val
            20                  25                  30

Leu Gly Trp Tyr Gln Gln Lys Pro Gly Lys Ala Pro Lys Arg Leu Ile
        35                  40                  45

Tyr Asp Val Ser Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105

<210> SEQ ID NO 178
<211> LENGTH: 321
<212> TYPE: DNA
<213> ORGANISM: Artificial Sequence
<220> FEATURE:
<223> OTHER INFORMATION: 2B10_O7D8; VL

<400> SEQUENCE: 178
gatatccaga tgacccagtc tccatcctcc ctgtctgcat ctgtcggaga ccgggtcacc 60
atcacctgcc gggcaagtca gagcattcgt aatgttttag gctggtacca gcagaagcca 120
gggaaagccc ctaagcgcct gatctatgat gtgtccagtt tgcagagtgg cgtcccatca 180
aggttcagcg gcggtggatc cgggacagag ttcactctca ccatcagcag cttgcagcct 240
gaagattttg ccacctatta ctgcttgcag aatggtctgc agcccgcgac gtttggccag 300
ggcaccaaag tcgagatcaa g 321

<210> SEQ ID NO 179
<211> LENGTH: 121
<212> TYPE: PRT
<213> ORGANISM: Artificial Sequence
<220> FEATURE:
<223> OTHER INFORMATION: 2B10_O7D8; VH

<400> SEQUENCE: 179

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120

<210> SEQ ID NO 180
<211> LENGTH: 363
<212> TYPE: DNA
<213> ORGANISM: Artificial Sequence
<220> FEATURE:
<223> OTHER INFORMATION: 2B10_O7D8; VH

<400> SEQUENCE: 180
caggtgcaat tggtgcagtc tggggctgag gtgaagaagc ctgggtcctc ggtgaaggtc 60
tcctgcaagg cctccggagg cacattcagc agctacgcta taagctgggt gcgacaggcc 120
cctggacaag ggctcgagtg gatgggaggg atcatcccta tctttggtac agcaaactac 180
gcacagaagt tccagggcag ggtcaccatt actgcagaca aatccacgag cacagcctac 240
atggagctga gcagcctgag atctgaggac accgccgtgt attactgtgc gagactgtac 300
ggttacgctt actacggtgc ttttgactac tggggccaag ggaccaccgt gaccgtctcc 360
tca 363

<210> SEQ ID NO 181
<211> LENGTH: 107
<212> TYPE: PRT
<213> ORGANISM: Artificial Sequence
<220> FEATURE:
<223> OTHER INFORMATION: 2B10_O1F7; VL

<400> SEQUENCE: 181

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Asn Val
20 25 30

Leu Gly Trp Tyr Gln Gln Lys Pro Gly Lys Ala Pro Lys Arg Leu Ile
35 40 45

Tyr Asp Ala Ser Ser Leu Gln Ser Gly Val Pro Ser Arg Phe Ser Gly
50 55 60

Gly Gly Ser Gly Thr Glu Phe Thr Leu Thr Ile Ser Ser Leu Gln Pro
65 70 75 80

Glu Asp Phe Ala Thr Tyr Tyr Cys Leu Gln Asn Gly Leu Gln Pro Ala
85 90 95

Thr Phe Gly Gln Gly Thr Lys Val Glu Ile Lys
100 105

<210> SEQ ID NO 182
<211> LENGTH: 321
<212> TYPE: DNA
<213> ORGANISM: Artificial Sequence
<220> FEATURE:
<223> OTHER INFORMATION: 2B10_O1F7; VL

<400> SEQUENCE: 182
gatatccaga tgacccagtc tccatcctcc ctgtctgcat ctgtcggaga ccgggtcacc 60
atcacctgcc gggcaagtca gggcattcgt aatgttttag gctggtacca gcagaagcca 120
gggaaagccc ctaagcgcct gatctatgat gcgtccagtt tgcagagtgg cgtcccatca 180
aggttcagcg gcggtggatc cgggacagag ttcactctca ccatcagcag cttgcagcct 240
gaagattttg ccacctatta ctgcctgcag aatggtctgc agcccgcgac gtttggccag 300
ggcaccaaag tcgagatcaa g 321

<210> SEQ ID NO 183

<211> LENGTH: 121
<212> TYPE: PRT
<213> ORGANISM: Artificial Sequence
<220> FEATURE:
<223> OTHER INFORMATION: 2B10_O1F7; VH

<400> SEQUENCE: 183

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Leu Tyr Gly Tyr Ala Tyr Tyr Gly Ala Phe Asp Tyr Trp Gly
100 105 110

Gln Gly Thr Thr Val Thr Val Ser Ser
115 120

<210> SEQ ID NO 184
<211> LENGTH: 363
<212> TYPE: DNA
<213> ORGANISM: Artificial Sequence
<220> FEATURE:
<223> OTHER INFORMATION: 2B10_O1F7; VH

<400> SEQUENCE: 184
caggtgcaat tggtgcagtc tggggctgag gtgaagaagc ctgggtcctc ggtgaaggtc 60
tcctgcaagg cctccggagg cacattcagc agctacgcta taagctgggt gcgacaggcc 120
cctggacaag ggctcgagtg gatgggaggg atcatcccta tctttggtac agcaaactac 180
gcacagaagt tccagggcag ggtcaccatt actgcagaca aatccacgag cacagcctac 240
atggagctga gcagcctgag atctgaggac accgccgtgt attactgtgc gagactgtac 300
ggttacgctt actacggtgc ttttgactac tggggccaag ggaccaccgt gaccgtctcc 360
tca 363

<210> SEQ ID NO 185
<211> LENGTH: 107
<212> TYPE: PRT
<213> ORGANISM: Artificial Sequence
<220> FEATURE:
<223> OTHER INFORMATION: 2B10_6H10; VL

<400> SEQUENCE: 185

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Asn Val
20 25 30

Leu Gly Trp Tyr Gln Gln Lys Pro Gly Lys Ala Pro Lys Arg Leu Ile
35 40 45

Gln Ala Ala Thr Ser Leu Gln Ser Gly Val Pro Ser Arg Phe Ser Gly
50 55 60

Gly Gly Ser Gly Thr Glu Phe Thr Leu Thr Ile Ser Ser Leu Gln Pro

```
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105


<210> SEQ ID NO 186
<211> LENGTH: 321
<212> TYPE: DNA
<213> ORGANISM: Artificial Sequence
<220> FEATURE:
<223> OTHER INFORMATION: 2B10_6H10; VL

<400> SEQUENCE: 186

gacatccaga tgacccagtc tccatcctcc ctgtctgcat ctgtcggaga ccgggtcacc      60

atcacctgcc gggcaagtca gggcattcgt aatgttttag gctggtacca gcagaagcca     120

gggaaagccc ctaagcgcct gatccaggct gctaccagtt tgcagagtgg cgtcccatca     180

aggttcagcg gcggtggatc cgggacagag ttcactctca ccatcagcag cttgcagcct     240

gaagattttg ccacctatta ctgcttgcag aatggtctgc agcccgcgac gtttggccag     300

ggcaccaaag tcgagatcaa g                                               321


<210> SEQ ID NO 187
<211> LENGTH: 121
<212> TYPE: PRT
<213> ORGANISM: Artificial Sequence
<220> FEATURE:
<223> OTHER INFORMATION: 2B10_6H10; VH

<400> SEQUENCE: 187

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120


<210> SEQ ID NO 188
<211> LENGTH: 363
<212> TYPE: DNA
<213> ORGANISM: Artificial Sequence
<220> FEATURE:
<223> OTHER INFORMATION: 2B10_6H10; VH

<400> SEQUENCE: 188

caggtgcaat tggtgcagtc tggggctgag gtgaagaagc ctgggtcctc ggtgaaggtc      60

tcctgcaagg cctccggagg cacattcagc agctacgcta taagctgggt gcgacaggcc     120

cctggacaag ggctcgagtg gatgggaggg atcatcccta tctttggtac agcaaactac     180
```

gcacagaagt tccagggcag ggtcaccatt actgcagaca aatccacgag cacagcctac 240
atggagctga gcagcctgag atctgaggac accgccgtgt attactgtgc gagactgtac 300
ggttacgctt actacggtgc ttttgactac tggggccaag ggaccaccgt gaccgtctcc 360
tca 363

<210> SEQ ID NO 189
<211> LENGTH: 108
<212> TYPE: PRT
<213> ORGANISM: Artificial Sequence
<220> FEATURE:
<223> OTHER INFORMATION: CH1A1A; VL

<400> SEQUENCE: 189

Asp Ile Gln Met Thr Gln Ser Pro Ser Ser Leu Ser Ala Ser Val Gly
1 5 10 15

Asp Arg Val Thr Ile Thr Cys Lys Ala Ser Ala Ala Val Gly Thr Tyr
20 25 30

Val Ala Trp Tyr Gln Gln Lys Pro Gly Lys Ala Pro Lys Leu Leu Ile
35 40 45

Tyr Ser Ala Ser Tyr Arg Lys Arg Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys His Gln Tyr Tyr Thr Tyr Pro Leu
85 90 95

Phe Thr Phe Gly Gln Gly Thr Lys Leu Glu Ile Lys
100 105

<210> SEQ ID NO 190
<211> LENGTH: 324
<212> TYPE: DNA
<213> ORGANISM: Artificial Sequence
<220> FEATURE:
<223> OTHER INFORMATION: CH1A1A; VL

<400> SEQUENCE: 190
gatatccaga tgacccagtc tccatcctcc ctgtctgcat ctgtgggaga cagagtcacc 60
atcacttgca aggccagtgc ggctgtgggt acgtatgttg cgtggtatca gcagaaacca 120
gggaaagcac ctaagctcct gatctattcg gcatcctacc gcaaaagggg agtcccatca 180
aggttcagtg gcagtggatc tgggacagat ttcactctca ccatcagcag tctgcaacct 240
gaagatttcg caacttacta ctgtcaccaa tattacacct atcctctatt cacgtttggc 300
cagggcacca agctcgagat caag 324

<210> SEQ ID NO 191
<211> LENGTH: 121
<212> TYPE: PRT
<213> ORGANISM: Artificial Sequence
<220> FEATURE:
<223> OTHER INFORMATION: CH1A1A; VH

<400> SEQUENCE: 191

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Glu Phe
20 25 30

Gly Met Asn Trp Val Arg Gln Ala Pro Gly Gln Gly Leu Glu Trp Met 35 40 45

Gly Trp Ile Asn Thr Lys Thr Gly Glu Ala Thr Tyr Val Glu Glu Phe
50 55 60

Lys Gly Arg Val Thr Phe Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Trp Asp Phe Ala Tyr Tyr Val Glu Ala Met Asp Tyr Trp Gly
100 105 110

Gln Gly Thr Thr Val Thr Val Ser Ser
115 120

<210> SEQ ID NO 192
<211> LENGTH: 363
<212> TYPE: DNA
<213> ORGANISM: Artificial Sequence
<220> FEATURE:
<223> OTHER INFORMATION: CH1A1A; VH

<400> SEQUENCE: 192
caggtgcagc tggtgcagtc tggcgccgaa gtgaagaaac ctggagctag tgtgaaggtg 60
tcctgcaagg ccagcggcta caccttcacc gagttcggca tgaactgggt ccgacaggct 120
ccaggccagg gcctcgaatg gatgggctgg atcaacacca agaccggcga ggccacctac 180
gtggaagagt tcaagggcag agtgaccttc accacggaca ccagcaccag caccgcctac 240
atggaactgc ggagcctgag aagcgacgac accgccgtgt actactgcgc cagatgggac 300
ttcgcctatt acgtggaagc catggactac tggggccagg gcaccaccgt gaccgtgtct 360
agc 363

<210> SEQ ID NO 193
<211> LENGTH: 446
<212> TYPE: PRT
<213> ORGANISM: Artificial Sequence
<220> FEATURE:
<223> OTHER INFORMATION: 28H1 Fab HC-Fc hole (LALA P329G)

<400> SEQUENCE: 193

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser His
20 25 30

Ala Met Ser Trp Val Arg Gln Ala Pro Gly Lys Gly Leu Glu Trp Val
35 40 45

Ser Ala Ile Trp Ala Ser Gly Glu Gln Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Lys Gly Trp Leu Gly Asn Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly

```
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 194
<211> LENGTH: 1338
<212> TYPE: DNA
<213> ORGANISM: Artificial Sequence
<220> FEATURE:
<223> OTHER INFORMATION: 28H1 Fab HC-Fc hole (LALA P329G)

<400> SEQUENCE: 194

```
gaagtgcagc tgctggaatc cggcggaggc ctggtgcagc ctggcggatc tctgagactg     60

tcctgcgccg cctccggctt caccttctcc tcccacgcca tgtcctgggt ccgacaggct    120

cctggcaaag gcctggaatg ggtgtccgcc atctgggcct ccggcgagca gtactacgcc    180

gactctgtga agggccggtt caccatctcc cgggacaact ccaagaacac cctgtacctg    240

cagatgaact ccctgcgggc cgaggacacc gccgtgtact actgtgccaa gggctggctg    300

ggcaacttcg actactgggg acagggcacc ctggtcaccg tgtccagcgc tagcaccaag    360

ggcccctccg tgttccccct ggcccccagc agcaagagca ccagcggcgg cacagccgct    420
```

```
ctgggctgcc tggtcaagga ctacttcccc gagcccgtga ccgtgtcctg gaacagcgga    480

gccctgacct ccggcgtgca caccttcccc gccgtgctgc agagttctgg cctgtatagc    540

ctgagcagcg tggtcaccgt gccttctagc agcctgggca cccagaccta catctgcaac    600

gtgaaccaca agcccagcaa caccaaggtg gacaagaagg tggagcccaa gagctgcgac    660

aaaactcaca catgcccacc gtgcccagca cctgaagctg caggggggacc gtcagtcttc   720

ctcttccccc caaaacccaa ggacaccctc atgatctccc ggacccctga ggtcacatgc    780

gtggtggtgg acgtgagcca cgaagaccct gaggtcaagt tcaactggta cgtggacggc    840

gtggaggtgc ataatgccaa gacaaagccg cgggaggagc agtacaacag cacgtaccgt    900

gtggtcagcg tcctcaccgt cctgcaccag gactggctga atggcaagga gtacaagtgc    960

aaggtctcca acaaagccct cggcgccccc atcgagaaaa ccatctccaa agccaaaggg   1020

cagccccgag aaccacaggt gtgcaccctg cccccatccc gggatgagct gaccaagaac   1080

caggtcagcc tctcgtgcgc agtcaaaggc ttctatccca gcgacatcgc cgtggagtgg   1140

gagagcaatg ggcagccgga gaacaactac aagaccacgc ctcccgtgct ggactccgac   1200

ggctccttct tcctcgtgag caagctcacc gtggacaaga gcaggtggca gcaggggaac   1260

gtcttctcat gctccgtgat gcatgaggct ctgcacaacc actacacgca gaagagcctc   1320

tccctgtctc cgggtaaa                                                 1338


<210> SEQ ID NO 195
<211> LENGTH: 592
<212> TYPE: PRT
<213> ORGANISM: Artificial Sequence
<220> FEATURE:
<223> OTHER INFORMATION: 28H1 Fab HC-Fc knob (LALA P329G)-IL-2 qm

<400> SEQUENCE: 195

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

```
Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Cys Arg Asp Glu Leu Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Gly Gly Gly
        435                 440                 445

Gly Ser Gly Gly Gly Gly Ser Gly Gly Gly Gly Ala Pro Ala Ser Ser
    450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Arg Met Leu Thr Ala Lys Phe Ala Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Gly Ala Gln Ser Lys Asn Phe His Leu Arg Pro Arg Asp Leu
    530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Ala Gln Ser Ile Ile Ser Thr Leu Thr
            580                 585                 590
```

<210> SEQ ID NO 196
<211> LENGTH: 1776
<212> TYPE: DNA

<213> ORGANISM: Artificial Sequence
<220> FEATURE:
<223> OTHER INFORMATION: 28H1 Fab HC-Fc knob (LALA P329G)-IL-2 qm

<400> SEQUENCE: 196
gaagtgcagc tgctggaatc cggcggaggc ctggtgcagc ctggcggatc tctgagactg 60
tcctgcgccg cctccggctt caccttctcc tcccacgcca tgtcctgggt ccgacaggct 120
cctggcaaag gcctggaatg ggtgtccgcc atctgggcct ccggcgagca gtactacgcc 180
gactctgtga agggccggtt caccatctcc cgggacaact ccaagaacac cctgtacctg 240
cagatgaact ccctgcgggc cgaggacacc gccgtgtact actgtgccaa gggctggctg 300
ggcaacttcg actactgggg acagggcacc ctggtcaccg tgtccagcgc tagcaccaag 360
ggcccatcgg tcttccccct ggcaccctcc tccaagagca cctctggggg cacagcggcc 420
ctgggctgcc tggtcaagga ctacttcccc gaaccggtga cggtgtcgtg gaactcaggc 480
gccctgacca gcggcgtgca caccttcccg gctgtcctac agtcctcagg actctactcc 540
ctcagcagcg tggtgaccgt gccctccagc agcttgggca cccagaccta catctgcaac 600
gtgaatcaca agcccagcaa caccaaggtg gacaagaaag ttgagcccaa atcttgtgac 660
aaaactcaca catgcccacc gtgcccagca cctgaagctg caggggggacc gtcagtcttc 720 ctcttccccc caaaacccaa ggacaccctc atgatctccc ggacccctga ggtcacatgc 780
gtggtggtgg acgtgagcca cgaagaccct gaggtcaagt tcaactggta cgtggacggc 840
gtggaggtgc ataatgccaa gacaaagccg cgggaggagc agtacaacag cacgtaccgt 900
gtggtcagcg tcctcaccgt cctgcaccag gactggctga atggcaagga gtacaagtgc 960
aaggtctcca acaaagccct cggcgccccc atcgagaaaa ccatctccaa agccaaaggg 1020
cagccccgag aaccacaggt gtacaccctg cccccatgcc gggatgagct gaccaagaac 1080
caggtcagcc tgtggtgcct ggtcaaaggc ttctatccca gcgacatcgc cgtggagtgg 1140
gagagcaatg ggcagccgga gaacaactac aagaccacgc ctcccgtgct ggactccgac 1200
ggctccttct tcctctacag caagctcacc gtggacaaga gcaggtggca gcaggggaac 1260
gtcttctcat gctccgtgat gcatgaggct ctgcacaacc actacacgca gaagagcctc 1320
tccctgtctc cgggtggcgg cggaggctcc ggaggcggag gttctggcgg aggtggcgct 1380
cctgcctcct ccagcaccaa gaaaacccag ctccagctgg aacatctcct gctggatctg 1440
cagatgatcc tgaacggcat caacaactac aagaacccca agctgacccg gatgctgacc 1500
gccaagttcg ccatgcccaa gaaggccacc gagctgaaac atctgcagtg cctggaagag 1560
gaactgaagc ctctggaaga ggtgctgaac ggcgcccagt ccaagaactt ccacctgagg 1620
cctcgggacc tgatctccaa catcaacgtg atcgtgctgg aactgaaggg ctccgagaca 1680
accttcatgt gcgagtacgc cgacgagaca gctaccatcg tggaatttct gaaccggtgg 1740
atcaccttcg cccagtccat catctccacc ctgacc 1776

<210> SEQ ID NO 197
<211> LENGTH: 592
<212> TYPE: PRT
<213> ORGANISM: Artificial Sequence
<220> FEATURE:
<223> OTHER INFORMATION: 28H1 Fab HC-Fc knob (LALA P329G)-IL-2 wt

<400> SEQUENCE: 197

Glu Val Gln Leu Leu Glu Ser Gly Gly Gly Leu Val Gln Pro Gly Gly
1 5 10 15

-continued

```
Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Cys Arg Asp Glu Leu Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Gly Gly Gly
```

```
        435                 440                 445

Gly Ser Gly Gly Gly Gly Ser Gly Gly Gly Gly Ala Pro Thr Ser Ser
    450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Arg Met Leu Thr Phe Lys Phe Tyr Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Leu Ala Gln Ser Lys Asn Phe His Leu Arg Pro Arg Asp Leu
    530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Ala Gln Ser Ile Ile Ser Thr Leu Thr
            580                 585                 590


<210> SEQ ID NO 198
<211> LENGTH: 1776
<212> TYPE: DNA
<213> ORGANISM: Artificial Sequence
<220> FEATURE:
<223> OTHER INFORMATION: 28H1 Fab HC-Fc knob (LALA P329G)-IL-2 wt

<400> SEQUENCE: 198

gaagtgcagc tgctggaatc cggcggaggc ctggtgcagc ctggcggatc tctgagactg     60

tcctgcgccg cctccggctt caccttctcc tcccacgcca tgtcctgggt ccgacaggct    120

cctggcaaag gcctggaatg ggtgtccgcc atctgggcct ccggcgagca gtactacgcc    180

gactctgtga agggccggtt caccatctcc cgggacaact ccaagaacac cctgtacctg    240

cagatgaact ccctgcgggc cgaggacacc gccgtgtact actgtgccaa gggctggctg    300

ggcaacttcg actactgggg acagggcacc ctggtcaccg tgtccagcgc tagcaccaag    360

ggcccatcgg tcttcccct ggcaccctcc tccaagagca cctctggggg cacagcggcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgaccgt gccctccagc agcttgggca cccagaccta catctgcaac    600

gtgaatcaca agcccagcaa caccaaggtg gacaagaaag ttgagcccaa atcttgtgac    660

aaaactcaca catgcccacc gtgcccagca cctgaagctg caggggggacc gtcagtcttc    720

ctcttccccc caaaacccaa ggacaccctc atgatctccc ggacccctga ggtcacatgc    780

gtggtggtgg acgtgagcca cgaagaccct gaggtcaagt tcaactggta cgtggacggc    840

gtggaggtgc ataatgccaa gacaaagccg cgggaggagc agtacaacag cacgtaccgt    900

gtggtcagcg tcctcaccgt cctgcaccag gactggctga atggcaagga gtacaagtgc    960

aaggtctcca acaaagccct cggcgccccc atcgagaaaa ccatctccaa agccaaaggg   1020

cagccccgag aaccacaggt gtacaccctg cccccatgcc gggatgagct gaccaagaac   1080

caggtcagcc tgtggtgcct ggtcaaaggc ttctatccca gcgacatcgc cgtggagtgg   1140

gagagcaatg ggcagccgga gaacaactac aagaccacgc ctcccgtgct ggactccgac   1200
```

```
ggctccttct tcctctacag caagctcacc gtggacaaga gcaggtggca gcaggggaac   1260

gtcttctcat gctccgtgat gcatgaggct ctgcacaacc actacacgca gaagagcctc   1320

tccctgtctc cgggtggcgg cggaggctcc ggaggcggag gttctggcgg aggtggcgct   1380

cctacatcct ccagcaccaa gaaaacccag ctccagctgg aacatctcct gctggatctg   1440

cagatgatcc tgaacggcat caacaactac aagaacccca agctgacccg gatgctgacc   1500

ttcaagttct acatgcccaa gaaggccacc gagctgaaac atctgcagtg cctggaagag   1560

gaactgaagc ctctggaaga ggtgctgaac ctggcccagt ccaagaactt ccacctgagg   1620

cctcgggacc tgatctccaa catcaacgtg atcgtgctgg aactgaaggg ctccgagaca   1680

accttcatgt gcgagtacgc cgacgagaca gctaccatcg tggaatttct gaaccggtgg   1740

atcaccttcg cccagtccat catctccacc ctgacc                             1776
```

<210> SEQ ID NO 199
<211> LENGTH: 574
<212> TYPE: PRT
<213> ORGANISM: Artificial Sequence
<220> FEATURE:
<223> OTHER INFORMATION: 28H1 Fab HC-Fc knob (LALA P329G)-IL-15
(E53A N79A)

<400> SEQUENCE: 199

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255
```

```
Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Cys Arg Asp Glu Leu Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Ser Gly Gly
        435                 440                 445

Gly Gly Ser Gly Gly Gly Gly Ser Gly Gly Gly Gly Asn Trp Val Asn
    450                 455                 460

Val Ile Ser Asp Leu Lys Lys Ile Glu Asp Leu Ile Gln Ser Met His
465                 470                 475                 480

Ile Asp Ala Thr Leu Tyr Thr Glu Ser Asp Val His Pro Ser Cys Lys
                485                 490                 495

Val Thr Ala Met Lys Cys Phe Leu Leu Glu Leu Gln Val Ile Ser Leu
            500                 505                 510

Ala Ser Gly Asp Ala Ser Ile His Asp Thr Val Glu Asn Leu Ile Ile
        515                 520                 525

Leu Ala Asn Asn Ser Leu Ser Ser Asn Gly Ala Val Thr Glu Ser Gly
    530                 535                 540

Cys Lys Glu Cys Glu Glu Leu Glu Glu Lys Asn Ile Lys Glu Phe Leu
545                 550                 555                 560

Gln Ser Phe Val His Ile Val Gln Met Phe Ile Asn Thr Ser
                565                 570
```

<210> SEQ ID NO 200
<211> LENGTH: 1722
<212> TYPE: DNA
<213> ORGANISM: Artificial Sequence
<220> FEATURE:
<223> OTHER INFORMATION: 28H1 Fab HC-Fc knob (LALA P329G)-IL-15
(E53A N79A)

<400> SEQUENCE: 200

```
gaagtgcagc tgctggaatc cggcggaggc ctggtgcagc ctggcggatc tctgagactg      60

tcctgcgccg cctccggctt caccttctcc tcccacgcca tgtcctgggt ccgacaggct     120

cctggcaaag gcctggaatg ggtgtccgcc atctgggcct ccggcgagca gtactacgcc     180

gactctgtga agggccggtt caccatctcc cgggacaact ccaagaacac cctgtacctg     240
```

```
cagatgaact ccctgcgggc cgaggacacc gccgtgtact actgtgccaa gggctggctg    300

ggcaacttcg actactgggg acagggcacc ctggtcaccg tgtccagcgc tagcaccaag    360

ggcccatcgg tcttccccct ggcaccctcc tccaagagca cctctggggg cacagcggcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgaccgt gccctccagc agcttgggca cccagaccta catctgcaac    600

gtgaatcaca agcccagcaa caccaaggtg gacaagaaag ttgagcccaa atcttgtgac    660

aaaactcaca catgcccacc gtgcccagca cctgaagctg caggggggacc gtcagtcttc    720

ctcttccccc caaaacccaa ggacaccctc atgatctccc ggacccctga ggtcacatgc    780

gtggtggtgg acgtgagcca cgaagaccct gaggtcaagt tcaactggta cgtggacggc    840

gtggaggtgc ataatgccaa gacaaagccg cgggaggagc agtacaacag cacgtaccgt    900

gtggtcagcg tcctcaccgt cctgcaccag gactggctga atggcaagga gtacaagtgc    960

aaggtctcca acaaagccct cggcgccccc atcgagaaaa ccatctccaa agccaaaggg   1020

cagccccgag aaccacaggt gtacaccctg cccccatgcc gggatgagct gaccaagaac   1080

caggtcagcc tgtggtgcct ggtcaaaggc ttctatccca gcgacatcgc cgtggagtgg   1140

gagagcaatg ggcagccgga gaacaactac aagaccacgc ctcccgtgct ggactccgac   1200

ggctccttct tcctctacag caagctcacc gtggacaaga gcaggtggca gcaggggaac   1260

gtcttctcat gctccgtgat gcatgaggct ctgcacaacc actacacgca gaagagcctc   1320

tccctgtctc cgggttccgg cggcggaggc tccggaggcg gaggttctgg cggaggtggc   1380

aactgggtga atgtaataag tgatttgaaa aaaattgaag atcttattca atctatgcat   1440

attgatgcta ctttatatac ggaaagtgat gttcacccca gttgcaaagt aacagcaatg   1500

aagtgctttc tcttggagtt acaagttatt tcacttgcgt ccggagatgc aagtattcat   1560

gatacagtag aaaatctgat catcctagca aacaacagtt tgtcttctaa tggggctgta   1620

acagaatctg gatgcaaaga atgtgaggaa ctggaggaaa aaaatattaa agaatttttg   1680

cagagttttg tacatattgt ccaaatgttc atcaacactt ct                        1722
```

<210> SEQ ID NO 201
<211> LENGTH: 447
<212> TYPE: PRT
<213> ORGANISM: Artificial Sequence
<220> FEATURE:
<223> OTHER INFORMATION: 4G8 Fab HC-Fc hole (LALA P329G)

<400> SEQUENCE: 201

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
```

-continued

```
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Cys Thr Leu Pro
            340                 345                 350

Pro Ser Arg Asp Glu Leu Thr Lys Asn Gln Val Ser Leu Ser Cys Ala
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 202
<211> LENGTH: 1341
<212> TYPE: DNA
<213> ORGANISM: Artificial Sequence
<220> FEATURE:
<223> OTHER INFORMATION: 4G8 Fab HC-Fc hole (LALA P329G)

<400> SEQUENCE: 202

```
gaggtgcaat tgttggagtc tgggggaggc ttggtacagc ctggggggtc cctgagactc      60

tcctgtgcag cctccggatt cacctttagc agttatgcca tgagctgggt ccgccaggct     120
```

-continued

```
ccagggaagg ggctggagtg ggtctcagct attagtggta gtggtggtag cacatactac     180

gcagactccg tgaagggccg gttcaccatc tccagagaca attccaagaa cacgctgtat     240

ctgcagatga acagcctgag agccgaggac acggccgtat attactgtgc gaaagggtgg     300

ctgggtaatt ttgactactg gggccaagga accctggtca ccgtctcgag tgctagcacc     360

aagggcccct ccgtgttccc cctggccccc agcagcaaga gcaccagcgg cggcacagcc     420

gctctgggct gcctggtcaa ggactacttc cccgagcccg tgaccgtgtc ctggaacagc     480

ggagccctga cctccggcgt gcacaccttc cccgccgtgc tgcagagttc tggcctgtat     540

agcctgagca gcgtggtcac cgtgccttct agcagcctgg gcacccagac ctacatctgc     600

aacgtgaacc acaagcccag caacaccaag gtggacaaga aggtggagcc caagagctgc     660

gacaaaactc acacatgccc accgtgccca gcacctgaag ctgcaggggg accgtcagtc     720

ttcctcttcc ccccaaaacc caaggacacc ctcatgatct cccggacccc tgaggtcaca     780

tgcgtggtgg tggacgtgag ccacgaagac cctgaggtca agttcaactg gtacgtggac     840

ggcgtggagg tgcataatgc caagacaaag ccgcgggagg agcagtacaa cagcacgtac     900

cgtgtggtca gcgtcctcac cgtcctgcac caggactggc tgaatggcaa ggagtacaag     960

tgcaaggtct ccaacaaagc cctcggcgcc cccatcgaga aaaccatctc caaagccaaa    1020

gggcagcccc gagaaccaca ggtgtgcacc ctgcccccat cccgggatga gctgaccaag    1080

aaccaggtca gcctctcgtg cgcagtcaaa ggcttctatc ccagcgacat cgccgtggag    1140

tgggagagca atgggcagcc ggagaacaac tacaagacca cgcctcccgt gctggactcc    1200

gacggctcct tcttcctcgt gagcaagctc accgtggaca agagcaggtg gcagcagggg    1260

aacgtcttct catgctccgt gatgcatgag gctctgcaca accactacac gcagaagagc    1320

ctctccctgt ctccgggtaa a                                               1341
```

<210> SEQ ID NO 203
<211> LENGTH: 593
<212> TYPE: PRT
<213> ORGANISM: Artificial Sequence
<220> FEATURE:
<223> OTHER INFORMATION: 4G8 Fab HC-Fc knob (LALA P329G)-IL-2 qm

<400> SEQUENCE: 203

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140
```

-continued

```
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Arg Asp Glu Leu Thr Lys Asn Gln Val Ser Leu Trp Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Gly Ser Gly Gly Gly Gly Ala Pro Ala Ser
    450                 455                 460

Ser Ser Thr Lys Lys Thr Gln Leu Gln Leu Glu His Leu Leu Leu Asp
465                 470                 475                 480

Leu Gln Met Ile Leu Asn Gly Ile Asn Asn Tyr Lys Asn Pro Lys Leu
                485                 490                 495

Thr Arg Met Leu Thr Ala Lys Phe Ala Met Pro Lys Lys Ala Thr Glu
            500                 505                 510

Leu Lys His Leu Gln Cys Leu Glu Glu Glu Leu Lys Pro Leu Glu Glu
        515                 520                 525

Val Leu Asn Gly Ala Gln Ser Lys Asn Phe His Leu Arg Pro Arg Asp
    530                 535                 540

Leu Ile Ser Asn Ile Asn Val Ile Val Leu Glu Leu Lys Gly Ser Glu
545                 550                 555                 560

Thr Thr Phe Met Cys Glu Tyr Ala Asp Glu Thr Ala Thr Ile Val Glu
```

```
                565                 570                 575

Phe Leu Asn Arg Trp Ile Thr Phe Ala Gln Ser Ile Ile Ser Thr Leu
            580                 585                 590

Thr


<210> SEQ ID NO 204
<211> LENGTH: 1779
<212> TYPE: DNA
<213> ORGANISM: Artificial Sequence
<220> FEATURE:
<223> OTHER INFORMATION: 4G8 Fab HC-Fc knob (LALA P329G)-IL-2 qm

<400> SEQUENCE: 204

gaggtgcaat tgttggagtc tgggggaggc ttggtacagc ctggggggtc cctgagactc     60
tcctgtgcag cctccggatt cacctttagc agttatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaagggtgg    300
ctgggtaatt ttgactactg gggccaagga accctggtca ccgtctcgag tgctagcacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga aagttgagcc caaatcttgt    660
gacaaaactc acacatgccc accgtgccca gcacctgaag ctgcaggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcggcgcc cccatcgaga aaaccatctc caaagccaaa   1020
gggcagcccc gagaaccaca ggtgtacacc ctgcccccat gccgggatga gctgaccaag   1080
aaccaggtca gcctgtggtg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctccgggtgg cggcggaggc tccggaggcg gaggttctgg cggaggtggc   1380
gctcctgcct cctccagcac caagaaaacc cagctccagc tggaacatct cctgctggat   1440
ctgcagatga tcctgaacgg catcaacaac tacaagaacc ccaagctgac ccggatgctg   1500
accgccaagt tcgccatgcc caagaaggcc accgagctga aacatctgca gtgcctggaa   1560
gaggaactga agcctctgga agaggtgctg aacggcgccc agtccaagaa cttccacctg   1620
aggcctcggg acctgatctc caacatcaac gtgatcgtgc tggaactgaa gggctccgag   1680
acaaccttca tgtgcgagta cgccgacgag acagctacca tcgtggaatt tctgaaccgg   1740
tggatcacct tcgcccagtc catcatctcc accctgacc                           1779


<210> SEQ ID NO 205
```

<211> LENGTH: 215
<212> TYPE: PRT
<213> ORGANISM: Artificial Sequence
<220> FEATURE:
<223> OTHER INFORMATION: 4G8 Fab LC

<400> SEQUENCE: 205

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Arg Ser
20 25 30

Tyr Leu Ala Trp Tyr Gln Gln Lys Pro Gly Gln Ala Pro Arg Leu Leu
35 40 45

Ile Ile Gly Ala Ser Thr Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Gly Gln Val Ile Pro
85 90 95

Pro Thr Phe Gly Gln Gly Thr Lys Val Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 206
<211> LENGTH: 645
<212> TYPE: DNA
<213> ORGANISM: Artificial Sequence
<220> FEATURE:
<223> OTHER INFORMATION: 4G8 Fab LC

<400> SEQUENCE: 206
gagatcgtgc tgacccagtc ccccggcacc ctgtctctga gccctggcga gagagccacc 60
ctgtcctgca gagcctccca gtccgtgtcc cggtcctacc tcgcctggta tcagcagaag 120
cccggccagg cccctcggct gctgatcatc ggcgcctcta ccagagccac cggcatccct 180
gaccggttct ccggctctgg ctccggcacc gacttcaccc tgaccatctc ccggctggaa 240
cccgaggact tcgccgtgta ctactgccag cagggccagg tcatccctcc cacctttggc 300
cagggcacca aggtggaaat caagcgtacg gtggctgcac catctgtctt catcttcccg 360
ccatctgatg agcagttgaa atctggaact gcctctgttg tgtgcctgct gaataacttc 420
tatcccagag aggccaaagt acagtggaag gtggataacg ccctccaatc gggtaactcc 480
caggagagtg tcacagagca ggacagcaag gacagcacct acagcctcag cagcaccctg 540
acgctgagca aagcagacta cgagaaacac aaagtctacg cctgcgaagt cacccatcag 600
ggcctgagct cgcccgtcac aaagagcttc aacaggggag agtgt 645

<210> SEQ ID NO 207
<211> LENGTH: 447
<212> TYPE: PRT
<213> ORGANISM: Artificial Sequence
<220> FEATURE:
<223> OTHER INFORMATION: 4B9 Fab HC-Fc hole (LALA P329G)

<400> SEQUENCE: 207

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ile Gly Ser Gly Ala Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Trp Phe Gly Gly Phe Asn Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Lys Val Glu Pro Lys Ser Cys Asp Lys Thr His
210 215 220

Thr Cys Pro Pro Cys Pro Ala Pro Glu Ala Ala Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Gly Ala Pro Ile Glu Lys Thr Ile
325 330 335

Ser Lys Ala Lys Gly Gln Pro Arg Glu Pro Gln Val Cys Thr Leu Pro
340 345 350

-continued

```
Pro Ser Arg Asp Glu Leu Thr Lys Asn Gln Val Ser Leu Ser Cys Ala
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 208
<211> LENGTH: 1341
<212> TYPE: DNA
<213> ORGANISM: Artificial Sequence
<220> FEATURE:
<223> OTHER INFORMATION: 4B9 Fab HC-Fc hole (LALA P329G)

<400> SEQUENCE: 208

```
gaggtgcagc tgctcgaaag cggcggagga ctggtgcagc ctggcggcag cctgagactg      60

tcttgcgccg ccagcggctt caccttcagc agctacgcca tgagctgggt ccgccaggcc     120

cctggcaagg gactggaatg ggtgtccgcc atcatcggct ctggcgccag cacctactac     180

gccgacagcg tgaagggccg gttcaccatc agccgggaca acagcaagaa caccctgtac     240

ctgcagatga acagcctgcg ggccgaggac accgccgtgt actactgcgc caagggatgg     300

ttcggcggct tcaactactg gggacagggc accctggtca cagtgtccag cgctagcacc     360

aagggcccct ccgtgttccc cctggccccc agcagcaaga gcaccagcgg cggcacagcc     420

gctctgggct gcctggtcaa ggactacttc cccgagcccg tgaccgtgtc ctggaacagc     480

ggagccctga cctccggcgt gcacaccttc cccgccgtgc tgcagagttc tggcctgtat     540

agcctgagca gcgtggtcac cgtgccttct agcagcctgg gcacccagac ctacatctgc     600

aacgtgaacc acaagcccag caacaccaag gtggacaaga aggtggagcc caagagctgc     660

gacaaaactc acacatgccc accgtgccca gcacctgaag ctgcaggggg accgtcagtc     720

ttcctcttcc ccccaaaacc caaggacacc ctcatgatct cccggacccc tgaggtcaca     780

tgcgtggtgg tggacgtgag ccacgaagac cctgaggtca agttcaactg gtacgtggac     840

ggcgtggagg tgcataatgc caagacaaag ccgcgggagg agcagtacaa cagcacgtac     900

cgtgtggtca gcgtcctcac cgtcctgcac caggactggc tgaatggcaa ggagtacaag     960

tgcaaggtct ccaacaaagc cctcggcgcc cccatcgaga aaaccatctc caaagccaaa    1020

gggcagcccc gagaaccaca ggtgtgcacc ctgcccccat cccgggatga gctgaccaag    1080

aaccaggtca gcctctcgtg cgcagtcaaa ggcttctatc ccagcgacat cgccgtggag    1140

tgggagagca atgggcagcc ggagaacaac tacaagacca cgcctcccgt gctggactcc    1200

gacggctcct tcttcctcgt gagcaagctc accgtggaca agagcaggtg gcagcagggg    1260

aacgtcttct catgctccgt gatgcatgag gctctgcaca accactacac gcagaagagc    1320

ctctccctgt ctccgggtaa a                                              1341
```

<210> SEQ ID NO 209
<211> LENGTH: 593
<212> TYPE: PRT
<213> ORGANISM: Artificial Sequence
<220> FEATURE:
<223> OTHER INFORMATION: 4B9 Fab HC-Fc knob (LALA P329G)-IL-2 qm

<400> SEQUENCE: 209

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ile Gly Ser Gly Ala Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Trp Phe Gly Gly Phe Asn Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Lys Val Glu Pro Lys Ser Cys Asp Lys Thr His
210 215 220

Thr Cys Pro Pro Cys Pro Ala Pro Glu Ala Ala Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Gly Ala Pro Ile Glu Lys Thr Ile
325 330 335

Ser Lys Ala Lys Gly Gln Pro Arg Glu Pro Gln Val Tyr Thr Leu Pro
340 345 350

Pro Cys Arg Asp Glu Leu Thr Lys Asn Gln Val Ser Leu Trp Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

```
Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Gly Ser Gly Gly Gly Gly Ala Pro Ala Ser
    450                 455                 460

Ser Ser Thr Lys Lys Thr Gln Leu Gln Leu Glu His Leu Leu Leu Asp
465                 470                 475                 480

Leu Gln Met Ile Leu Asn Gly Ile Asn Asn Tyr Lys Asn Pro Lys Leu
                485                 490                 495

Thr Arg Met Leu Thr Ala Lys Phe Ala Met Pro Lys Lys Ala Thr Glu
            500                 505                 510

Leu Lys His Leu Gln Cys Leu Glu Glu Glu Leu Lys Pro Leu Glu Glu
        515                 520                 525

Val Leu Asn Gly Ala Gln Ser Lys Asn Phe His Leu Arg Pro Arg Asp
    530                 535                 540

Leu Ile Ser Asn Ile Asn Val Ile Val Leu Glu Leu Lys Gly Ser Glu
545                 550                 555                 560

Thr Thr Phe Met Cys Glu Tyr Ala Asp Glu Thr Ala Thr Ile Val Glu
                565                 570                 575

Phe Leu Asn Arg Trp Ile Thr Phe Ala Gln Ser Ile Ile Ser Thr Leu
            580                 585                 590

Thr


<210> SEQ ID NO 210
<211> LENGTH: 1779
<212> TYPE: DNA
<213> ORGANISM: Artificial Sequence
<220> FEATURE:
<223> OTHER INFORMATION: 4B9 Fab HC-Fc knob (LALA P329G)-IL-2 qm

<400> SEQUENCE: 210

gaggtgcagc tgctcgaaag cggcggagga ctggtgcagc ctggcggcag cctgagactg      60

tcttgcgccg ccagcggctt caccttcagc agctacgcca tgagctgggt ccgccaggcc     120

cctggcaagg gactggaatg ggtgtccgcc atcatcggct ctggcgccag cacctactac     180

gccgacagcg tgaagggccg gttcaccatc agccgggaca acagcaagaa caccctgtac     240

ctgcagatga acagcctgcg ggccgaggac accgccgtgt actactgcgc caagggatgg     300

ttcggcggct tcaactactg gggacagggc accctggtca cagtgtccag cgctagcacc     360

aagggcccat cggtcttccc cctggcaccc tcctccaaga gcacctctgg gggcacagcg     420

gccctgggct gcctggtcaa ggactacttc cccgaaccgg tgacggtgtc gtggaactca     480

ggcgccctga ccagcggcgt gcacaccttc ccggctgtcc tacagtcctc aggactctac     540

tccctcagca gcgtggtgac cgtgccctcc agcagcttgg gcacccagac ctacatctgc     600

aacgtgaatc acaagcccag caacaccaag gtggacaaga aagttgagcc caaatcttgt     660

gacaaaactc acacatgccc accgtgccca gcacctgaag ctgcaggggg accgtcagtc     720

ttcctcttcc ccccaaaacc caaggacacc ctcatgatct cccggacccc tgaggtcaca     780

tgcgtggtgg tggacgtgag ccacgaagac cctgaggtca agttcaactg gtacgtggac     840

ggcgtggagg tgcataatgc caagacaaag ccgcgggagg agcagtacaa cagcacgtac     900
```

-continued

```
cgtgtggtca gcgtcctcac cgtcctgcac caggactggc tgaatggcaa ggagtacaag    960

tgcaaggtct ccaacaaagc cctcggcgcc cccatcgaga aaaccatctc caaagccaaa   1020

gggcagcccc gagaaccaca ggtgtacacc ctgcccccat gccgggatga gctgaccaag   1080

aaccaggtca gcctgtggtg cctggtcaaa ggcttctatc ccagcgacat cgccgtggag   1140

tgggagagca atgggcagcc ggagaacaac tacaagacca cgcctcccgt gctggactcc   1200

gacggctcct tcttcctcta cagcaagctc accgtggaca agagcaggtg gcagcagggg   1260

aacgtcttct catgctccgt gatgcatgag gctctgcaca accactacac gcagaagagc   1320

ctctccctgt ctccgggtgg cggcggaggc tccggaggcg gaggttctgg cggaggtggc   1380

gctcctgcct cctccagcac caagaaaacc cagctccagc tggaacatct cctgctggat   1440

ctgcagatga tcctgaacgg catcaacaac tacaagaacc ccaagctgac ccggatgctg   1500

accgccaagt tcgccatgcc caagaaggcc accgagctga aacatctgca gtgcctggaa   1560

gaggaactga agcctctgga agaggtgctg aacggcgccc agtccaagaa cttccacctg   1620

aggcctcggg acctgatctc caacatcaac gtgatcgtgc tggaactgaa gggctccgag   1680

acaaccttca tgtgcgagta cgccgacgag acagctacca tcgtggaatt tctgaaccgg   1740

tggatcacct tcgcccagtc catcatctcc accctgacc                          1779
```

```
<210> SEQ ID NO 211
<211> LENGTH: 215
<212> TYPE: PRT
<213> ORGANISM: Artificial Sequence
<220> FEATURE:
<223> OTHER INFORMATION: 3F2 Fab LC

<400> SEQUENCE: 211

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205
```

```
Ser Phe Asn Arg Gly Glu Cys
    210                 215


<210> SEQ ID NO 212
<211> LENGTH: 645
<212> TYPE: DNA
<213> ORGANISM: Artificial Sequence
<220> FEATURE:
<223> OTHER INFORMATION: 3F2 Fab LC

<400> SEQUENCE: 212

gagatcgtgc tgacccagtc ccccggcacc ctgtctctga gccctggcga gagagccacc      60

ctgtcctgca gagcctccca gtccgtgacc tcctcctacc tcgcctggta tcagcagaag     120

cccggccagg cccctcggct gctgatcaac gtgggcagtc ggagagccac cggcatccct     180

gaccggttct ccggctctgg ctccggcacc gacttcaccc tgaccatctc ccggctggaa     240

cccgaggact tcgccgtgta ctactgccag cagggcatca tgctgccccc cacctttggc     300

cagggcacca aggtggaaat caagcgtacg gtggccgctc cctccgtgtt catcttccca     360

ccctccgacg agcagctgaa gtccggcacc gcctccgtcg tgtgcctgct gaacaacttc     420

tacccccgcg aggccaaggt gcagtggaag gtggacaacg ccctgcagtc cggcaactcc     480

caggaatccg tcaccgagca ggactccaag gacagcacct actccctgtc ctccaccctg     540

accctgtcca aggccgacta cgagaagcac aaggtgtacg cctgcgaagt gacccaccag     600

ggcctgtcca gccccgtgac caagtccttc aaccggggcg agtgc                     645


<210> SEQ ID NO 213
<211> LENGTH: 446
<212> TYPE: PRT
<213> ORGANISM: Artificial Sequence
<220> FEATURE:
<223> OTHER INFORMATION: L19 Fab HC-Fc hole (LALA P329G)

<400> SEQUENCE: 213

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
```

-continued

```
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 214
<211> LENGTH: 1338
<212> TYPE: DNA
<213> ORGANISM: Artificial Sequence
<220> FEATURE:
<223> OTHER INFORMATION: L19 Fab HC-Fc hole (LALA P329G)

<400> SEQUENCE: 214

```
gaggtgcagc tgttggagtc tgggggaggc ttggtacagc ctggggggtc cctgagactc     60

tcctgtgcag cctctggatt cacctttagc agtttttcga tgagctgggt ccgccaggct    120

ccagggaagg ggctggagtg ggtctcatct atttccggta gttcgggtac cacatactac    180

gcagactccg tgaagggccg gttcaccatc tccagagaca attccaagaa cacgctgtat    240

ctgcaaatga acagcctgag agccgaggac acggccgtat attactgtgc gaaaccgttt    300

ccgtattttg actactgggg ccagggaacc ctggtcaccg tctcgagtgc tagcaccaag    360

ggcccctccg tgttccccct ggcccccagc agcaagagca ccagcggcgg cacagccgct    420

ctgggctgcc tggtcaagga ctacttcccc gagcccgtga ccgtgtcctg gaacagcgga    480

gccctgacct ccggcgtgca caccttcccc gccgtgctgc agagttctgg cctgtatagc    540

ctgagcagcg tggtcaccgt gccttctagc agcctgggca cccagaccta catctgcaac    600
```

```
gtgaaccaca agcccagcaa caccaaggtg gacaagaagg tggagcccaa gagctgcgac    660

aaaactcaca catgcccacc gtgcccagca cctgaagctg caggggggacc gtcagtcttc    720

ctcttccccc caaaacccaa ggacaccctc atgatctccc ggacccctga ggtcacatgc    780

gtggtggtgg acgtgagcca cgaagaccct gaggtcaagt tcaactggta cgtggacggc    840

gtggaggtgc ataatgccaa gacaaagccg cgggaggagc agtacaacag cacgtaccgt    900

gtggtcagcg tcctcaccgt cctgcaccag gactggctga atggcaagga gtacaagtgc    960

aaggtctcca acaaagccct cggcgccccc atcgagaaaa ccatctccaa agccaaaggg   1020

cagccccgag aaccacaggt gtgcaccctg cccccatccc gggatgagct gaccaagaac   1080

caggtcagcc tctcgtgcgc agtcaaaggc ttctatccca gcgacatcgc cgtggagtgg   1140

gagagcaatg ggcagccgga gaacaactac aagaccacgc ctcccgtgct ggactccgac   1200

ggctccttct tcctcgtgag caagctcacc gtggacaaga gcaggtggca gcaggggaac   1260

gtcttctcat gctccgtgat gcatgaggct ctgcacaacc actacacgca gaagagcctc   1320

tccctgtctc cgggtaaa                                                 1338
```

<210> SEQ ID NO 215
<211> LENGTH: 592
<212> TYPE: PRT
<213> ORGANISM: Artificial Sequence
<220> FEATURE:
<223> OTHER INFORMATION: L19 Fab HC-Fc knob (LALA P329G)-IL-2 qm

<400> SEQUENCE: 215

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220
```

```
Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Cys Arg Asp Glu Leu Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Gly Gly Gly
        435                 440                 445

Gly Ser Gly Gly Gly Gly Ser Gly Gly Gly Gly Ala Pro Ala Ser Ser
    450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Arg Met Leu Thr Ala Lys Phe Ala Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Gly Ala Gln Ser Lys Asn Phe His Leu Arg Pro Arg Asp Leu
    530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Ala Gln Ser Ile Ile Ser Thr Leu Thr
            580                 585                 590
```

<210> SEQ ID NO 216
<211> LENGTH: 1776
<212> TYPE: DNA
<213> ORGANISM: Artificial Sequence
<220> FEATURE:
<223> OTHER INFORMATION: L19 Fab HC-Fc knob (LALA P329G)-IL-2 qm

<400> SEQUENCE: 216

```
gaggtgcagc tgttggagtc tgggggaggc ttggtacagc ctggggggtc cctgagactc     60
tcctgtgcag cctctggatt cacctttagc agtttttcga tgagctgggt ccgccaggct    120
ccagggaagg ggctggagtg ggtctcatct atttccggta gttcgggtac cacatactac    180
gcagactccg tgaagggccg gttcaccatc tccagagaca attccaagaa cacgctgtat    240
ctgcaaatga acagcctgag agccgaggac acggccgtat attactgtgc gaaaccgttt    300
ccgtattttg actactgggg ccagggaacc ctggtcaccg tctcgagtgc tagcaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaagctg caggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cggcgccccc atcgagaaaa ccatctccaa agccaaaggg   1020
cagccccgag aaccacaggt gtacaccctg cccccatgcc gggatgagct gaccaagaac   1080
caggtcagcc tgtggtgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtctc cgggtggcgg cggaggctcc ggaggcggag gttctggcgg aggtggcgct   1380
cctgcctcct ccagcaccaa gaaaacccag ctccagctgg aacatctcct gctggatctg   1440
cagatgatcc tgaacggcat caacaactac aagaacccca agctgacccg gatgctgacc   1500
gccaagttcg ccatgcccaa gaaggccacc gagctgaaac atctgcagtg cctggaagag   1560
gaactgaagc ctctggaaga ggtgctgaac ggcgcccagt ccaagaactt ccacctgagg   1620
cctcgggacc tgatctccaa catcaacgtg atcgtgctgg aactgaaggg ctccgagaca   1680
accttcatgt gcgagtacgc cgacgagaca gctaccatcg tggaatttct gaaccggtgg   1740
atcaccttcg cccagtccat catctccacc ctgacc                              1776
```

```
<210> SEQ ID NO 217
<211> LENGTH: 215
<212> TYPE: PRT
<213> ORGANISM: Artificial Sequence
<220> FEATURE:
<223> OTHER INFORMATION: L19 Fab LC

<400> SEQUENCE: 217

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45
```

Ile Tyr Tyr Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Thr Gly Arg Ile Pro
85 90 95

Pro Thr Phe Gly Gln Gly Thr Lys Val Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 218
<211> LENGTH: 645
<212> TYPE: DNA
<213> ORGANISM: Artificial Sequence
<220> FEATURE:
<223> OTHER INFORMATION: L19 Fab LC

<400> SEQUENCE: 218
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat tatgcatcca gcagggccac tggcatccca 180
gacaggttca gtggcagtgg gtctgggaca gacttcactc tcaccatcag cagactggag 240
cctgaagatt ttgcagtgta ttactgtcag cagacgggtc gtattcctcc gacgttcggc 300
caagggacca aggtggaaat caaacgtacg gtggctgcac catctgtctt catcttcccg 360
ccatctgatg agcagttgaa atctggaact gcctctgttg tgtgcctgct gaataacttc 420
tatcccagag aggccaaagt acagtggaag gtggataacg ccctccaatc gggtaactcc 480
caggagagtg tcacagagca ggacagcaag gacagcacct acagcctcag cagcaccctg 540
acgctgagca aagcagacta cgagaaacac aaagtctacg cctgcgaagt cacccatcag 600
ggcctgagct cgcccgtcac aaagagcttc aacaggggag agtgt 645

<210> SEQ ID NO 219
<211> LENGTH: 445
<212> TYPE: PRT
<213> ORGANISM: Artificial Sequence
<220> FEATURE:
<223> OTHER INFORMATION: DP47 GS Fab HC-Fc hole (LALA P329G)

<400> SEQUENCE: 219

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr

-continued

```
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Cys Thr Leu Pro Pro Ser
            340                 345                 350

Arg Asp Glu Leu Thr Lys Asn Gln Val Ser Leu Ser Cys Ala Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Val Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 220
<211> LENGTH: 1335
<212> TYPE: DNA
<213> ORGANISM: Artificial Sequence
<220> FEATURE:
<223> OTHER INFORMATION: DP47 GS Fab HC-Fc hole (LALA P329G)

<400> SEQUENCE: 220

```
gaggtgcaat tgttggagtc tgggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaaggcagc    300

ggatttgact actggggcca aggaaccctg gtcaccgtct cgagtgctag caccaagggc    360

ccctccgtgt tccccctggc ccccagcagc aagagcacca gcggcggcac agccgctctg    420

ggctgcctgg tcaaggacta cttccccgag cccgtgaccg tgtcctggaa cagcggagcc    480

ctgacctccg gcgtgcacac cttccccgcc gtgctgcaga gttctggcct gtatagcctg    540

agcagcgtgg tcaccgtgcc ttctagcagc ctgggcaccc agacctacat ctgcaacgtg    600

aaccacaagc ccagcaacac caaggtggac aagaaggtgg agcccaagag ctgcgacaaa    660

actcacacat gcccaccgtg cccagcacct gaagctgcag gggaccgtc agtcttcctc     720

ttccccccaa aacccaagga caccctcatg atctcccgga cccctgaggt cacatgcgtg    780

gtggtggacg tgagccacga agaccctgag gtcaagttca actggtacgt ggacggcgtg    840

gaggtgcata atgccaagac aaagccgcgg gaggagcagt acaacagcac gtaccgtgtg    900

gtcagcgtcc tcaccgtcct gcaccaggac tggctgaatg gcaaggagta caagtgcaag    960

gtctccaaca aagccctcgg cgcccccatc gagaaaacca tctccaaagc caaagggcag   1020

ccccgagaac cacaggtgtg caccctgccc ccatcccggg atgagctgac caagaaccag   1080

gtcagcctct cgtgcgcagt caaaggcttc tatcccagcg acatcgccgt ggagtgggag   1140

agcaatgggc agccggagaa caactacaag accacgcctc ccgtgctgga ctccgacggc   1200

tccttcttcc tcgtgagcaa gctcaccgtg gacaagagca ggtggcagca ggggaacgtc   1260

ttctcatgct ccgtgatgca tgaggctctg cacaaccact acacgcagaa gagcctctcc   1320

ctgtctccgg gtaaa                                                    1335
```

<210> SEQ ID NO 221
<211> LENGTH: 591
<212> TYPE: PRT
<213> ORGANISM: Artificial Sequence
<220> FEATURE:
<223> OTHER INFORMATION: DP47 GS Fab HC-Fc knob (LALA P329G)-IL-2 qm

<400> SEQUENCE: 221

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Tyr Thr Leu Pro Pro Cys
            340                 345                 350

Arg Asp Glu Leu Thr Lys Asn Gln Val Ser Leu Trp Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Gly Gly Gly Gly
        435                 440                 445

Ser Gly Gly Gly Gly Ser Gly Gly Gly Gly Ala Pro Ala Ser Ser Ser
    450                 455                 460

Thr Lys Lys Thr Gln Leu Gln Leu Glu His Leu Leu Leu Asp Leu Gln
465                 470                 475                 480

Met Ile Leu Asn Gly Ile Asn Asn Tyr Lys Asn Pro Lys Leu Thr Arg
```

-continued

```
                485                 490                 495

Met Leu Thr Ala Lys Phe Ala Met Pro Lys Lys Ala Thr Glu Leu Lys
            500                 505                 510

His Leu Gln Cys Leu Glu Glu Glu Leu Lys Pro Leu Glu Glu Val Leu
        515                 520                 525

Asn Gly Ala Gln Ser Lys Asn Phe His Leu Arg Pro Arg Asp Leu Ile
    530                 535                 540

Ser Asn Ile Asn Val Ile Val Leu Glu Leu Lys Gly Ser Glu Thr Thr
545                 550                 555                 560

Phe Met Cys Glu Tyr Ala Asp Glu Thr Ala Thr Ile Val Glu Phe Leu
                565                 570                 575

Asn Arg Trp Ile Thr Phe Ala Gln Ser Ile Ile Ser Thr Leu Thr
            580                 585                 590


<210> SEQ ID NO 222
<211> LENGTH: 1773
<212> TYPE: DNA
<213> ORGANISM: Artificial Sequence
<220> FEATURE:
<223> OTHER INFORMATION: DP47 GS Fab HC-Fc knob (LALA P329G)-IL-2 qm

<400> SEQUENCE: 222

gaggtgcaat tgttggagtc tgggggaggc ttggtacagc ctggggggtc cctgagactc      60

tcctgtgcag cctccggatt cacctttagc agttatgcca tgagctgggt ccgccaggct     120

ccagggaagg ggctggagtg ggtctcagct attagtggta gtggtggtag cacatactac     180

gcagactccg tgaagggccg gttcaccatc tccagagaca attccaagaa cacgctgtat     240

ctgcagatga acagcctgag agccgaggac acggccgtat attactgtgc gaaaggcagc     300

ggatttgact actggggcca aggaaccctg gtcaccgtct cgagtgctag caccaagggc     360

ccatcggtct tccccctggc accctcctcc aagagcacct ctgggggcac agcggccctg     420

ggctgcctgg tcaaggacta cttccccgaa ccggtgacgg tgtcgtggaa ctcaggcgcc     480

ctgaccagcg gcgtgcacac cttcccggct gtcctacagt cctcaggact ctactccctc     540

agcagcgtgg tgaccgtgcc ctccagcagc ttgggcaccc agacctacat ctgcaacgtg     600

aatcacaagc ccagcaacac caaggtggac aagaaagttg agcccaaatc ttgtgacaaa     660

actcacacat gcccaccgtg cccagcacct gaagctgcag ggggaccgtc agtcttcctc     720

ttccccccaa aacccaagga caccctcatg atctcccgga cccctgaggt cacatgcgtg     780

gtggtggacg tgagccacga agaccctgag gtcaagttca actggtacgt ggacggcgtg     840

gaggtgcata atgccaagac aaagccgcgg gaggagcagt acaacagcac gtaccgtgtg     900

gtcagcgtcc tcaccgtcct gcaccaggac tggctgaatg gcaaggagta caagtgcaag     960

gtctccaaca aagccctcgg cgcccccatc gagaaaacca tctccaaagc caaagggcag    1020

ccccgagaac cacaggtgta caccctgccc ccatgccggg atgagctgac caagaaccag    1080

gtcagcctgt ggtgcctggt caaaggcttc tatcccagcg acatcgccgt ggagtgggag    1140

agcaatgggc agccggagaa caactacaag accacgcctc ccgtgctgga ctccgacggc    1200

tccttcttcc tctacagcaa gctcaccgtg gacaagagca ggtggcagca ggggaacgtc    1260

ttctcatgct ccgtgatgca tgaggctctg cacaaccact acacgcagaa gagcctctcc    1320

ctgtctccgg gtggcggcgg aggctccgga ggcggaggtt ctggcggagg tggcgctcct    1380

gcctcctcca gcaccaagaa aacccagctc cagctggaac atctcctgct ggatctgcag    1440

atgatcctga acggcatcaa caactacaag aaccccaagc tgacccggat gctgaccgcc    1500
```

```
aagttcgcca tgcccaagaa ggccaccgag ctgaaacatc tgcagtgcct ggaagaggaa   1560

ctgaagcctc tggaagaggt gctgaacggc gcccagtcca agaacttcca cctgaggcct   1620

cgggacctga tctccaacat caacgtgatc gtgctggaac tgaagggctc cgagacaacc   1680

ttcatgtgcg agtacgccga cgagacagct accatcgtgg aatttctgaa ccggtggatc   1740

accttcgccc agtccatcat ctccaccctg acc                                1773


<210> SEQ ID NO 223
<211> LENGTH: 591
<212> TYPE: PRT
<213> ORGANISM: Artificial Sequence
<220> FEATURE:
<223> OTHER INFORMATION: DP47GL Fab HC-Fc knob (LALA P329G)- IL-2 wt

<400> SEQUENCE: 223

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
```

```
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Tyr Thr Leu Pro Pro Cys
            340                 345                 350

Arg Asp Glu Leu Thr Lys Asn Gln Val Ser Leu Trp Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Gly Gly Gly Gly
        435                 440                 445

Ser Gly Gly Gly Gly Ser Gly Gly Gly Gly Ala Pro Thr Ser Ser Ser
    450                 455                 460

Thr Lys Lys Thr Gln Leu Gln Leu Glu His Leu Leu Leu Asp Leu Gln
465                 470                 475                 480

Met Ile Leu Asn Gly Ile Asn Asn Tyr Lys Asn Pro Lys Leu Thr Arg
                485                 490                 495

Met Leu Thr Phe Lys Phe Tyr Met Pro Lys Lys Ala Thr Glu Leu Lys
            500                 505                 510

His Leu Gln Cys Leu Glu Glu Glu Leu Lys Pro Leu Glu Glu Val Leu
        515                 520                 525

Asn Leu Ala Gln Ser Lys Asn Phe His Leu Arg Pro Arg Asp Leu Ile
    530                 535                 540

Ser Asn Ile Asn Val Ile Val Leu Glu Leu Lys Gly Ser Glu Thr Thr
545                 550                 555                 560

Phe Met Cys Glu Tyr Ala Asp Glu Thr Ala Thr Ile Val Glu Phe Leu
                565                 570                 575

Asn Arg Trp Ile Thr Phe Ala Gln Ser Ile Ile Ser Thr Leu Thr
            580                 585                 590


<210> SEQ ID NO 224
<211> LENGTH: 1773
<212> TYPE: DNA
<213> ORGANISM: Artificial Sequence
<220> FEATURE:
<223> OTHER INFORMATION: DP47GS Fab HC-Fc knob (LALA P329G)- IL-2 wt

<400> SEQUENCE: 224

gaggtgcaat tgttggagtc tgggggaggc ttggtacagc ctgggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaaggcagc    300

ggatttgact actggggcca aggaaccctg gtcaccgtct cgagtgctag caccaagggc    360

ccatcggtct tccccctggc accctcctcc aagagcacct ctgggggcac agcggccctg    420

ggctgcctgg tcaaggacta cttccccgaa ccggtgacgg tgtcgtggaa ctcaggcgcc    480
```

-continued

```
ctgaccagcg gcgtgcacac cttcccggct gtcctacagt cctcaggact ctactccctc    540

agcagcgtgg tgaccgtgcc ctccagcagc ttgggcaccc agacctacat ctgcaacgtg    600

aatcacaagc ccagcaacac caaggtggac aagaaagttg agcccaaatc ttgtgacaaa    660

actcacacat gcccaccgtg cccagcacct gaagctgcag gggaccgtc agtcttcctc    720

ttccccccaa aacccaagga caccctcatg atctcccgga cccctgaggt cacatgcgtg    780

gtggtggacg tgagccacga agaccctgag gtcaagttca actggtacgt ggacggcgtg    840

gaggtgcata atgccaagac aaagccgcgg gaggagcagt acaacagcac gtaccgtgtg    900

gtcagcgtcc tcaccgtcct gcaccaggac tggctgaatg gcaaggagta caagtgcaag    960

gtctccaaca aagccctcgg cgcccccatc gagaaaacca tctccaaagc caaagggcag   1020

ccccgagaac cacaggtgta caccctgccc ccatgccggg atgagctgac caagaaccag   1080

gtcagcctgt ggtgcctggt caaaggcttc tatcccagcg acatcgccgt ggagtgggag   1140

agcaatgggc agccggagaa caactacaag accacgcctc ccgtgctgga ctccgacggc   1200

tccttcttcc tctacagcaa gctcaccgtg gacaagagca ggtggcagca ggggaacgtc   1260

ttctcatgct ccgtgatgca tgaggctctg cacaaccact acacgcagaa gagcctctcc   1320

ctgtctccgg gtggcggcgg aggctccgga ggcggaggtt ctggcggagg tggcgctcct   1380

acatcctcca gcaccaagaa aacccagctc cagctggaac atctcctgct ggatctgcag   1440

atgatcctga acggcatcaa caactacaag aaccccaagc tgacccggat gctgaccttc   1500

aagttctaca tgcccaagaa ggccaccgag ctgaaacatc tgcagtgcct ggaagaggaa   1560

ctgaagcctc tggaagaggt gctgaacctg gcccagtcca agaacttcca cctgaggcct   1620

cgggacctga tctccaacat caacgtgatc gtgctggaac tgaagggctc cgagacaacc   1680

ttcatgtgcg agtacgccga cgagacagct accatcgtgg aatttctgaa ccggtggatc   1740

accttcgccc agtccatcat ctccaccctg acc                                1773
```

<210> SEQ ID NO 225
<211> LENGTH: 215
<212> TYPE: PRT
<213> ORGANISM: Artificial Sequence
<220> FEATURE:
<223> OTHER INFORMATION: DP47GS Fab LC

<400> SEQUENCE: 225

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
```

```
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 226
<211> LENGTH: 645
<212> TYPE: DNA
<213> ORGANISM: Artificial Sequence
<220> FEATURE:
<223> OTHER INFORMATION: DP47GS Fab LC

<400> SEQUENCE: 226

gaaatcgtgt taacgcagtc tccaggcacc ctgtctttgt ctccagggga aagagccacc     60

ctctcttgca gggccagtca gagtgttagc agcagctact tagcctggta ccagcagaaa    120

cctggccagg ctcccaggct cctcatctat ggagcatcca gcagggccac tggcatccca    180

gacaggttca gtggcagtgg atccgggaca gacttcactc tcaccatcag cagactggag    240

cctgaagatt ttgcagtgta ttactgtcag cagtatggta gctcaccgct gacgttcggc    300

caggggacca aagtggaaat caaacgtacg gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgt                    645


<210> SEQ ID NO 227
<211> LENGTH: 451
<212> TYPE: PRT
<213> ORGANISM: Artificial Sequence
<220> FEATURE:
<223> OTHER INFORMATION: CH1A1A Fab HC-Fc hole (wt)

<400> SEQUENCE: 227

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110
```

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 228
<211> LENGTH: 1353
<212> TYPE: DNA
<213> ORGANISM: Artificial Sequence
<220> FEATURE:
<223> OTHER INFORMATION: CH1A1A Fab HC-Fc hole (wt)

<400> SEQUENCE: 228
caggtgcagc tggtgcagtc tggcgccgaa gtgaagaaac ctggagctag tgtgaaggtg     60

```
tcctgcaagg ccagcggcta caccttcacc gagttcggca tgaactgggt ccgacaggct    120

ccaggccagg gcctcgaatg gatgggctgg atcaacacca agaccggcga ggccacctac    180

gtggaagagt tcaagggcag agtgaccttc accacggaca ccagcaccag caccgcctac    240

atggaactgc ggagcctgag aagcgacgac accgccgtgt actactgcgc cagatgggac    300

ttcgcctatt acgtggaagc catggactac tggggccagg gcaccaccgt gaccgtgtct    360

agcgctagca ccaagggccc aagcgtgttc cctctggccc ccagcagcaa gagcacaagc    420

ggcggaacag ccgccctggg ctgcctggtc aaggactact tccccgagcc cgtgacagtg    480

tcctggaaca gcggagccct gaccagcggc gtgcacacct tccagccgt gctgcagagc     540

agcggcctgt acagcctgag cagcgtggtc acagtgccta gcagcagcct gggcacccag    600

acctacatct gcaacgtgaa ccacaagccc agcaacacca aggtggacaa gaaggtggag    660

cccaagagct gcgacaagac ccacacctgt ccccccttgtc ctgcccctga gctgctgggc    720

ggacccagcg tgttcctgtt ccccccaaag cccaaggaca ccctgatgat cagccggacc    780

cccgaagtga cctgcgtggt ggtggacgtg tcccacgagg accctgaagt gaagttcaat    840

tggtacgtgg acggcgtgga ggtgcacaat gccaagacca agccccggga ggaacagtac    900

aacagcacct accgggtggt gtccgtgctg accgtgctgc accaggactg gctgaacggc    960

aaagagtaca agtgcaaggt ctccaacaag gccctgcctg cccccatcga gaaaaccatc   1020

agcaaggcca agggccagcc cagagaaccc caggtgtgca ccctgccccc cagcagagat   1080

gagctgacca agaaccaggt gtccctgagc tgtgccgtca agggcttcta ccccagcgat   1140

atcgccgtgg agtgggagag caacggccag cctgagaaca actacaagac caccccccct   1200

gtgctggaca gcgacggcag cttcttcctg gtgtccaaac tgaccgtgga caagagccgg   1260

tggcagcagg gcaacgtgtt cagctgcagc gtgatgcacg aggccctgca caaccactac   1320

acccagaagt ccctgagcct gagccccggc aag                                1353
```

<210> SEQ ID NO 229
<211> LENGTH: 599
<212> TYPE: PRT
<213> ORGANISM: Artificial Sequence
<220> FEATURE:
<223> OTHER INFORMATION: CH1A1A Fab HC-Fc knob (wt)-IL-2 qm

<400> SEQUENCE: 229

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
```

-continued

```
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Asp Glu Leu Thr Lys Asn Gln Val Ser
        355                 360                 365

Leu Trp Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Ser Gly Gly Gly Gly Ser Gly Gly Gly Gly Ser Gly Gly
    450                 455                 460

Gly Gly Ala Pro Ala Ser Ser Ser Thr Lys Lys Thr Gln Leu Gln Leu
465                 470                 475                 480

Glu His Leu Leu Leu Asp Leu Gln Met Ile Leu Asn Gly Ile Asn Asn
                485                 490                 495

Tyr Lys Asn Pro Lys Leu Thr Arg Met Leu Thr Ala Lys Phe Ala Met
            500                 505                 510

Pro Lys Lys Ala Thr Glu Leu Lys His Leu Gln Cys Leu Glu Glu Glu
        515                 520                 525

Leu Lys Pro Leu Glu Glu Val Leu Asn Gly Ala Gln Ser Lys Asn Phe
    530                 535                 540

His Leu Arg Pro Arg Asp Leu Ile Ser Asn Ile Asn Val Ile Val Leu
545                 550                 555                 560
```

Glu Leu Lys Gly Ser Glu Thr Thr Phe Met Cys Glu Tyr Ala Asp Glu
565 570 575

Thr Ala Thr Ile Val Glu Phe Leu Asn Arg Trp Ile Thr Phe Ala Gln
580 585 590

Ser Ile Ile Ser Thr Leu Thr
595

<210> SEQ ID NO 230
<211> LENGTH: 1797
<212> TYPE: DNA
<213> ORGANISM: Artificial Sequence
<220> FEATURE:
<223> OTHER INFORMATION: CH1A1A Fab HC-Fc knob (wt)-IL-2 qm

<400> SEQUENCE: 230
caggtgcagc tggtgcagtc tggcgccgaa gtgaagaaac ctggagctag tgtgaaggtg 60
tcctgcaagg ccagcggcta caccttcacc gagttcggca tgaactgggt ccgacaggct 120
ccaggccagg gcctcgaatg gatgggctgg atcaacacca agaccggcga ggccacctac 180
gtggaagagt tcaagggcag agtgaccttc accacggaca ccagcaccag caccgcctac 240
atggaactgc ggagcctgag aagcgacgac accgccgtgt actactgcgc cagatgggac 300
ttcgcctatt acgtggaagc catggactac tggggccagg gcaccaccgt gaccgtgtct 360
agcgctagca ccaagggccc aagcgtgttc cctctggccc ccagcagcaa gagcacaagc 420
ggcggaacag ccgccctggg ctgcctggtc aaggactact tccccgagcc cgtgacagtg 480
tcctggaaca gcggagccct gaccagcggc gtgcacacct ttccagccgt gctgcagagc 540
agcggcctgt acagcctgag cagcgtggtc acagtgccta gcagcagcct gggcacccag 600
acctacatct gcaacgtgaa ccacaagccc agcaacacca aggtggacaa gaaggtggag 660
cccaagagct gcgacaagac ccacacctgt ccccccttgtc ctgcccctga gctgctgggc 720
ggacccagcg tgttcctgtt cccccccaaag cccaaggaca ccctgatgat cagccggacc 780
cccgaagtga cctgcgtggt ggtggacgtg tcccacgagg accctgaagt gaagttcaat 840
tggtacgtgg acggcgtgga ggtgcacaat gccaagacca agccccggga ggaacagtac 900
aacagcacct accgggtggt gtccgtgctg accgtgctgc accaggactg gctgaacggc 960
aaagagtaca agtgcaaggt ctccaacaag gccctgcctg cccccatcga gaaaaccatc 1020
agcaaggcca agggccagcc cagagaaccc caggtgtaca ccctgccccc ctgcagagat 1080
gagctgacca agaaccaggt gtccctgtgg tgtctggtca agggcttcta ccccagcgat 1140
atcgccgtgg agtgggagag caacggccag cctgagaaca actacaagac caccccccct 1200
gtgctggaca gcgacggcag cttcttcctg tactccaaac tgaccgtgga caagagccgg 1260
tggcagcagg gcaacgtgtt cagctgcagc gtgatgcacg aggccctgca caaccactac 1320
acccagaagt ccctgagcct gagccccggc aagtccggag gcggaggctc cggcggcgga 1380
ggttctggcg gaggtggcgc tcctgcctcc tccagcacca agaaaaccca gctccagctg 1440
gaacatctcc tgctggatct gcagatgatc ctgaacggca tcaacaacta caagaacccc 1500
aagctgaccc ggatgctgac cgccaagttc gccatgccca agaaggccac cgagctgaaa 1560
catctgcagt gcctggaaga ggaactgaag cctctggaag aggtgctgaa cggcgcccag 1620
tccaagaact tccacctgag gcctcgggac ctgatctcca acatcaacgt gatcgtgctg 1680
gaactgaagg gctccgagac aaccttcatg tgcgagtacg ccgacgagac agctaccatc 1740
gtggaatttc tgaaccggtg gatcaccttc gcccagtcca tcatctccac cctgacc 1797

<210> SEQ ID NO 231
<211> LENGTH: 215
<212> TYPE: PRT
<213> ORGANISM: Artificial Sequence
<220> FEATURE:
<223> OTHER INFORMATION: 2F1 Fab LC

<400> SEQUENCE: 231

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 232
<211> LENGTH: 645
<212> TYPE: DNA
<213> ORGANISM: Artificial Sequence
<220> FEATURE:
<223> OTHER INFORMATION: 2F1 Fab LC

<400> SEQUENCE: 232

```
gatatccaga tgacccagtc tccatcctcc ctgtctgcat ctgtgggaga cagagtcacc     60

atcacttgca aggccagtgc ggctgtgggt acgtatgttg cgtggtatca gcagaaacca    120

gggaaagcac ctaagctcct gatctattcg gcatcctacc gcaaaagggg agtcccatca    180

aggttcagtg gcagtggatc tgggacagat ttcactctca ccatcagcag tctgcaacct    240

gaagatttcg caacttacta ctgtcaccaa tattacacct atcctctatt cacgtttggc    300

cagggcacca agctcgagat caagcgtacg gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480
```

caggagagtg tcacagagca ggacagcaag gacagcacct acagcctcag cagcaccctg 540
acgctgagca aagcagacta cgagaaacac aaagtctacg cctgcgaagt cacccatcag 600
ggcctgagct cgcccgtcac aaagagcttc aacaggggag agtgt 645

<210> SEQ ID NO 233
<211> LENGTH: 451
<212> TYPE: PRT
<213> ORGANISM: Artificial Sequence
<220> FEATURE:
<223> OTHER INFORMATION: 2B10 Fab HC-Fc knob (LALA P329G)

<400> SEQUENCE: 233

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Leu Tyr Gly Tyr Ala Tyr Tyr Gly Ala Phe Asp Tyr Trp Gly
100 105 110

Gln Gly Thr Thr Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Lys Val Glu Pro Lys Ser Cys
210 215 220

Asp Lys Thr His Thr Cys Pro Pro Cys Pro Ala Pro Glu Ala Ala Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

Glu Asp Pro Glu Val Lys Phe Asn Trp Tyr Val Asp Gly Val Glu Val
275 280 285

His Asn Ala Lys Thr Lys Pro Arg Glu Glu Gln Tyr Asn Ser Thr Tyr
290 295 300

Arg Val Val Ser Val Leu Thr Val Leu His Gln Asp Trp Leu Asn Gly
305 310 315 320

Lys Glu Tyr Lys Cys Lys Val Ser Asn Lys Ala Leu Gly Ala Pro Ile
325 330 335

```
Glu Lys Thr Ile Ser Lys Ala Lys Gly Gln Pro Arg Glu Pro Gln Val
            340                 345                 350

Tyr Thr Leu Pro Pro Cys Arg Asp Glu Leu Thr Lys Asn Gln Val Ser
        355                 360                 365

Leu Trp Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 234
<211> LENGTH: 1353
<212> TYPE: DNA
<213> ORGANISM: Artificial Sequence
<220> FEATURE:
<223> OTHER INFORMATION: 2B10 Fab HC-Fc knob (LALA P329G)

<400> SEQUENCE: 234

caggtgcaat tggtgcagtc tggggctgag gtgaagaagc ctgggtcctc ggtgaaggtc     60

tcctgcaagg cctccggagg cacattcagc agctacgcta taagctgggt gcgacaggcc    120

cctggacaag ggctcgagtg gatgggaggg atcatcccta tctttggtac agcaaactac    180

gcacagaagt tccagggcag ggtcaccatt actgcagaca aatccacgag cacagcctac    240

atggagctga gcagcctgag atctgaggac accgccgtgt attactgtgc gagactgtac    300

ggttacgctt actacggtgc ttttgactac tggggccaag ggaccaccgt gaccgtctcc    360

tcagctagca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggacaa gaaagttgag    660

cccaaatctt gtgacaaaac tcacacatgc ccaccgtgcc cagcacctga agctgcaggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgcggga ggagcagtac    900

aacagcacgt accgtgtggt cagcgtcctc accgtcctgc accaggactg gctgaatggc    960

aaggagtaca agtgcaaggt ctccaacaaa gccctcggcg cccccatcga gaaaaccatc   1020

tccaaagcca aagggcagcc ccgagaacca caggtgtaca ccctgccccc atgccgggat   1080

gagctgacca agaaccaggt cagcctgtgg tgcctggtca aaggcttcta tcccagcgac   1140

atcgccgtgg agtgggagag caatgggcag ccggagaaca actacaagac cacgcctccc   1200

gtgctggact ccgacggctc cttcttcctc tacagcaagc tcaccgtgga caagagcagg   1260

tggcagcagg ggaacgtctt ctcatgctcc gtgatgcatg aggctctgca caaccactac   1320

acgcagaaga gcctctccct gtctccgggt aaa                                1353
```

<210> SEQ ID NO 235
<211> LENGTH: 805
<212> TYPE: PRT
<213> ORGANISM: Artificial Sequence
<220> FEATURE:
<223> OTHER INFORMATION: 2B10 Fab HC-Fc hole (LALA P329G)-scIL-10

<400> SEQUENCE: 235

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

```
Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Gly Gly Gly Gly Ser Gly Gly Gly Gly Ser Gly Gly Gly Gly
    450                 455                 460

Ser Ser Pro Gly Gln Gly Thr Gln Ser Glu Asn Ser Cys Thr His Phe
465                 470                 475                 480

Pro Gly Asn Leu Pro Asn Met Leu Arg Asp Leu Arg Asp Ala Phe Ser
                485                 490                 495

Arg Val Lys Thr Phe Phe Gln Met Lys Asp Gln Leu Asp Asn Leu Leu
            500                 505                 510

Leu Lys Glu Ser Leu Leu Glu Asp Phe Lys Gly Tyr Leu Gly Cys Gln
        515                 520                 525

Ala Leu Ser Glu Met Ile Gln Phe Tyr Leu Glu Glu Val Met Pro Gln
    530                 535                 540

Ala Glu Asn Gln Asp Pro Asp Ile Lys Ala His Val Asn Ser Leu Gly
545                 550                 555                 560

Glu Asn Leu Lys Thr Leu Arg Leu Arg Leu Arg Arg Cys His Arg Phe
                565                 570                 575

Leu Pro Cys Glu Asn Lys Ser Lys Ala Val Glu Gln Val Lys Asn Ala
            580                 585                 590

Phe Asn Lys Leu Gln Glu Lys Gly Ile Tyr Lys Ala Met Ser Glu Phe
        595                 600                 605

Asp Ile Phe Ile Asn Tyr Ile Glu Ala Tyr Met Thr Met Lys Ile Arg
    610                 615                 620

Asn Gly Gly Gly Gly Ser Gly Gly Gly Gly Ser Gly Gly Gly Gly Ser
625                 630                 635                 640

Gly Gly Gly Gly Ser Ser Pro Gly Gln Gly Thr Gln Ser Glu Asn Ser
                645                 650                 655

Cys Thr His Phe Pro Gly Asn Leu Pro Asn Met Leu Arg Asp Leu Arg
            660                 665                 670

Asp Ala Phe Ser Arg Val Lys Thr Phe Phe Gln Met Lys Asp Gln Leu
        675                 680                 685

Asp Asn Leu Leu Leu Lys Glu Ser Leu Leu Glu Asp Phe Lys Gly Tyr
    690                 695                 700

Leu Gly Cys Gln Ala Leu Ser Glu Met Ile Gln Phe Tyr Leu Glu Glu
705                 710                 715                 720

Val Met Pro Gln Ala Glu Asn Gln Asp Pro Asp Ile Lys Ala His Val
                725                 730                 735

Asn Ser Leu Gly Glu Asn Leu Lys Thr Leu Arg Leu Arg Leu Arg Arg
            740                 745                 750

Cys His Arg Phe Leu Pro Cys Glu Asn Lys Ser Lys Ala Val Glu Gln
        755                 760                 765

Val Lys Asn Ala Phe Asn Lys Leu Gln Glu Lys Gly Ile Tyr Lys Ala
    770                 775                 780
```

Met Ser Glu Phe Asp Ile Phe Ile Asn Tyr Ile Glu Ala Tyr Met Thr
785 790 795 800

Met Lys Ile Arg Asn
805

<210> SEQ ID NO 236
<211> LENGTH: 2415
<212> TYPE: DNA
<213> ORGANISM: Artificial Sequence
<220> FEATURE:
<223> OTHER INFORMATION: 2B10 Fab HC-Fc hole (LALA P329G)-scIL-10

<400> SEQUENCE: 236
caggtgcaat tggtgcagtc tggggctgag gtgaagaagc ctgggtcctc ggtgaaggtc 60
tcctgcaagg cctccggagg cacattcagc agctacgcta taagctgggt gcgacaggcc 120
cctggacaag ggctcgagtg gatgggaggg atcatcccta tctttggtac agcaaactac 180
gcacagaagt tccagggcag ggtcaccatt actgcagaca aatccacgag cacagcctac 240
atggagctga gcagcctgag atctgaggac accgccgtgt attactgtgc gagactgtac 300
ggttacgctt actacggtgc ttttgactac tggggccaag ggaccaccgt gaccgtctcc 360
tcagctagca ccaagggccc atcggtcttc cccctggcac cctcctccaa gagcacctct 420
gggggcacag cggccctggg ctgcctggtc aaggactact tccccgaacc ggtgacggtg 480
tcgtggaact caggcgccct gaccagcggc gtgcacacct tcccggctgt cctacagtcc 540
tcaggactct actccctcag cagcgtggtg accgtgccct ccagcagctt gggcacccag 600
acctacatct gcaacgtgaa tcacaagccc agcaacacca aggtggacaa gaaagttgag 660
cccaaatctt gtgacaaaac tcacacatgc ccaccgtgcc cagcacctga agctgcaggg 720
ggaccgtcag tcttcctctt ccccccaaaa cccaaggaca ccctcatgat ctcccggacc 780
cctgaggtca catgcgtggt ggtggacgtg agccacgaag accctgaggt caagttcaac 840
tggtacgtgg acggcgtgga ggtgcataat gccaagacaa agccgcggga ggagcagtac 900
aacagcacgt accgtgtggt cagcgtcctc accgtcctgc accaggactg gctgaatggc 960
aaggagtaca agtgcaaggt ctccaacaaa gccctcggcg cccccatcga gaaaaccatc 1020
tccaaagcca aagggcagcc ccgagaacca caggtgtgca ccctgccccc atcccgggat 1080
gagctgacca agaaccaggt cagcctctcg tgcgcagtca aaggcttcta tcccagcgac 1140
atcgccgtgg agtgggagag caatgggcag ccggagaaca actacaagac cacgcctccc 1200
gtgctggact ccgacggctc cttcttcctc gtgagcaagc tcaccgtgga caagagcagg 1260
tggcagcagg ggaacgtctt ctcatgctcc gtgatgcatg aggctctgca caaccactac 1320
acgcagaaga gcctctccct gtctccgggt ggcggcggag gctccggagg cggaggatct 1380
gggggaggcg gaagtagccc gggccagggc acccagagcg agaacagctg cacccacttc 1440
cccggcaacc tgcccaacat gctgcgggac ctgagggacg ccttcagcag agtgaaaacc 1500
ttcttccaga tgaaggacca gctggacaac ctgctgctga aagagagcct gctggaagat 1560
ttcaagggct acctgggctg tcaggccctg agcgagatga tccagttcta cctggaagaa 1620
gtgatgcccc aggccgagaa ccaggacccc gacatcaagg cccacgtgaa cagcctgggc 1680
gagaacctga aaaccctgcg gctgagactg cggcggtgcc acagatttct gccctgcgag 1740
aacaagagca aggccgtgga acaggtgaag aacgccttca acaagctgca ggaaaagggc 1800
atctacaagg ccatgtccga gttcgacatc ttcatcaact acatcgaagc ttacatgacc 1860
atgaagatca gaaacggcgg aggcggatct ggcggcggtg gaagtggagg cggaggatct 1920

```
gggggaggcg gaagtagccc gggccagggc acccagagcg agaacagctg cacccacttc   1980

cccggcaacc tgcccaacat gctgcgggac ctgagggacg ccttcagcag agtgaaaacc   2040

ttcttccaga tgaaggacca gctggacaac ctgctgctga aagagagcct gctggaagat   2100

ttcaagggct acctgggctg tcaggccctg agcgagatga tccagttcta cctggaagaa   2160

gtgatgcccc aggccgagaa ccaggacccc gacatcaagg cccacgtgaa cagcctgggc   2220

gagaacctga aaaccctgcg gctgagactg cggcggtgcc acagatttct gccctgcgag   2280

aacaagagca aggccgtgga acaggtgaag aacgccttca acaagctgca ggaaaagggc   2340

atctacaagg ccatgtccga gttcgacatc ttcatcaact acatcgaggc ctacatgaca   2400

atgaaaatcc gcaat                                                    2415


<210> SEQ ID NO 237
<211> LENGTH: 631
<212> TYPE: PRT
<213> ORGANISM: Artificial Sequence
<220> FEATURE:
<223> OTHER INFORMATION: 2B10 Fab HC-Fc hole (LALA P329G)-IL-10M1

<400> SEQUENCE: 237

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270
```

```
Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Gly Gly Gly Gly Ser Gly Gly Gly Gly Ser Gly Gly Gly Gly
    450                 455                 460

Ser Ser Pro Gly Gln Gly Thr Gln Ser Glu Asn Ser Cys Thr His Phe
465                 470                 475                 480

Pro Gly Asn Leu Pro Asn Met Leu Arg Asp Leu Arg Asp Ala Phe Ser
                485                 490                 495

Arg Val Lys Thr Phe Phe Gln Met Lys Asp Gln Leu Asp Asn Leu Leu
            500                 505                 510

Leu Lys Glu Ser Leu Leu Glu Asp Phe Lys Gly Tyr Leu Gly Cys Gln
        515                 520                 525

Ala Leu Ser Glu Met Ile Gln Phe Tyr Leu Glu Glu Val Met Pro Gln
    530                 535                 540

Ala Glu Asn Gln Asp Pro Asp Ile Lys Ala His Val Asn Ser Leu Gly
545                 550                 555                 560

Glu Asn Leu Lys Thr Leu Arg Leu Arg Leu Arg Arg Cys His Arg Phe
                565                 570                 575

Leu Pro Cys Glu Asn Gly Gly Gly Ser Gly Gly Lys Ser Lys Ala Val
            580                 585                 590

Glu Gln Val Lys Asn Ala Phe Asn Lys Leu Gln Glu Lys Gly Ile Tyr
        595                 600                 605

Lys Ala Met Ser Glu Phe Asp Ile Phe Ile Asn Tyr Ile Glu Ala Tyr
    610                 615                 620

Met Thr Met Lys Ile Arg Asn
625                 630
```

<210> SEQ ID NO 238
<211> LENGTH: 1893
<212> TYPE: DNA
<213> ORGANISM: Artificial Sequence
<220> FEATURE:
<223> OTHER INFORMATION: 2B10 Fab HC-Fc hole (LALA P329G)-IL-10M1

<400> SEQUENCE: 238

```
caggtgcaat tggtgcagtc tggggctgag gtgaagaagc ctgggtcctc ggtgaaggtc     60
tcctgcaagg cctccggagg cacattcagc agctacgcta taagctgggt gcgacaggcc    120
cctggacaag ggctcgagtg gatgggaggg atcatcccta tctttggtac agcaaactac    180
gcacagaagt tccagggcag ggtcaccatt actgcagaca aatccacgag cacagcctac    240
atggagctga gcagcctgag atctgaggac accgccgtgt attactgtgc gagactgtac    300
ggttacgctt actacggtgc ttttgactac tggggccaag ggaccaccgt gaccgtctcc    360
tcagctagca ccaagggccc atcggtcttc cccctggcac cctcctccaa gagcacctct    420
gggggcacag cggccctggg ctgcctggtc aaggactact tccccgaacc ggtgacggtg    480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga agctgcaggg    720
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcggcg cccccatcga gaaaaccatc   1020
tccaaagcca aagggcagcc ccgagaacca caggtgtgca ccctgccccc atcccgggat   1080
gagctgacca agaaccaggt cagcctctcg tgcgcagtca aaggcttcta tcccagcgac   1140
atcgccgtgg agtgggagag caatgggcag ccggagaaca actacaagac cacgcctccc   1200
gtgctggact ccgacggctc cttcttcctc gtgagcaagc tcaccgtgga caagagcagg   1260
tggcagcagg ggaacgtctt ctcatgctcc gtgatgcatg aggctctgca caaccactac   1320
acgcagaaga gcctctccct gtctccgggt ggcggcggag gctccggagg cggaggaagt   1380
ggcggcggtg gcagctctcc aggccagggc acccagagcg agaacagctg cacccacttc   1440
cccggcaacc tgcccaacat gctgcgggac ctgagggacg ccttcagcag agtgaaaacc   1500
ttcttccaga tgaaggacca gctggacaac ctgctgctga aagagagcct gctggaagat   1560
ttcaagggct acctgggctg tcaggccctg agcgagatga tccagttcta cctggaagaa   1620
gtgatgcccc aggccgagaa ccaggacccc gacatcaagg cccacgtgaa cagcctgggc   1680
gagaacctga aaccctgcg gctgagactg cggcggtgcc acagatttct gccctgcgag   1740
aacggcggag gctctggcgg aaagtccaag gccgtggaac aggtgaagaa cgccttcaac   1800
aagctgcagg aaaagggcat ctacaaggcc atgagcgagt tcgacatctt catcaactac   1860
atcgaagctt acatgacaat gaagatacga aac                                 1893
```

<210> SEQ ID NO 239
<211> LENGTH: 214
<212> TYPE: PRT
<213> ORGANISM: Artificial Sequence
<220> FEATURE:
<223> OTHER INFORMATION: 2B10 Fab LC

<400> SEQUENCE: 239

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
```

```
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 240
<211> LENGTH: 642
<212> TYPE: DNA
<213> ORGANISM: Artificial Sequence
<220> FEATURE:
<223> OTHER INFORMATION: 2B10 Fab LC

<400> SEQUENCE: 240

gatatccaga tgacccagtc tccatcctcc ctgtctgcat ctgtcggaga ccgggtcacc     60

atcacctgcc gggcaagtca gggcattaga aatgatttag gctggtacca gcagaagcca    120

gggaaagccc ctaagcgcct gatctatgct gcatccagtt tgcagagtgg cgtcccatca    180

aggttcagcg gcggtggatc cgggacagag ttcactctca ccatcagcag cttgcagcct    240

gaagattttg ccacctatta ctgcttgcag aatggtctgc agcccgcgac gtttggccag    300

ggcaccaaag tcgagatcaa gcgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642


<210> SEQ ID NO 241
<211> LENGTH: 447
<212> TYPE: PRT
<213> ORGANISM: Artificial Sequence
<220> FEATURE:
<223> OTHER INFORMATION: 4G8 Fab HC-Fc knob (LALA P329G)

<400> SEQUENCE: 241
```

-continued

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Arg Asp Glu Leu Thr Lys Asn Gln Val Ser Leu Trp Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415
```

```
Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 242
<211> LENGTH: 1341
<212> TYPE: DNA
<213> ORGANISM: Artificial Sequence
<220> FEATURE:
<223> OTHER INFORMATION: 4G8 Fab HC-Fc knob (LALA P329G)

<400> SEQUENCE: 242

```
gaggtgcaat tgttggagtc tgggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaagggtgg    300

ctgggtaatt ttgactactg gggccaagga accctggtca ccgtctcgag tgctagcacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga aagttgagcc caaatcttgt    660

gacaaaactc acacatgccc accgtgccca gcacctgaag ctgcaggggg accgtcagtc    720

ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840

ggcgtggagg tgcataatgc caagacaaag ccgcgggagg agcagtacaa cagcacgtac    900

cgtgtggtca gcgtcctcac cgtcctgcac caggactggc tgaatggcaa ggagtacaag    960

tgcaaggtct ccaacaaagc cctcggcgcc cccatcgaga aaaccatctc caaagccaaa   1020

gggcagcccc gagaaccaca ggtgtacacc ctgcccccat gccgggatga gctgaccaag   1080

aaccaggtca gcctgtggtg cctggtcaaa ggcttctatc ccagcgacat cgccgtggag   1140

tgggagagca atgggcagcc ggagaacaac tacaagacca cgcctcccgt gctggactcc   1200

gacggctcct tcttcctcta cagcaagctc accgtggaca agagcaggtg gcagcagggg   1260

aacgtcttct catgctccgt gatgcatgag gctctgcaca accactacac gcagaagagc   1320

ctctccctgt ctccgggtaa a                                              1341
```

<210> SEQ ID NO 243
<211> LENGTH: 801
<212> TYPE: PRT
<213> ORGANISM: Artificial Sequence
<220> FEATURE:
<223> OTHER INFORMATION: 4G8 Fab HC-Fc hole (LALA P329G)-scIL-10

<400> SEQUENCE: 243

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
```

```
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Cys Thr Leu Pro
            340                 345                 350

Pro Ser Arg Asp Glu Leu Thr Lys Asn Gln Val Ser Leu Ser Cys Ala
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Gly Ser Gly Gly Gly Gly Ser Ser Pro Gly
    450                 455                 460
```

Gln Gly Thr Gln Ser Glu Asn Ser Cys Thr His Phe Pro Gly Asn Leu
465 470 475 480

Pro Asn Met Leu Arg Asp Leu Arg Asp Ala Phe Ser Arg Val Lys Thr
485 490 495

Phe Phe Gln Met Lys Asp Gln Leu Asp Asn Leu Leu Leu Lys Glu Ser
500 505 510

Leu Leu Glu Asp Phe Lys Gly Tyr Leu Gly Cys Gln Ala Leu Ser Glu
515 520 525

Met Ile Gln Phe Tyr Leu Glu Glu Val Met Pro Gln Ala Glu Asn Gln
530 535 540

Asp Pro Asp Ile Lys Ala His Val Asn Ser Leu Gly Glu Asn Leu Lys
545 550 555 560

Thr Leu Arg Leu Arg Leu Arg Arg Cys His Arg Phe Leu Pro Cys Glu
565 570 575

Asn Lys Ser Lys Ala Val Glu Gln Val Lys Asn Ala Phe Asn Lys Leu
580 585 590

Gln Glu Lys Gly Ile Tyr Lys Ala Met Ser Glu Phe Asp Ile Phe Ile
595 600 605

Asn Tyr Ile Glu Ala Tyr Met Thr Met Lys Ile Arg Asn Gly Gly Gly
610 615 620

Gly Ser Gly Gly Gly Gly Ser Gly Gly Gly Gly Ser Gly Gly Gly Gly
625 630 635 640

Ser Ser Pro Gly Gln Gly Thr Gln Ser Glu Asn Ser Cys Thr His Phe
645 650 655

Pro Gly Asn Leu Pro Asn Met Leu Arg Asp Leu Arg Asp Ala Phe Ser
660 665 670

Arg Val Lys Thr Phe Phe Gln Met Lys Asp Gln Leu Asp Asn Leu Leu
675 680 685

Leu Lys Glu Ser Leu Leu Glu Asp Phe Lys Gly Tyr Leu Gly Cys Gln
690 695 700

Ala Leu Ser Glu Met Ile Gln Phe Tyr Leu Glu Glu Val Met Pro Gln
705 710 715 720

Ala Glu Asn Gln Asp Pro Asp Ile Lys Ala His Val Asn Ser Leu Gly
725 730 735

Glu Asn Leu Lys Thr Leu Arg Leu Arg Leu Arg Arg Cys His Arg Phe
740 745 750

Leu Pro Cys Glu Asn Lys Ser Lys Ala Val Glu Gln Val Lys Asn Ala
755 760 765

Phe Asn Lys Leu Gln Glu Lys Gly Ile Tyr Lys Ala Met Ser Glu Phe
770 775 780

Asp Ile Phe Ile Asn Tyr Ile Glu Ala Tyr Met Thr Met Lys Ile Arg
785 790 795 800

Asn

<210> SEQ ID NO 244
<211> LENGTH: 2403
<212> TYPE: DNA
<213> ORGANISM: Artificial Sequence
<220> FEATURE:
<223> OTHER INFORMATION: 4G8 Fab HC-Fc hole (LALA P329G)-scIL-10

<400> SEQUENCE: 244
gaggtgcaat tgttggagtc tgggggaggc ttggtacagc ctggggggtc cctgagactc 60
tcctgtgcag cctccggatt cacctttagc agttatgcca tgagctgggt ccgccaggct 120

```
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaagggtgg    300
ctgggtaatt ttgactactg gggccaagga accctggtca ccgtctcgag tgctagcacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga aagttgagcc caaatcttgt    660
gacaaaactc acacatgccc accgtgccca gcacctgaag ctgcaggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcggcgcc cccatcgaga aaaccatctc caaagccaaa   1020
gggcagcccc gagaaccaca ggtgtgcacc ctgcccccat cccgggatga gctgaccaag   1080
aaccaggtca gcctctcgtg cgcagtcaaa ggcttctatc ccagcgacat cgccgtggag   1140
tgggagagca atgggcagcc ggagaacaac tacaagacca cgcctcccgt gctggactcc   1200
gacggctcct tcttcctcgt gagcaagctc accgtggaca agagcaggtg gcagcagggg   1260
aacgtcttct catgctccgt gatgcatgag gctctgcaca accactacac gcagaagagc   1320
ctctccctgt ctccgggtgg cggcggaggc tccggaggcg gaggatctgg gggaggcgga   1380
agtagcccgg gccagggcac ccagagcgag aacagctgca cccacttccc cggcaacctg   1440
cccaacatgc tgcgggacct gagggacgcc ttcagcagag tgaaaacctt cttccagatg   1500
aaggaccagc tggacaacct gctgctgaaa gagagcctgc tggaagattt caagggctac   1560
ctgggctgtc aggccctgag cgagatgatc cagttctacc tggaagaagt gatgccccag   1620
gccgagaacc aggaccccga catcaaggcc cacgtgaaca gcctgggcga gaacctgaaa   1680
accctgcggc tgagactgcg gcggtgccac agatttctgc cctgcgagaa caagagcaag   1740
gccgtggaac aggtgaagaa cgccttcaac aagctgcagg aaaagggcat ctacaaggcc   1800
atgtccgagt tcgacatctt catcaactac atcgaagctt acatgaccat gaagatcaga   1860
aacggcggag gcggatctgg cggcggtgga agtggaggcg gaggatctgg gggaggcgga   1920
agtagcccgg gccagggcac ccagagcgag aacagctgca cccacttccc cggcaacctg   1980
cccaacatgc tgcgggacct gagggacgcc ttcagcagag tgaaaacctt cttccagatg   2040
aaggaccagc tggacaacct gctgctgaaa gagagcctgc tggaagattt caagggctac   2100
ctgggctgtc aggccctgag cgagatgatc cagttctacc tggaagaagt gatgccccag   2160
gccgagaacc aggaccccga catcaaggcc cacgtgaaca gcctgggcga gaacctgaaa   2220
accctgcggc tgagactgcg gcggtgccac agatttctgc cctgcgagaa caagagcaag   2280
gccgtggaac aggtgaagaa cgccttcaac aagctgcagg aaaagggcat ctacaaggcc   2340
atgtccgagt tcgacatctt catcaactac atcgaggcct acatgacaat gaaaatccgc   2400
aat                                                                 2403
```

<210> SEQ ID NO 245
<211> LENGTH: 627
<212> TYPE: PRT
<213> ORGANISM: Artificial Sequence
<220> FEATURE:
<223> OTHER INFORMATION: 4G8 Fab HC-Fc hole (LALA P329G)-IL-10M1

<400> SEQUENCE: 245

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Cys Thr Leu Pro
            340                 345                 350

Pro Ser Arg Asp Glu Leu Thr Lys Asn Gln Val Ser Leu Ser Cys Ala
        355                 360                 365
```

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Gly Ser Gly Gly Gly Gly Ser Ser Pro Gly
    450                 455                 460

Gln Gly Thr Gln Ser Glu Asn Ser Cys Thr His Phe Pro Gly Asn Leu
465                 470                 475                 480

Pro Asn Met Leu Arg Asp Leu Arg Asp Ala Phe Ser Arg Val Lys Thr
                485                 490                 495

Phe Phe Gln Met Lys Asp Gln Leu Asp Asn Leu Leu Leu Lys Glu Ser
            500                 505                 510

Leu Leu Glu Asp Phe Lys Gly Tyr Leu Gly Cys Gln Ala Leu Ser Glu
        515                 520                 525

Met Ile Gln Phe Tyr Leu Glu Glu Val Met Pro Gln Ala Glu Asn Gln
    530                 535                 540

Asp Pro Asp Ile Lys Ala His Val Asn Ser Leu Gly Glu Asn Leu Lys
545                 550                 555                 560

Thr Leu Arg Leu Arg Leu Arg Arg Cys His Arg Phe Leu Pro Cys Glu
                565                 570                 575

Asn Gly Gly Gly Ser Gly Gly Lys Ser Lys Ala Val Glu Gln Val Lys
            580                 585                 590

Asn Ala Phe Asn Lys Leu Gln Glu Lys Gly Ile Tyr Lys Ala Met Ser
        595                 600                 605

Glu Phe Asp Ile Phe Ile Asn Tyr Ile Glu Ala Tyr Met Thr Met Lys
    610                 615                 620

Ile Arg Asn
625

<210> SEQ ID NO 246
<211> LENGTH: 1881
<212> TYPE: DNA
<213> ORGANISM: Artificial Sequence
<220> FEATURE:
<223> OTHER INFORMATION: 4G8 Fab HC-Fc hole (LALA P329G)-IL-10M1

<400> SEQUENCE: 246
gaggtgcaat tgttggagtc tgggggaggc ttggtacagc ctggggggtc cctgagactc 60
tcctgtgcag cctccggatt cacctttagc agttatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcagatga acagcctgag agccgaggac acggccgtat attactgtgc gaaagggtgg 300
ctgggtaatt ttgactactg gggccaagga accctggtca ccgtctcgag tgctagcacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540

```
tccctcagca gcgtggtgac cgtgccctcc agcagcttgg gcacccagac ctacatctgc    600

aacgtgaatc acaagcccag caacaccaag gtggacaaga aagttgagcc caaatcttgt    660

gacaaaactc acacatgccc accgtgccca gcacctgaag ctgcaggggg accgtcagtc    720

ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840

ggcgtggagg tgcataatgc caagacaaag ccgcgggagg agcagtacaa cagcacgtac    900

cgtgtggtca gcgtcctcac cgtcctgcac caggactggc tgaatggcaa ggagtacaag    960

tgcaaggtct ccaacaaagc cctcggcgcc cccatcgaga aaaccatctc caaagccaaa   1020

gggcagcccc gagaaccaca ggtgtgcacc ctgcccccat cccgggatga gctgaccaag   1080

aaccaggtca gcctctcgtg cgcagtcaaa ggcttctatc ccagcgacat cgccgtggag   1140

tgggagagca atgggcagcc ggagaacaac tacaagacca cgcctcccgt gctggactcc   1200

gacggctcct tcttcctcgt gagcaagctc accgtggaca agagcaggtg gcagcagggg   1260

aacgtcttct catgctccgt gatgcatgag gctctgcaca accactacac gcagaagagc   1320

ctctccctgt ctccgggtgg cggcggaggc tccggaggcg gaggaagtgg cggcggtggc   1380

agctctccag gccagggcac ccagagcgag aacagctgca cccacttccc cggcaacctg   1440

cccaacatgc tgcgggacct gagggacgcc ttcagcagag tgaaaacctt cttccagatg   1500

aaggaccagc tggacaacct gctgctgaaa gagagcctgc tggaagattt caagggctac   1560

ctgggctgtc aggccctgag cgagatgatc cagttctacc tggaagaagt gatgccccag   1620

gccgagaacc aggaccccga catcaaggcc cacgtgaaca gcctgggcga gaacctgaaa   1680

accctgcggc tgagactgcg gcggtgccac agatttctgc cctgcgagaa cggcggaggc   1740

tctggcggaa agtccaaggc cgtggaacag gtgaagaacg ccttcaacaa gctgcaggaa   1800

aagggcatct acaaggccat gagcgagttc gacatcttca tcaactacat cgaagcttac   1860

atgacaatga agatacgaaa c                                             1881
```

<210> SEQ ID NO 247
<211> LENGTH: 366
<212> TYPE: PRT
<213> ORGANISM: Artificial Sequence
<220> FEATURE:
<223> OTHER INFORMATION: IL-2 qm-Fc knob (LALA P329G) (IL-2 N-terminal)

<400> SEQUENCE: 247

```
Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Ala Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Gly Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125
```

```
Ile Ser Thr Leu Thr Ser Gly Gly Gly Gly Ser Asp Lys Thr His Thr
    130                 135                 140

Cys Pro Pro Cys Pro Ala Pro Glu Ala Ala Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Gly Ala Pro Ile Glu Lys Thr Ile Ser
                245                 250                 255

Lys Ala Lys Gly Gln Pro Arg Glu Pro Gln Val Tyr Thr Leu Pro Pro
            260                 265                 270

Cys Arg Asp Glu Leu Thr Lys Asn Gln Val Ser Leu Trp Cys Leu Val
        275                 280                 285

Lys Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
        355                 360                 365
```

<210> SEQ ID NO 248
<211> LENGTH: 1098
<212> TYPE: DNA
<213> ORGANISM: Artificial Sequence
<220> FEATURE:
<223> OTHER INFORMATION: IL-2 qm-Fc knob (LALA P329G) (IL-2 N-terminal)

<400> SEQUENCE: 248

```
gctcctgcct cctccagcac caagaaaacc cagctccagc tggaacatct cctgctggat      60

ctgcagatga tcctgaacgg catcaacaac tacaagaacc ccaagctgac ccggatgctg     120

accgccaagt tcgccatgcc caagaaggcc accgagctga aacatctgca gtgcctggaa     180

gaggaactga agcctctgga agaggtgctg aacggcgccc agtccaagaa cttccacctg     240

aggcctcggg acctgatctc caacatcaac gtgatcgtgc tggaactgaa gggctccgag     300

acaaccttca tgtgcgagta cgccgacgag acagctacca tcgtggaatt tctgaaccgg     360

tggatcacct tcgcccagtc catcatctcc accctgacct ccggtggtgg cggatccgac     420

aaaactcaca catgcccacc gtgcccagca cctgaagctg caggggggacc gtcagtcttc    480

ctcttccccc caaaacccaa ggacaccctc atgatctccc ggacccctga ggtcacatgc     540

gtggtggtgg acgtgagcca cgaagaccct gaggtcaagt tcaactggta cgtggacggc     600

gtggaggtgc ataatgccaa gacaaagccg cgggaggagc agtacaacag cacgtaccgt     660

gtggtcagcg tcctcaccgt cctgcaccag gactggctga atggcaagga gtacaagtgc     720
```

```
aaggtctcca acaaagccct cggcgccccc atcgagaaaa ccatctccaa agccaaaggg    780

cagccccgag aaccacaggt gtacaccctg cccccatgcc gggatgagct gaccaagaac    840

caggtcagcc tgtggtgcct ggtcaaaggc ttctatccca gcgacatcgc cgtggagtgg    900

gagagcaatg ggcagccgga gaacaactac aagaccacgc ctcccgtgct ggactccgac    960

ggctccttct tcctctacag caagctcacc gtggacaaga gcaggtggca gcaggggaac   1020

gtcttctcat gctccgtgat gcatgaggct ctgcacaacc actacacgca gaagagcctc   1080

tccctgtctc cgggtaaa                                                 1098


<210> SEQ ID NO 249
<211> LENGTH: 384
<212> TYPE: PRT
<213> ORGANISM: Artificial Sequence
<220> FEATURE:
<223> OTHER INFORMATION: IL-7-Fc knob (LALA P329G) (IL-7 N-terminal)

<400> SEQUENCE: 249

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His Gly Gly Gly Gly Ser Asp Lys Thr
145                 150                 155                 160

His Thr Cys Pro Pro Cys Pro Ala Pro Glu Ala Ala Gly Gly Pro Ser
                165                 170                 175

Val Phe Leu Phe Pro Pro Lys Pro Lys Asp Thr Leu Met Ile Ser Arg
            180                 185                 190

Thr Pro Glu Val Thr Cys Val Val Val Asp Val Ser His Glu Asp Pro
        195                 200                 205

Glu Val Lys Phe Asn Trp Tyr Val Asp Gly Val Glu Val His Asn Ala
    210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Ala Leu Gly Ala Pro Ile Glu Lys Thr
            260                 265                 270

Ile Ser Lys Ala Lys Gly Gln Pro Arg Glu Pro Gln Val Tyr Thr Leu
        275                 280                 285
```

-continued

```
Pro Pro Cys Arg Asp Glu Leu Thr Lys Asn Gln Val Ser Leu Trp Cys
    290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Lys Leu Thr Val Asp Lys Ser
            340                 345                 350

Arg Trp Gln Gln Gly Asn Val Phe Ser Cys Ser Val Met His Glu Ala
        355                 360                 365

Leu His Asn His Tyr Thr Gln Lys Ser Leu Ser Leu Ser Pro Gly Lys
    370                 375                 380


<210> SEQ ID NO 250
<211> LENGTH: 1152
<212> TYPE: DNA
<213> ORGANISM: Artificial Sequence
<220> FEATURE:
<223> OTHER INFORMATION: IL-7-Fc knob (LALA P329G) (IL-7 N-terminal)

<400> SEQUENCE: 250

gattgtgata ttgaaggtaa agatggcaaa caatatgaga gtgttctaat ggtcagcatc      60

gatcaattat tggacagcat gaaagaaatt ggtagcaatt gcctgaataa tgaatttaac     120

ttttttaaaa gacatatctg tgatgctaat aaggaaggta tgtttttatt ccgtgctgct     180

cgcaagttga ggcaatttct taaaatgaat agcactggtg attttgatct ccacttatta     240

aaagtttcag aaggcacaac aatactgttg aactgcactg gccaggttaa aggaagaaaa     300

ccagctgccc tgggtgaagc ccaaccaaca aagagtttgg aagaaaataa atctttaaag     360

gaacagaaaa aactgaatga cttgtgtttc ctaaagagac tattacaaga gataaaaact     420

tgttggaata aaattttgat gggcactaaa gaacacggtg gtggcggatc cgacaaaact     480

cacacatgcc caccgtgccc agcacctgaa gctgcagggg gaccgtcagt cttcctcttc     540

cccccaaaac ccaaggacac cctcatgatc tcccggaccc ctgaggtcac atgcgtggtg     600

gtggacgtga gccacgaaga ccctgaggtc aagttcaact ggtacgtgga cggcgtggag     660

gtgcataatg ccaagacaaa gccgcgggag gagcagtaca acagcacgta ccgtgtggtc     720

agcgtcctca ccgtcctgca ccaggactgg ctgaatggca aggagtacaa gtgcaaggtc     780

tccaacaaag ccctcggcgc ccccatcgag aaaaccatct ccaaagccaa agggcagccc     840

cgagaaccac aggtgtacac cctgccccca tgccgggatg agctgaccaa gaaccaggtc     900

agcctgtggt gcctggtcaa aggcttctat cccagcgaca tcgccgtgga gtgggagagc     960

aatgggcagc cggagaacaa ctacaagacc acgcctcccg tgctggactc cgacggctcc    1020

ttcttcctct acagcaagct caccgtggac aagagcaggt ggcagcaggg gaacgtcttc    1080

tcatgctccg tgatgcatga ggctctgcac aaccactaca cgcagaagag cctctccctg    1140

tctccgggta aa                                                        1152


<210> SEQ ID NO 251
<211> LENGTH: 398
<212> TYPE: PRT
<213> ORGANISM: Artificial Sequence
<220> FEATURE:
<223> OTHER INFORMATION: IFN-a-Fc knob (LALA P329G) (IFN-a N-terminal)

<400> SEQUENCE: 251

Ser Cys Asp Leu Pro Gln Thr His Ser Leu Gly Ser Arg Arg Thr Leu
```

-continued

```
1               5                   10                  15

Met Leu Leu Ala Gln Met Arg Lys Ile Ser Leu Phe Ser Cys Leu Lys
            20                  25                  30

Asp Arg His Asp Phe Gly Phe Pro Gln Glu Glu Phe Gly Asn Gln Phe
        35                  40                  45

Gln Lys Ala Glu Thr Ile Pro Val Leu His Glu Met Ile Gln Gln Ile
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu Gly Gly Gly Gly Ser Asp Lys Thr His Thr
                165                 170                 175

Cys Pro Pro Cys Pro Ala Pro Glu Ala Ala Gly Gly Pro Ser Val Phe
            180                 185                 190

Leu Phe Pro Pro Lys Pro Lys Asp Thr Leu Met Ile Ser Arg Thr Pro
        195                 200                 205

Glu Val Thr Cys Val Val Val Asp Val Ser His Glu Asp Pro Glu Val
    210                 215                 220

Lys Phe Asn Trp Tyr Val Asp Gly Val Glu Val His Asn Ala Lys Thr
225                 230                 235                 240

Lys Pro Arg Glu Glu Gln Tyr Asn Ser Thr Tyr Arg Val Val Ser Val
                245                 250                 255

Leu Thr Val Leu His Gln Asp Trp Leu Asn Gly Lys Glu Tyr Lys Cys
            260                 265                 270

Lys Val Ser Asn Lys Ala Leu Gly Ala Pro Ile Glu Lys Thr Ile Ser
        275                 280                 285

Lys Ala Lys Gly Gln Pro Arg Glu Pro Gln Val Tyr Thr Leu Pro Pro
    290                 295                 300

Cys Arg Asp Glu Leu Thr Lys Asn Gln Val Ser Leu Trp Cys Leu Val
305                 310                 315                 320

Lys Gly Phe Tyr Pro Ser Asp Ile Ala Val Glu Trp Glu Ser Asn Gly
                325                 330                 335

Gln Pro Glu Asn Asn Tyr Lys Thr Thr Pro Pro Val Leu Asp Ser Asp
            340                 345                 350

Gly Ser Phe Phe Leu Tyr Ser Lys Leu Thr Val Asp Lys Ser Arg Trp
        355                 360                 365

Gln Gln Gly Asn Val Phe Ser Cys Ser Val Met His Glu Ala Leu His
    370                 375                 380

Asn His Tyr Thr Gln Lys Ser Leu Ser Leu Ser Pro Gly Lys
385                 390                 395
```

<210> SEQ ID NO 252
<211> LENGTH: 1194
<212> TYPE: DNA
<213> ORGANISM: Artificial Sequence
<220> FEATURE:
<223> OTHER INFORMATION: IFN-a-Fc knob (LALA P329G) (IFN-a N-terminal)

<400> SEQUENCE: 252

```
agctgtgacc tgcctcagac acacagcctg ggcagccggc ggaccctgat gctgctggcc     60
cagatgcgga agatcagcct gttcagctgc ctgaaggacc ggcacgactt cggcttccct    120
caggaagagt tcggcaacca gttccagaag gccgagacaa tccccgtgct gcacgagatg    180
atccagcaga ttttcaacct gttcagcacc aaggacagca gcgccgcctg ggacgagaca    240
ctgctggaca agttctacac cgagctgtac cagcagctga acgacctgga agcctgcgtg    300
atccagggcg tgggcgtgac cgagacaccc ctgatgaagg aagatagcat cctggccgtg    360
cggaagtatt tccagcggat caccctgtac ctgaaagaga agaagtacag cccctgcgcc    420
tgggaggtcg tgcgggccga gatcatgcgg agcttcagcc tgagcaccaa cctgcaggaa    480
agcctgcgga gcaaagaggg tggtggcgga tccgacaaaa ctcacacatg cccaccgtgc    540
ccagcacctg aagctgcagg gggaccgtca gtcttcctct tccccccaaa acccaaggac    600
accctcatga tctcccggac ccctgaggtc acatgcgtgg tggtggacgt gagccacgaa    660
gaccctgagg tcaagttcaa ctggtacgtg gacggcgtgg aggtgcataa tgccaagaca    720
aagccgcggg aggagcagta caacagcacg taccgtgtgg tcagcgtcct caccgtcctg    780
caccaggact ggctgaatgg caaggagtac aagtgcaagg tctccaacaa agccctcggc    840
gcccccatcg agaaaaccat ctccaaagcc aaagggcagc cccgagaacc acaggtgtac    900
accctgcccc catgccggga tgagctgacc aagaaccagg tcagcctgtg gtgcctggtc    960
aaaggcttct atcccagcga catcgccgtg gagtgggaga gcaatgggca gccggagaac   1020
aactacaaga ccacgcctcc cgtgctggac tccgacggct ccttcttcct ctacagcaag   1080
ctcaccgtgg acaagagcag gtggcagcag gggaacgtct tctcatgctc cgtgatgcat   1140
gaggctctgc acaaccacta cacgcagaag agcctctccc tgtctccggg taaa         1194
```

<210> SEQ ID NO 253
<211> LENGTH: 593
<212> TYPE: PRT
<213> ORGANISM: Artificial Sequence
<220> FEATURE:
<223> OTHER INFORMATION: 28H1 Fab HC-Fc (LALA P329G)-IL-2 qm

<400> SEQUENCE: 253

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125
```

```
Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Gly Gly Gly
        435                 440                 445

Gly Ser Gly Gly Gly Gly Ser Gly Gly Gly Gly Ser Ala Pro Ala Ser
    450                 455                 460

Ser Ser Thr Lys Lys Thr Gln Leu Gln Leu Glu His Leu Leu Leu Asp
465                 470                 475                 480

Leu Gln Met Ile Leu Asn Gly Ile Asn Asn Tyr Lys Asn Pro Lys Leu
                485                 490                 495

Thr Arg Met Leu Thr Ala Lys Phe Ala Met Pro Lys Lys Ala Thr Glu
            500                 505                 510

Leu Lys His Leu Gln Cys Leu Glu Glu Glu Leu Lys Pro Leu Glu Glu
        515                 520                 525

Val Leu Asn Gly Ala Gln Ser Lys Asn Phe His Leu Arg Pro Arg Asp
    530                 535                 540

Leu Ile Ser Asn Ile Asn Val Ile Val Leu Glu Leu Lys Gly Ser Glu
```

545 550 555 560

Thr Thr Phe Met Cys Glu Tyr Ala Asp Glu Thr Ala Thr Ile Val Glu
565 570 575

Phe Leu Asn Arg Trp Ile Thr Phe Ala Gln Ser Ile Ile Ser Thr Leu
580 585 590

Thr

<210> SEQ ID NO 254
<211> LENGTH: 1779
<212> TYPE: DNA
<213> ORGANISM: Artificial Sequence
<220> FEATURE:
<223> OTHER INFORMATION: 28H1 Fab HC-Fc (LALA P329G)-IL-2 qm

<400> SEQUENCE: 254
gaagtgcagc tgctggaatc cggcggaggc ctggtgcagc ctggcggatc tctgagactg 60
tcctgcgccg cctccggctt caccttctcc tcccacgcca tgtcctgggt ccgacaggct 120
cctggcaaag gcctggaatg ggtgtccgcc atctgggcct ccggcgagca gtactacgcc 180
gactctgtga agggccggtt caccatctcc cgggacaact ccaagaacac cctgtacctg 240
cagatgaact ccctgcgggc cgaggacacc gccgtgtact actgtgccaa gggctggctg 300
ggcaacttcg actactgggg acagggcacc ctggtcaccg tgtccagcgc tagcaccaag 360
ggcccatcgg tcttccccct ggcaccctcc tccaagagca cctctggggg cacagcggcc 420
ctgggctgcc tggtcaagga ctacttcccc gaaccggtga cggtgtcgtg gaactcaggc 480
gccctgacca gcggcgtgca caccttcccg gctgtcctac agtcctcagg actctactcc 540
ctcagcagcg tggtgaccgt gccctccagc agcttgggca cccagaccta catctgcaac 600
gtgaatcaca agcccagcaa caccaaggtg gacaagaaag ttgagcccaa atcttgtgac 660
aaaactcaca catgcccacc gtgcccagca cctgaagctg caggggggacc gtcagtcttc 720 ctcttccccc caaaacccaa ggacaccctc atgatctccc ggacccctga ggtcacatgc 780
gtggtggtgg acgtgagcca cgaagaccct gaggtcaagt tcaactggta cgtggacggc 840
gtggaggtgc ataatgccaa gacaaagccg cgggaggagc agtacaacag cacgtaccgt 900
gtggtcagcg tcctcaccgt cctgcaccag gactggctga atggcaagga gtacaagtgc 960
aaggtctcca acaaagccct cggcgccccc atcgagaaaa ccatctccaa agccaaaggg 1020
cagccccgag aaccacaggt gtacaccctg cccccatccc gggatgagct gaccaagaac 1080
caggtcagcc tgacctgcct ggtcaaaggc ttctatccca gcgacatcgc cgtggagtgg 1140
gagagcaatg ggcagccgga gaacaactac aagaccacgc ctcccgtgct ggactccgac 1200
ggctccttct tcctctacag caagctcacc gtggacaaga gcaggtggca gcaggggaac 1260
gtcttctcat gctccgtgat gcatgaggct ctgcacaacc actacacgca gaagagcctc 1320
tccctgtctc cgggtggcgg cggaggctcc ggaggcggag gttctggcgg aggtggctcc 1380
gcacctgcct caagttctac aaagaaaaca cagctacaac tggagcattt actgctggat 1440
ttacagatga ttttgaatgg aattaataat tacaagaatc ccaaactcac caggatgctc 1500
acagccaagt ttgccatgcc caagaaggcc acagaactga aacatcttca gtgtctagaa 1560
gaagaactca aacctctgga ggaagtgcta aatggcgctc aaagcaaaaa ctttcactta 1620
agacccaggg acttaatcag caatatcaac gtaatagttc tggaactaaa gggatctgaa 1680
acaacattca tgtgtgaata tgctgatgag acagcaacca ttgtagaatt tctgaacaga 1740
tggattacct ttgcccaaag catcatctca acactgact 1779

<210> SEQ ID NO 255
<211> LENGTH: 473
<212> TYPE: PRT
<213> ORGANISM: Artificial Sequence
<220> FEATURE:
<223> OTHER INFORMATION: Murine IL-2R-beta-Fc(hole) fusion protein

<400> SEQUENCE: 255

Met Asp Met Arg Val Pro Ala Gln Leu Leu Gly Leu Leu Leu Leu Trp
1 5 10 15

Phe Pro Leu Leu Leu Leu Trp Phe Pro Gly Ala Arg Cys Ala Val Lys
20 25 30

Asn Cys Ser His Leu Glu Cys Phe Tyr Asn Ser Arg Ala Asn Val Ser
35 40 45

Cys Met Trp Ser His Glu Glu Ala Leu Asn Val Thr Thr Cys His Val
50 55 60

His Ala Lys Ser Asn Leu Arg His Trp Asn Lys Thr Cys Glu Leu Thr
65 70 75 80

Leu Val Arg Gln Ala Ser Trp Ala Cys Asn Leu Ile Leu Gly Ser Phe
85 90 95

Pro Glu Ser Gln Ser Leu Thr Ser Val Asp Leu Leu Asp Ile Asn Val
100 105 110

Val Cys Trp Glu Glu Lys Gly Trp Arg Arg Val Lys Thr Cys Asp Phe
115 120 125

His Pro Phe Asp Asn Leu Arg Leu Val Ala Pro His Ser Leu Gln Val
130 135 140

Leu His Ile Asp Thr Gln Arg Cys Asn Ile Ser Trp Lys Val Ser Gln
145 150 155 160

Val Ser His Tyr Ile Glu Pro Tyr Leu Glu Phe Glu Ala Arg Arg Arg
165 170 175

Leu Leu Gly His Ser Trp Glu Asp Ala Ser Val Leu Ser Leu Lys Gln
180 185 190

Arg Gln Gln Trp Leu Phe Leu Glu Met Leu Ile Pro Ser Thr Ser Tyr
195 200 205

Glu Val Gln Val Arg Val Lys Ala Gln Arg Asn Asn Thr Gly Thr Trp
210 215 220

Ser Pro Trp Ser Gln Pro Leu Thr Phe Arg Thr Arg Pro Ala Asp Pro
225 230 235 240

Met Lys Glu Gly Ala Gln Asp Lys Thr His Thr Cys Pro Pro Cys Pro
245 250 255

Ala Pro Glu Leu Leu Gly Gly Pro Ser Val Phe Leu Phe Pro Pro Lys
260 265 270

Pro Lys Asp Thr Leu Met Ile Ser Arg Thr Pro Glu Val Thr Cys Val
275 280 285

Val Val Asp Val Ser His Glu Asp Pro Glu Val Lys Phe Asn Trp Tyr
290 295 300

Val Asp Gly Val Glu Val His Asn Ala Lys Thr Lys Pro Arg Glu Glu
305 310 315 320

Gln Tyr Asn Ser Thr Tyr Arg Val Val Ser Val Leu Thr Val Leu His
325 330 335

Gln Asp Trp Leu Asn Gly Lys Glu Tyr Lys Cys Lys Val Ser Asn Lys
340 345 350

Ala Leu Pro Ala Pro Ile Glu Lys Thr Ile Ser Lys Ala Lys Gly Gln
355 360 365

Pro Arg Glu Pro Gln Val Cys Thr Leu Pro Pro Ser Arg Asp Glu Leu
    370                 375                 380

Thr Lys Asn Gln Val Ser Leu Ser Cys Ala Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Val Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 256
<211> LENGTH: 1422
<212> TYPE: DNA
<213> ORGANISM: Artificial Sequence
<220> FEATURE:
<223> OTHER INFORMATION: Murine IL-2R-beta-Fc(hole) fusion protein

<400> SEQUENCE: 256
atggacatga gggtccccgc tcagctcctg ggcctcctgc tgctctggtt ccccctcctg 60
ctgctctggt tcccaggtgc caggtgtgca gtgaaaaact gttcccatct tgaatgcttc 120
tacaactcaa gagccaatgt ctcttgcatg tggagccatg aagaggctct gaatgtcaca 180
acctgccacg tccatgccaa gtcgaacctg cgacactgga acaaaacctg tgagctaact 240
cttgtgaggc aggcatcctg ggcctgcaac ctgatcctcg ggtcgttccc agagtcccag 300
tcactgacct ccgtggacct ccttgacata aatgtggtgt gctgggaaga gaagggttgg 360
cgtagggtaa agacctgcga cttccatccc tttgacaacc ttcgcctggt ggcccctcat 420
tccctccaag ttctgcacat tgatacccag agatgtaaca taagctggaa ggtctcccag 480
gtctctcact acattgaacc atacttggaa tttgaggccc gtagacgtct tctgggccac 540
agctgggagg atgcatccgt attaagcctc aagcagagac agcagtggct cttcttggag 600
atgctgatcc ctagtacctc atatgaggtc caggtgaggg tcaaagctca acgaaacaat 660
accgggacct ggagtccctg gagccagccc ctgacctttc ggacaaggcc agcagatccc 720
atgaaggagg gagctcagga caaaactcac acatgcccac cgtgcccagc acctgaactc 780
ctggggggac cgtcagtctt cctcttcccc ccaaaaccca aggacaccct catgatctcc 840
cggacccctg aggtcacatg cgtggtggtg gacgtgagcc acgaagaccc tgaggtcaag 900
ttcaactggt acgtggacgg cgtggaggtg cataatgcca agacaaagcc gcgggaggag 960
cagtacaaca gcacgtaccg tgtggtcagc gtcctcaccg tcctgcacca ggactggctg 1020
aatggcaagg agtacaagtg caaggtctcc aacaaagccc tcccagcccc catcgagaaa 1080
accatctcca aagccaaagg gcagccccga gaaccacagg tgtgcaccct gcccccatcc 1140
cgggatgagc tgaccaagaa ccaggtcagc ctctcgtgcg cagtcaaagg cttctatccc 1200
agcgacatcg ccgtggagtg ggagagcaat gggcagccgg agaacaacta caagaccacg 1260
cctcccgtgc tggactccga cggctccttc ttcctcgtga gcaagctcac cgtggacaag 1320
agcaggtggc agcaggggaa cgtcttctca tgctccgtga tgcatgaggc tctgcacaac 1380
cactacacgc agaagagcct ctccctgtct ccgggtaaat ga 1422

<210> SEQ ID NO 257
<211> LENGTH: 500
<212> TYPE: PRT
<213> ORGANISM: Artificial Sequence
<220> FEATURE:
<223> OTHER INFORMATION: Murine IL-2R-gamma-Fc(knob) fusion protein

<400> SEQUENCE: 257

```
Met Asp Met Arg Val Pro Ala Gln Leu Leu Gly Leu Leu Leu Leu Trp
1               5                   10                  15

Phe Pro Leu Leu Leu Leu Trp Phe Pro Gly Ala Arg Cys Trp Ser Ser
            20                  25                  30

Lys Val Leu Met Ser Ser Ala Asn Glu Asp Ile Lys Ala Asp Leu Ile
        35                  40                  45

Leu Thr Ser Thr Ala Pro Glu His Leu Ser Ala Pro Thr Leu Pro Leu
    50                  55                  60

Pro Glu Val Gln Cys Phe Val Phe Asn Ile Glu Tyr Met Asn Cys Thr
65                  70                  75                  80

Trp Asn Ser Ser Ser Glu Pro Gln Ala Thr Asn Leu Thr Leu His Tyr
                85                  90                  95

Arg Tyr Lys Val Ser Asp Asn Asn Thr Phe Gln Glu Cys Ser His Tyr
            100                 105                 110

Leu Phe Ser Lys Glu Ile Thr Ser Gly Cys Gln Ile Gln Lys Glu Asp
        115                 120                 125

Ile Gln Leu Tyr Gln Thr Phe Val Val Gln Leu Gln Asp Pro Gln Lys
    130                 135                 140

Pro Gln Arg Arg Ala Val Gln Lys Leu Asn Leu Gln Asn Leu Val Ile
145                 150                 155                 160

Pro Arg Ala Pro Glu Asn Leu Thr Leu Ser Asn Leu Ser Glu Ser Gln
                165                 170                 175

Leu Glu Leu Arg Trp Lys Ser Arg His Ile Lys Glu Arg Cys Leu Gln
            180                 185                 190

Tyr Leu Val Gln Tyr Arg Ser Asn Arg Asp Arg Ser Trp Thr Glu Leu
        195                 200                 205

Ile Val Asn His Glu Pro Arg Phe Ser Leu Pro Ser Val Asp Glu Leu
    210                 215                 220

Lys Arg Tyr Thr Phe Arg Val Arg Ser Arg Tyr Asn Pro Ile Cys Gly
225                 230                 235                 240

Ser Ser Gln Gln Trp Ser Lys Trp Ser Gln Pro Val His Trp Gly Ser
                245                 250                 255

His Thr Val Glu Glu Asn Pro Ser Leu Phe Ala Leu Glu Ala Gly Ala
            260                 265                 270

Gln Asp Lys Thr His Thr Cys Pro Pro Cys Pro Ala Pro Glu Leu Leu
        275                 280                 285

Gly Gly Pro Ser Val Phe Leu Phe Pro Pro Lys Pro Lys Asp Thr Leu
    290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
        355                 360                 365
```

```
Gly Lys Glu Tyr Lys Cys Lys Val Ser Asn Lys Ala Leu Pro Ala Pro
    370                 375                 380

Ile Glu Lys Thr Ile Ser Lys Ala Lys Gly Gln Pro Arg Glu Pro Gln
385                 390                 395                 400

Val Tyr Thr Leu Pro Pro Cys Arg Asp Glu Leu Thr Lys Asn Gln Val
                405                 410                 415

Ser Leu Trp Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly Lys
            500


<210> SEQ ID NO 258
<211> LENGTH: 1503
<212> TYPE: DNA
<213> ORGANISM: Artificial Sequence
<220> FEATURE:
<223> OTHER INFORMATION: Murine IL-2R-gamma-Fc(knob) fusion protein

<400> SEQUENCE: 258

atggacatga gggtccccgc tcagctcctg ggcctcctgc tgctctggtt ccccctcctg     60

ctgctctggt tcccaggtgc caggtgttgg agttccaagg tcctcatgtc cagtgcgaat    120

gaagacatca aagctgattt gatcctgact tctacagccc ctgaacacct cagtgctcct    180

actctgcccc ttccagaggt tcagtgcttt gtgttcaaca tagagtacat gaattgcact    240

tggaatagca gttctgagcc tcaggcaacc aacctcacgc tgcactatag gtacaaggta    300

tctgataata atacattcca ggagtgcagt cactatttgt tctccaaaga gattacttct    360

ggctgtcaga tacaaaaaga agatatccag ctctaccaga catttgttgt ccagctccag    420

gacccccaga aaccccagag gcgagctgta cagaagctaa acctacagaa tcttgtgatc    480

ccacgggctc cagaaaatct aacactcagc aatctgagtg aatcccagct agagctgaga    540

tggaaaagca gacatattaa agaacgctgt ttacaatact tggtgcagta ccggagcaac    600

agagatcgaa gctggacgga actaatagtg aatcatgaac ctagattctc cctgcctagt    660

gtggatgagc tgaaacggta cacatttcgg gttcggagcc gctataaccc aatctgtgga    720

agttctcaac agtggagtaa atggagccag cctgtccact gggggagtca tactgtagag    780

gagaatcctt ccttgtttgc actggaagct ggagctcagg acaaaactca cacatgccca    840

ccgtgcccag cacctgaact cctgggggga ccgtcagtct tcctcttccc cccaaaaccc    900

aaggacaccc tcatgatctc ccggacccct gaggtcacat gcgtggtggt ggacgtgagc    960

cacgaagacc ctgaggtcaa gttcaactgg tacgtggacg gcgtggaggt gcataatgcc   1020

aagacaaagc cgcgggagga gcagtacaac agcacgtacc gtgtggtcag cgtcctcacc   1080

gtcctgcacc aggactggct gaatggcaag gagtacaagt gcaaggtctc caacaaagcc   1140

ctcccagccc ccatcgagaa aaccatctcc aaagccaaag ggcagccccg agaaccacag   1200

gtgtacaccc tgcccccatg ccgggatgag ctgaccaaga accaggtcag cctgtggtgc   1260
```

ctggtcaaag gcttctatcc cagcgacatc gccgtggagt gggagagcaa tgggcagccg 1320
gagaacaact acaagaccac gcctcccgtg ctggactccg acggctcctt cttcctctac 1380
agcaagctca ccgtggacaa gagcaggtgg cagcagggga acgtcttctc atgctccgtg 1440
atgcatgagg ctctgcacaa ccactacacg cagaagagcc tctccctgtc tccgggtaaa 1500
tga 1503

<210> SEQ ID NO 259
<211> LENGTH: 213
<212> TYPE: PRT
<213> ORGANISM: Artificial Sequence
<220> FEATURE:
<223> OTHER INFORMATION: Murine IL-2R alpha subunit + Avi-tag + His-tag

<400> SEQUENCE: 259

Met Gly Trp Ser Cys Ile Ile Leu Phe Leu Val Ala Thr Ala Thr Gly
1 5 10 15

Val His Ser Glu Leu Cys Leu Tyr Asp Pro Pro Glu Val Pro Asn Ala
20 25 30

Thr Phe Lys Ala Leu Ser Tyr Lys Asn Gly Thr Ile Leu Asn Cys Glu
35 40 45

Cys Lys Arg Gly Phe Arg Arg Leu Lys Glu Leu Val Tyr Met Arg Cys
50 55 60

Leu Gly Asn Ser Trp Ser Ser Asn Cys Gln Cys Thr Ser Asn Ser His
65 70 75 80

Asp Lys Ser Arg Lys Gln Val Thr Ala Gln Leu Glu His Gln Lys Glu
85 90 95

Gln Gln Thr Thr Thr Asp Met Gln Lys Pro Thr Gln Ser Met His Gln
100 105 110

Glu Asn Leu Thr Gly His Cys Arg Glu Pro Pro Pro Trp Lys His Glu
115 120 125

Asp Ser Lys Arg Ile Tyr His Phe Val Glu Gly Gln Ser Val His Tyr
130 135 140

Glu Cys Ile Pro Gly Tyr Lys Ala Leu Gln Arg Gly Pro Ala Ile Ser
145 150 155 160

Ile Cys Lys Met Lys Cys Gly Lys Thr Gly Trp Thr Gln Pro Gln Leu
165 170 175

Thr Cys Val Asp Glu Gln Leu Tyr Phe Gln Gly Gly Ser Gly Leu Asn
180 185 190

Asp Ile Phe Glu Ala Gln Lys Ile Glu Trp His Glu Ala Arg Ala His
195 200 205

His His His His His
210

<210> SEQ ID NO 260
<211> LENGTH: 642
<212> TYPE: DNA
<213> ORGANISM: Artificial Sequence
<220> FEATURE:
<223> OTHER INFORMATION: Murine IL-2R alpha subunit + Avi-tag + His-tag

<400> SEQUENCE: 260
atgggatgga gctgtatcat cctcttcttg gtagcaacag ctaccggtgt gcattccgaa 60
ctgtgtctgt atgacccacc cgaggtcccc aatgccacat tcaaagccct ctcctacaag 120
aacggcacca tcctaaactg tgaatgcaag agaggtttcc gaagactaaa ggaattggtc 180

-continued

```
tatatgcgtt gcttaggaaa ctcctggagc agcaactgcc agtgcaccag caactcccat    240

gacaaatcga gaaagcaagt tacagctcaa cttgaacacc agaaagagca acaaaccaca    300

acagacatgc agaagccaac acagtctatg caccaagaga accttacagg tcactgcagg    360

gagccacctc cttggaaaca tgaagattcc aagagaatct atcatttcgt ggaaggacag    420

agtgttcact acgagtgtat tccgggatac aaggctctac agagaggtcc tgctattagc    480

atctgcaaga tgaagtgtgg gaaaacgggg tggactcagc cccagctcac atgtgtcgac    540

gaacagttat attttcaggg cggctcaggc ctgaacgaca tcttcgaggc ccagaagatc    600

gagtggcacg aggctcgagc tcaccaccat caccatcact ga                       642
```

```
<210> SEQ ID NO 261
<211> LENGTH: 480
<212> TYPE: PRT
<213> ORGANISM: Artificial Sequence
<220> FEATURE:
<223> OTHER INFORMATION: Cynomolgous IL-2R-beta-Fc(knob) fusion protein
      + Avi-tag

<400> SEQUENCE: 261

Met Gly Trp Ser Cys Ile Ile Leu Phe Leu Val Ala Thr Ala Thr Gly
1               5                   10                  15

Val His Ser Ala Val Asn Gly Thr Ser Arg Phe Thr Cys Phe Tyr Asn
            20                  25                  30

Ser Arg Ala Asn Ile Ser Cys Val Trp Ser Gln Asp Gly Ala Leu Gln
        35                  40                  45

Asp Thr Ser Cys Gln Val His Ala Trp Pro Asp Arg Arg Arg Trp Asn
    50                  55                  60

Gln Thr Cys Glu Leu Leu Pro Val Ser Gln Ala Ser Trp Ala Cys Asn
65                  70                  75                  80

Leu Ile Leu Gly Thr Pro Asp Ser Gln Lys Leu Thr Ala Val Asp Ile
                85                  90                  95

Val Thr Leu Arg Val Met Cys Arg Glu Gly Val Arg Trp Arg Met Met
            100                 105                 110

Ala Ile Gln Asp Phe Lys Pro Phe Glu Asn Leu Arg Leu Met Ala Pro
        115                 120                 125

Ile Ser Leu Gln Val Val His Val Glu Thr His Arg Cys Asn Ile Ser
    130                 135                 140

Trp Lys Ile Ser Gln Ala Ser His Tyr Phe Glu Arg His Leu Glu Phe
145                 150                 155                 160

Glu Ala Arg Thr Leu Ser Pro Gly His Thr Trp Glu Glu Ala Pro Leu
                165                 170                 175

Met Thr Leu Lys Gln Lys Gln Glu Trp Ile Cys Leu Glu Thr Leu Thr
            180                 185                 190

Pro Asp Thr Gln Tyr Glu Phe Gln Val Arg Val Lys Pro Leu Gln Gly
        195                 200                 205

Glu Phe Thr Thr Trp Ser Pro Trp Ser Gln Pro Leu Ala Phe Arg Thr
    210                 215                 220

Lys Pro Ala Ala Leu Gly Lys Asp Thr Gly Ala Gln Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
```

```
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
        355                 360                 365

Pro Cys Arg Asp Glu Leu Thr Lys Asn Gln Val Ser Leu Trp Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys Ser
    450                 455                 460

Gly Gly Leu Asn Asp Ile Phe Glu Ala Gln Lys Ile Glu Trp His Glu
465                 470                 475                 480
```

<210> SEQ ID NO 262
<211> LENGTH: 1443
<212> TYPE: DNA
<213> ORGANISM: Artificial Sequence
<220> FEATURE:
<223> OTHER INFORMATION: Cynomolgous IL-2R-beta-Fc(knob) fusion protein + Avi-tag

<400> SEQUENCE: 262

```
atgggatgga gctgtatcat cctcttcttg gtagcaacag ctaccggtgt gcattccgcg      60

gtcaacggca cttcccggtt cacatgcttc tacaactcga gagccaacat ctcctgtgtc     120

tggagccaag atggggctct gcaggacact tcctgccaag tccacgcctg gccggacaga     180

cggcggtgga accaaacctg tgagctgctc cctgtgagtc aagcatcctg ggcctgcaac     240

ctgatcctcg gaaccccaga ttctcagaaa ctgaccgcag tggatatcgt caccctgagg     300

gtgatgtgcc gtgaaggggt gcgatggagg atgatggcca tccaggactt caaacccttt     360

gagaaccttc gcctgatggc ccccatctcc ctccaagtcg tccacgtgga gacccacaga     420

tgcaacataa gctggaaaat ctcccaagcc tcccactact ttgaaagaca cctggagttt     480

gaggcccgga cgctgtcccc aggccacacc tgggaggagg ccccccctgat gaccctcaag     540

cagaagcagg aatggatctg cctggagacg ctcaccccag acacccagta tgagtttcag     600

gtgcgggtca agcctctgca aggcgagttc acgacctgga gcccctggag ccagcccctg     660

gccttcagga caaagcctgc agcccttggg aaggacaccg gagctcagga caaaactcac     720

acatgcccac cgtgcccagc acctgaactc ctgggggggac cgtcagtctt cctcttcccc     780

ccaaaaccca aggacaccct catgatctcc cggacccctg aggtcacatg cgtggtggtg     840

gacgtgagcc acgaagaccc tgaggtcaag ttcaactggt acgtggacgg cgtggaggtg     900
```

```
cataatgcca agacaaagcc gcgggaggag cagtacaaca gcacgtaccg tgtggtcagc    960

gtcctcaccg tcctgcacca ggactggctg aatggcaagg agtacaagtg caaggtctcc   1020

aacaaagccc tcccagcccc catcgagaaa accatctcca aagccaaagg gcagccccga   1080

gaaccacagg tgtacaccct gcccccatgc cgggatgagc tgaccaagaa ccaggtcagc   1140

ctgtggtgcc tggtcaaagg cttctatccc agcgacatcg ccgtggagtg ggagagcaat   1200

gggcagccgg agaacaacta caagaccacg cctcccgtgc tggactccga cggctccttc   1260

ttcctctaca gcaagctcac cgtggacaag agcaggtggc agcaggggaa cgtcttctca   1320

tgctccgtga tgcatgaggc tctgcacaac cactacacgc agaagagcct ctccctgtct   1380

ccgggtaaat ccggaggcct gaacgacatc ttcgaggccc agaagattga atggcacgag   1440

tga                                                                 1443
```

<210> SEQ ID NO 263
<211> LENGTH: 489
<212> TYPE: PRT
<213> ORGANISM: Artificial Sequence
<220> FEATURE:
<223> OTHER INFORMATION: Cynomolgous IL-2R-gamma-Fc(hole) fusion protein

<400> SEQUENCE: 263

```
Met Gly Trp Ser Cys Ile Ile Leu Phe Leu Val Ala Thr Ala Thr Gly
1               5                   10                  15

Val His Ser Leu Asn Thr Thr Ile Leu Thr Pro Asn Gly Asn Glu Asp
            20                  25                  30

Ala Thr Thr Asp Phe Phe Leu Thr Ser Met Pro Thr Asp Ser Leu Ser
        35                  40                  45

Val Ser Thr Leu Pro Leu Pro Glu Val Gln Cys Phe Val Phe Asn Val
    50                  55                  60

Glu Tyr Met Asn Cys Thr Trp Asn Ser Ser Ser Glu Pro Gln Pro Thr
65                  70                  75                  80

Asn Leu Thr Leu His Tyr Trp Tyr Lys Asn Ser Asp Asn Asp Lys Val
                85                  90                  95

Gln Lys Cys Ser His Tyr Leu Phe Ser Glu Glu Ile Thr Ser Gly Cys
            100                 105                 110

Gln Leu Gln Lys Lys Glu Ile His Leu Tyr Gln Thr Phe Val Val Gln
        115                 120                 125

Leu Gln Asp Pro Arg Glu Pro Arg Arg Gln Ala Thr Gln Met Leu Lys
    130                 135                 140

Leu Gln Asn Leu Val Ile Pro Trp Ala Pro Glu Asn Leu Thr Leu Arg
145                 150                 155                 160

Lys Leu Ser Glu Ser Gln Leu Glu Leu Asn Trp Asn Asn Arg Phe Leu
                165                 170                 175

Asn His Cys Leu Glu His Leu Val Gln Tyr Arg Thr Asp Trp Asp His
            180                 185                 190

Ser Trp Thr Glu Gln Ser Val Asp Tyr Arg His Lys Phe Ser Leu Pro
        195                 200                 205

Ser Val Asp Gly Gln Lys Arg Tyr Thr Phe Arg Val Arg Ser Arg Phe
    210                 215                 220

Asn Pro Leu Cys Gly Ser Ala Gln His Trp Ser Glu Trp Ser His Pro
225                 230                 235                 240

Ile His Trp Gly Ser Asn Ser Ser Lys Glu Asn Pro Phe Leu Phe Ala
                245                 250                 255

Leu Glu Ala Gly Ala Gln Asp Lys Thr His Thr Cys Pro Pro Cys Pro
```

-continued

```
            260                 265                 270

Ala Pro Glu Leu Leu Gly Gly Pro Ser Val Phe Leu Phe Pro Pro Lys
        275                 280                 285

Pro Lys Asp Thr Leu Met Ile Ser Arg Thr Pro Glu Val Thr Cys Val
    290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
                325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
        355                 360                 365

Ala Leu Gly Ala Pro Ile Glu Lys Thr Ile Ser Lys Ala Lys Gly Gln
    370                 375                 380

Pro Arg Glu Pro Gln Val Cys Thr Leu Pro Pro Ser Arg Asp Glu Leu
385                 390                 395                 400

Thr Lys Asn Gln Val Ser Leu Ser Cys Ala Val Lys Gly Phe Tyr Pro
                405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
        435                 440                 445

Val Ser Lys Leu Thr Val Asp Lys Ser Arg Trp Gln Gln Gly Asn Val
    450                 455                 460

Phe Ser Cys Ser Val Met His Glu Ala Leu His Asn His Tyr Thr Gln
465                 470                 475                 480

Lys Ser Leu Ser Leu Ser Pro Gly Lys
                485
```

```
<210> SEQ ID NO 264
<211> LENGTH: 1470
<212> TYPE: DNA
<213> ORGANISM: Artificial Sequence
<220> FEATURE:
<223> OTHER INFORMATION: Cynomolgous IL-2R-gamma-Fc(hole) fusion protein

<400> SEQUENCE: 264

atgggatgga gctgtatcat cctcttcttg gtagcaacag ctaccggtgt gcattccctg      60

aacacgacaa ttctgacgcc caatgggaat gaagacgcca caactgattt cttcctgacc     120

tctatgccca ctgactccct cagtgtttcc actctgcccc tcccagaggt tcagtgtttt     180

gtgttcaatg tcgagtacat gaattgcact tggaacagca gctctgagcc ccagcctacc     240

aacctcactc tgcattattg gtacaagaat tcggataatg ataaagtcca gaagtgcagc     300

cactatctat tctctgaaga aatcacttct ggctgtcagt tgcaaaaaaa ggagatccac     360

ctctaccaaa cgtttgttgt tcagctccag gacccacggg aacccaggag acaggccaca     420

cagatgctaa aactgcagaa tctggtgatc ccctgggctc cggagaacct aacacttcgc     480

aaactgagtg aatcccagct agaactgaac tggaacaaca gattcttgaa ccactgtttg     540

gagcacttgg tgcagtaccg gactgactgg gaccacagct ggactgaaca atcagtggat     600

tatagacata agttctcctt gcctagtgtg gatgggcaga aacgctacac gtttcgtgtc     660

cggagccgct ttaacccact ctgtggaagt gctcagcatt ggagtgaatg gagccaccca     720

atccactggg ggagcaatag ttcaaaagag aatcctttcc tgtttgcatt ggaagccgga     780
```

gctcaggaca aaactcacac atgcccaccg tgcccagcac ctgaactcct gggggaccg 840 tcagtcttcc tcttcccccc aaaacccaag gacaccctca tgatctcccg gacccctgag 900
gtcacatgcg tggtggtgga cgtgagccac gaagaccctg aggtcaagtt caactggtac 960
gtggacggcg tggaggtgca taatgccaag acaaagccgc gggaggagca gtacaacagc 1020
acgtaccgtg tggtcagcgt cctcaccgtc ctgcaccagg actggctgaa tggcaaggag 1080
tacaagtgca aggtctccaa caaagccctc ggcgccccca tcgagaaaac catctccaaa 1140
gccaaagggc agccccgaga accacaggtg tgcaccctgc ccccatcccg ggatgagctg 1200
accaagaacc aggtcagcct ctcgtgcgca gtcaaaggct tctatcccag cgacatcgcc 1260
gtggagtggg agagcaatgg gcagccggag aacaactaca agaccacgcc tcccgtgctg 1320
gactccgacg gctccttctt cctcgtgagc aagctcaccg tggacaagag caggtggcag 1380
caggggaacg tcttctcatg ctccgtgatg catgaggctc tgcacaacca ctacacgcag 1440
aagagcctct ccctgtctcc gggtaaatga 1470

<210> SEQ ID NO 265
<211> LENGTH: 217
<212> TYPE: PRT
<213> ORGANISM: Artificial Sequence
<220> FEATURE:
<223> OTHER INFORMATION: Cynomolgous IL-2R alpha subunit + Avi-tag + His-tag

<400> SEQUENCE: 265

Met Gly Trp Ser Cys Ile Ile Leu Phe Leu Val Ala Thr Ala Thr Gly
1 5 10 15

Glu Leu Cys Asp Asp Asp Pro Pro Lys Ile Thr His Ala Thr Phe Lys
20 25 30

Ala Met Ala Tyr Lys Glu Gly Thr Met Leu Asn Cys Glu Cys Lys Arg
35 40 45

Gly Phe Arg Arg Ile Lys Ser Gly Ser Pro Tyr Met Leu Cys Thr Gly
50 55 60

Asn Ser Ser His Ser Ser Trp Asp Asn Gln Cys Gln Cys Thr Ser Ser
65 70 75 80

Ala Ala Arg Asn Thr Thr Lys Gln Val Thr Pro Gln Pro Glu Glu Gln
85 90 95

Lys Glu Arg Lys Thr Thr Glu Met Gln Ser Gln Met Gln Leu Ala Asp
100 105 110

Gln Val Ser Leu Pro Gly His Cys Arg Glu Pro Pro Pro Trp Glu Asn
115 120 125

Glu Ala Thr Glu Arg Ile Tyr His Phe Val Val Gly Gln Thr Val Tyr
130 135 140

Tyr Gln Cys Val Gln Gly Tyr Arg Ala Leu His Arg Gly Pro Ala Glu
145 150 155 160

Ser Val Cys Lys Met Thr His Gly Lys Thr Arg Trp Thr Gln Pro Gln
165 170 175

Leu Ile Cys Thr Gly Glu Val Asp Glu Gln Leu Tyr Phe Gln Gly Gly
180 185 190

Ser Gly Leu Asn Asp Ile Phe Glu Ala Gln Lys Ile Glu Trp His Glu
195 200 205

Ala Arg Ala His His His His His His
210 215

<210> SEQ ID NO 266
<211> LENGTH: 654
<212> TYPE: DNA
<213> ORGANISM: Artificial Sequence
<220> FEATURE:
<223> OTHER INFORMATION: Cynomolgous IL-2R alpha subunit + Avi-tag + His-tag

<400> SEQUENCE: 266

```
atgggatgga gctgtatcat cctcttcttg gtagcaacag ctaccggtga gctctgtgac     60

gatgacccgc caaaaatcac acatgccaca ttcaaagcca tggcctacaa ggaaggaacc    120

atgttgaact gtgaatgcaa gagaggtttc cgcagaataa aaagcgggtc accctatatg    180

ctctgtacag gaaactctag ccactcgtcc tgggacaacc aatgtcaatg cacaagctct    240

gctgctcgga acacaacaaa acaagtgaca cctcaacctg aagaacagaa agaaagaaaa    300

accacagaaa tgcaaagtca aatgcagctg gcggaccaag tgagccttcc aggtcactgc    360

agggaacctc caccgtggga aaatgaagcc acagaaagaa tttatcattt cgtggtgggg    420

cagacggttt actaccagtg cgtccaggga tacagggctc tacacagagg tcctgctgag    480

agcgtctgca aaatgaccca cgggaagaca agatggaccc agccccagct catatgcaca    540

ggtgaagtcg acgaacagtt atattttcag ggcggctcag gcctgaacga catcttcgag    600

gcccagaaga tcgagtggca cgaggctcga gctcaccacc atcaccatca ctga          654
```

<210> SEQ ID NO 267
<211> LENGTH: 474
<212> TYPE: PRT
<213> ORGANISM: Artificial Sequence
<220> FEATURE:
<223> OTHER INFORMATION: Human IL-10R1-Fc fusion + Avi-tag

<400> SEQUENCE: 267

```
His Gly Thr Glu Leu Pro Ser Pro Pro Ser Val Trp Phe Glu Ala Glu
1               5                   10                  15

Phe Phe His His Ile Leu His Trp Thr Pro Ile Pro Asn Gln Ser Glu
            20                  25                  30

Ser Thr Cys Tyr Glu Val Ala Leu Leu Arg Tyr Gly Ile Glu Ser Trp
        35                  40                  45

Asn Ser Ile Ser Asn Cys Ser Gln Thr Leu Ser Tyr Asp Leu Thr Ala
    50                  55                  60

Val Thr Leu Asp Leu Tyr His Ser Asn Gly Tyr Arg Ala Arg Val Arg
65                  70                  75                  80

Ala Val Asp Gly Ser Arg His Ser Asn Trp Thr Val Thr Asn Thr Arg
                85                  90                  95

Phe Ser Val Asp Glu Val Thr Leu Thr Val Gly Ser Val Asn Leu Glu
            100                 105                 110

Ile His Asn Gly Phe Ile Leu Gly Lys Ile Gln Leu Pro Arg Pro Lys
        115                 120                 125

Met Ala Pro Ala Asn Asp Thr Tyr Glu Ser Ile Phe Ser His Phe Arg
    130                 135                 140

Glu Tyr Glu Ile Ala Ile Arg Lys Val Pro Gly Asn Phe Thr Phe Thr
145                 150                 155                 160

His Lys Lys Val Lys His Glu Asn Phe Ser Leu Leu Thr Ser Gly Glu
                165                 170                 175

Val Gly Glu Phe Cys Val Gln Val Lys Pro Ser Val Ala Ser Arg Ser
            180                 185                 190

Asn Lys Gly Met Trp Ser Lys Glu Glu Cys Ile Ser Leu Thr Arg Gln
```

-continued

```
        195                 200                 205

Tyr Phe Thr Val Thr Asn Val Asp Glu Gln Leu Tyr Phe Gln Gly Gly
    210                 215                 220

Ser Pro Lys Ser Ala Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Gly Gly Ser Gly Gly Leu Asn Asp Ile
    450                 455                 460

Phe Glu Ala Gln Lys Ile Glu Trp His Glu
465                 470
```

<210> SEQ ID NO 268
<211> LENGTH: 1422
<212> TYPE: DNA
<213> ORGANISM: Artificial Sequence
<220> FEATURE:
<223> OTHER INFORMATION: Human IL-10R1-Fc fusion + Avi-tag

<400> SEQUENCE: 268

```
catgggacag agctgcccag ccctccgtct gtgtggtttg aagcagaatt tttccaccac     60

atcctccact ggacacccat cccaaatcag tctgaaagta cctgctatga agtggcactc    120

ctgaggtatg gaatagagtc ctggaactcc atctccaact gtagccagac cctgtcctat    180

gaccttaccg cagtgacctt ggacctgtac cacagcaatg gctaccgggc cagagtgcgg    240

gctgtggacg gcagccggca ctccaactgg accgtcacca acacccgctt ctctgtggat    300

gaagtgactc tgacagttgg cagtgtgaac ctagagatcc acaatggctt catcctcggg    360

aagattcagc tacccaggcc caagatggcc cccgcaaatg acacatatga aagcatcttc    420

agtcacttcc gagagtatga gattgccatt cgcaaggtgc cgggaaactt cacgttcaca    480
```

-continued

```
cacaagaaag taaaacatga aaacttcagc ctcctaacct ctggagaagt gggagagttc    540

tgtgtccagg tgaaaccatc tgtcgcttcc cgaagtaaca aggggatgtg gtctaaagag    600

gagtgcatct ccctcaccag gcagtatttc accgtgacca acgtcgacga acagttatat    660

tttcagggcg gctcacccaa atctgcagac aaaactcaca catgcccacc gtgcccagca    720

cctgaactcc tgggggggacc gtcagtcttc ctcttccccc caaaacccaa ggacaccctc    780

atgatctccc ggacccctga ggtcacatgc gtggtggtgg acgtgagcca cgaagaccct    840

gaggtcaagt tcaactggta cgtggacggc gtggaggtgc ataatgccaa gacaaagccg    900

cgggaggagc agtacaacag cacgtaccgt gtggtcagcg tcctcaccgt cctgcaccag    960

gactggctga atggcaagga gtacaagtgc aaggtctcca acaaagccct cccagccccc   1020

atcgagaaaa ccatctccaa agccaaaggg cagccccgag aaccacaggt gtacaccctg   1080

cccccatccc gggatgagct gaccaagaac caggtcagcc tgacctgcct ggtcaaaggc   1140

ttctatccca gcgacatcgc cgtggagtgg gagagcaatg ggcagccgga gaacaactac   1200

aagaccacgc ctcccgtgct ggactccgac ggctccttct tcctctacag caagctcacc   1260

gtggacaaga gcaggtggca gcaggggaac gtcttctcat gctccgtgat gcatgaggct   1320

ctgcacaacc actacacgca gaagagcctc tccctgtctc cgggtggcgg gtccggaggc   1380

ctgaacgaca tcttcgaggc ccagaagatt gaatggcacg ag                      1422
```

<210> SEQ ID NO 269
<211> LENGTH: 593
<212> TYPE: PRT
<213> ORGANISM: Artificial Sequence
<220> FEATURE:
<223> OTHER INFORMATION: 28H1 Fab HC-Fc knob (LALA P329G)-IL-2 qm (2)

<400> SEQUENCE: 269

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
```

```
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Cys Arg Asp Glu Leu Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Gly Gly Gly
        435                 440                 445

Gly Ser Gly Gly Gly Gly Ser Gly Gly Gly Gly Ser Ala Pro Ala Ser
    450                 455                 460

Ser Ser Thr Lys Lys Thr Gln Leu Gln Leu Glu His Leu Leu Leu Asp
465                 470                 475                 480

Leu Gln Met Ile Leu Asn Gly Ile Asn Asn Tyr Lys Asn Pro Lys Leu
                485                 490                 495

Thr Arg Met Leu Thr Ala Lys Phe Ala Met Pro Lys Lys Ala Thr Glu
            500                 505                 510

Leu Lys His Leu Gln Cys Leu Glu Glu Glu Leu Lys Pro Leu Glu Glu
        515                 520                 525

Val Leu Asn Gly Ala Gln Ser Lys Asn Phe His Leu Arg Pro Arg Asp
    530                 535                 540

Leu Ile Ser Asn Ile Asn Val Ile Val Leu Glu Leu Lys Gly Ser Glu
545                 550                 555                 560

Thr Thr Phe Met Cys Glu Tyr Ala Asp Glu Thr Ala Thr Ile Val Glu
                565                 570                 575

Phe Leu Asn Arg Trp Ile Thr Phe Ala Gln Ser Ile Ile Ser Thr Leu
            580                 585                 590

Thr
```

<210> SEQ ID NO 270
<211> LENGTH: 1779

<212> TYPE: DNA
<213> ORGANISM: Artificial Sequence
<220> FEATURE:
<223> OTHER INFORMATION: 28H1 Fab HC-Fc knob (LALA P329G)-IL-2 qm (2)

<400> SEQUENCE: 270

```
gaagtgcagc tgctggaatc cggcggaggc ctggtgcagc ctggcggatc tctgagactg     60

tcctgcgccg cctccggctt caccttctcc tcccacgcca tgtcctgggt ccgacaggct    120

cctggcaaag gcctggaatg ggtgtccgcc atctgggcct ccggcgagca gtactacgcc    180

gactctgtga agggccggtt caccatctcc cgggacaact ccaagaacac cctgtacctg    240

cagatgaact ccctgcgggc cgaggacacc gccgtgtact actgtgccaa gggctggctg    300

ggcaacttcg actactgggg acagggcacc ctggtcaccg tgtccagcgc tagcaccaag    360

ggcccatcgg tcttccccct ggcaccctcc tccaagagca cctctggggg cacagcggcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgaccgt gccctccagc agcttgggca cccagaccta catctgcaac    600

gtgaatcaca agcccagcaa caccaaggtg gacaagaaag ttgagcccaa atcttgtgac    660

aaaactcaca catgcccacc gtgcccagca cctgaagctg caggggggacc gtcagtcttc    720

ctcttccccc caaaacccaa ggacaccctc atgatctccc ggacccctga ggtcacatgc    780

gtggtggtgg acgtgagcca cgaagaccct gaggtcaagt tcaactggta cgtggacggc    840

gtggaggtgc ataatgccaa gacaaagccg cgggaggagc agtacaacag cacgtaccgt    900

gtggtcagcg tcctcaccgt cctgcaccag gactggctga atggcaagga gtacaagtgc    960

aaggtctcca acaaagccct cggcgccccc atcgagaaaa ccatctccaa agccaaaggg   1020

cagccccgag aaccacaggt gtacaccctg cccccatgcc gggatgagct gaccaagaac   1080

caggtcagcc tgtggtgcct ggtcaaaggc ttctatccca gcgacatcgc cgtggagtgg   1140

gagagcaatg ggcagccgga gaacaactac aagaccacgc ctcccgtgct ggactccgac   1200

ggctccttct tcctctacag caagctcacc gtggacaaga gcaggtggca gcaggggaac   1260

gtcttctcat gctccgtgat gcatgaggct ctgcacaacc actacacgca gaagagcctc   1320

tccctgtctc cgggtggcgg cggaggctcc ggaggcggag gttctggcgg aggtggctcc   1380

gcacctgcct caagttctac aaagaaaaca cagctacaac tggagcattt actgctggat   1440

ttacagatga ttttgaatgg aattaataat tacaagaatc ccaaactcac caggatgctc   1500

acagccaagt ttgccatgcc caagaaggcc acagaactga aacatcttca gtgtctagaa   1560

gaagaactca aacctctgga ggaagtgcta aatggcgctc aaagcaaaaa ctttcactta   1620

agacccaggg acttaatcag caatatcaac gtaatagttc tggaactaaa gggatctgaa   1680

acaacattca tgtgtgaata tgctgatgag acagcaacca ttgtagaatt tctgaacaga   1740

tggattacct ttgcccaaag catcatctca acactgact                          1779
```

<210> SEQ ID NO 271
<211> LENGTH: 594
<212> TYPE: PRT
<213> ORGANISM: Artificial Sequence
<220> FEATURE:
<223> OTHER INFORMATION: 4B9 Fab HC-Fc knob (LALA P329G)-IL-2 qm (2)

<400> SEQUENCE: 271

```
Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Arg Asp Glu Leu Thr Lys Asn Gln Val Ser Leu Trp Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430
```

```
His Asn His Tyr Thr Gln Lys Ser Leu Ser Leu Ser Pro Gly Gly Gly
        435                 440                 445

Gly Gly Ser Gly Gly Gly Gly Ser Gly Gly Gly Gly Ser Ala Pro Ala
    450                 455                 460

Ser Ser Ser Thr Lys Lys Thr Gln Leu Gln Leu Glu His Leu Leu Leu
465                 470                 475                 480

Asp Leu Gln Met Ile Leu Asn Gly Ile Asn Asn Tyr Lys Asn Pro Lys
                485                 490                 495

Leu Thr Arg Met Leu Thr Ala Lys Phe Ala Met Pro Lys Lys Ala Thr
            500                 505                 510

Glu Leu Lys His Leu Gln Cys Leu Glu Glu Glu Leu Lys Pro Leu Glu
        515                 520                 525

Glu Val Leu Asn Gly Ala Gln Ser Lys Asn Phe His Leu Arg Pro Arg
    530                 535                 540

Asp Leu Ile Ser Asn Ile Asn Val Ile Val Leu Glu Leu Lys Gly Ser
545                 550                 555                 560

Glu Thr Thr Phe Met Cys Glu Tyr Ala Asp Glu Thr Ala Thr Ile Val
                565                 570                 575

Glu Phe Leu Asn Arg Trp Ile Thr Phe Ala Gln Ser Ile Ile Ser Thr
            580                 585                 590

Leu Thr
```

<210> SEQ ID NO 272
<211> LENGTH: 1782
<212> TYPE: DNA
<213> ORGANISM: Artificial Sequence
<220> FEATURE:
<223> OTHER INFORMATION: 4B9 Fab HC-Fc knob (LALA P329G)-IL-2 qm (2)

<400> SEQUENCE: 272

```
gaggtgcagc tgctcgaaag cggcggagga ctggtgcagc ctggcggcag cctgagactg     60

tcttgcgccg ccagcggctt caccttcagc agctacgcca tgagctgggt ccgccaggcc    120

cctggcaagg gactggaatg ggtgtccgcc atcatcggct ctggcgccag cacctactac    180

gccgacagcg tgaagggccg gttcaccatc agccgggaca acagcaagaa caccctgtac    240

ctgcagatga acagcctgcg ggccgaggac accgccgtgt actactgcgc caagggatgg    300

ttcggcggct tcaactactg gggacagggc accctggtca cagtgtccag cgctagcacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga aagttgagcc caaatcttgt    660

gacaaaactc acacatgccc accgtgccca gcacctgaag ctgcaggggg accgtcagtc    720

ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840

ggcgtggagg tgcataatgc caagacaaag ccgcgggagg agcagtacaa cagcacgtac    900

cgtgtggtca gcgtcctcac cgtcctgcac caggactggc tgaatggcaa ggagtacaag    960

tgcaaggtct ccaacaaagc cctcggcgcc cccatcgaga aaaccatctc caaagccaaa   1020

gggcagcccc gagaaccaca ggtgtacacc ctgcccccat gccgggatga gctgaccaag   1080

aaccaggtca gcctgtggtg cctggtcaaa ggcttctatc ccagcgacat cgccgtggag   1140
```

```
tgggagagca atgggcagcc ggagaacaac tacaagacca cgcctcccgt gctggactcc   1200

gacggctcct tcttcctcta cagcaagctc accgtggaca agagcaggtg gcagcagggg   1260

aacgtcttct catgctccgt gatgcatgag gctctgcaca accactacac gcagaagagc   1320

ctctccctgt ctccgggtgg cggcggaggc tccggaggcg gaggttctgg cggaggtggc   1380

tccgcacctg cctcaagttc tacaaagaaa acacagctac aactggagca tttactgctg   1440

gatttacaga tgattttgaa tggaattaat aattacaaga atcccaaact caccaggatg   1500

ctcacagcca agtttgccat gcccaagaag gccacagaac tgaaacatct tcagtgtcta   1560

gaagaagaac tcaaacctct ggaggaagtg ctaaatggcg ctcaaagcaa aaactttcac   1620

ttaagaccca gggacttaat cagcaatatc aacgtaatag ttctggaact aaagggatct   1680

gaaacaacat tcatgtgtga atatgctgat gagacagcaa ccattgtaga atttctgaac   1740

agatggatta cctttgccca aagcatcatc tcaacactga ct                      1782
```

<210> SEQ ID NO 273
<211> LENGTH: 594
<212> TYPE: PRT
<213> ORGANISM: Artificial Sequence
<220> FEATURE:
<223> OTHER INFORMATION: 4B9 Fab HC-Fc knob (LALA P329G)-IL-2 wt

<400> SEQUENCE: 273

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
```

```
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Arg Asp Glu Leu Thr Lys Asn Gln Val Ser Leu Trp Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Gly Ser Gly Gly Gly Gly Ser Ala Pro Thr
    450                 455                 460

Ser Ser Ser Thr Lys Lys Thr Gln Leu Gln Leu Glu His Leu Leu Leu
465                 470                 475                 480

Asp Leu Gln Met Ile Leu Asn Gly Ile Asn Asn Tyr Lys Asn Pro Lys
                485                 490                 495

Leu Thr Arg Met Leu Thr Phe Lys Phe Tyr Met Pro Lys Lys Ala Thr
            500                 505                 510

Glu Leu Lys His Leu Gln Cys Leu Glu Glu Glu Leu Lys Pro Leu Glu
        515                 520                 525

Glu Val Leu Asn Leu Ala Gln Ser Lys Asn Phe His Leu Arg Pro Arg
    530                 535                 540

Asp Leu Ile Ser Asn Ile Asn Val Ile Val Leu Glu Leu Lys Gly Ser
545                 550                 555                 560

Glu Thr Thr Phe Met Cys Glu Tyr Ala Asp Glu Thr Ala Thr Ile Val
                565                 570                 575

Glu Phe Leu Asn Arg Trp Ile Thr Phe Ala Gln Ser Ile Ile Ser Thr
            580                 585                 590

Leu Thr
```

<210> SEQ ID NO 274
<211> LENGTH: 1782
<212> TYPE: DNA
<213> ORGANISM: Artificial Sequence
<220> FEATURE:
<223> OTHER INFORMATION: 4B9 Fab HC-Fc knob (LALA P329G)-IL-2 wt

<400> SEQUENCE: 274

```
gaggtgcagc tgctcgaaag cggcggagga ctggtgcagc ctggcggcag cctgagactg      60
```

```
tcttgcgccg ccagcggctt caccttcagc agctacgcca tgagctgggt ccgccaggcc    120

cctggcaagg gactggaatg ggtgtccgcc atcatcggct ctggcgccag cacctactac    180

gccgacagcg tgaagggccg gttcaccatc agccgggaca acagcaagaa caccctgtac    240

ctgcagatga acagcctgcg ggccgaggac accgccgtgt actactgcgc caagggatgg    300

ttcggcggct tcaactactg gggacagggc accctggtca cagtgtccag cgctagcacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga aagttgagcc caaatcttgt    660

gacaaaactc acacatgccc accgtgccca gcacctgaag ctgcaggggg accgtcagtc    720

ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840

ggcgtggagg tgcataatgc caagacaaag ccgcgggagg agcagtacaa cagcacgtac    900

cgtgtggtca gcgtcctcac cgtcctgcac caggactggc tgaatggcaa ggagtacaag    960

tgcaaggtct ccaacaaagc cctcggcgcc cccatcgaga aaaccatctc caaagccaaa   1020

gggcagcccc gagaaccaca ggtgtacacc ctgcccccat gccgggatga gctgaccaag   1080

aaccaggtca gcctgtggtg cctggtcaaa ggcttctatc ccagcgacat cgccgtggag   1140

tgggagagca atgggcagcc ggagaacaac tacaagacca cgcctcccgt gctggactcc   1200

gacggctcct tcttcctcta cagcaagctc accgtggaca agagcaggtg gcagcagggg   1260

aacgtcttct catgctccgt gatgcatgag gctctgcaca accactacac gcagaagagc   1320

ctctccctgt ctccgggtgg cggcggaggc tccggaggcg gaggttctgg aggcggaggc   1380

tccgcaccta cttcaagttc tacaaagaaa acacagctac aactggagca tttactgctg   1440

gatttacaga tgattttgaa tggaattaat aattacaaga atcccaaact caccaggatg   1500

ctcacattta agttttacat gcccaagaag gccacagaac tgaaacatct tcagtgtcta   1560

gaagaagaac tcaaacctct ggaggaagtg ctaaatttag ctcaaagcaa aaactttcac   1620

ttaagaccca gggacttaat cagcaatatc aacgtaatag ttctggaact aaagggatct   1680

gaaacaacat tcatgtgtga atatgctgat gagacagcaa ccattgtaga atttctgaac   1740

agatggatta cctttgccca aagcatcatc tcaacactga ct                      1782
```

<210> SEQ ID NO 275
<211> LENGTH: 599
<212> TYPE: PRT
<213> ORGANISM: Artificial Sequence
<220> FEATURE:
<223> OTHER INFORMATION: CH1A1A 98/99 2F1 Fab HC-Fc knob
(LALA P329G)-IL-2 qm

<400> SEQUENCE: 275

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
```

```
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Asp Glu Leu Thr Lys Asn Gln Val Ser
        355                 360                 365

Leu Trp Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Ser Gly Gly Gly Gly Ser Gly Gly Gly Gly Ser Gly Gly
    450                 455                 460

Gly Gly Ala Pro Ala Ser Ser Ser Thr Lys Lys Thr Gln Leu Gln Leu
465                 470                 475                 480
```

```
Glu His Leu Leu Leu Asp Leu Gln Met Ile Leu Asn Gly Ile Asn Asn
                485                 490                 495

Tyr Lys Asn Pro Lys Leu Thr Arg Met Leu Thr Ala Lys Phe Ala Met
            500                 505                 510

Pro Lys Lys Ala Thr Glu Leu Lys His Leu Gln Cys Leu Glu Glu Glu
        515                 520                 525

Leu Lys Pro Leu Glu Glu Val Leu Asn Gly Ala Gln Ser Lys Asn Phe
    530                 535                 540

His Leu Arg Pro Arg Asp Leu Ile Ser Asn Ile Asn Val Ile Val Leu
545                 550                 555                 560

Glu Leu Lys Gly Ser Glu Thr Thr Phe Met Cys Glu Tyr Ala Asp Glu
                565                 570                 575

Thr Ala Thr Ile Val Glu Phe Leu Asn Arg Trp Ile Thr Phe Ala Gln
            580                 585                 590

Ser Ile Ile Ser Thr Leu Thr
        595


<210> SEQ ID NO 276
<211> LENGTH: 1797
<212> TYPE: DNA
<213> ORGANISM: Artificial Sequence
<220> FEATURE:
<223> OTHER INFORMATION: CH1A1A 98/99 2F1 Fab HC-Fc knob
      (LALA P329G)-IL-2 qm

<400> SEQUENCE: 276

caggtgcagc tggtgcagtc tggcgccgaa gtgaagaaac ctggagctag tgtgaaggtg     60

tcctgcaagg ccagcggcta caccttcacc gagttcggca tgaactgggt ccgacaggct    120

ccaggccagg gcctcgaatg gatgggctgg atcaacacca agaccggcga ggccacctac    180

gtggaagagt tcaagggcag agtgaccttc accacggaca ccagcaccag caccgcctac    240

atggaactgc ggagcctgag aagcgacgac accgccgtgt actactgcgc cagatgggac    300

ttcgcctatt acgtggaagc catggactac tggggccagg gcaccaccgt gaccgtgtct    360

agcgctagca ccaagggccc aagcgtgttc cctctggccc ccagcagcaa gagcacaagc    420

ggcggaacag ccgccctggg ctgcctggtc aaggactact tccccgagcc cgtgacagtg    480

tcctggaaca gcggagccct gaccagcggc gtgcacacct ttccagccgt gctgcagagc    540

agcggcctgt acagcctgag cagcgtggtc acagtgccta gcagcagcct gggcacccag    600

acctacatct gcaacgtgaa ccacaagccc agcaacacca aggtggacaa gaaggtggag    660

cccaagagct gcgacaagac ccacacctgt ccccccttgtc ctgcccctga gctgctgggc    720

ggacccagcg tgttcctgtt ccccccaaag cccaaggaca ccctgatgat cagccggacc    780

cccgaagtga cctgcgtggt ggtggacgtg tcccacgagg accctgaagt gaagttcaat    840

tggtacgtgg acggcgtgga ggtgcacaat gccaagacca agccccggga ggaacagtac    900

aacagcacct accgggtggt gtccgtgctg accgtgctgc accaggactg gctgaacggc    960

aaagagtaca agtgcaaggt ctccaacaag gccctgcctg cccccatcga gaaaaccatc   1020

agcaaggcca agggccagcc cagagaaccc caggtgtaca ccctgccccc ctgcagagat   1080

gagctgacca agaaccaggt gtccctgtgg tgtctggtca agggcttcta ccccagcgat   1140

atcgccgtgg agtgggagag caacggccag cctgagaaca actacaagac caccccccct   1200

gtgctggaca gcgacggcag cttcttcctg tactccaaac tgaccgtgga caagagccgg   1260

tggcagcagg gcaacgtgtt cagctgcagc gtgatgcacg aggccctgca caaccactac   1320
```

acccagaagt ccctgagcct gagccccggc aagtccggag gcggaggctc cggcggcgga 1380
ggttctggcg gaggtggcgc tcctgcctcc tccagcacca agaaaaccca gctccagctg 1440
gaacatctcc tgctggatct gcagatgatc ctgaacggca tcaacaacta caagaacccc 1500
aagctgaccc ggatgctgac cgccaagttc gccatgccca agaaggccac cgagctgaaa 1560
catctgcagt gcctggaaga ggaactgaag cctctggaag aggtgctgaa cggcgcccag 1620
tccaagaact tccacctgag gcctcgggac ctgatctcca acatcaacgt gatcgtgctg 1680
gaactgaagg gctccgagac aaccttcatg tgcgagtacg ccgacgagac agctaccatc 1740
gtggaatttc tgaaccggtg gatcaccttc gcccagtcca tcatctccac cctgacc 1797

<210> SEQ ID NO 277
<211> LENGTH: 598
<212> TYPE: PRT
<213> ORGANISM: Artificial Sequence
<220> FEATURE:
<223> OTHER INFORMATION: CH1A1A 98/99 2F1 Fab HC-Fc knob (LALA P329G)-IL-2 qm (2)

<400> SEQUENCE: 277

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Glu Phe
20 25 30

Gly Met Asn Trp Val Arg Gln Ala Pro Gly Gln Gly Leu Glu Trp Met
35 40 45

Gly Trp Ile Asn Thr Lys Thr Gly Glu Ala Thr Tyr Val Glu Glu Phe
50 55 60

Lys Gly Arg Val Thr Phe Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Trp Asp Phe Ala Tyr Tyr Val Glu Ala Met Asp Tyr Trp Gly
100 105 110

Gln Gly Thr Thr Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Lys Val Glu Pro Lys Ser Cys
210 215 220

Asp Lys Thr His Thr Cys Pro Pro Cys Pro Ala Pro Glu Ala Ala Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

-continued

```
Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Asp Glu Leu Thr Lys Asn Gln Val Ser
        355                 360                 365

Leu Trp Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Gly Gly Gly Gly Ser Gly Gly Gly Gly Ser Gly Gly Gly Gly
    450                 455                 460

Ser Ala Pro Ala Ser Ser Ser Thr Lys Lys Thr Gln Leu Gln Leu Glu
465                 470                 475                 480

His Leu Leu Leu Asp Leu Gln Met Ile Leu Asn Gly Ile Asn Asn Tyr
                485                 490                 495

Lys Asn Pro Lys Leu Thr Arg Met Leu Thr Ala Lys Phe Ala Met Pro
            500                 505                 510

Lys Lys Ala Thr Glu Leu Lys His Leu Gln Cys Leu Glu Glu Glu Leu
        515                 520                 525

Lys Pro Leu Glu Glu Val Leu Asn Gly Ala Gln Ser Lys Asn Phe His
    530                 535                 540

Leu Arg Pro Arg Asp Leu Ile Ser Asn Ile Asn Val Ile Val Leu Glu
545                 550                 555                 560

Leu Lys Gly Ser Glu Thr Thr Phe Met Cys Glu Tyr Ala Asp Glu Thr
                565                 570                 575

Ala Thr Ile Val Glu Phe Leu Asn Arg Trp Ile Thr Phe Ala Gln Ser
            580                 585                 590

Ile Ile Ser Thr Leu Thr
        595


<210> SEQ ID NO 278
<211> LENGTH: 1794
<212> TYPE: DNA
<213> ORGANISM: Artificial Sequence
<220> FEATURE:
<223> OTHER INFORMATION: CH1A1A 98/99 2F1 Fab HC-Fc knob
      (LALA P329G)-IL-2 qm (2)

<400> SEQUENCE: 278

caggtgcagc tggtgcagtc tggcgccgaa gtgaagaaac ctggagctag tgtgaaggtg     60

tcctgcaagg ccagcggcta caccttcacc gagttcggca tgaactgggt ccgacaggct    120

ccaggccagg gcctcgaatg gatgggctgg atcaacacca agaccggcga ggccacctac    180
```

```
gtggaagagt tcaagggcag agtgaccttc accacggaca ccagcaccag caccgcctac    240

atggaactgc ggagcctgag aagcgacgac accgccgtgt actactgcgc cagatgggac    300

ttcgcctatt acgtggaagc catggactac tggggccagg gcaccaccgt gaccgtgtct    360

agcgctagca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggacaa gaaagttgag    660

cccaaatctt gtgacaaaac tcacacatgc ccaccgtgcc cagcacctga agctgcaggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgcggga ggagcagtac    900

aacagcacgt accgtgtggt cagcgtcctc accgtcctgc accaggactg gctgaatggc    960

aaggagtaca agtgcaaggt ctccaacaaa gccctcggcg cccccatcga gaaaaccatc   1020

tccaaagcca aagggcagcc ccgagaacca caggtgtaca ccctgccccc atgccgggat   1080

gagctgacca agaaccaggt cagcctgtgg tgcctggtca aaggcttcta tcccagcgac   1140

atcgccgtgg agtgggagag caatgggcag ccggagaaca actacaagac cacgcctccc   1200

gtgctggact ccgacggctc cttcttcctc tacagcaagc tcaccgtgga caagagcagg   1260

tggcagcagg ggaacgtctt ctcatgctcc gtgatgcatg aggctctgca caaccactac   1320

acgcagaaga gcctctccct gtctccgggt ggcggcggag gctccggagg cggaggttct   1380

ggcggaggtg gctccgcacc tgcctcaagt tctacaaaga aaacacagct acaactggag   1440

catttactgc tggatttaca gatgattttg aatggaatta ataattacaa gaatcccaaa   1500

ctcaccagga tgctcacagc caagtttgcc atgcccaaga aggccacaga actgaaacat   1560

cttcagtgtc tagaagaaga actcaaacct ctggaggaag tgctaaatgg cgctcaaagc   1620

aaaaactttc acttaagacc cagggactta atcagcaata tcaacgtaat agttctggaa   1680

ctaaagggat ctgaaacaac attcatgtgt gaatatgctg atgagacagc aaccattgta   1740

gaatttctga acagatggat tacctttgcc caaagcatca tctcaacact gact         1794
```

<210> SEQ ID NO 279
<211> LENGTH: 598
<212> TYPE: PRT
<213> ORGANISM: Artificial Sequence
<220> FEATURE:
<223> OTHER INFORMATION: CH1A1A 98/99 2F1 Fab HC-Fc knob
(LALA P329G)-IL-2 wt

<400> SEQUENCE: 279

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
```

```
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Asp Glu Leu Thr Lys Asn Gln Val Ser
        355                 360                 365

Leu Trp Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Gly Gly Gly Gly Ser Gly Gly Gly Gly Ser Gly Gly Gly Gly
    450                 455                 460

Ser Ala Pro Thr Ser Ser Ser Thr Lys Lys Thr Gln Leu Gln Leu Glu
465                 470                 475                 480

His Leu Leu Leu Asp Leu Gln Met Ile Leu Asn Gly Ile Asn Asn Tyr
                485                 490                 495
```

```
Lys Asn Pro Lys Leu Thr Arg Met Leu Thr Phe Lys Phe Tyr Met Pro
            500                 505                 510

Lys Lys Ala Thr Glu Leu Lys His Leu Gln Cys Leu Glu Glu Glu Leu
        515                 520                 525

Lys Pro Leu Glu Glu Val Leu Asn Leu Ala Gln Ser Lys Asn Phe His
    530                 535                 540

Leu Arg Pro Arg Asp Leu Ile Ser Asn Ile Asn Val Ile Val Leu Glu
545                 550                 555                 560

Leu Lys Gly Ser Glu Thr Thr Phe Met Cys Glu Tyr Ala Asp Glu Thr
                565                 570                 575

Ala Thr Ile Val Glu Phe Leu Asn Arg Trp Ile Thr Phe Ala Gln Ser
            580                 585                 590

Ile Ile Ser Thr Leu Thr
        595
```

<210> SEQ ID NO 280
<211> LENGTH: 1794
<212> TYPE: DNA
<213> ORGANISM: Artificial Sequence
<220> FEATURE:
<223> OTHER INFORMATION: CH1A1A 98/99 2F1 Fab HC-Fc knob (LALA P329G)-IL-2 wt

<400> SEQUENCE: 280

```
caggtgcagc tggtgcagtc tggcgccgaa gtgaagaaac ctggagctag tgtgaaggtg     60

tcctgcaagg ccagcggcta caccttcacc gagttcggca tgaactgggt ccgacaggct    120

ccaggccagg gcctcgaatg gatgggctgg atcaacacca agaccggcga ggccacctac    180

gtggaagagt tcaagggcag agtgaccttc accacggaca ccagcaccag caccgcctac    240

atggaactgc ggagcctgag aagcgacgac accgccgtgt actactgcgc cagatgggac    300

ttcgcctatt acgtggaagc catggactac tggggccagg gcaccaccgt gaccgtgtct    360

agcgctagca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggacaa gaaagttgag    660

cccaaatctt gtgacaaaac tcacacatgc ccaccgtgcc cagcacctga agctgcaggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgcggga ggagcagtac    900

aacagcacgt accgtgtggt cagcgtcctc accgtcctgc accaggactg gctgaatggc    960

aaggagtaca agtgcaaggt ctccaacaaa gccctcggcg cccccatcga gaaaaccatc   1020

tccaaagcca aagggcagcc ccgagaacca caggtgtaca ccctgccccc atgccgggat   1080

gagctgacca agaaccaggt cagcctgtgg tgcctggtca aaggcttcta tcccagcgac   1140

atcgccgtgg agtgggagag caatgggcag ccggagaaca actacaagac cacgcctccc   1200

gtgctggact ccgacggctc cttcttcctc tacagcaagc tcaccgtgga caagagcagg   1260

tggcagcagg ggaacgtctt ctcatgctcc gtgatgcatg aggctctgca caaccactac   1320

acgcagaaga gcctctccct gtctccgggt ggcggcggag gctccggagg cggaggttct   1380
```

```
ggaggcggag gctccgcacc tacttcaagt tctacaaaga aaacacagct acaactggag   1440

catttactgc tggatttaca gatgattttg aatggaatta ataattacaa gaatcccaaa   1500

ctcaccagga tgctcacatt taagttttac atgcccaaga aggccacaga actgaaacat   1560

cttcagtgtc tagaagaaga actcaaacct ctggaggaag tgctaaattt agctcaaagc   1620

aaaaactttc acttaagacc cagggactta atcagcaata tcaacgtaat agttctggaa   1680

ctaaagggat ctgaaacaac attcatgtgt gaatatgctg atgagacagc aaccattgta   1740

gaatttctga acagatggat tacctttgcc caaagcatca tctcaacact gact         1794


<210> SEQ ID NO 281
<211> LENGTH: 451
<212> TYPE: PRT
<213> ORGANISM: Artificial Sequence
<220> FEATURE:
<223> OTHER INFORMATION: CH1A1A 98/99 2F1 Fab HC-Fc hole (LALA P329G)

<400> SEQUENCE: 281

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
```

```
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 282
<211> LENGTH: 1353
<212> TYPE: DNA
<213> ORGANISM: Artificial Sequence
<220> FEATURE:
<223> OTHER INFORMATION: CH1A1A 98/99 2F1 Fab HC-Fc hole (LALA P329G)

<400> SEQUENCE: 282

caggtgcagc tggtgcagtc tggcgccgaa gtgaagaaac ctggagctag tgtgaaggtg     60

tcctgcaagg ccagcggcta caccttcacc gagttcggca tgaactgggt ccgacaggct    120

ccaggccagg gcctcgaatg gatgggctgg atcaacacca agaccggcga ggccacctac    180

gtggaagagt tcaagggcag agtgaccttc accacggaca ccagcaccag caccgcctac    240

atggaactgc ggagcctgag aagcgacgac accgccgtgt actactgcgc cagatgggac    300

ttcgcctatt acgtggaagc catggactac tggggccagg gcaccaccgt gaccgtgtct    360

agcgctagca ccaagggccc ctccgtgttc cccctggccc ccagcagcaa gagcaccagc    420

ggcggcacag ccgctctggg ctgcctggtc aaggactact tccccgagcc cgtgaccgtg    480

tcctggaaca gcggagccct gacctccggc gtgcacacct tccccgccgt gctgcagagt    540

tctggcctgt atagcctgag cagcgtggtc accgtgcctt ctagcagcct gggcacccag    600

acctacatct gcaacgtgaa ccacaagccc agcaacacca aggtggacaa gaaggtggag    660

cccaagagct gcgacaaaac tcacacatgc ccaccgtgcc cagcacctga agctgcaggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgcggga ggagcagtac    900

aacagcacgt accgtgtggt cagcgtcctc accgtcctgc accaggactg gctgaatggc    960

aaggagtaca agtgcaaggt ctccaacaaa gccctcggcg cccccatcga gaaaaccatc   1020

tccaaagcca aagggcagcc ccgagaacca caggtgtgca ccctgccccc atcccgggat   1080

gagctgacca agaaccaggt cagcctctcg tgcgcagtca aaggcttcta tcccagcgac   1140
```

atcgccgtgg agtgggagag caatgggcag ccggagaaca actacaagac cacgcctccc 1200
gtgctggact ccgacggctc cttcttcctc gtgagcaagc tcaccgtgga caagagcagg 1260
tggcagcagg ggaacgtctt ctcatgctcc gtgatgcatg aggctctgca caaccactac 1320
acgcagaaga gcctctccct gtctccgggt aaa 1353

<210> SEQ ID NO 283
<211> LENGTH: 215
<212> TYPE: PRT
<213> ORGANISM: Artificial Sequence
<220> FEATURE:
<223> OTHER INFORMATION: CH1A1A 98/99 2F1 Fab LC

<400> SEQUENCE: 283

Asp Ile Gln Met Thr Gln Ser Pro Ser Ser Leu Ser Ala Ser Val Gly
1 5 10 15

Asp Arg Val Thr Ile Thr Cys Lys Ala Ser Ala Ala Val Gly Thr Tyr
20 25 30

Val Ala Trp Tyr Gln Gln Lys Pro Gly Lys Ala Pro Lys Leu Leu Ile
35 40 45

Tyr Ser Ala Ser Tyr Arg Lys Arg Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys His Gln Tyr Tyr Thr Tyr Pro Leu
85 90 95

Phe Thr Phe Gly Gln Gly Thr Lys Leu Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 284
<211> LENGTH: 645
<212> TYPE: DNA
<213> ORGANISM: Artificial Sequence
<220> FEATURE:
<223> OTHER INFORMATION: CH1A1A 98/99 2F1 Fab LC

<400> SEQUENCE: 284
gatatccaga tgacccagtc tccatcctcc ctgtctgcat ctgtgggaga cagagtcacc 60
atcacttgca aggccagtgc ggctgtgggt acgtatgttg cgtggtatca gcagaaacca 120
gggaaagcac ctaagctcct gatctattcg gcatcctacc gcaaaagggg agtcccatca 180
aggttcagtg gcagtggatc tgggacagat ttcactctca ccatcagcag tctgcaacct 240

```
gaagatttcg caacttacta ctgtcaccaa tattacacct atcctctatt cacgtttggc    300

cagggcacca agctcgagat caagcgtacg gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgt                    645


<210> SEQ ID NO 285
<211> LENGTH: 598
<212> TYPE: PRT
<213> ORGANISM: Artificial Sequence
<220> FEATURE:
<223> OTHER INFORMATION: 2B10 Fab HC-Fc knob (LALA P329G)-IL-2 qm

<400> SEQUENCE: 285

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
```

```
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Asp Glu Leu Thr Lys Asn Gln Val Ser
        355                 360                 365

Leu Trp Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Gly Gly Gly Gly Ser Gly Gly Gly Gly Ser Gly Gly Gly Gly
    450                 455                 460

Ser Ala Pro Ala Ser Ser Ser Thr Lys Lys Thr Gln Leu Gln Leu Glu
465                 470                 475                 480

His Leu Leu Leu Asp Leu Gln Met Ile Leu Asn Gly Ile Asn Asn Tyr
                485                 490                 495

Lys Asn Pro Lys Leu Thr Arg Met Leu Thr Ala Lys Phe Ala Met Pro
            500                 505                 510

Lys Lys Ala Thr Glu Leu Lys His Leu Gln Cys Leu Glu Glu Glu Leu
        515                 520                 525

Lys Pro Leu Glu Glu Val Leu Asn Gly Ala Gln Ser Lys Asn Phe His
    530                 535                 540

Leu Arg Pro Arg Asp Leu Ile Ser Asn Ile Asn Val Ile Val Leu Glu
545                 550                 555                 560

Leu Lys Gly Ser Glu Thr Thr Phe Met Cys Glu Tyr Ala Asp Glu Thr
                565                 570                 575

Ala Thr Ile Val Glu Phe Leu Asn Arg Trp Ile Thr Phe Ala Gln Ser
            580                 585                 590

Ile Ile Ser Thr Leu Thr
        595


<210> SEQ ID NO 286
<211> LENGTH: 1794
<212> TYPE: DNA
<213> ORGANISM: Artificial Sequence
<220> FEATURE:
<223> OTHER INFORMATION: 2B10 Fab HC-Fc knob (LALA P329G)-IL-2 qm

<400> SEQUENCE: 286

caggtgcaat tggtgcagtc tggggctgag gtgaagaagc ctgggtcctc ggtgaaggtc      60

tcctgcaagg cctccggagg cacattcagc agctacgcta taagctgggt gcgacaggcc     120

cctggacaag ggctcgagtg gatgggaggg atcatcccta tctttggtac agcaaactac     180

gcacagaagt tccagggcag ggtcaccatt actgcagaca aatccacgag cacagcctac     240

atggagctga gcagcctgag atctgaggac accgccgtgt attactgtgc gagactgtac     300
```

-continued

```
ggttacgctt actacggtgc ttttgactac tggggccaag ggaccaccgt gaccgtctcc    360
tcagctagca ccaagggccc atcggtcttc cccctggcac cctcctccaa gagcacctct    420
gggggcacag cggccctggg ctgcctggtc aaggactact tccccgaacc ggtgacggtg    480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga agctgcaggg    720
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcggcg cccccatcga gaaaaccatc   1020
tccaaagcca aagggcagcc ccgagaacca caggtgtaca ccctgccccc atgccgggat   1080
gagctgacca agaaccaggt cagcctgtgg tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt ggcggcggag gctccggagg cggaggttct   1380
ggcggaggtg gctccgcacc tgcctcaagt tctacaaaga aaacacagct acaactggag   1440
catttactgc tggatttaca gatgattttg aatggaatta ataattacaa gaatcccaaa   1500
ctcaccagga tgctcacagc caagtttgcc atgcccaaga aggccacaga actgaaacat   1560
cttcagtgtc tagaagaaga actcaaacct ctggaggaag tgctaaatgg cgctcaaagc   1620
aaaaactttc acttaagacc cagggactta atcagcaata tcaacgtaat agttctggaa   1680
ctaaagggat ctgaaacaac attcatgtgt gaatatgctg atgagacagc aaccattgta   1740
gaatttctga acagatggat tacctttgcc caaagcatca tctcaacact gact         1794
```

<210> SEQ ID NO 287
<211> LENGTH: 451
<212> TYPE: PRT
<213> ORGANISM: Artificial Sequence
<220> FEATURE:
<223> OTHER INFORMATION: 2B10 Fab HC-Fc hole (LALA P329G)

<400> SEQUENCE: 287

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
```

```
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 288
<211> LENGTH: 1353
<212> TYPE: DNA
<213> ORGANISM: Artificial Sequence
<220> FEATURE:
<223> OTHER INFORMATION: 2B10 Fab HC-Fc hole (LALA P329G)

<400> SEQUENCE: 288

caggtgcaat tggtgcagtc tggggctgag gtgaagaagc ctgggtcctc ggtgaaggtc      60
```

```
tcctgcaagg cctccggagg cacattcagc agctacgcta taagctgggt gcgacaggcc    120

cctggacaag ggctcgagtg gatgggaggg atcatcccta tctttggtac agcaaactac    180

gcacagaagt tccagggcag ggtcaccatt actgcagaca aatccacgag cacagcctac    240

atggagctga gcagcctgag atctgaggac accgccgtgt attactgtgc gagactgtac    300

ggttacgctt actacggtgc ttttgactac tggggccaag ggaccaccgt gaccgtctcc    360

tcagctagca ccaagggccc ctccgtgttc cccctggccc ccagcagcaa gagcaccagc    420

ggcggcacag ccgctctggg ctgcctggtc aaggactact tccccgagcc cgtgaccgtg    480

tcctggaaca gcggagccct gacctccggc gtgcacacct tccccgccgt gctgcagagt    540

tctggcctgt atagcctgag cagcgtggtc accgtgcctt ctagcagcct gggcacccag    600

acctacatct gcaacgtgaa ccacaagccc agcaacacca aggtggacaa gaaggtggag    660

cccaagagct gcgacaaaac tcacacatgc ccaccgtgcc cagcacctga agctgcaggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgcggga ggagcagtac    900

aacagcacgt accgtgtggt cagcgtcctc accgtcctgc accaggactg gctgaatggc    960

aaggagtaca agtgcaaggt ctccaacaaa gccctcggcg cccccatcga gaaaaccatc   1020

tccaaagcca aagggcagcc ccgagaacca caggtgtgca ccctgccccc atcccgggat   1080

gagctgacca agaaccaggt cagcctctcg tgcgcagtca aaggcttcta tcccagcgac   1140

atcgccgtgg agtgggagag caatgggcag ccggagaaca actacaagac cacgcctccc   1200

gtgctggact ccgacggctc cttcttcctc gtgagcaagc tcaccgtgga caagagcagg   1260

tggcagcagg ggaacgtctt ctcatgctcc gtgatgcatg aggctctgca caaccactac   1320

acgcagaaga gcctctccct gtctccgggt aaa                                1353
```

<210> SEQ ID NO 289
<211> LENGTH: 592
<212> TYPE: PRT
<213> ORGANISM: Artificial Sequence
<220> FEATURE:
<223> OTHER INFORMATION: DP47GS Fab HC-Fc knob (LALA P329G)-IL-2 qm

<400> SEQUENCE: 289

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125
```

-continued

```
Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Tyr Thr Leu Pro Pro Cys
            340                 345                 350

Arg Asp Glu Leu Thr Lys Asn Gln Val Ser Leu Trp Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Gly Gly Gly Gly
        435                 440                 445

Ser Gly Gly Gly Gly Ser Gly Gly Gly Gly Ser Ala Pro Ala Ser Ser
    450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Arg Met Leu Thr Ala Lys Phe Ala Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Gly Ala Gln Ser Lys Asn Phe His Leu Arg Pro Arg Asp Leu
    530                 535                 540

Ile Ser Asn Ile Asn Val Ile Val Leu Glu Leu Lys Gly Ser Glu Thr
```

545 550 555 560

Thr Phe Met Cys Glu Tyr Ala Asp Glu Thr Ala Thr Ile Val Glu Phe
565 570 575

Leu Asn Arg Trp Ile Thr Phe Ala Gln Ser Ile Ile Ser Thr Leu Thr
580 585 590

<210> SEQ ID NO 290
<211> LENGTH: 1776
<212> TYPE: DNA
<213> ORGANISM: Artificial Sequence
<220> FEATURE:
<223> OTHER INFORMATION: DP47GS Fab HC-Fc knob (LALA P329G)-IL-2 qm

<400> SEQUENCE: 290
gaggtgcaat tgttggagtc tgggggaggc ttggtacagc ctgggggtc cctgagactc 60 tcctgtgcag cctccggatt cacctttagc agttatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcagatga acagcctgag agccgaggac acggccgtat attactgtgc gaaaggcagc 300
ggatttgact actggggcca aggaaccctg gtcaccgtct cgagtgctag caccaagggc 360
ccatcggtct tccccctggc accctcctcc aagagcacct ctgggggcac agcggccctg 420
ggctgcctgg tcaaggacta cttccccgaa ccggtgacgg tgtcgtggaa ctcaggcgcc 480
ctgaccagcg gcgtgcacac cttcccggct gtcctacagt cctcaggact ctactccctc 540
agcagcgtgg tgaccgtgcc ctccagcagc ttgggcaccc agacctacat ctgcaacgtg 600
aatcacaagc ccagcaacac caaggtggac aagaaagttg agcccaaatc ttgtgacaaa 660
actcacacat gcccaccgtg cccagcacct gaagctgcag gggaccgtc agtcttcctc 720 ttccccccaa aacccaagga caccctcatg atctcccgga cccctgaggt cacatgcgtg 780
gtggtggacg tgagccacga agaccctgag gtcaagttca actggtacgt ggacggcgtg 840
gaggtgcata atgccaagac aaagccgcgg gaggagcagt acaacagcac gtaccgtgtg 900
gtcagcgtcc tcaccgtcct gcaccaggac tggctgaatg gcaaggagta caagtgcaag 960
gtctccaaca aagccctcgg cgcccccatc gagaaaacca tctccaaagc caaagggcag 1020
ccccgagaac cacaggtgta caccctgccc ccatgccggg atgagctgac caagaaccag 1080
gtcagcctgt ggtgcctggt caaaggcttc tatcccagcg acatcgccgt ggagtgggag 1140
agcaatgggc agccggagaa caactacaag accacgcctc ccgtgctgga ctccgacggc 1200
tccttcttcc tctacagcaa gctcaccgtg gacaagagca ggtggcagca ggggaacgtc 1260
ttctcatgct ccgtgatgca tgaggctctg cacaaccact acacgcagaa gagcctctcc 1320
ctgtctccgg gtggcggcgg aggctccgga ggcggaggtt ctggcggagg tggctccgca 1380
cctgcctcaa gttctacaaa gaaaacacag ctacaactgg agcatttact gctggattta 1440
cagatgattt tgaatggaat taataattac aagaatccca aactcaccag gatgctcaca 1500
gccaagtttg ccatgcccaa gaaggccaca gaactgaaac atcttcagtg tctagaagaa 1560
gaactcaaac ctctggagga agtgctaaat ggcgctcaaa gcaaaaactt tcacttaaga 1620
cccagggact taatcagcaa tatcaacgta atagttctgg aactaaaggg atctgaaaca 1680
acattcatgt gtgaatatgc tgatgagaca gcaaccattg tagaatttct gaacagatgg 1740
attacctttg cccaaagcat catctcaaca ctgact 1776

<210> SEQ ID NO 291
<211> LENGTH: 592
<212> TYPE: PRT
<213> ORGANISM: Artificial Sequence
<220> FEATURE:
<223> OTHER INFORMATION: DP47GS Fab HC-Fc knob (LALA P329G)-IL-2 wt (2)

<400> SEQUENCE: 291

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Tyr Thr Leu Pro Pro Cys
            340                 345                 350

Arg Asp Glu Leu Thr Lys Asn Gln Val Ser Leu Trp Cys Leu Val Lys
        355                 360                 365

Gly Phe Tyr Pro Ser Asp Ile Ala Val Glu Trp Glu Ser Asn Gly Gln
```

370 375 380

Pro Glu Asn Asn Tyr Lys Thr Thr Pro Pro Val Leu Asp Ser Asp Gly
385 390 395 400

Ser Phe Phe Leu Tyr Ser Lys Leu Thr Val Asp Lys Ser Arg Trp Gln
405 410 415

Gln Gly Asn Val Phe Ser Cys Ser Val Met His Glu Ala Leu His Asn
420 425 430

His Tyr Thr Gln Lys Ser Leu Ser Leu Ser Pro Gly Gly Gly Gly Gly
435 440 445

Ser Gly Gly Gly Gly Ser Gly Gly Gly Gly Ser Ala Pro Thr Ser Ser
450 455 460

Ser Thr Lys Lys Thr Gln Leu Gln Leu Glu His Leu Leu Leu Asp Leu
465 470 475 480

Gln Met Ile Leu Asn Gly Ile Asn Asn Tyr Lys Asn Pro Lys Leu Thr
485 490 495

Arg Met Leu Thr Phe Lys Phe Tyr Met Pro Lys Lys Ala Thr Glu Leu
500 505 510

Lys His Leu Gln Cys Leu Glu Glu Glu Leu Lys Pro Leu Glu Glu Val
515 520 525

Leu Asn Leu Ala Gln Ser Lys Asn Phe His Leu Arg Pro Arg Asp Leu
530 535 540

Ile Ser Asn Ile Asn Val Ile Val Leu Glu Leu Lys Gly Ser Glu Thr
545 550 555 560

Thr Phe Met Cys Glu Tyr Ala Asp Glu Thr Ala Thr Ile Val Glu Phe
565 570 575

Leu Asn Arg Trp Ile Thr Phe Ala Gln Ser Ile Ile Ser Thr Leu Thr
580 585 590

<210> SEQ ID NO 292
<211> LENGTH: 1776
<212> TYPE: DNA
<213> ORGANISM: Artificial Sequence
<220> FEATURE:
<223> OTHER INFORMATION: DP47GS Fab HC-Fc knob (LALA P329G)-IL-2 wt (2)

<400> SEQUENCE: 292
gaggtgcaat tgttggagtc tgggggaggc ttggtacagc ctggggggtc cctgagactc 60
tcctgtgcag cctccggatt cacctttagc agttatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcagatga acagcctgag agccgaggac acggccgtat attactgtgc gaaaggcagc 300
ggatttgact actggggcca aggaaccctg gtcaccgtct cgagtgctag caccaagggc 360
ccatcggtct tccccctggc accctcctcc aagagcacct ctgggggcac agcggccctg 420
ggctgcctgg tcaaggacta cttccccgaa ccggtgacgg tgtcgtggaa ctcaggcgcc 480
ctgaccagcg gcgtgcacac cttcccggct gtcctacagt cctcaggact ctactccctc 540
agcagcgtgg tgaccgtgcc ctccagcagc ttgggcaccc agacctacat ctgcaacgtg 600
aatcacaagc ccagcaacac caaggtggac aagaaagttg agcccaaatc ttgtgacaaa 660
actcacacat gcccaccgtg cccagcacct gaagctgcag gggaccgtc agtcttcctc 720 ttccccccaa aacccaagga caccctcatg atctcccgga cccctgaggt cacatgcgtg 780
gtggtggacg tgagccacga agaccctgag gtcaagttca actggtacgt ggacggcgtg 840

-continued

```
gaggtgcata atgccaagac aaagccgcgg gaggagcagt acaacagcac gtaccgtgtg    900

gtcagcgtcc tcaccgtcct gcaccaggac tggctgaatg gcaaggagta caagtgcaag    960

gtctccaaca aagccctcgg cgcccccatc gagaaaacca tctccaaagc caaagggcag   1020

ccccgagaac cacaggtgta caccctgccc ccatgccggg atgagctgac caagaaccag   1080

gtcagcctgt ggtgcctggt caaaggcttc tatcccagcg acatcgccgt ggagtgggag   1140

agcaatgggc agccggagaa caactacaag accacgcctc ccgtgctgga ctccgacggc   1200

tccttcttcc tctacagcaa gctcaccgtg gacaagagca ggtggcagca ggggaacgtc   1260

ttctcatgct ccgtgatgca tgaggctctg cacaaccact acacgcagaa gagcctctcc   1320

ctgtctccgg gtggcggcgg aggctccgga ggcggaggtt ctggaggcgg aggctccgca   1380

cctacttcaa gttctacaaa gaaaacacag ctacaactgg agcatttact gctggattta   1440

cagatgattt tgaatggaat taataattac aagaatccca aactcaccag gatgctcaca   1500

tttaagtttt acatgcccaa gaaggccaca gaactgaaac atcttcagtg tctagaagaa   1560

gaactcaaac ctctggagga agtgctaaat ttagctcaaa gcaaaaactt tcacttaaga   1620

cccagggact taatcagcaa tatcaacgta atagttctgg aactaaaggg atctgaaaca   1680

acattcatgt gtgaatatgc tgatgagaca gcaaccattg tagaatttct gaacagatgg   1740

attacctttg cccaaagcat catctcaaca ctgact                             1776
```

<210> SEQ ID NO 293
<211> LENGTH: 108
<212> TYPE: PRT
<213> ORGANISM: Artificial Sequence
<220> FEATURE:
<223> OTHER INFORMATION: CH1A1A 98/99 2F1; VL

<400> SEQUENCE: 293

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys
            100                 105
```

<210> SEQ ID NO 294
<211> LENGTH: 324
<212> TYPE: DNA
<213> ORGANISM: Artificial Sequence
<220> FEATURE:
<223> OTHER INFORMATION: CH1A1A 98/99 2F1; VL

<400> SEQUENCE: 294

```
gatatccaga tgacccagtc tccatcctcc ctgtctgcat ctgtgggaga cagagtcacc     60

atcacttgca aggccagtgc ggctgtgggt acgtatgttg cgtggtatca gcagaaacca    120

gggaaagcac ctaagctcct gatctattcg gcatcctacc gcaaaagggg agtcccatca    180
```

aggttcagtg gcagtggatc tgggacagat ttcactctca ccatcagcag tctgcaacct 240
gaagatttcg caacttacta ctgtcaccaa tattacacct atcctctatt cacgtttggc 300
cagggcacca agctcgagat caag 324

<210> SEQ ID NO 295
<211> LENGTH: 121
<212> TYPE: PRT
<213> ORGANISM: Artificial Sequence
<220> FEATURE:
<223> OTHER INFORMATION: CH1A1A 98/99 2F1; VH

<400> SEQUENCE: 295

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Glu Phe
20 25 30

Gly Met Asn Trp Val Arg Gln Ala Pro Gly Gln Gly Leu Glu Trp Met
35 40 45

Gly Trp Ile Asn Thr Lys Thr Gly Glu Ala Thr Tyr Val Glu Glu Phe
50 55 60

Lys Gly Arg Val Thr Phe Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Trp Asp Phe Ala Tyr Tyr Val Glu Ala Met Asp Tyr Trp Gly
100 105 110

Gln Gly Thr Thr Val Thr Val Ser Ser
115 120

<210> SEQ ID NO 296
<211> LENGTH: 363
<212> TYPE: DNA
<213> ORGANISM: Artificial Sequence
<220> FEATURE:
<223> OTHER INFORMATION: CH1A1A 98/99 2F1; VH

<400> SEQUENCE: 296
caggtgcagc tggtgcagtc tggcgccgaa gtgaagaaac ctggagctag tgtgaaggtg 60
tcctgcaagg ccagcggcta caccttcacc gagttcggca tgaactgggt ccgacaggct 120
ccaggccagg gcctcgaatg gatgggctgg atcaacacca agaccggcga ggccacctac 180
gtggaagagt tcaagggcag agtgaccttc accacggaca ccagcaccag caccgcctac 240
atggaactgc ggagcctgag aagcgacgac accgccgtgt actactgcgc cagatgggac 300
ttcgcctatt acgtggaagc catggactac tggggccagg gcaccaccgt gaccgtgtct 360
agc 363

<210> SEQ ID NO 297
<211> LENGTH: 108
<212> TYPE: PRT
<213> ORGANISM: Artificial Sequence
<220> FEATURE:
<223> OTHER INFORMATION: DP47GS VL

<400> SEQUENCE: 297

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Leu Thr Phe Gly Gln Gly Thr Lys Val Glu Ile Lys
100 105

<210> SEQ ID NO 298
<211> LENGTH: 324
<212> TYPE: DNA
<213> ORGANISM: Artificial Sequence
<220> FEATURE:
<223> OTHER INFORMATION: DP47GS VL

<400> SEQUENCE: 298
gaaatcgtgt taacgcagtc tccaggcacc ctgtctttgt ctccagggga aagagccacc 60
ctctcttgca gggccagtca gagtgttagc agcagctact tagcctggta ccagcagaaa 120
cctggccagg ctcccaggct cctcatctat ggagcatcca gcagggccac tggcatccca 180
gacaggttca gtggcagtgg atccgggaca gacttcactc tcaccatcag cagactggag 240
cctgaagatt ttgcagtgta ttactgtcag cagtatggta gctcaccgct gacgttcggc 300
caggggacca aagtggaaat caaa 324

<210> SEQ ID NO 299
<211> LENGTH: 115
<212> TYPE: PRT
<213> ORGANISM: Artificial Sequence
<220> FEATURE:
<223> OTHER INFORMATION: DP47GS VH

<400> SEQUENCE: 299

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Ser Gly Phe Asp Tyr Trp Gly Gln Gly Thr Leu Val Thr
100 105 110

Val Ser Ser
115

<210> SEQ ID NO 300
<211> LENGTH: 345
<212> TYPE: DNA
<213> ORGANISM: Artificial Sequence
<220> FEATURE:
<223> OTHER INFORMATION: DP47GS VH -continued

```
<400> SEQUENCE: 300

gaggtgcaat tgttggagtc tgggggaggc ttggtacagc ctgggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaaggcagc    300

ggatttgact actggggcca aggaaccctg gtcaccgtct cgagt                    345
```

IMMUNOCONJUGATES

CROSS-REFERENCE TO RELATED APPLICATIONS

This application is a continuation of U.S. application Ser. No. 13/457,039, filed Apr. 26, 2012, now U.S. Pat. No. 9,447,159, issued Sep. 20, 2016, which claims benefit under 35 U.S.C. § 119 to European Patent Application No. 11164237.7, filed Apr. 29, 2011, the contents of which are hereby incorporated by reference.

The instant application contains a Sequence Listing which has been submitted electronically in ASCII format and is hereby incorporated by reference in its entirety. Said ASCII copy, created Mar. 9, 2018, is named P27307_US_3_SeqListing.txt and is 494,061 bytes in size.

FIELD OF THE INVENTION

The present invention generally relates to antigen-specific immunoconjugates for selectively delivering effector moieties that influence cellular activity. In addition, the present invention relates to polynucleotides encoding such immunoconjugates, and vectors and host cells comprising such polynucleotides. The invention further relates to methods for producing the immunoconjugates of the invention, and to methods of using these immunoconjugates in the treatment of disease.

BACKGROUND

The selective destruction of an individual cell or a specific cell type is often desirable in a variety of clinical settings. For example, it is a primary goal of cancer therapy to specifically destroy tumor cells, while leaving healthy cells and tissues intact and undamaged. A multitude of signal transduction pathways in the cell are linked to the cell's survival and/or death. Accordingly, the direct delivery of a pathway factor involved in cell survival or death can be used to contribute to the cell's maintenance or destruction. Similarly, specific factors may be delivered that stimulate immune effector cells in a tumor microenvironment, such as natural killer (NK) cells or cytotoxic T lymphocytes (CTLs), to attack and destroy tumor cells.

Cytokines are cell signaling molecules that participate in regulation of the immune system. When used in cancer therapy, cytokines can act as immunomodulatory agents that have anti-tumor effects and which can increase the immunogenicity of some types of tumors. However, rapid blood clearance and lack of tumor specificity require systemic administration of high doses of the cytokine in order to achieve a concentration of the cytokine at the tumor site sufficient to activate an immune response or have an anti-tumor effect. These high levels of systemic cytokine can lead to severe toxicity and adverse reactions.

For use in therapy, it is therefore desirable to specifically deliver a signal transduction pathway factor, such as a cytokine, to a specific site in vivo (e.g. a tumor or tumor microenvironment in the case of cancer therapy). This can be achieved by conjugating the factor to a targeting moiety, e.g. an antibody or an antibody fragment, specific for the site. Early strategies aimed at delivering signal transduction pathway factors, such as cytokines, to a specific site in vivo included immunoglobulin heavy chains conjugated to various cytokines, including lymphotoxin, tumor necrosis factor-α (TNF-α), interleukin-2 (IL-2), and granulocyte macrophage-colony stimulating factor (GM-CSF) (reviewed e.g. in Lode et al., Pharmacol Ther 80, 277-292 (1998)).

Researchers observed that, not only were they able to target cytokines to specific sites in vivo, they were also able to take advantage of the fact that monoclonal antibodies have longer serum half-lives than most other proteins. Given the systemic toxicity associated with high doses of certain unconjugated cytokines, e.g. IL-2, the ability of an immunoglobulin-cytokine fusion protein to maximize therapeutically beneficial biological activities at a desired site, e.g. in a tumor, whilst keeping systemic side effects to a minimum at a lower dose led researchers to believe that immunoglobulin-cytokine immunoconjugates were optimal therapeutic agents.

Nevertheless, there are certain disadvantages associated with the immunoglobulin-cytokine immunoconjugtates known in the art. For example, these immunoconjugates have at least one cytokine coupled to each of the two immunoglobulin heavy chains, resulting in an immunoconjugate with bivalent target binding and two or more cytokine moieties (reviewed e.g. in Chang et al., Expert Opin Drug Discovery 4, 181-194 (2009), or Ortiz-Sanchez et al., Expert Opin Biol Ther 8, 609-632 (2008)). FIG. 1 depicts a conventional immunoglobulin-cytokine immunoconjugate as it is known in the art, where a cytokine is fused to the C-terminus of each of the two antibody heavy chains. Due to the presence of two or more cytokine moieties, such an immunoconjugate has a high avidity to the respective cytokine receptor (for example, picomolar affinity in the case of IL-2), and thus is targeted rather to the immune effector cells expressing the cytokine receptor than to the target antigen of the immunoglobulin (nM affinity) to which the cytokine is linked. Moreover, conventional immunoconjugates are known to be associated with infusion reactions (see e.g. King et al., J Clin Oncol 22, 4463-4473 (2004)), resulting at least partially from activation of cytokine receptors on immune effector cells in peripheral blood by the immunoconjugate's cytokine moieties.

Additionally, via their Fc domain, immunoglobulin-cytokine immunoconjugates can activate complement and interact with Fc receptors. This inherent immunoglobulin feature has been viewed unfavorably because therapeutic immunoconjugates may be targeted to cells expressing Fc receptors rather than the preferred antigen-bearing cells. Moreover, the simultaneous activation of cytokine receptors and Fc receptor signaling pathways leading to cytokine release, especially in combination with the long half-life of immunoglobulin fusion proteins, make their application in a therapeutic setting difficult due to systemic toxicity.

One approach to overcoming this problem is the use of immunoglobulin fragments devoid of an Fc domain, such as scFv or Fab fragments, in immunoconjugates. Examples of immunoglobulin fragment-cytokine immunoconjugates include the scFv-IL-2 immunoconjugate as set forth in PCT publication WO 2001/062298, the scFv-IL-12-scFv immunoconjugate as set forth in PCT publication WO 2006/119897 (wherein each of the two scFv fragments is connected to a subunit of the IL-12 heterodimer that is held together by disulfide bond(s)) or the Fab-IL-2-Fab immunoconjugates as set forth in PCT publication WO 2011/020783. Both the tumor-binding reactivity of the immunoglobulin parent molecule and the functional activity of the cytokine are maintained in most of these types of immunoconjugates, however the half-life of such constructs is considerably shorter than of immunoglobulin fusion proteins.

Therefore there remains a need for immunoconjugates with improved properties, for greater therapeutic effectiveness and a reduction in the number and severity of the side effects of these products (e.g., toxicity, destruction of non-tumor cells, etc.).

The present invention provides immunoglobulin-like immunoconjugates that exhibit improved efficacy, high specificity of action, reduced toxicity, and improved half-life and stability in blood relative to known immunoconjugates.

SUMMARY OF THE INVENTION

The present invention is based, in part, on the inventors' recognition that immunoconjugates comprising more than one effector moiety, such as e.g. a cytokine, may be targeted to the respective effector moiety receptor rather than the target antigen of the antigen binding moiety of the immunoconjugate. Therefore, in one aspect the invention provides an immunoconjugate comprising a first antigen binding moiety, an Fc domain consisting of two subunits, and an effector moiety, wherein not more than one effector moiety is present. In one embodiment the effector moiety is fused to the amino- or carboxy-terminal amino acid of one of the two subunits of the Fc domain, optionally through a linker peptide. In one embodiment the first antigen binding moiety is fused to the amino-terminal amino acid of one of the two subunits of the Fc domain, optionally through a linker peptide or an immunoglobulin hinge region.

In one embodiment the first antigen binding moiety comprises an antigen binding domain of an antibody. In a particular embodiment the first antigen binding moiety is a Fab molecule. In certain embodiments the Fc domain comprises a modification promoting heterodimerization of two non-identical polypeptide chains. In a specific embodiment said modification is a knob-into-hole modification, comprising a knob modification in one of the subunits of the Fc domain and a hole modification in the other one of the two subunits of the Fc domain. In a particular embodiment the effector moiety is fused to the amino- or carboxy-terminal amino acid of the subunit of the Fc domain comprising the knob modification.

In one embodiment the Fc domain is an IgG Fc domain, particularly an $IgG_1$ Fc domain. In a particular embodiment the Fc domain is human.

In certain embodiments of the invention the Fc domain is engineered to have altered binding to an Fc receptor, specifically altered binding to an Fcγ receptor, and/or altered effector function, specifically altered antibody-dependent cell-mediated cytotoxicity (ADCC).

Although the presence of an Fc domain is essential for prolonging the half-life of the immunoconjugate, the inventors realize that in some situations it will be beneficial to eliminate effector functions associated with engagement of Fc receptors by the Fc domain. Hence, in particular embodiments the altered binding to an Fc receptor and/or effector function is reduced binding and/or effector function. In a specific such embodiment the Fc domain comprises one or more amino acid mutation that reduces the binding of the Fc domain to an Fc receptor, particularly an Fcγ receptor. Preferably, such an amino acid mutation does not reduce binding to FcRn receptors. In one embodiment the Fc domain comprises an amino acid substitution at position P329. In a particular embodiment the Fc domain comprises the amino acid substitutions L234A, L235A and P329G in each of its subunits.

On the other hand, there may be situations where it is desirable to enhance the effector functions of immunoconjugates. Hence, in certain embodiments the Fc domain of the immunoconjugate of the invention is engineered to have altered binding to an Fc receptor, specifically an Fcγ receptor, more specifically an FcγIIIa receptor, and/or altered effector function, wherein the altered binding and/or effector function is increased binding and/or effector function. In one such embodiment the Fc domain is engineered to have an altered oligosaccharide structure, as compared to a non-engineered Fc domain. In a particular such embodiment the Fc domain comprises an increased proportion of non-fucosylated oligosaccharides, as compared to a non-engineered Fc domain. In a more specific embodiment the Fc domain comprises at least 20%, particularly at least 50%, more particularly at least 70% non-fucosylated oligosaccharides. In another specific embodiment the Fc domain comprises an increased proportion of bisected oligosaccharides, as compared to a non-engineered Fc domain. In yet another specific embodiment the Fc domain comprises an increased proportion of bisected, non-fucosylated oligosaccharides, compared to a non-engineered Fc domain. In some embodiments said altered oligosaccharide structure results from increased β(1,4)-N-acetylglucosaminyltransferase III (GnTIII) activity in a host cell used for expression of the immunoconjugate.

In a particular aspect, the invention provides immunoconjugates that comprise a first and a second antigen binding moiety, an Fc domain consisting of two subunits, and an effector moiety, wherein not more than one effector moiety is present. In one embodiment the first and the second antigen binding moiety and the Fc domain are part of an immunoglobulin molecule. In certain embodiments the immunoconjugate essentially consists of an immunoglobulin molecule and an effector moiety and optionally one or more linker sequences. In a particular embodiment the immunoglobulin molecule is an IgG class immunoglobulin. In an even more particular embodiment the immunoglobulin is an $IgG_1$ subclass immunoglobulin. In one embodiment the effector moiety is fused to the carboxy-terminal amino acid of one of the immunoglobulin heavy chains, optionally through a linker peptide.

In a particular embodiment the immunconjugate of the invention comprises an immunoglobulin molecule comprising two antigen binding moieties and an Fc domain, and an effector moiety fused to the carboxy-terminal amino acid of one of the immunoglobulin heavy chains, wherein not more than one effector moiety is present and wherein the Fc domain is engineered to have reduced binding to an Fc receptor, specifically altered binding to an Fcγ receptor, and/or reduced effector function.

In certain embodiments said first antigen binding moiety, or said first and said second antigen binding moiety, is directed to an antigen associated with a pathological condition, such as an antigen presented on a tumor cell or in a tumor cell environment, at a site of inflammation, or on a virus-infected cell. In a more specific embodiment said antigen is selected from the group of Fibroblast Activation Protein (FAP), the A1 domain of Tenascin-C (TNC A1), the A2 domain of Tenascin-C (TNC A2), the Extra Domain B of Fibronectin (EDB), Carcinoembryonic Antigen (CEA), and Melanoma-associated Chondroitin Sulfate Proteoglycan (MCSP).

In certain embodiments the effector moiety is a single chain effector moiety. In a particular embodiment the effector moiety is a cytokine. In one embodiment said cytokine is selected from the group of IL-2, IL-7, IL-10, IL-12, IL-15, IFN-α and IFN-γ. In a particular embodiment said cytokine is IL-2. In an even more particular embodiment said cytokine is a mutant IL-2 polypeptide having reduced binding affinity to the α-subunit of the IL-2 receptor. In a specific embodiment said mutant IL-2 polypeptide comprises an amino acid substitution at one or more positions selected from the positions corresponding to residues 42, 45 and 72 of human IL-2. In another particular embodiment the cytokine is IL-10. In yet another embodiment, the cytokine is IL-15, particularly a mutant IL-15 polypeptide having reduced binding affinity to the α-subunit of the IL-15 receptor. In another embodiment, the cytokine is IFN-α.

According to another aspect of the invention there is provided an isolated polynucleotide encoding an immunoconjugate of the invention or a fragment thereof. The invention further provides an expression vector comprising the isolated polynucleotide of the invention, and a host cell comprising the isolated polynucleotide or the expression vector of the invention. In some embodiments the host cell is a eukaryotic cell, particularly a mammalian cell. In some embodiments, the host cell has been manipulated to express increased levels of one or more polypeptides having β(1,4)-N-acetylglucosaminyltransferase III (GnTIII) activity. In one such embodiment the host cell has been further manipulated to express increased levels of one or more polypeptides having α-mannosidase II (ManII) activity.

In another aspect is provided a method of producing the immunoconjugates of the invention, comprising the steps of a) culturing the host cell of the invention under conditions suitable for the expression of the immunoconjugate and b) recovering the immunoconjugate. The invention also encompasses an immunoconjugate produced by the method of the invention.

The invention further provides a pharmaceutical composition comprising an immunoconjugate of the invention and a pharmaceutically acceptable carrier.

Also encompassed by the invention are methods of using the immunoconjugates and pharmaceutical compositions of the invention. In one aspect the invention provides an immunoconjugate or a pharmaceutical composition of the invention for use as a medicament. In one aspect is provided an immunoconjugate or a pharmaceutical composition according to the invention for use in the treatment of a disease in an individual in need thereof. In a specific embodiment the disease is cancer. In other embodiments the disease is an inflammatory disorder. In a particular such embodiment the immunoconjugate comprises an IL-10 effector moiety.

Also provided is the use of an immunoconjugate of the invention for the manufacture of a medicament for the treatment of a disease in an individual in need thereof as well as a method of treating a disease in an individual, comprising administering to said individual a therapeutically effective amount of a composition comprising the immunoconjugate according to the invention in a pharmaceutically acceptable form. In a specific embodiment the disease is cancer. In other embodiments the disease is an inflammatory disorder. In a particular such embodiment the immunoconjugate comprises an IL-10 effector moiety.

In any of the above embodiments the individual preferably is a mammal, particularly a human.

In a further aspect, the invention provides a conjugate comprising a first Fab molecule which does not specifically bind any antigen, an Fc domain consisting of two subunits, and an effector moiety, wherein not more than one effector moiety is present. In a particular embodiment the first Fab molecule comprises the heavy chain variable region sequence of SEQ ID NO: 299 and the light chain variable region sequence of SEQ ID NO: 297. In one embodiment, the effector moiety is fused to the amino- or carboxy-terminal amino acid of one of the two subunits of the Fc domain, optionally through a linker peptide. In another embodiment, the first Fab molecule is fused to the amino-terminal amino acid of one of said two subunits of the Fc domain, optionally through a linker peptide or an immunoglobulin hinge region. In one embodiment, the conjugate comprises (i) an immunoglobulin molecule, comprising a first and a second Fab molecule which do not specifically bind any antigen and an Fc domain, and (ii) an effector moiety, wherein not more than one effector moiety is present. In one embodiment the immunoglobulin molecule is an IgG class immunoglobulin, particularly an IgG1 subclass immunoglobulin. In a particular embodiment the immunoglobulin molecule comprises the heavy chain variable region sequence of SEQ ID NO: 299 and the light chain variable region sequence of SEQ ID NO: 297.

Specifically, the heavy chain variable region sequence of SEQ ID NO: 299 and the light chain variable region sequence of SEQ ID NO: 297 are comprised in the first and the second Fab molecule of the immunoglobulin molecule. In one embodiment, the effector moiety is fused to the carboxy-terminal amino acid of one of the immunoglobulin heavy chains, optionally through a linker peptide.

In certain embodiments the Fc domain of the conjugate comprises a modification promoting heterodimerization of the non-identical polypeptide chains. In a specific embodiment, said modification is a knob-into-hole modification, comprising a knob modification in one of the subunits of the Fc domain and a hole modification in the other one of the two subunits of the Fc domain. In a particular embodiment, the effector moiety is fused to the amino- or carboxy-terminal amino acid of the subunit of the Fc domain comprising the knob modification. In one embodiment, the Fc domain is an IgG Fc domain, particularly an $IgG_1$ Fc domain. In a particular embodiment, the Fc domain is human. In some embodiments, the Fc domain is engineered to have altered binding to an Fc receptor, specifically altered binding to an Fcγ receptor, and/or altered effector function, specifically altered ADCC. In some embodiments the Fc domain of the conjugate is engineered to have reduced binding to an Fc receptor, specifically reduced binding to an Fcγ receptor, and/or reduced effector function, specifically reduced ADCC. In one embodiment, the Fc domain comprises one or more amino acid mutation that reduces the binding of the Fc domain to an Fc receptor, particularly an Fcγ receptor. In a specific embodiment the amino acid mutation is an amino acid substitution at position P329. In a particular embodiment, the Fc domain of the conjugate comprises the amino acid substitutions L234A, L235A and P329G in each of its subunits. In another embodiment of the conjugate of the invention, the Fc domain is engineered to have altered binding to an Fc receptor and/or altered effector function, wherein said altered binding and/or effector function is increased binding and/or effector function. In one embodiment of the conjugate of the invention, the Fc domain is engineered to have an altered oligosaccharide structure, as compared to a non-engineered Fc domain. In a specific embodiment, the Fc domain described above comprises an increased proportion of non-fucosylated oligosaccharides, as compared to a non-engineered Fc domain.

In a further embodiment of the conjugate of the invention, the conjugate comprises a first and a second Fab molecule. In one embodiment, the first and the second Fab molecule each comprises the heavy chain variable region sequence of SEQ ID NO: 299 and the light chain variable region sequence of SEQ ID NO: 297. In one embodiment, the first and said second Fab molecule and said Fc domain are part of an immunoglobulin molecule. In a particular embodiment, the immunoglobulin molecule is an IgG class immunoglobulin. In an even more particular embodiment, the immunoglobulin molecule is an $IgG_1$ subclass immunoglobulin. In one embodiment, the effector moiety is fused to the carboxy-terminal amino acid of one of the immunoglobulin heavy chains, optionally through a linker peptide.

In some embodiments of the conjugate of the invention, said effector moiety is a single chain effector moiety. In one embodiment the effector moiety is a cytokine, particularly IL-2. In another embodiment, said cytokine is a mutant IL-2 polypeptide having reduced binding affinity to the α-subunit of the IL-2 receptor. In a specific embodiment, said mutant IL-2 polypeptide comprises an amino acid substitution at one or more positions selected from the positions corresponding to residues 42, 45 and 72 of human IL-2.

Additionally, the conjugate can incorporate, alone or in combination, any of the features described herein in relation to the formats, the Fc domain or the effector moiety of the immunoconjugates of the invention.

The invention also provides an isolated polynucleotide encoding the conjugate of the invention of a fragment thereof, as described above. In a specific embodiment, the isolated polynucleotide comprises a sequence that is at least about 80%, 85%, 90%, 95%, 96%, 97%, 98%, 99% or 100% identical to the sequence of SEQ ID NO: 298 or SEQ ID NO: 300. The invention further provides an expression vector comprising the isolated polynucleotide, and a host cell comprising the isolated polynucleotide or the expression vector of the invention. In another aspect is provided a method of producing the conjugate of the invention described above, comprising the steps of a) culturing the host cell of the invention under conditions suitable for the expression of the conjugate and b) recovering the conjugate. The invention also encompasses a conjugate, described above, produced by the method of the invention, comprising the steps of a) culturing the host cell of the invention under conditions suitable for the expression of the conjugate and b) recovering the conjugate.

The invention further provides a pharmaceutical composition comprising the conjugate of the invention described above and a pharmaceutically acceptable carrier. Furthermore, the conjugate can be employed in the methods of use described herein for the immunoconjugates of the invention. In one embodiment, the conjugate as described above, or the pharmaceutical composition described above, is for use in the treatment of a disease in an individual in need thereof or for the manufacture of a medicament for the treatment of a disease in an individual in need thereof.

In a further aspect of the invention, a method of treating a disease in an individual is provided, comprising administering to said individual a therapeutically effective amount of a composition comprising the conjugate of the invention as described above, in a pharmaceutically acceptable form.

BRIEF DESCRIPTION OF THE DRAWINGS

FIG. 3A) Elution profile of the Protein A affinity chromatography step. FIG. 3B) Elution profile of the size exclusion chromatography step. FIG. 3C) Analytical SDS-PAGE (NuPAGE Novex Bis-Tris Mini Gel, Invitrogen, MOPS running buffer) of the final product. FIG. 3D) Analytical size exclusion chromatography of the final product on a Superdex 200 column (97% monomer content).

FIG. 4A) Elution profile of the Protein A affinity chromatography step. FIG. 4B) Elution profile of the size exclusion chromatography step. FIG. 4C) Analytical SDS-PAGE (reduced: NuPAGE Novex Bis-Tris Mini Gel, Invitrogen, MOPS running buffer; non-reduced: NuPAGE Tris-Acetate, Invitrogen, Tris-Acetate running buffer) of the final product. FIG. 4D) Analytical size exclusion chromatography of the final product on a Superdex 200 column (100% monomer content).

FIGS. 5A-D. Purification of FAP-targeted 28H1-based IgG-IL-2 qm immunoconjugate from CHO cells. FIG. 5A) Elution profile of the Protein A affinity chromatography step. FIG. 5B) Elution profile of the size exclusion chromatography step. FIG. 5C) Analytical SDS-PAGE (NuPAGE Novex Bis-Tris Mini Gel, Invitrogen, MOPS running buffer) of the final product. FIG. 5D) Analytical size exclusion chromatography of the final product on a Superdex 200 column (100% monomer content).

FIG. 6A) Elution profile of the Protein A affinity chromatography step. FIG. 6B) Elution profile of the size exclusion chromatography step. FIG. 6C) Analytical SDS-PAGE (NuPAGE Novex Bis-Tris Mini Gel, Invitrogen, MOPS running buffer) of the final product. FIG. 6D) Analytical size exclusion chromatography of the final product on a Superdex 200 column (100% monomer content).

FIGS. 7A-D. Purification of CEA-targeted CH1A1A 98/99 2F1-based IgG-IL-2 qm immunoconjugate. FIG. 7A) Elution profile of the Protein A affinity chromatography step. FIG. 7B) Elution profile of the size exclusion chromatography step. FIG. 7C) Analytical capillary electrophoresis SDS (Caliper) of the final product. FIG. 7D) Analytical size exclusion chromatography of the final product on a TSKgel G3000 SW XL column (98.8% monomer content).

FIG. 8A) Elution profile of the Protein A affinity chromatography step. FIG. 8B) Elution profile of the size exclusion chromatography step. FIG. 8C) Analytical capillary electrophoresis SDS (Caliper) of the final product. FIG. 8D) Analytical size exclusion chromatography of the final product on a TSKgel G3000 SW XL column (100% monomer content).

FIG. 9A) Elution profile of the Protein A affinity chromatography step. FIG. 9B) Elution profile of the size exclusion chromatography step. FIG. 9C) Analytical SDS-PAGE (NuPAGE Novex Bis-Tris Mini Gel, Invitrogen, MOPS running buffer) of the final product. FIG.

9D) Analytical size exclusion chromatography of the final product on a Superdex 200 column (100% monomer content).

Figure 10:
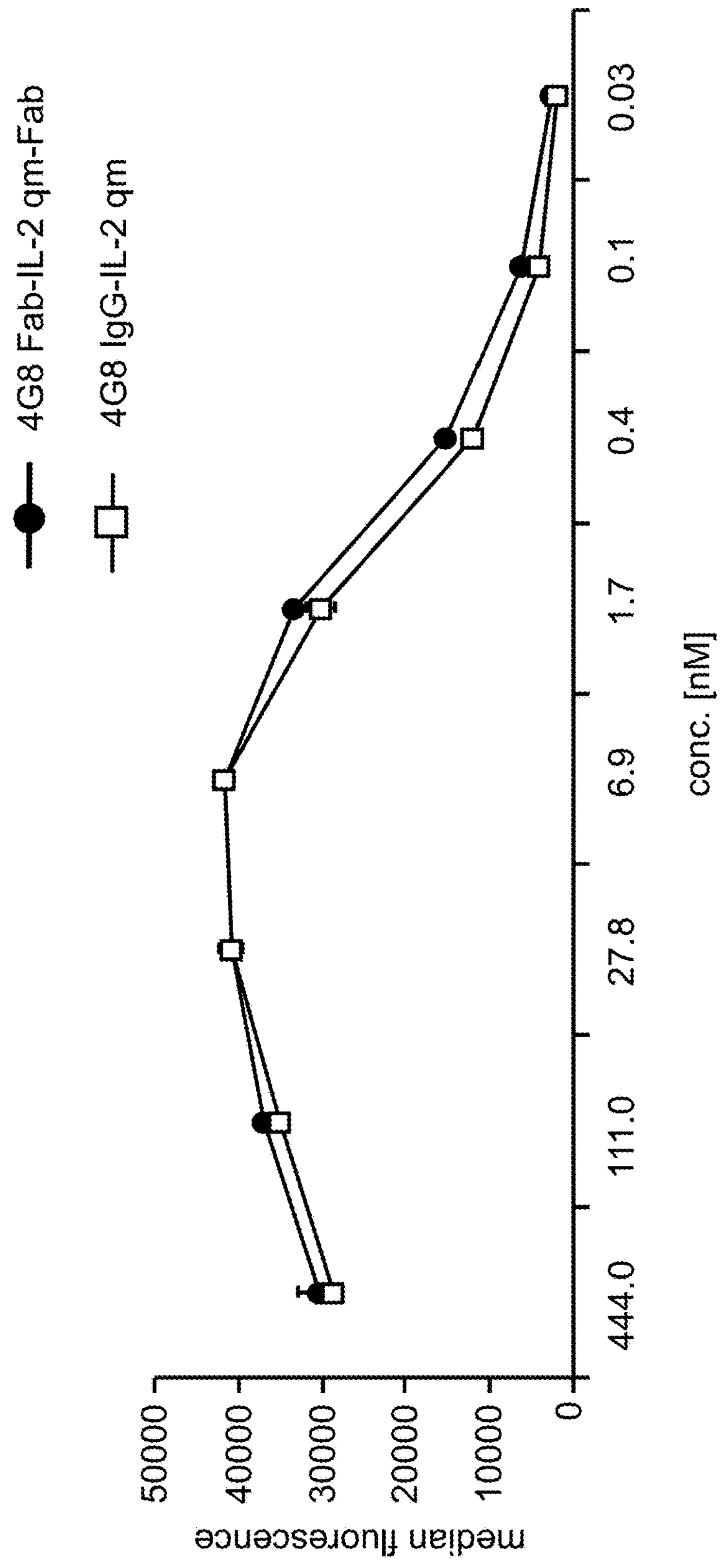

FIG. 10. Binding of FAP-targeted 4G8-based IgG-IL-2 qm immunoconjugate to human FAP expressed on stably transfected HEK 293 cells as measured by FACS, compared to the corresponding Fab-IL-2 qm-Fab construct.

Figure 11:
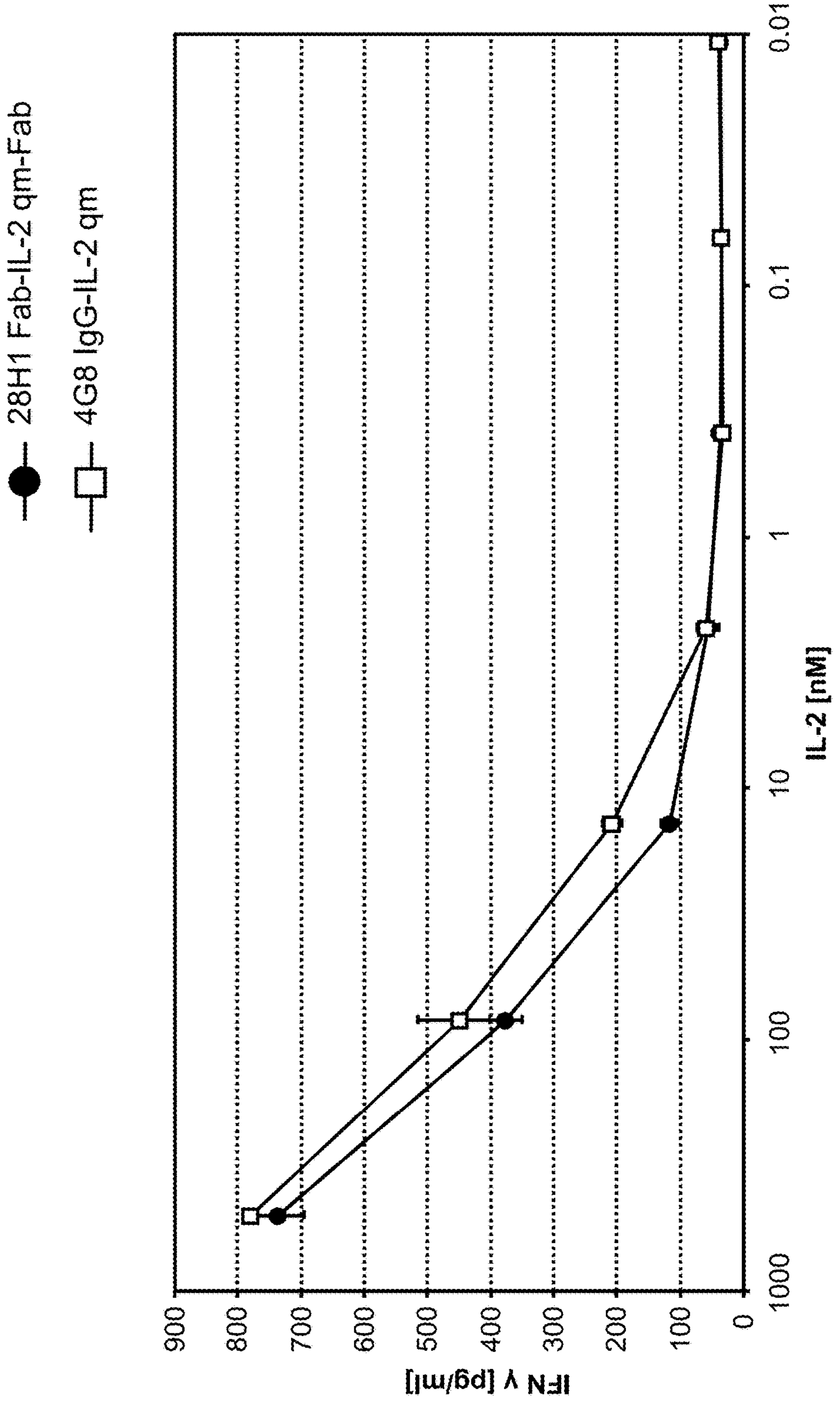

FIG. 11. Interferon (IFN)-γ release on NK92 cells induced by FAP-targeted 4G8-based IgG-IL-2 qm immunoconjugate in solution, compared to the 28H1-based Fab-IL-2 qm-Fab construct.

Figures 12A, 12B, 12C, 12D:
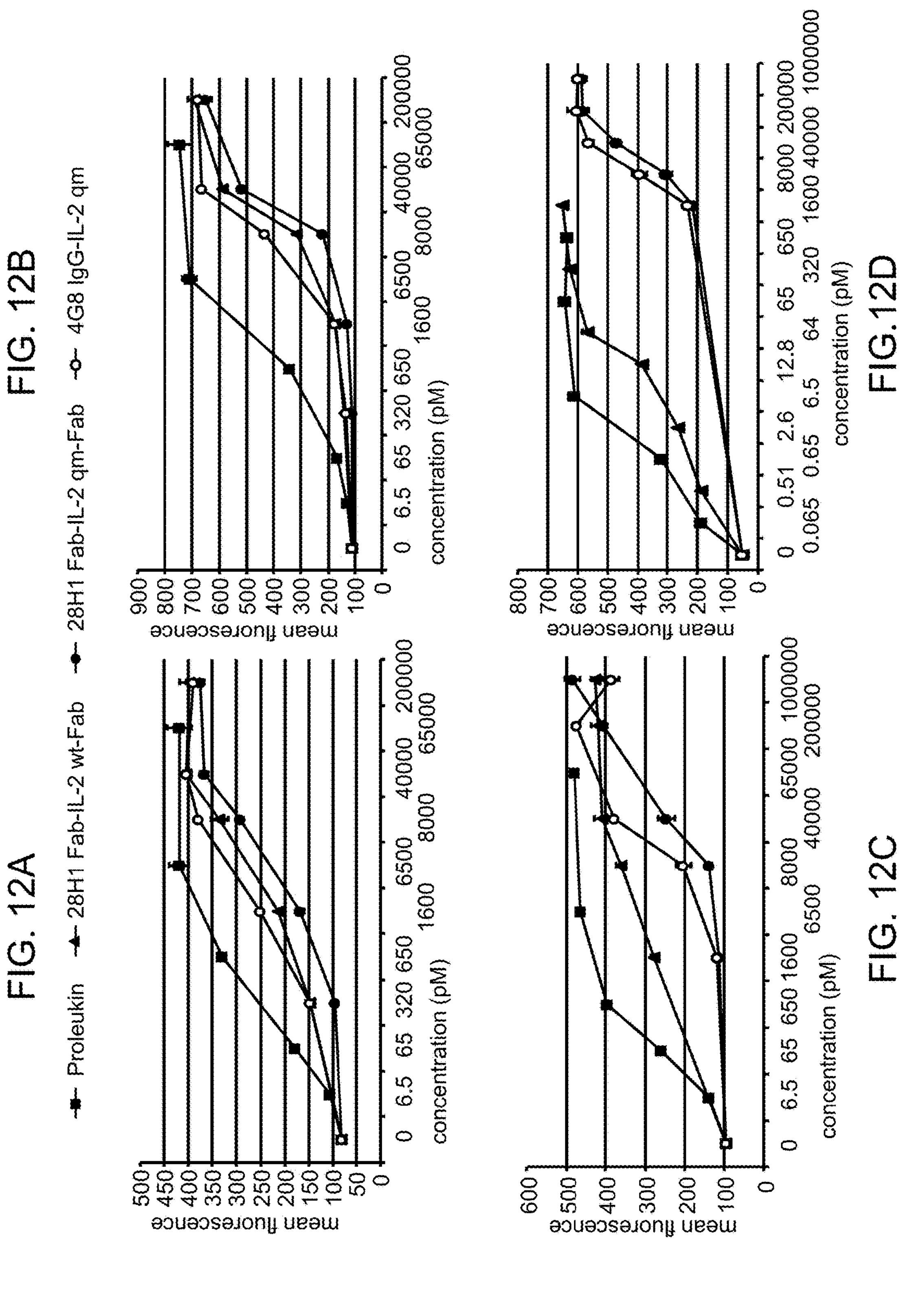

FIGS. 12A-D. Detection of phosphorylated STAT5 by FACS in different cell types after stimulation for 20 min with FAP-targeted 4G8-based IgG-IL-2 qm immunoconjugate in solution, compared to the 28H1-based Fab-IL-2-Fab and Fab-IL-2 qm-Fab constructs as well as Proleukin. FIG. 12A) NK cells ($CD3^-CD56^+$); FIG. 12B) $CD8^+$ T cells ($CD3^+CD8^+$); FIG. 12C) $CD4^+$ T cells ($CD3^+CD4^+CD25^-CD127^+$); FIG. 12D) regulatory T cells ($CD4^+CD25^+FOXP3^+$).

Figure 13:
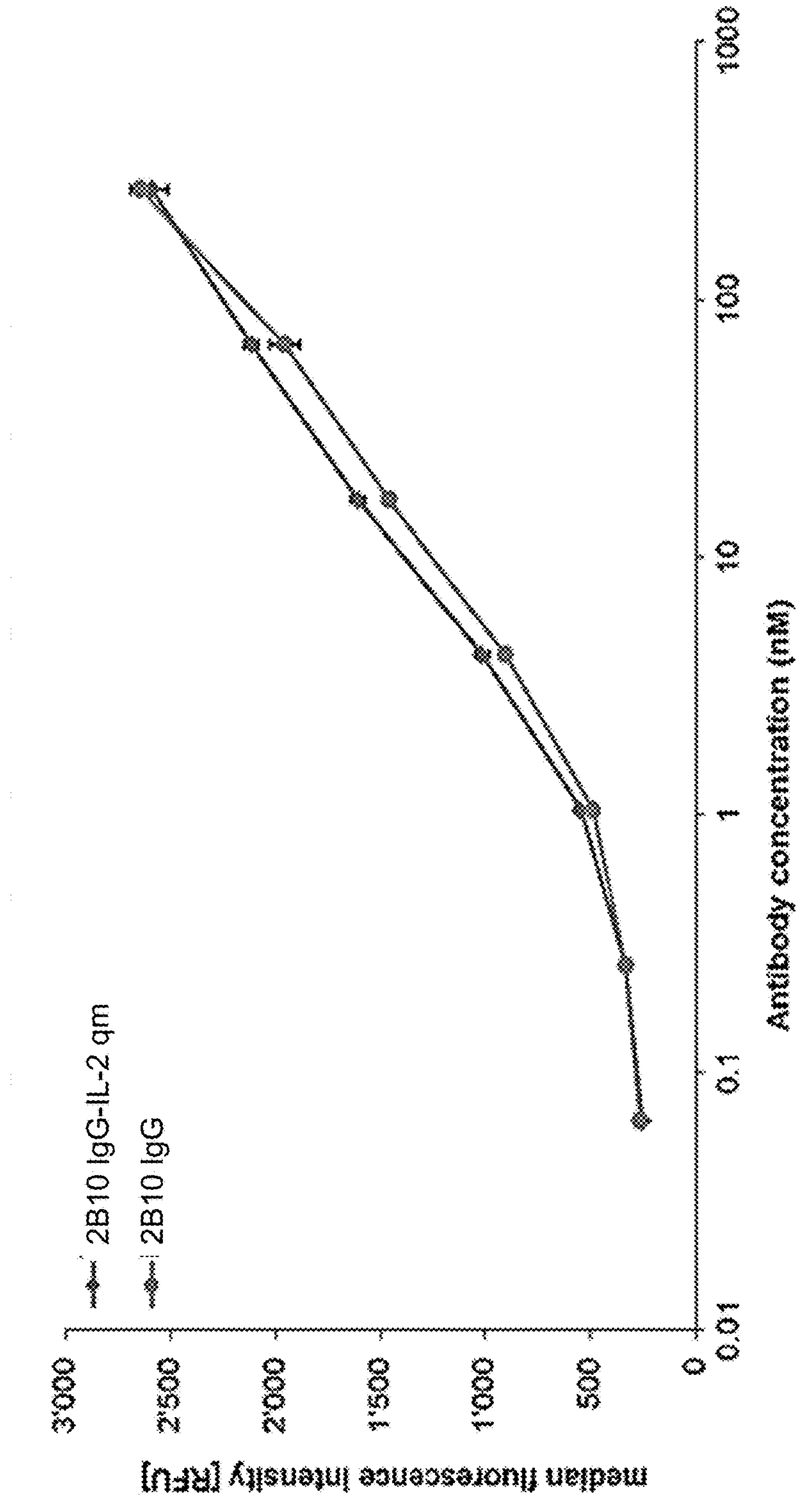

FIG. 13. Binding of TNC A2-targeted 2B10 IgG-IL-2 qm and corresponding unconjugated IgG to TNC A2-expressing U87MG cells, as measured by FACS.

Figure 14:
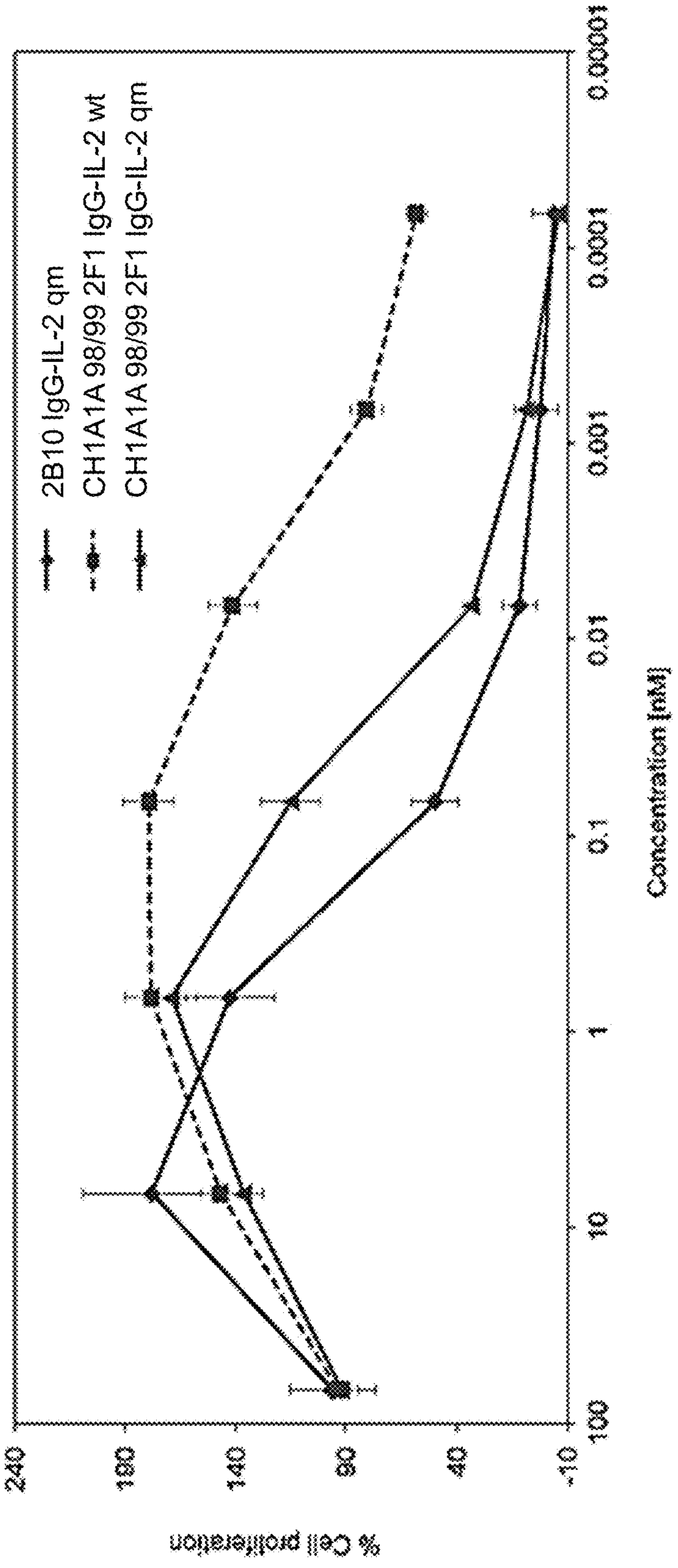

FIG. 14. Induction of NK92 cell proliferation by TNC A2-targeted 2B10 IgG-IL-2 qm, CEA-targeted CH1A1A 98/99 2F1 IgG-IL-2 qm and CH1A1A 98/99 2F1 IgG-IL-2 wt immunoconjugates.

Figure 15:
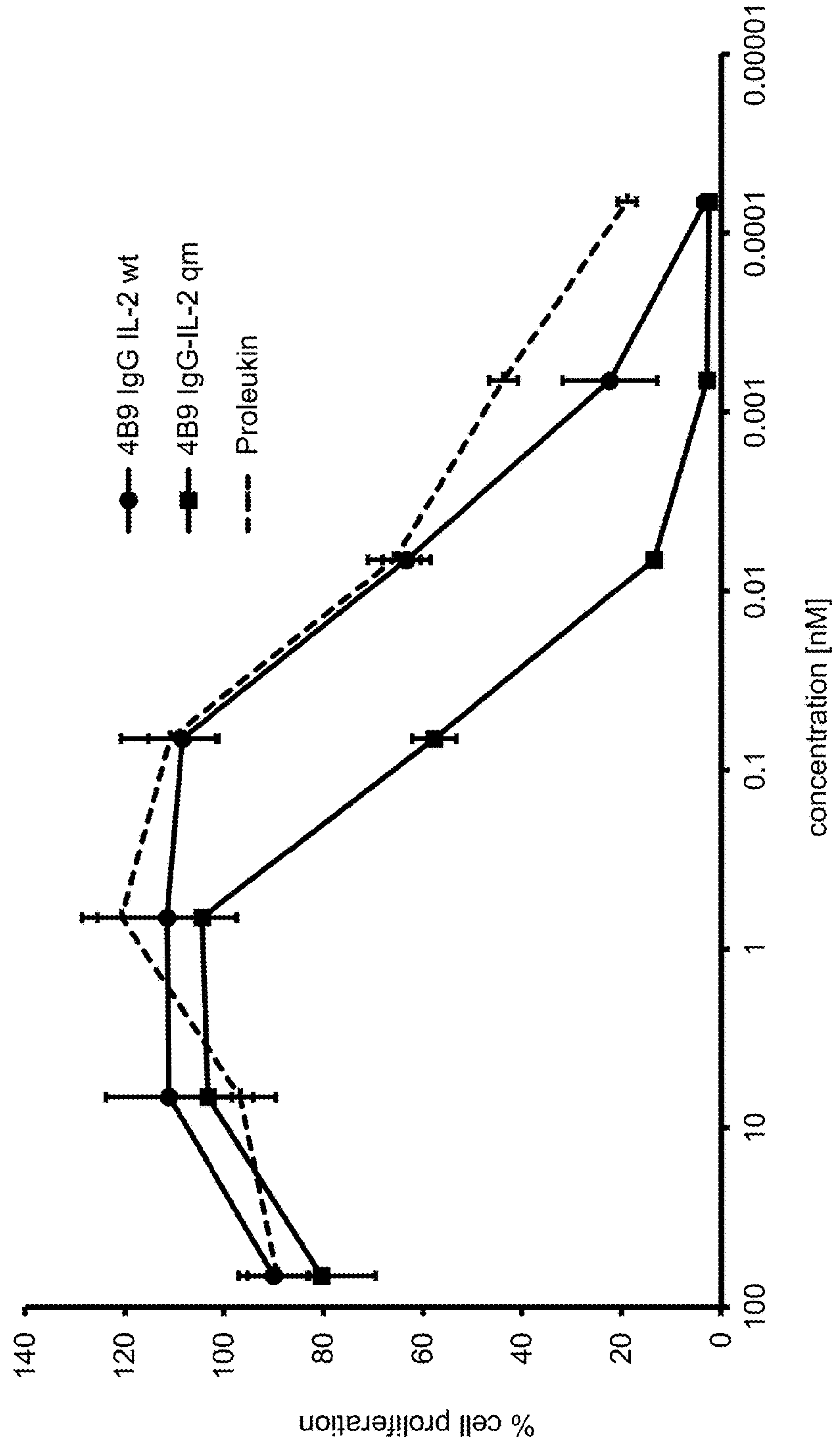

FIG. 15. Induction of NK92 cell proliferation by FAP-targeted 4B9 IgG-IL-2 qm and 4B9 IgG-IL-2 wt immunoconjugates.

Figure 16:
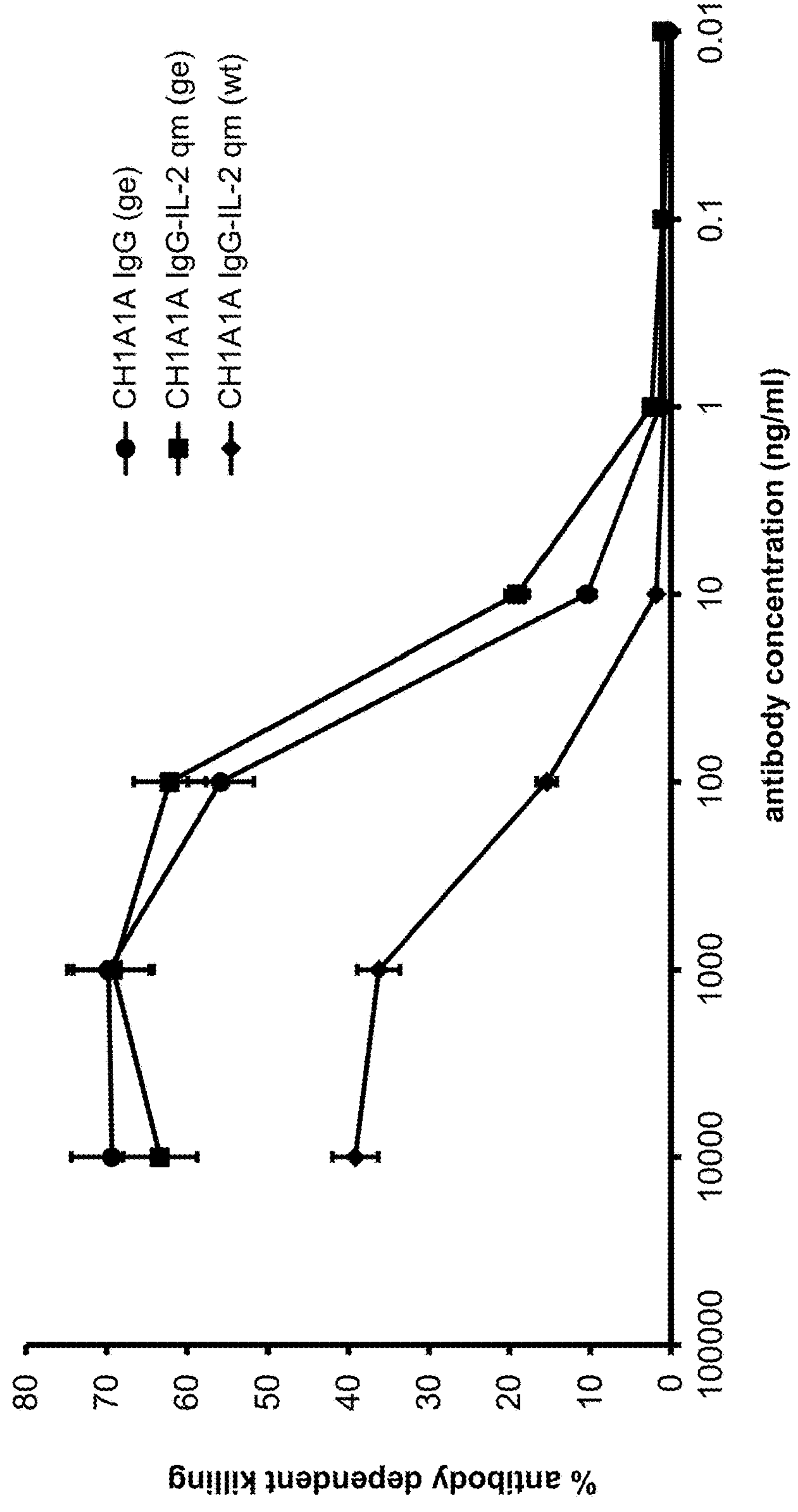

FIG. 16. Killing (as measured by LDH release) of CEA-overexpressing A549 tumor cells by PBMCs through ADCC mediated by glycoengineered (ge) and wildtype (wt) CH1A1A IgG-IL-2 qm immunoconjugates, compared to unconjugated glycoengineered CH1A1A IgG.

Figures 17A, 17B, 17C, 17D:
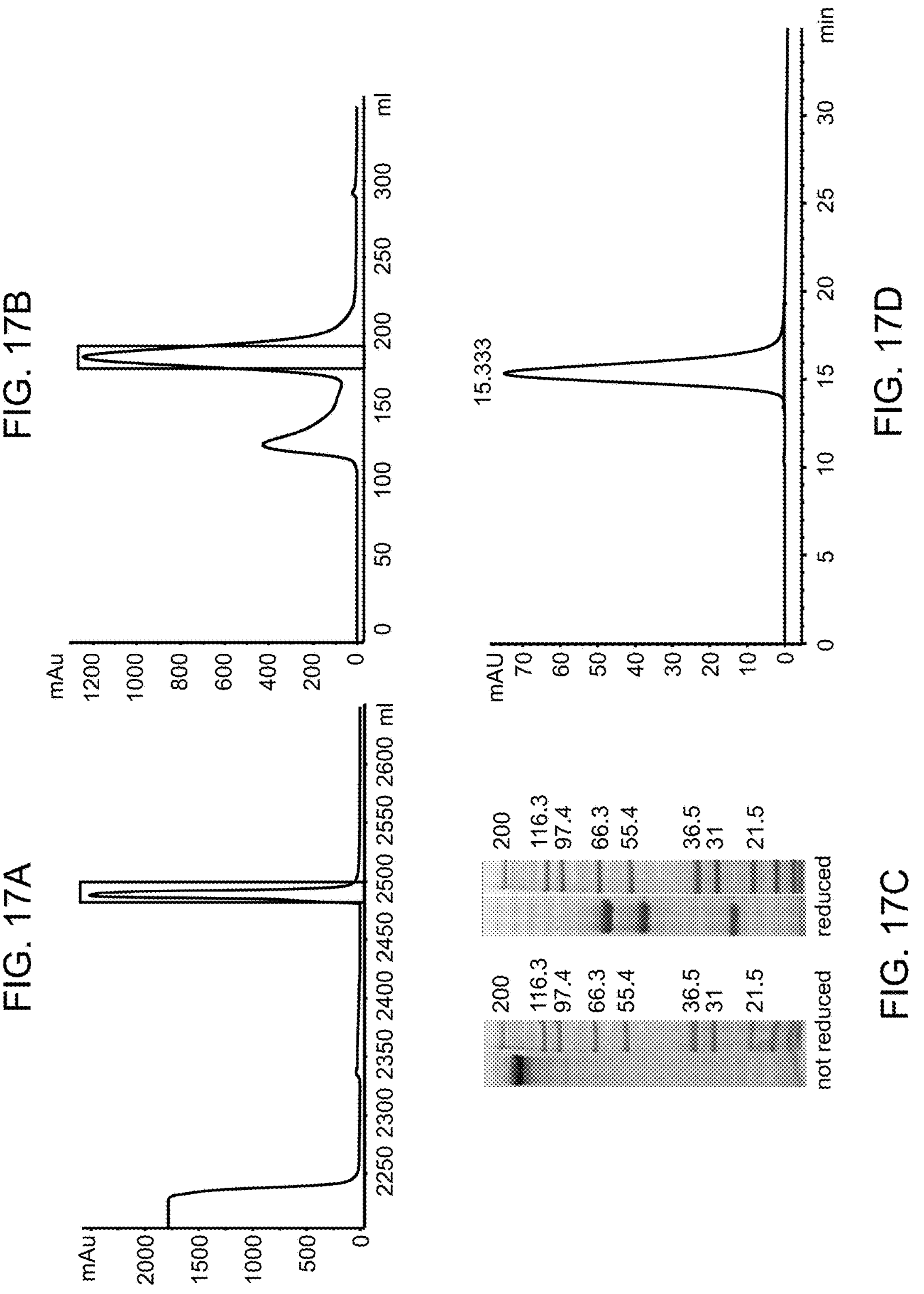

FIGS. 17A-D. Purification of untargeted DP47GS IgG-IL-2 wt immunoconjugate. FIG. 17A) Elution profile of the Protein A affinity chromatography step. FIG. 17B) Elution profile of the size exclusion chromatography step. FIG. 17C) Analytical SDS-PAGE (NuPAGE Novex Bis-Tris Mini Gel, Invitrogen, MOPS running buffer) of the final product. FIG. 17D) Analytical size exclusion chromatography of the final product on a Superdex 200 column (99.6% monomer content).

FIGS. 18A-D. Purification of 28H1-based FAP-targeted 28H1 IgG-IL-2 wt immunoconjugate. FIG. 18A) Elution profile of the Protein A affinity chromatography step. FIG. 18B) Elution profile of the size exclusion chromatography step. FIG. 18C) Analytical SDS-PAGE (NuPAGE Novex Bis-Tris Mini Gel, Invitrogen, MOPS running buffer) of the final product. FIG. 18D) Analytical size exclusion chromatography of the final product on a Superdex 200 column (99.6% monomer content).

Figures 19A, 19B, 19C, 19D:
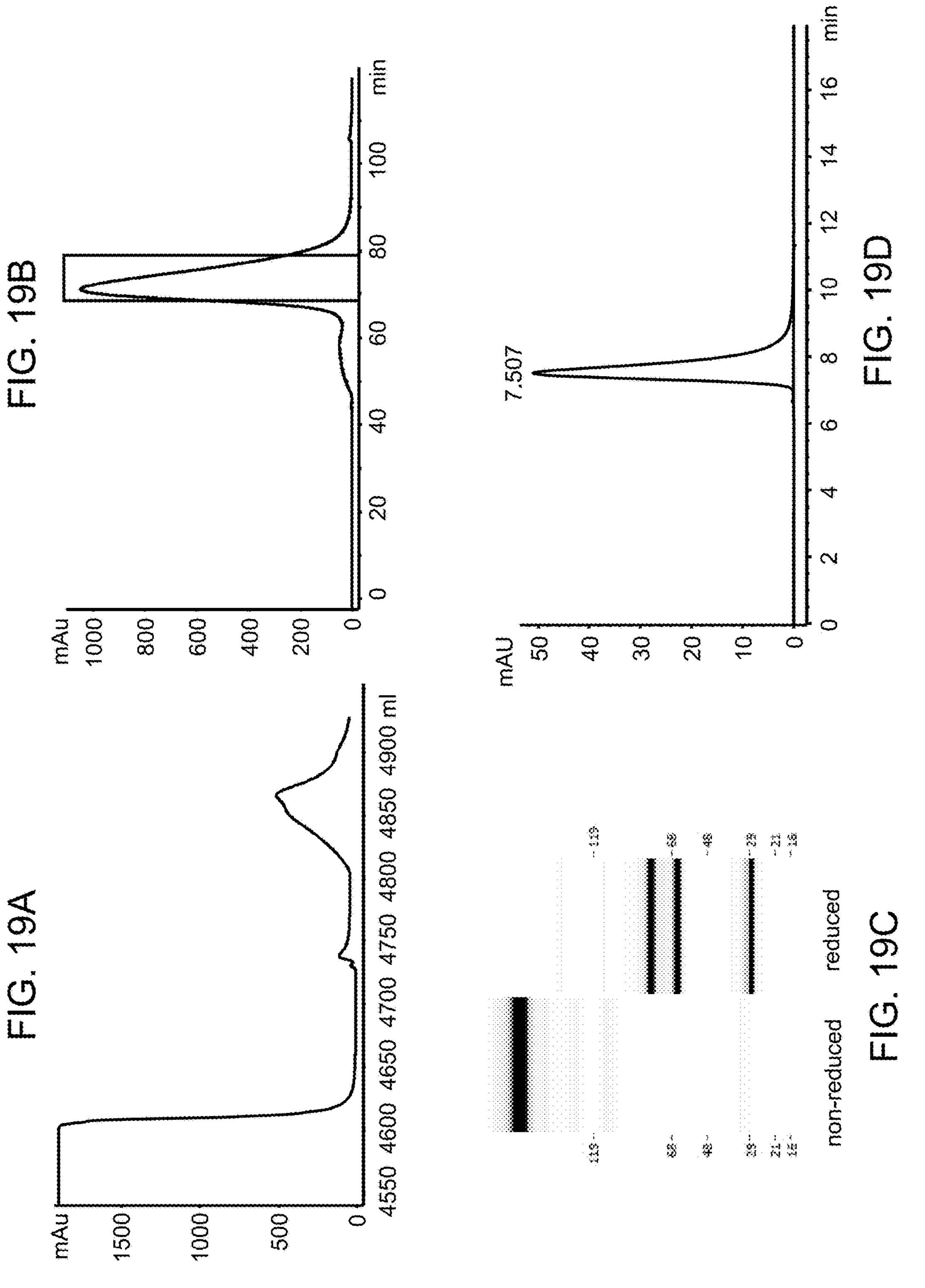

FIGS. 19A-D. Purification of CEA-targeted CH1A1A 98/99 2F1-based IgG-IL-2 wt immunoconjugate. FIG. 19A) Elution profile of the Protein A affinity chromatography step. FIG. 19B) Elution profile of the size exclusion chromatography step. FIG. 19C) Analytical capillary electrophoresis SDS (Caliper) of the final product. FIG. 19D) Analytical size exclusion chromatography of the final product on a TSKgel G3000 SW XL column (100% monomer content).

Figure 20A:
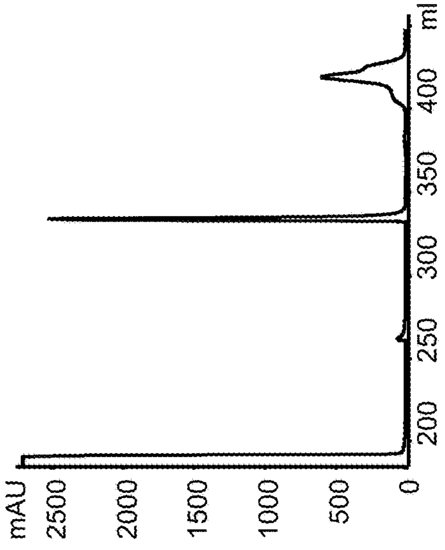
Figure 20B:
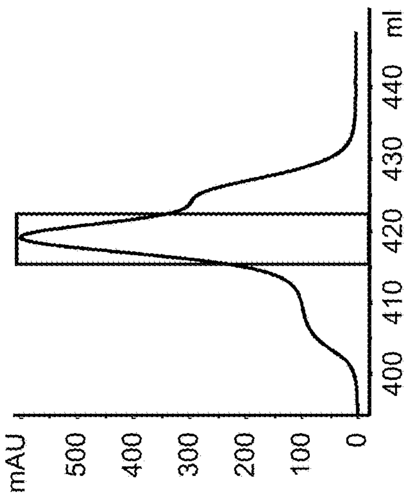
Figure 20C:
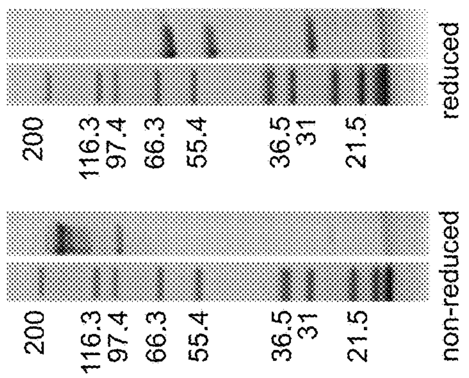
Figure 20D:
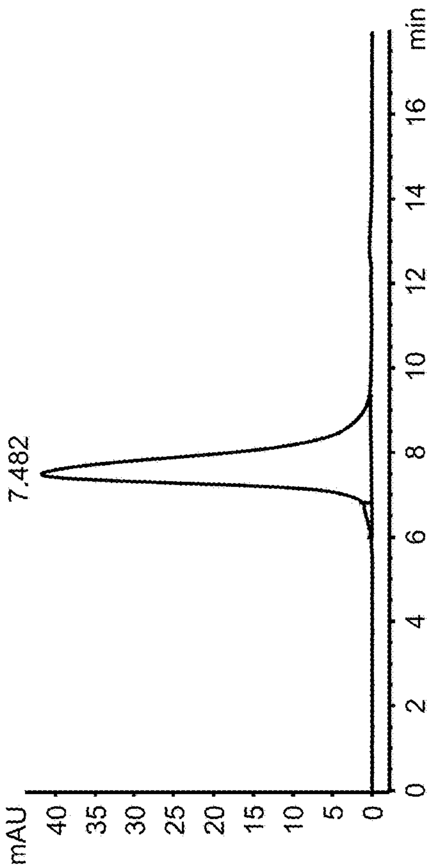

FIGS. 20A-D. Purification of FAP-targeted 4B9-based IgG-IL-2 wt immunoconjugate. FIG. 20A) Elution profile of the combined Protein A affinity and size exclusion chromatography. FIG. 20B) Zoom on the elution profile of the size exclusion chromatography step in A. FIG. 20C) Analytical SDS-PAGE (NuPAGE Novex Bis-Tris Mini Gel, Invitrogen, MOPS running buffer) of the final product. FIG. 20D) Analytical size exclusion chromatography of the final product on a TSKgel G3000 SW XL column (98.5% monomer content).

Figure 21A:
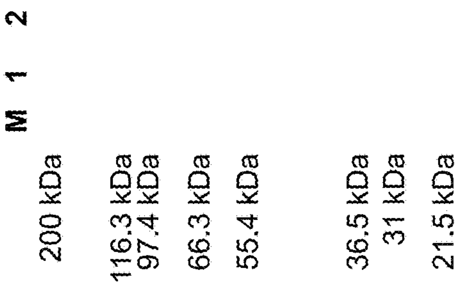
Figure 21B:
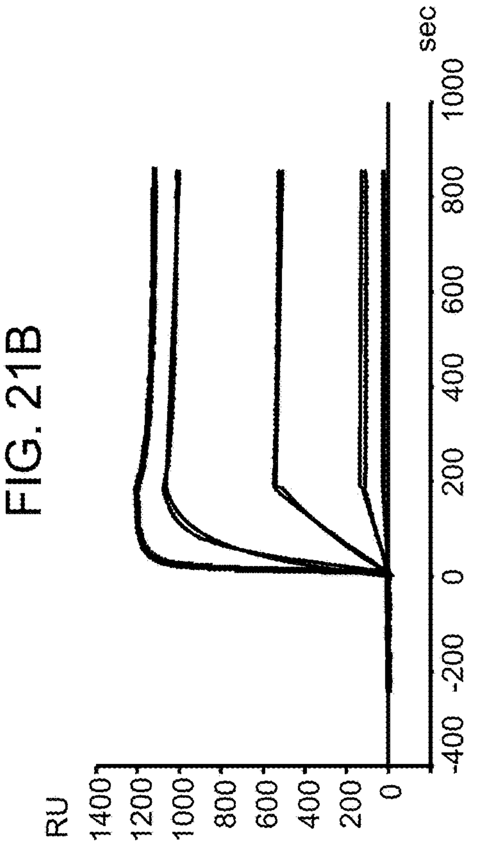
Figure 21C:
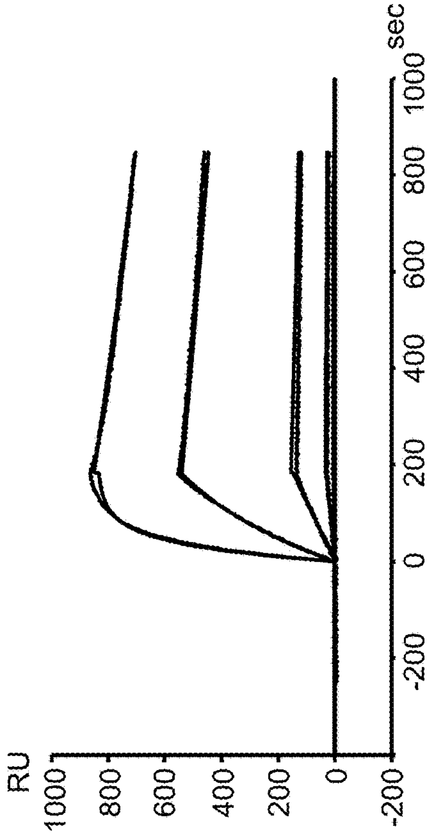

FIGS. 21A-C. FIG. 21A) Analytical SDS-PAGE (NuPAGE Novex Bis-Tris Mini Gel (Invitrogen), NuPAGE LDS sample buffer (4×), heated for 10 min at 70° C., MOPS buffer, 160 V, 60 min, MW marker Mark 12, unstained standard (Invitrogen, M) of reduced (1) and non-reduced (2) 2B10 IgG-IL-10M1. FIG. 21B) SPR-based affinity determination (ProteOn XPR36) of 2B10 IgG-IL-10M1 to human TNC A2 fitted globally to a 1:1 interaction model. (chip: NLC; ligand: TNCA2 (250 RU); analyte: TNCA2 2B10 IgG-IL-10M1 164 kDa; concentration range analyte: 50, 10, 2, 0.4, 0.08, 0 nM; association time: 180 s; dissociation time: 600 s; flow rate: 50 μl/min; $k_{on}$ $1.80\times10^6$ 1/Ms; $k_{off}$: $9.35\times10^{-5}$ 1/s; $K_D$: 52 pM). FIG. 21C) SPR-based affinity determination (ProteOn XPR36) of 2B10 IgG-IL-10M1 to human IL-10R1 fitted globally to a 1:1 interaction model (chip: NLC; ligand: IL-10R1 (1600RU); analyte: TNCA2 2B10 IgG-IL-10M1 164 kDa; concentration range analyte: 50, 10, 2, 0.4, 0.08, 0 nM; association time: 180 s; dissociation time: 600 s; flow rate: 50 μl/min; $k_{on}$ $5.56\times10^5$ 1/Ms; $k_{off}$: $2.89\times10^{-4}$ 1/s; $K_D$: 520 pM).

FIGS. 22A-C. FIG. 22A) Analytical SDS-PAGE (NuPAGE Novex Bis-Tris Mini Gel (Invitrogen), NuPAGE LDS sample buffer (4×), heated for 10 min at 70° C., MOPS buffer, 160 V, 60 min, MW marker Mark 12, unstained standard (Invitrogen, M) of reduced (1) and non-reduced (2) 4G8 IgG-IL-10M1. FIG. 22B) SPR-based affinity determination (ProteOn XPR36) of 4G8 IgG-IL-10M1 to human FAP fitted globally to a 1:1 interaction model (chip: GLM; ligand: huFAP (500RU); analyte: FAP 4G8 IgG-IL-10M1 164 kDa; concentration range analyte: 10, 2, 0.4, 0.08, 0 nM; association time: 180 s; dissociation time: 600 s; flow rate: 50 μl/min; $k_{on}$ $6.68\times10^5$ 1/Ms; $k_{off}$: $1.75\times10^{-5}$ 1/s; $K_D$: 26 pM). FIG. 22C) SPR-based affinity determination (ProteOn XPR36) of 4G8 IgG-IL-10M1 to human IL-10R1 fitted globally to a 1:1 interaction model (chip: NLC; ligand: IL 10R1 (1600RU); analyte: FAP 4G8 IgG-IL-10M1 164 kDa; concentration range analyte: 50, 10, 2, 0.4, 0.08, 0 nM; association time: 180 s; dissociation time: 600 s; flow rate: 50 μl/min; $k_{on}$: $3.64\times10^5$ 1/Ms; $k_{off}$: $2.96\times10^{-4}$ 1/s; $K_D$: 815 pM).

FIGS. 23A-C. Purification of FAP-targeted 4B9-based "1+1" IgG-IL-2 qm immunoconjugate. FIG. 23A) Elution profile of the combined Protein A affinity and size exclusion chromatography. FIG. 23B) Analytical SDS-PAGE (NuPAGE Novex Bis-Tris Mini Gel, Invitrogen, MOPS running buffer) of the final product. FIG. 23C) Analytical size exclusion chromatography of the final product on a TSKgel G3000 SW XL column (99.2% monomer content).

Figure 24A:
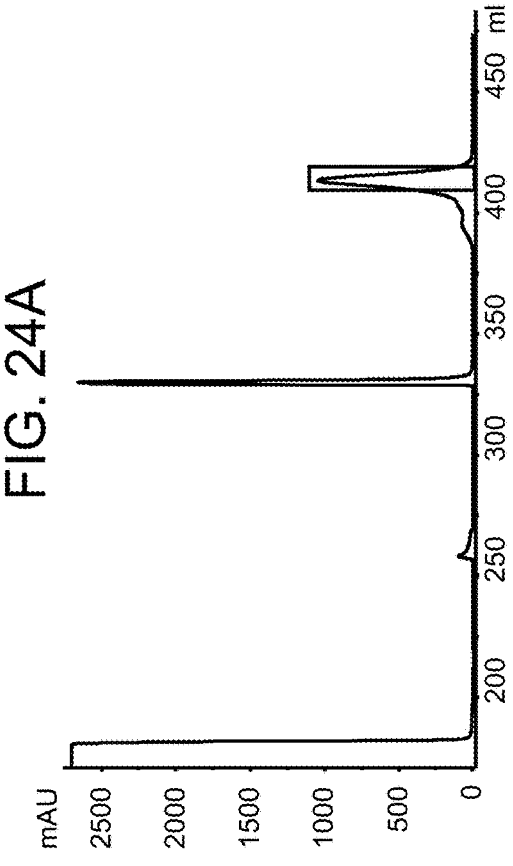
Figure 24B:
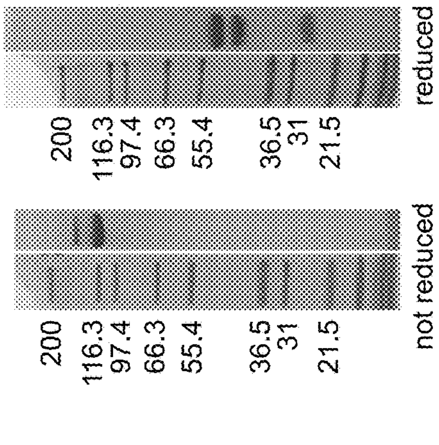
Figure 24C:
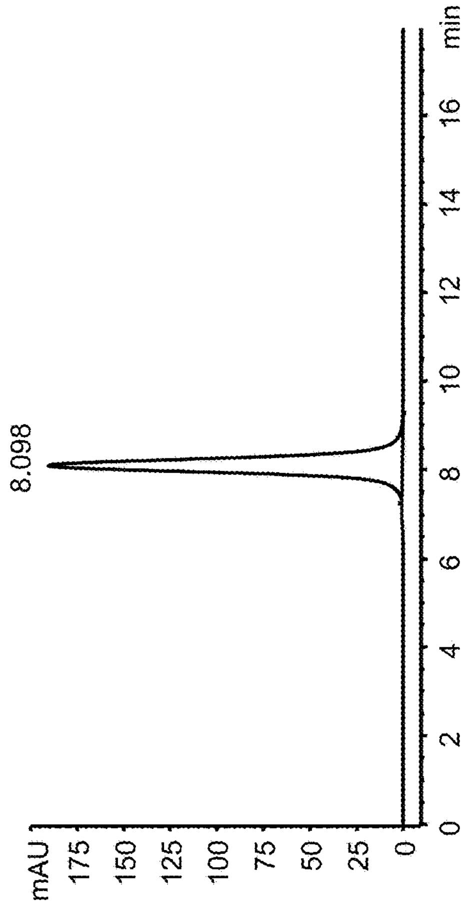

FIGS. 24A-C. Purification of FAP-targeted 28H1-based "1+1" IgG-IL-2 qm immunoconjugate. FIG. 24A) Elution profile of the combined Protein A affinity and size exclusion chromatography. FIG. 24B) Analytical SDS-PAGE (NuPAGE Novex Bis-Tris Mini Gel, Invitrogen, MOPS running buffer) of the final product. FIG. 24C) Analytical size exclusion chromatography of the final product on a TSKgel G3000 SW XL column (100% monomer content).

Figure 25A:
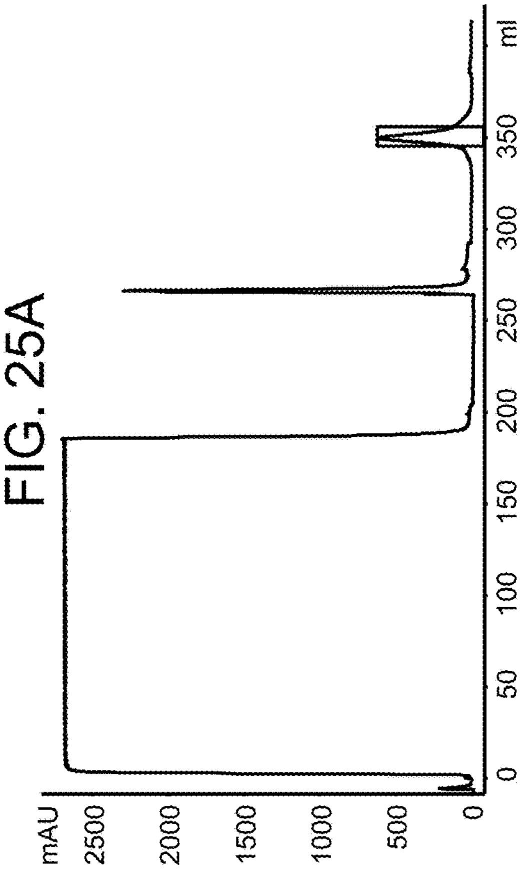
Figure 25B:
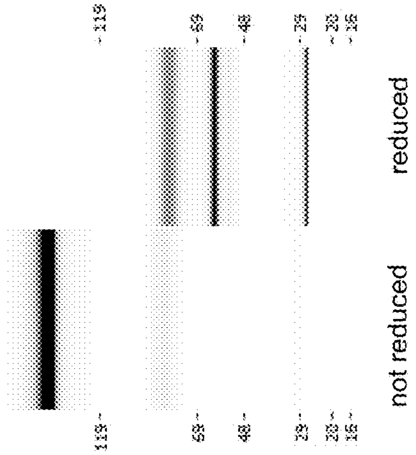
Figure 25C:
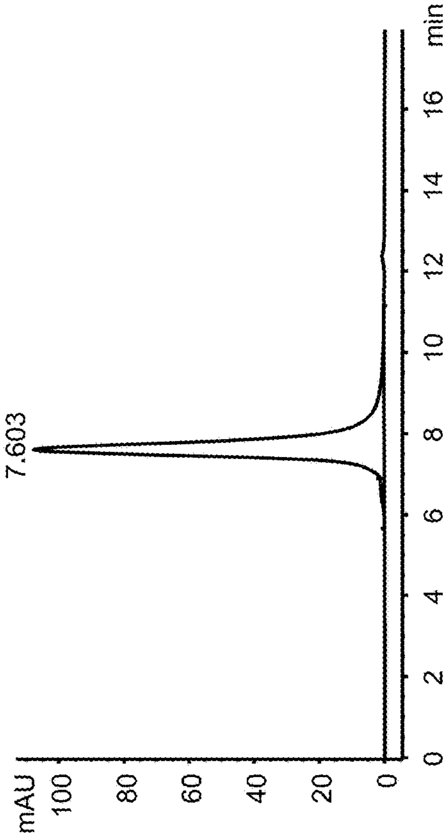

FIGS. 25A-C. Purification of FAP-targeted 4B9-based "1+1" IgG-IL-7 immunoconjugate. FIG. 25A) Elution profile of the combined Protein A affinity and size exclusion chromatography. FIG. 25B) Analytical capillary electrophoresis SDS (Caliper) of the final product. FIG. 25C) Analytical size exclusion chromatography of the final product on a TSKgel G3000 SW XL column (98.6% monomer content).

FIGS. 26A-D. Purification of FAP-targeted 4B9-based "1+1" IgG-IFN-α immunoconjugate. FIG. 26A) Elution profile of the Protein A affinity chromatography step. FIG. 26B) Elution profile of the size exclusion chromatography step. FIG. 26C) Analytical capillary electrophoresis SDS (Caliper) of the final product. FIG. 26D) Analytical size exclusion chromatography of the final product on a TSKgel G3000 SW XL column (92.8% monomer content).

Figure 27:
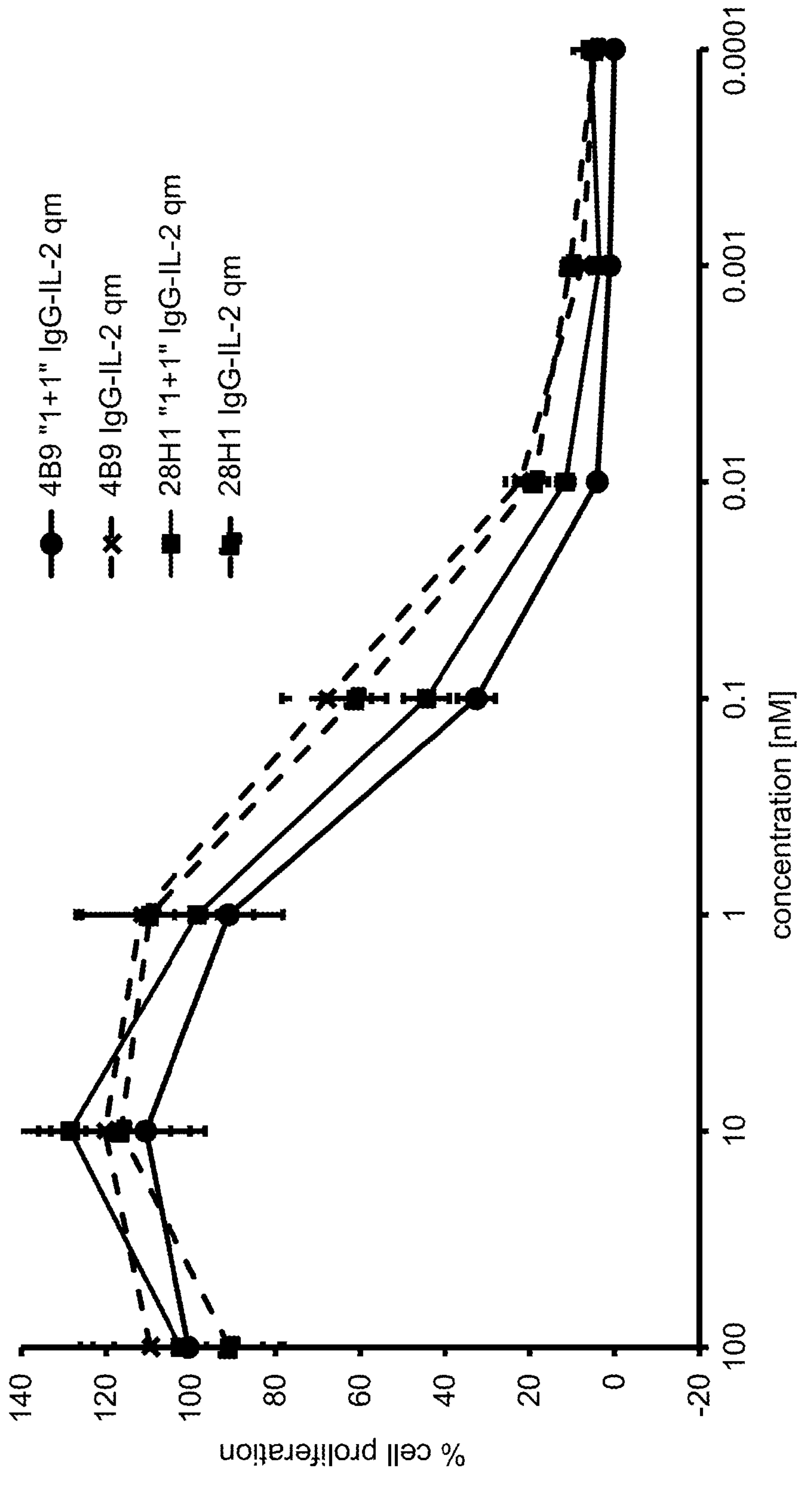

FIG. 27. Induction of NK92 cell proliferation by FAP-targeted 4B9 "1+1" IgG-IL-2 qm and 28H1 "1+1" IgG-IL-2 wt immunoconjugates, compared to corresponding IgG-IL-2 constructs.

Figure 28B:
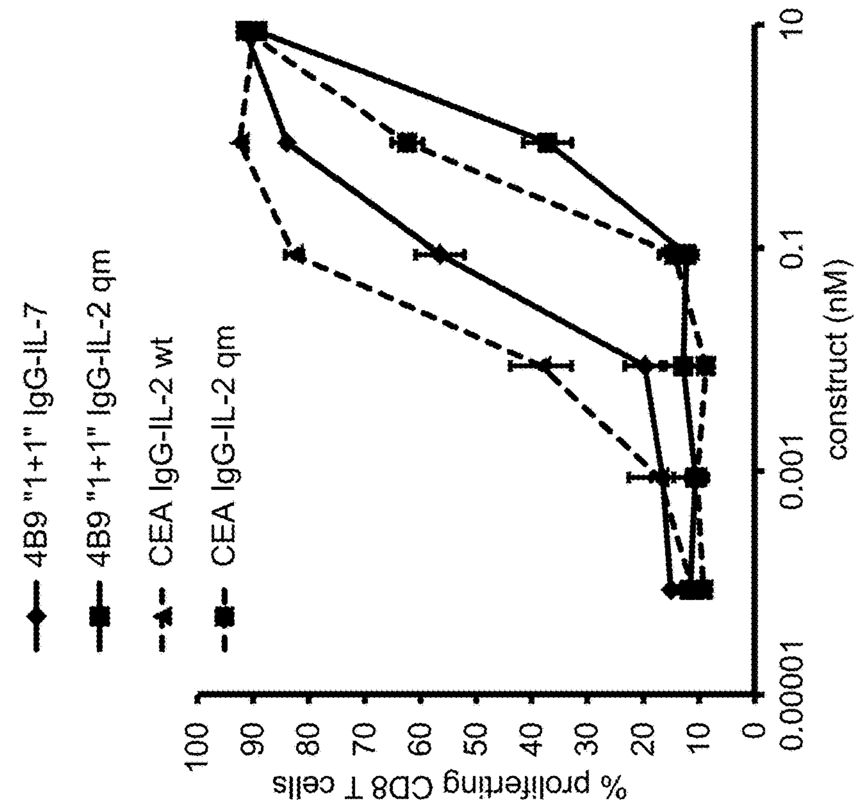
Figure 28A:
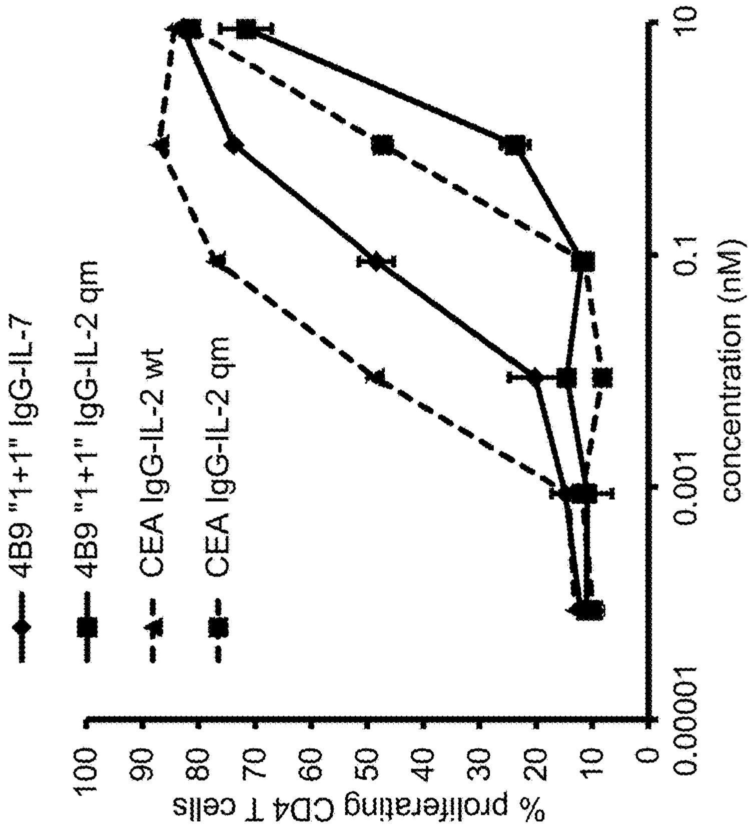

FIGS. 28A-B. Proliferation of PHA-activated (FIG. 28A) CD4 and (FIG. 28B) CD8 T cells induced by 4B9 "1+1" IgG-IL-7 and 4B9 "1+1" IgG-IL-2 qm immunoconjugates, compared to IgG-IL-2 qm and IgG-IL-2 wt constructs.

Figure 29:
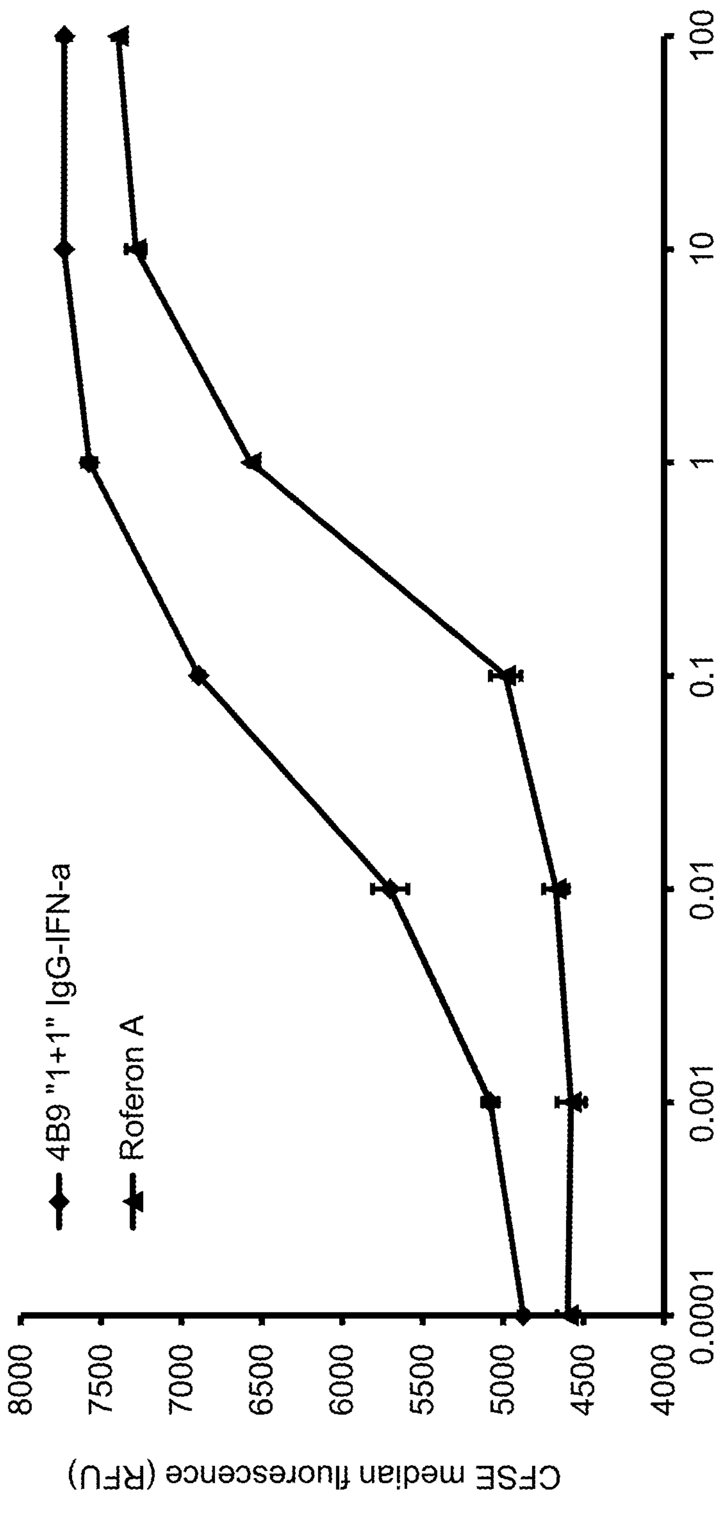

FIG. 29. Induction of Daudi cell proliferation by 4B9 "1+1" IgG-IFN-α, compared to Roferon A.

Figure 30A:
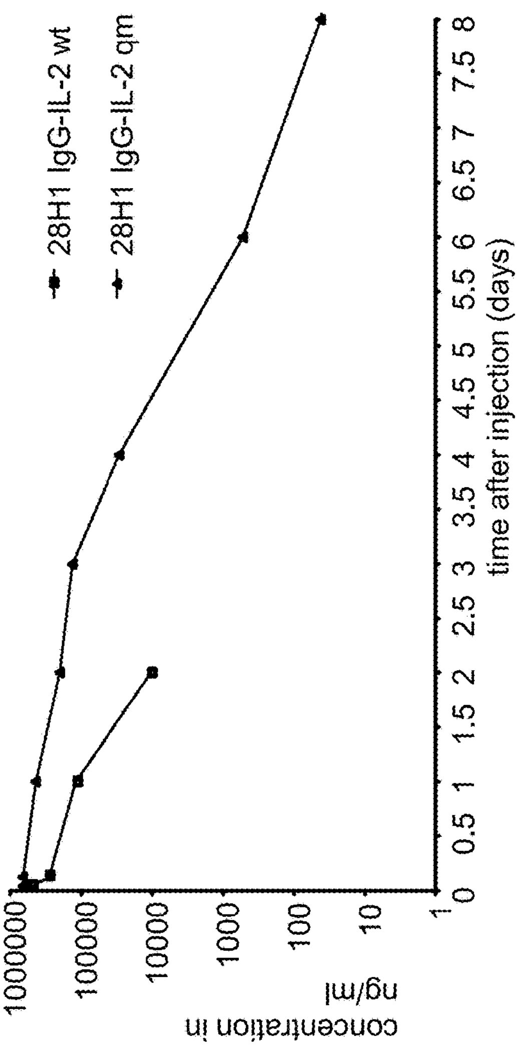
Figure 30B:
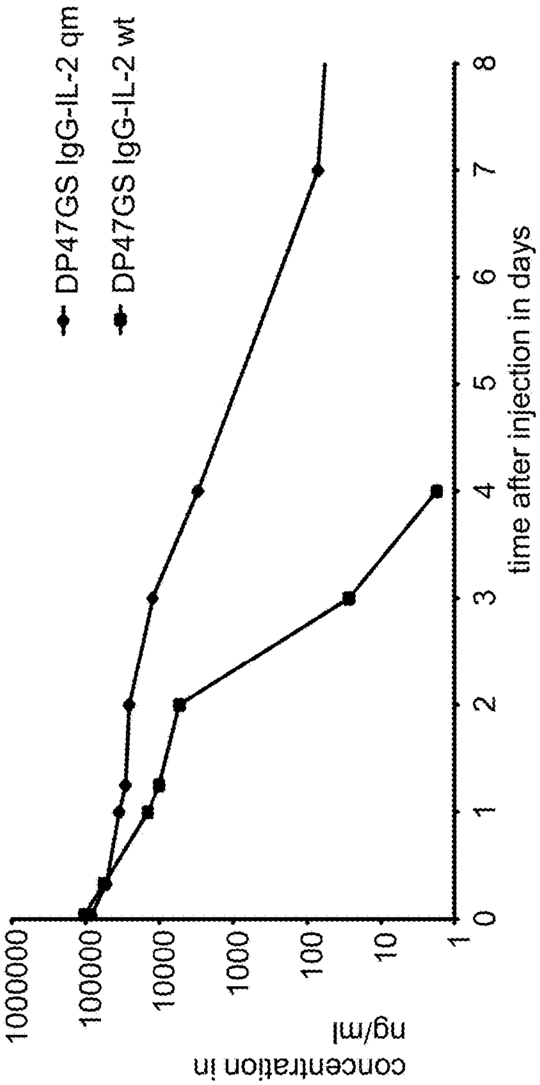

FIGS. 30A-B. Serum concentrations of IL-2 immunoconjugates after a single i.v. administration of FAP-targeted (FIG. 30A) and untargeted (FIG. 30B) IgG-IL-2 constructs comprising either wild-type (wt) or quadruple mutant (qm) IL-2.

Figure 31:
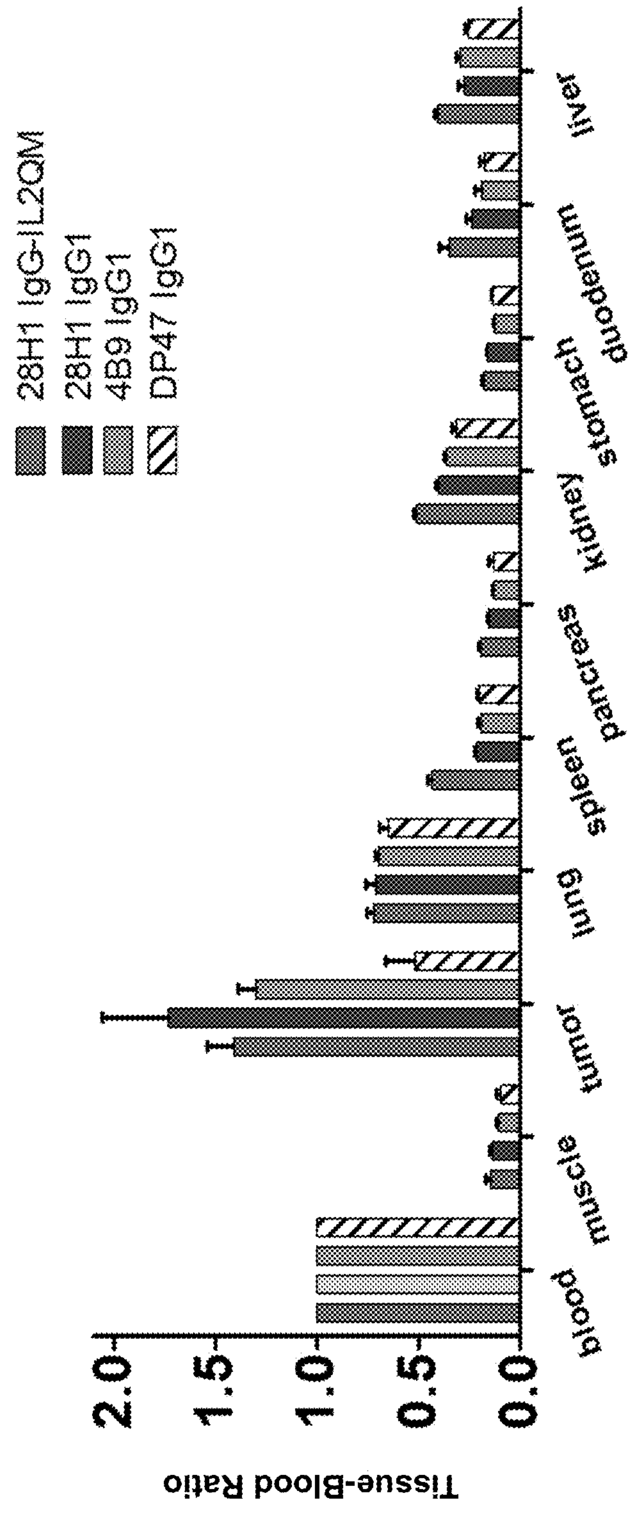

FIG. 31. Tissue distribution of FAP-targeted 28H1 IgG-IL qm compared to unconjugated FAP-targeted 28H1 IgG and 4B9 IgG, as well as untargeted DP47GS IgG, 24 hours after i.v. injection.

Figure 32:
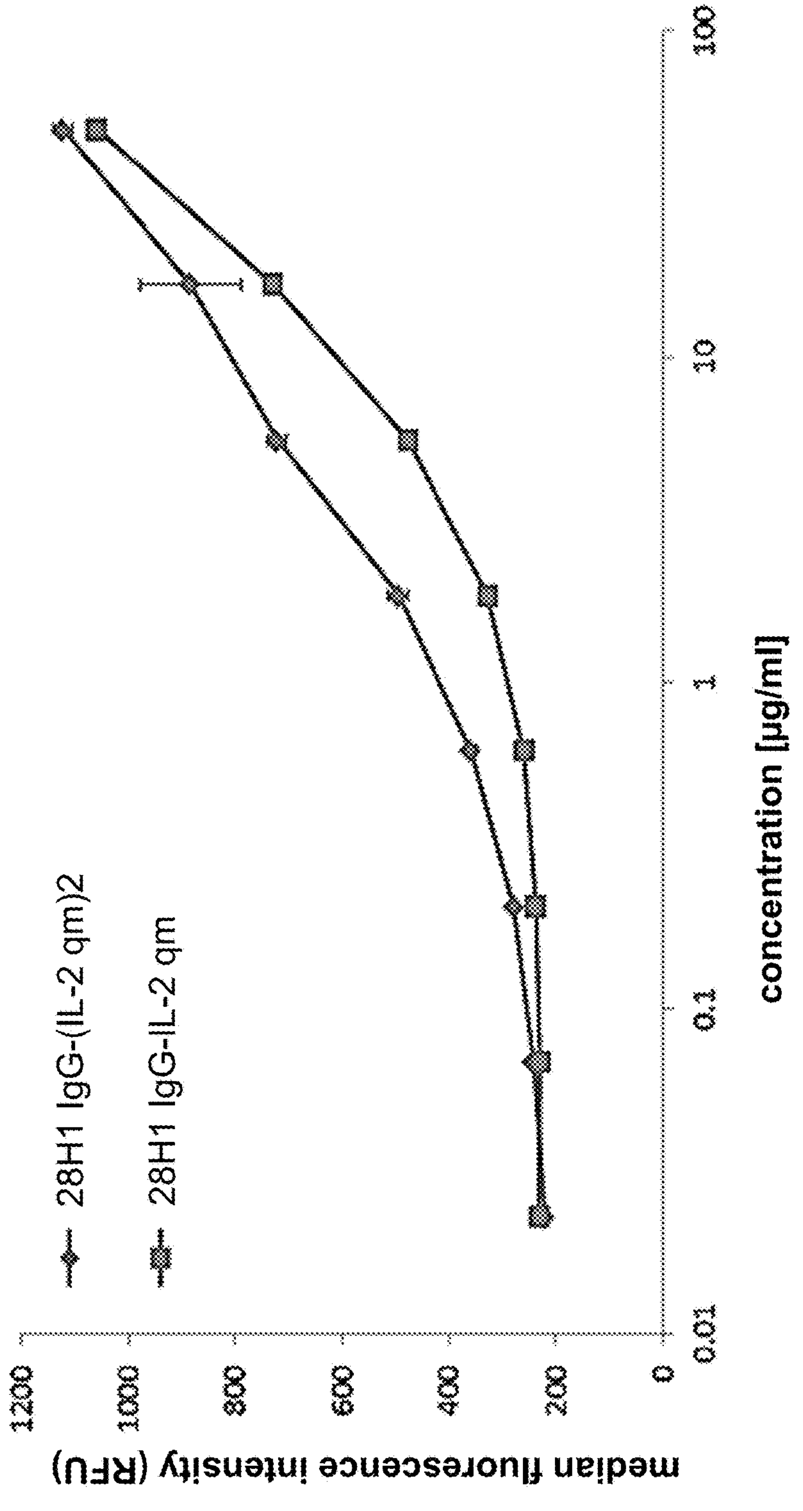

FIG. 32. Binding of 28H1 IgG-IL-2 qm and 28H1 IgG-(IL-2 qm)$_2$ immunoconjugates to NK92 cells as determined by FACS.

FIGS. 33A-C. Proliferation of NK cells upon incubation with different FAP-targeted 28H1 IL-2 immunoconjugates or Proleukin for 4 (FIG. 33A), 5 (FIG. 33B) or 6 (FIG. 33C) days.

FIGS. 34A-C. Proliferation of CD4 T-cells upon incubation with different FAP-targeted 28H1 IL-2 immunoconjugates or Proleukin for 4 (FIG. 34A), 5 (FIG. 34B) or 6 (FIG. 34C) days.

FIGS. 35A-C. Proliferation of CD8 T-cells upon incubation with different FAP-targeted 28H1 IL-2 immunoconjugates or Proleukin for 4 (FIG. 35A), 5 (FIG. 35B) or 6 (FIG. 35C) days.

FIGS. 36A-B. Proliferation of pre-activated CD8 (FIG. 36A) and CD4 (FIG. 36B) T cells after six days incubation with different IL-2 immunoconjugates.

Figure 37:
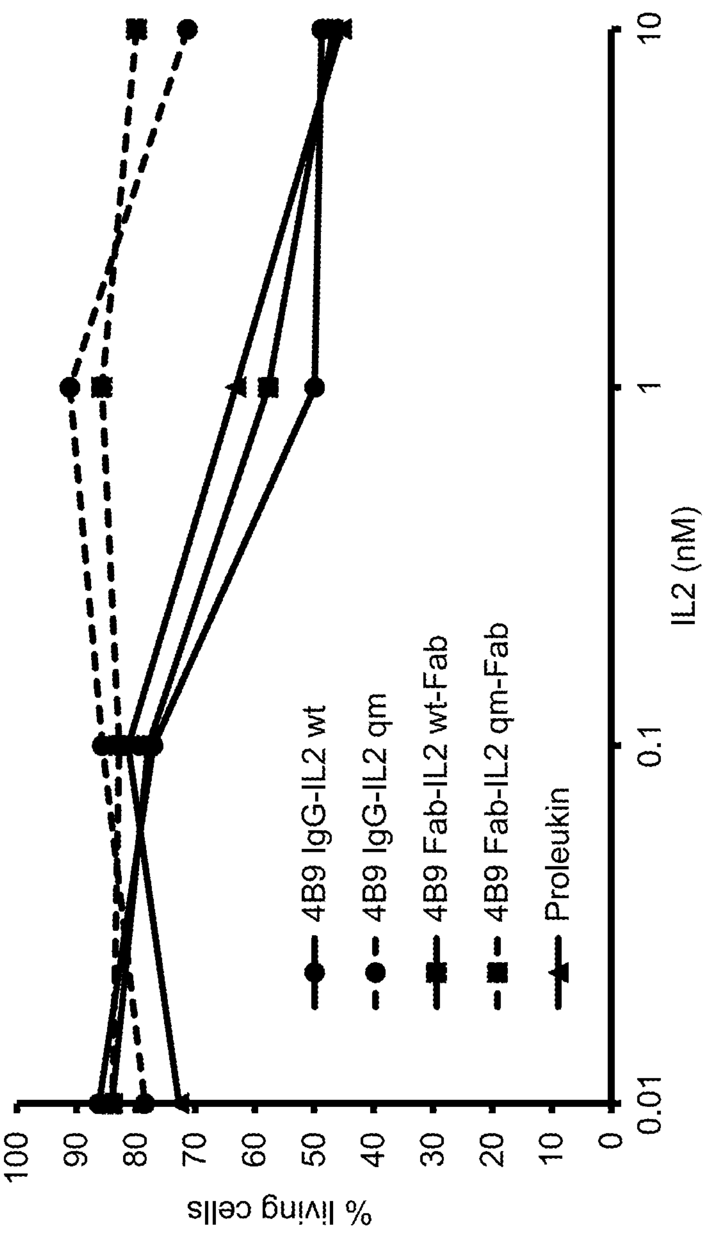

FIG. 37. Activation induced cell death of CD3$^+$ T cells after six days incubation with different IL-2 immunoconjugates and overnight treatment with anti-Fas antibody.

FIGS. 38A-B. Serum concentrations of IL-2 immunoconjugates after a single i.v. administration of untargeted DP47GS IgG-IL-2 constructs comprising either wild-type (FIG. 38A) or quadruple mutant IL-2 (FIG. 38B).

Figure 39:
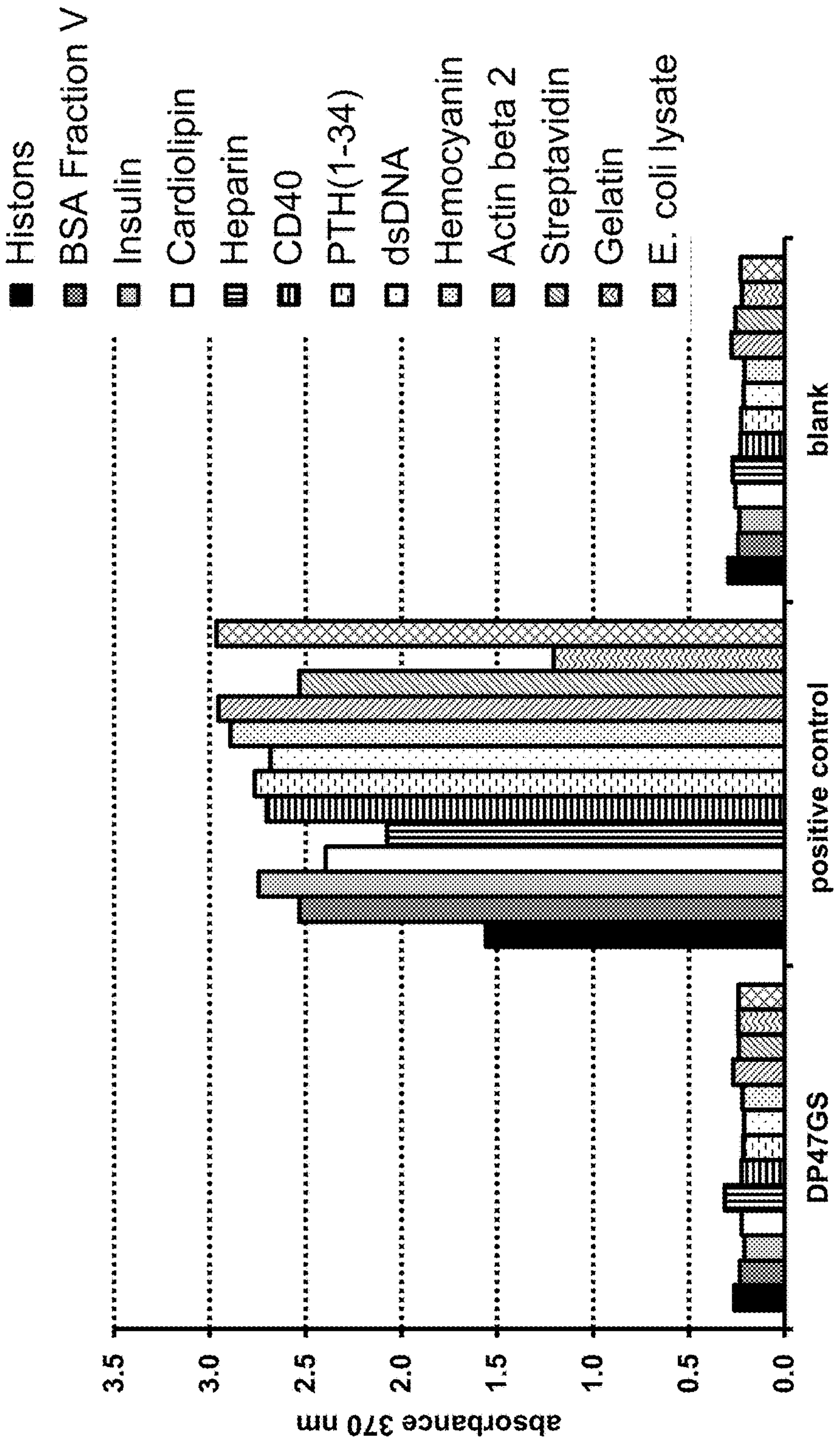
Figures 40A, 40B, 40C, 40D:
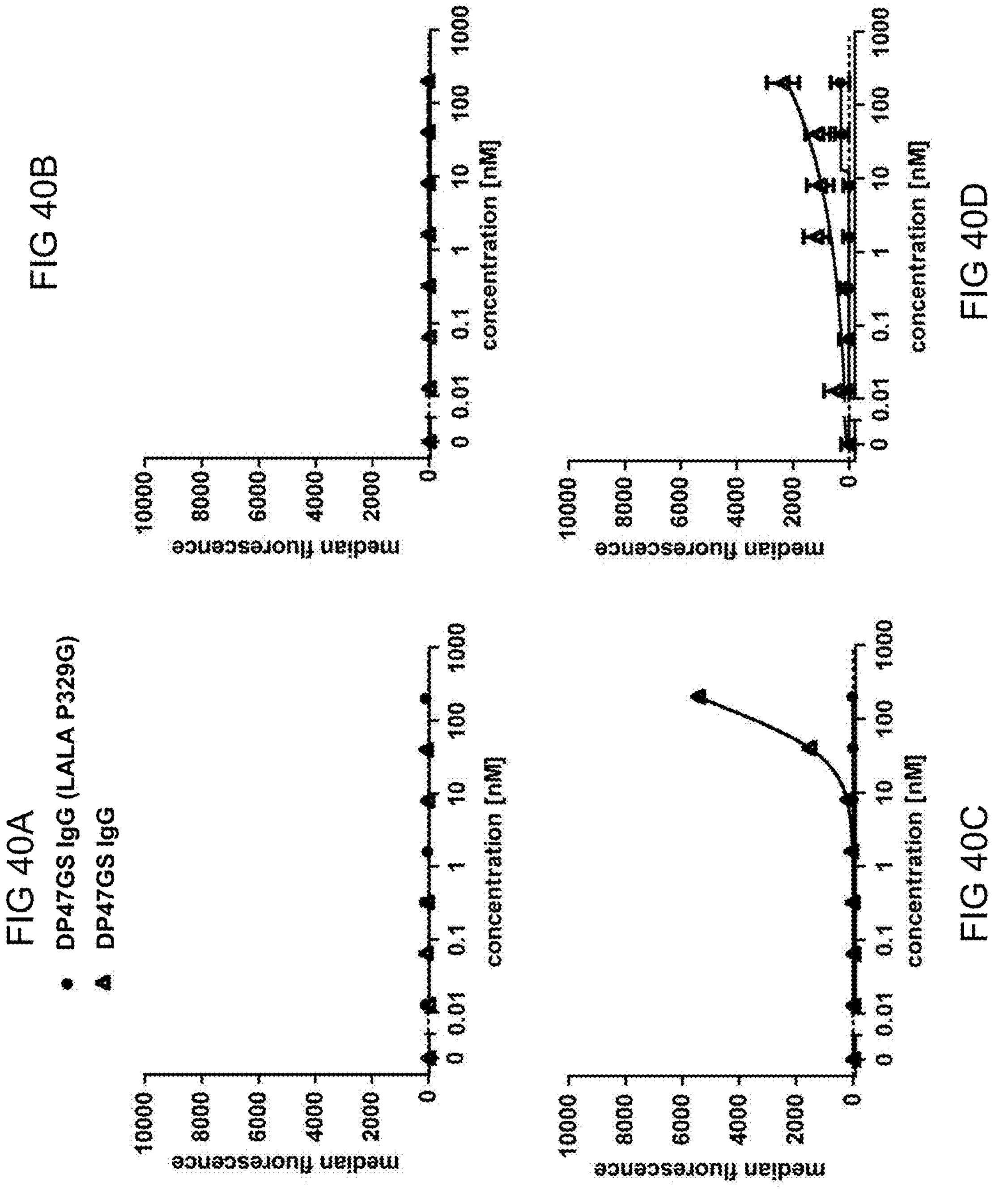
Figures 40E, 40F, 40G, 40H:
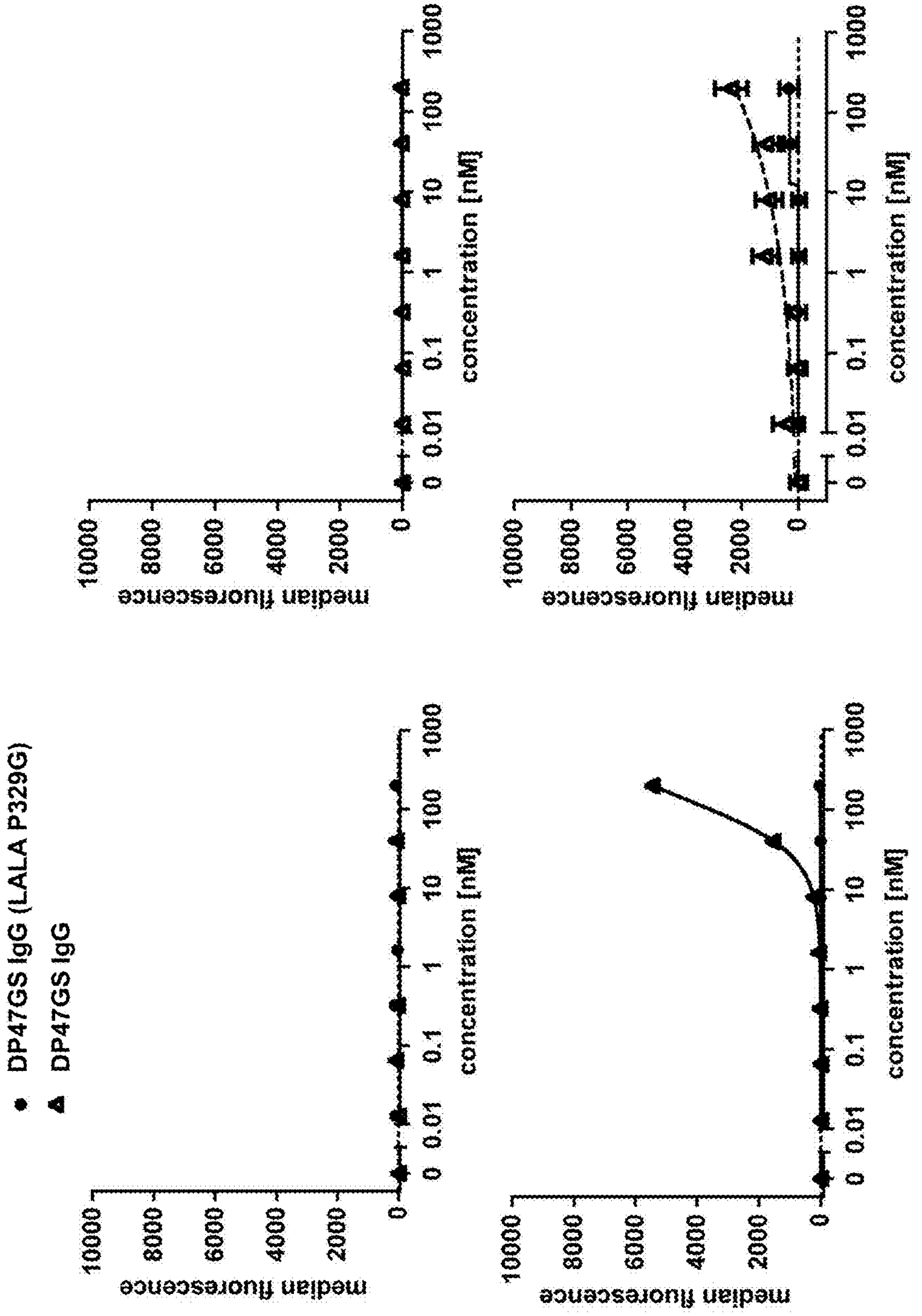
Figures 40I, 40J, 40K, 40L:
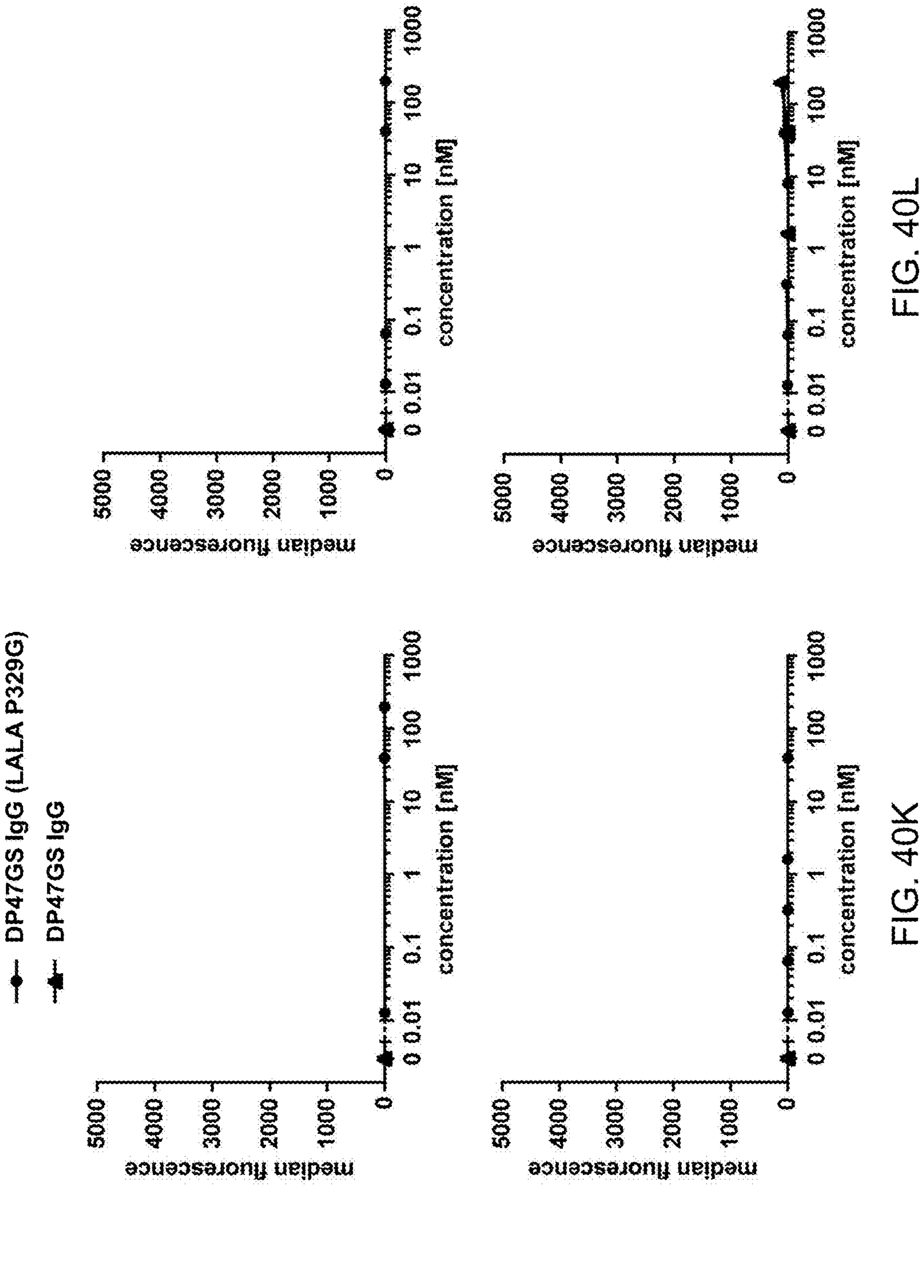

FIG. 39. Binding of DP47GS IgG to different antigens. Binding was detected in an ELISA-based assay with the antigens captured on the plate. A human IgG1 antibody which exhibits unspecific binding to almost all of the captured antigens was used as positive control, blank samples did not contain any antibody.

FIGS. 40A-L. Binding of DP47GS IgG with or without LALA P329G mutation in the Fc domain to subsets of fresh (FIGS. 40A-D), PHA-L activated (FIGS. 40E-H) and re-stimulated (FIGS. 40I-L) human PBMCs, as determined by FACS analysis. Upper left panel: B cells (in FIG. 40A and FIG. 40E) or CD4$^+$ T cells (in FIG. 40I); upper right panel: CD8$^+$ T cells (in FIG. 40B, FIG. 40F and FIG. 40J); lower left panel (in FIG. 40C, FIG. 40G, and FIG. 40K): NK cells; lower right panel (in FIG. 40D, FIG. 40H, and FIG. 40L): CD14$^+$ cells (monocytes/neutrophils).

DETAILED DESCRIPTION OF THE INVENTION

Definitions

Terms are used herein as generally used in the art, unless otherwise defined in the following.

As used herein, the term "conjugate" refers to a fusion polypeptide molecule that includes one effector moiety and a further peptide molecule, particularly an immunoglobulin molecule.

As used herein, the term "immunoconjugate" refers to a fusion polypeptide molecule that includes one effector moiety, at least one antigen binding moiety and an Fc domain, provided that not more than one effector moiety is present. In certain embodiments, the immunoconjugate comprises one effector moiety, two antigen binding moieties, and an Fc domain. Particular immunoconjugates according to the invention essentially consist of one effector moiety, two antigen binding moieties, and an Fc domain, joined by one or more linker sequences. The antigen binding moiety and the effector moiety can be joined to the Fc domain by a variety of interactions and in a variety of configurations as described herein. In a particular embodiment, the two antigen binding moieties and the Fc domain are joined to each other in a configuration so as to form a full immunoglobulin molecule. An immunoconjugate as referred to herein, is a fusion protein, i.e. the components of the immunoconjugate are linked to each other by peptide-bonds, either directly or through linker peptides.

As used herein, the term "antigen binding moiety" refers to a polypeptide molecule that specifically binds to an antigenic determinant. In one embodiment, an antigen binding moiety is able to direct the entity to which it is attached (e.g. an effector moiety or a second antigen binding moiety) to a target site, for example to a specific type of tumor cell or tumor stroma bearing the antigenic determinant. Antigen binding moieties include antibodies and fragments thereof as further defined herein. Particular antigen binding moieties include an antigen binding domain of an antibody, comprising an antibody heavy chain variable region and an antibody light chain variable region. In certain embodiments, the antigen binding moieties may comprise antibody constant regions as further defined herein and known in the art. Useful heavy chain constant regions include any of the five isotypes: α, δ, ε, γ, or μ. Useful light chain constant regions include any of the two isotypes: κ and λ.

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex.

Useful antigenic determinants can be found, for example, on the surfaces of tumor cells, on the surfaces of virus-infected cells, on the surfaces of other diseased cells, free in blood serum, and/or in the extracellular matrix (ECM). In a particular embodiment the antigenic determinant is a human antigen.

By "specifically binds" is meant that the binding is selective for the antigen and can be discriminated from unwanted or non-specific interactions. The ability of an antigen-binding moiety to bind to a specific antigenic determinant can be measured either through an enzyme-linked immunosorbent assay (ELISA) or other techniques familiar to one of skill in the art, e.g. surface plasmon resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding moiety to an unrelated protein is less than about 10% of the binding of the antigen binding moiety to the antigen as measured, e.g., by SPR. In certain embodiments, an antigen binding moiety that binds to the antigen, or an immunoconjugate comprising that antigen binding moiety, has a dissociation constant ($K_D$) of ≤1 μM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M).

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., receptor and a ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well established methods known in the art, including those described herein. A particular method for measuring affinity is Surface Plasmon Resonance (SPR).

"Reduced binding", for example reduced binding to an Fc receptor or to CD25, refers to a decrease in affinity for the respective interaction, as measured for example by SPR. For clarity the term includes also reduction of the affinity to zero (or below the detection limit of the analytic method), i.e. complete abolishment of the interaction. Conversely, "increased binding" refers to an increase in binding affinity for the respective interaction.

As used herein, the terms "first" and "second" with respect to antigen-binding moieties etc., are used for convenience of distinguishing when there is more than one of each type of moiety. Use of these terms is not intended to confer a specific order or orientation of the immunoconjugate unless explicitly so stated.

As used herein, the term "effector moiety" refers to a polypeptide, e.g., a protein or glycoprotein, that influences cellular activity, for example, through signal transduction or other cellular pathways. Accordingly, the effector moiety of the invention can be associated with receptor-mediated signaling that transmits a signal from outside the cell membrane to modulate a response in a cell bearing one or more receptors for the effector moiety. In one embodiment, an effector moiety can elicit a cytotoxic response in cells bearing one or more receptors for the effector moiety. In another embodiment, an effector moiety can elicit a proliferative response in cells bearing one or more receptors for the effector moiety. In another embodiment, an effector moiety can elicit differentiation in cells bearing receptors for the effector moiety. In another embodiment, an effector moiety can alter expression (i.e. upregulate or downregulate) of an endogenous cellular protein in cells bearing receptors for the effector moiety. Non-limiting examples of effector moieties include cytokines, growth factors, hormones, enzymes, substrates, and cofactors. The effector moiety can be associated with an antigen-binding moiety or an Fc domain in a variety of configurations to form an immunoconjugate.

As used herein, the term "cytokine" refers to a molecule that mediates and/or regulates a biological or cellular function or process (e.g. immunity, inflammation, and hematopoiesis). The term "cytokine" as used herein includes "lymphokines," "chemokines," "monokines," and "interleukins". Examples of useful cytokines include, but are not limited to, GM-CSF, IL-1α, IL-1β, IL-2, IL-3, IL-4, IL-5, IL-6, IL-7, IL-8, IL-10, IL-12, IFN-α, IFN-β, IFN-γ, MIP-1α, MIP-1β, TGF-β, TNF-α, and TNF-β. Particular cytokines are IL-2, IL-7, IL-10, IL-12, IL-15, IFN-α and IFN-γ. In particular embodiments the cytokine is a human cytokine. The term "cytokine" as used herein is meant to also include cytokine variants comprising one or more amino acid mutations in the amino acid sequences of the corresponding wild-type cytokine, such as for example the IL-2 variants described in Sauvé et al., Proc Natl Acad Sci USA 88, 4636-40 (1991); Hu et al., Blood 101, 4853-4861 (2003) and US Pat. Publ. No. 2003/0124678; Shanafelt et al., Nature Biotechnol 18, 1197-1202 (2000); Heaton et al., Cancer Res 53, 2597-602 (1993) and U.S. Pat. No. 5,229,109; US Pat. Publ. No. 2007/0036752; WO 2008/0034473; WO 2009/061853; or PCT patent application no. PCT/EP2012/051991. Further cytokine variants, for example variants of IL-15, are described herein. In certain embodiments cytokines have been mutated to eliminate glycosylation.

As used herein, the term "single-chain" refers to a molecule comprising amino acid monomers linearly linked by peptide bonds. In one embodiment, the effector moiety is a single-chain effector moiety. Non-limiting examples of single-chain effector moieties include cytokines, growth factors, hormones, enzymes, substrates, and cofactors. When the effector moiety is a cytokine and the cytokine of interest is normally found as a multimer in nature, each subunit of the multimeric cytokine is sequentially encoded by the single-chain of the effector moiety. Accordingly, non-limiting examples of useful single-chain effector moieties include GM-CSF, IL-1α, IL-1β, IL-2, IL-3, IL-4, IL-5, IL-6, IL-7, IL-8, IL-10, IL-12, IL-15, IFN-α, IFN-β, IFN-γ, MIP-1α, MIP-1β, TGF-β, TNF-α, and TNF-β.

As used herein, the term "control effector moiety" refers to an unconjugated effector moiety. For example, when comparing an IL-2 immunoconjugate as described herein with a control effector moiety, the control effector moiety is free, unconjugated IL-2. Likewise, e.g., when comparing an IL-12 immunoconjugate with a control effector moiety, the control effector moiety is free, unconjugated IL-12 (e.g. existing as a heterodimeric protein wherein the p40 and p35 subunits share only disulfide bond(s)).

As used herein, the term "effector moiety receptor" refers to a polypeptide molecule capable of binding specifically to an effector moiety. For example, where IL-2 is the effector moiety, the effector moiety receptor that binds to an IL-2 molecule (e.g. an immunoconjugate comprising IL-2) is the IL-2 receptor. Similarly, e.g., where IL-12 is the effector moiety of an immunoconjugate, the effector moiety receptor is the IL-12 receptor. Where an effector moiety specifically binds to more than one receptor, all receptors that specifically bind to the effector moiety are "effector moiety receptors" for that effector moiety.

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfidebonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The heavy chain of an immunoglobulin may be assigned to one of five types, called α (IgA), δ (IgD), ε (IgE), γ (IgG), or μ (IgM), some of which may be further divided into subtypes, e.g. $\gamma_1$ ($IgG_1$), $\gamma_2$ ($IgG_2$), $\gamma_3$ ($IgG_3$), $\gamma_4$ ($IgG_4$), $\alpha_1$ ($IgA_1$) and $\alpha_2$ ($IgA_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

The term "antibody" herein is used in the broadest sense and encompasses various antibody structures, including but not limited to monoclonal antibodies, polyclonal antibodies, and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$, diabodies, linear antibodies, single-chain antibody molecules (e.g. scFv), and single-domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and $F(ab')_2$ fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g. U.S. Pat. No. 6,248,516 B1). Antibody fragments can be made by various techniques, including but not limited to proteolytic digestion of an intact antibody as well as production by recombinant host cells (e.g. *E. coli* or phage), as described herein.

The term "antigen binding domain" refers to the part of an antibody that comprises the area which specifically binds to and is complementary to part or all of an antigen. An antigen binding domain may be provided by, for example, one or more antibody variable domains (also called antibody variable regions). Particularly, an antigen binding domain comprises an antibody light chain variable region (VL) and an antibody heavy chain variable region (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, $6^{th}$ ed., W.H. Freeman and Co., page 91 (2007). A single VH or VL domain may be sufficient to confer antigen-binding specificity.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition.

With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

| CDR | Kabat | Chothia | AbM[2] |
|---|---|---|---|
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table 1 is according to the numbering conventions set forth by Kabat et al. (see below).
[2]"AbM" with a lowercase "b" as used in Table 1 refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

The polypeptide sequences of the sequence listing (i.e., SEQ ID NOs 23, 25, 27, 29, 31, etc.) are not numbered according to the Kabat numbering system. However, it is well within the ordinary skill of one in the art to convert the numbering of the sequences of the Sequence Listing to Kabat numbering.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991. A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

A "modification promoting heterodimerization" is a manipulation of the peptide backbone or the post-translational modifications of a polypeptide that reduces or prevents the association of the polypeptide with an identical polypeptide to form a homodimer. A modification promoting heterodimerization as used herein particularly includes separate modifications made to each of two polypeptides desired to form a dimer, wherein the modifications are complementary to each other so as to promote association of the two polypeptides. For example, a modification promoting heterodimerization may alter the structure or charge of one or both of the polypeptides desired to form a dimer so as to make their association sterically or electrostatically favorable, respectively. Heterodimerization occurs between two non-identical polypeptides, such as two subunits of an Fc domain wherein further immunoconjugate components fused to each of the subunits (e.g. antigen binding moiety, effector moiety) are not the same. In the immunoconjugates according to the present invention, the modification promoting heterodimerization is in the Fc domain. In some embodiments the modification promoting heterodimerziation comprises an amino acid mutation, specifically an amino acid substitution. In a particular embodiment, the modification promoting heterodimerization comprises a separate amino acid mutation, specifically an amino acid substitution, in each of the two subunits of the Fc domain.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches. "Engineering", particularly with the prefix "glyco-", as well as the term "glycosylation engineering" includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation. In one embodiment, the glycosylation engineering is an alteration in glycosyltransferase activity. In a particular embodiment, the engineering results in altered glucosaminyltransferase activity and/or fucosyltransferase activity. Glycosylation engineering can be used to obtain a "host cell having increased GnTIII activity", a "host cell having increased ManII activity", or a "host cell having decreased α(1,6) fucosyltransferase activity".

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or reduced binding to CD25. Amino acid sequence deletions and insertions include amino- and/or carboxy-terminal deletions and insertions of amino acids. Particular amino acid mutations are amino acid substitutions. For the purpose of altering e.g. the binding characteristics of an Fc region or a cytokine such as IL-2, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, $G_{329}$, P329G, or Pro329Gly.

As used herein, term "polypeptide" refers to a molecule composed of monomers (amino acids) linearly linked by amide bonds (also known as peptide bonds). The term "polypeptide" refers to any chain of two or more amino acids, and does not refer to a specific length of the product. Thus, peptides, dipeptides, tripeptides, oligopeptides, "protein," "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

By an "isolated" polypeptide or a variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a therapeutic polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode immunoconjugates of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode immunoconjugates of the invention or fragments thereof.

The term "artificial" refers to a synthetic, or non-host cell derived composition, e.g. a chemically-synthesized oligonucleotide.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages.

Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the immunoconjugates used for the present invention. In one embodiment, the host cell is engineered to allow the production of an immunoconjugate with modified oligosaccharides in its Fc region. In certain embodiments, the host cells have been manipulated to express increased levels of one or more polypeptides having β(1,4)-N-acetylglucosaminyltransferase III (GnTIII) activity. In certain embodiments the host cells have been further manipulated to express increased levels of one or more polypeptides having α-mannosidase II (ManII) activity. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

As used herein, the term "polypeptide having GnTIII activity" refers to polypeptides that are able to catalyze the addition of a N-acetylglucosamine (GlcNAc) residue in β-1,4 linkage to the β-linked mannoside of the trimannosyl core of N-linked oligosaccharides. This includes fusion polypeptides exhibiting enzymatic activity similar to, but not necessarily identical to, an activity of β(1,4)-N-acetylglucosaminyltransferase III, also known as β-1,4-mannosyl-glycoprotein 4-beta-N-acetylglucosaminyl-transferase (EC 2.4.1.144), according to the Nomenclature Committee of the International Union of Biochemistry and Molecular Biology (NC-IUBMB), as measured in a particular biological assay, with or without dose dependency. In the case where dose dependency does exist, it need not be identical to that of GnTIII, but rather substantially similar to the dose-dependency in a given activity as compared to the GnTIII (i.e. the candidate polypeptide will exhibit greater activity or not more than about 25-fold less and, preferably, not more than about ten-fold less activity, and most preferably, not more than about three-fold less activity relative to the GnTIII). In certain embodiments the polypeptide having GnTIII activity is a fusion polypeptide comprising the catalytic domain of GnTIII and the Golgi localization domain of a heterologous Golgi resident polypeptide. Particularly, the Golgi localization domain is the localization domain of mannosidase II or GnTI, most particularly the localization domain of mannosidase II. Alternatively, the Golgi localization domain is selected from the group consisting of: the localization domain of mannosidase I, the localization domain of GnTII, and the localization domain of α1,6 core fucosyltransferase. Methods for generating such fusion polypeptides and using them to produce antibodies with increased effector functions are disclosed in WO 2004/065540, U.S. Provisional Pat. Appl. No. 60/495,142 and U.S. Pat. Appl. Publ. No. 2004/0241817, the entire contents of which are expressly incorporated herein by reference.

As used herein, the term "Golgi localization domain" refers to the amino acid sequence of a Golgi resident polypeptide which is responsible for anchoring the polypeptide to a location within the Golgi complex. Generally, localization domains comprise amino terminal "tails" of an enzyme.

As used herein, the term "polypeptide having ManII activity" refers to polypeptides that are able to catalyze the hydrolysis of the terminal 1,3- and 1,6-linked α-D-mannose residues in the branched $GlcNAcMan_5GlcNAc_2$ mannose intermediate of N-linked oligosaccharides. This includes polypeptides exhibiting enzymatic activity similar to, but not necessarily identical to, an activity of Golgi α-mannosidase II, also known as mannosyl oligosaccharide 1,3-1,6-α-mannosidase II (EC 3.2.1.114), according to the Nomenclature Committee of the International Union of Biochemistry and Molecular Biology (NC-IUBMB).

An "activating Fc receptor" is an Fc receptor that following engagement by an Fc region of an antibody (or immunoconjugate) elicits signaling events that stimulate the receptor-bearing cell to perform effector functions. Activating Fc receptors include FcγRIIIa (CD16a), FcγRI (CD64), FcγRIIa (CD32), and FcαRI (CD89).

Antibody-dependent cell-mediated cytotoxicity (ADCC) is an immune mechanism leading to the lysis of antibody-coated target cells by immune effector cells. The target cells are cells to which antibodies, immunoconjugates or fragments thereof comprising an Fc region specifically bind, generally via the protein part that is N-terminal to the Fc region. As used herein, the term "increased ADCC" is defined as either an increase in the number of target cells that are lysed in a given time, at a given concentration of immunoconjugate in the medium surrounding the target cells, by the mechanism of ADCC defined above, and/or a reduction in the concentration of immunoconjugate, in the medium surrounding the target cells, required to achieve the lysis of a given number of target cells in a given time, by the mechanism of ADCC. The increase in ADCC is relative to the ADCC mediated by the same immunoconjugate produced by the same type of host cells, using the same standard production, purification, formulation and storage methods (which are known to those skilled in the art), but that has not been engineered. For example the increase in ADCC mediated by an immunoconjugate produced by host cells engineered to have an altered pattern of glycosylation (e.g. to express the glycosyltransferase, GnTIII, or other glycosyltransferases) by the methods described herein, is relative to the ADCC mediated by the same immunoconjugate produced by the same type of non-engineered host cells.

By "immunoconjugate having increased antibody dependent cell-mediated cytotoxicity (ADCC)" is meant an immunoconjugate having increased ADCC as determined by any suitable method known to those of ordinary skill in the art. One accepted in vitro ADCC assay is as follows:

1) the assay uses target cells that are known to express the target antigen recognized by the antigen binding moiety of the immunoconjugate;
2) the assay uses human peripheral blood mononuclear cells (PBMCs), isolated from blood of a randomly chosen healthy donor, as effector cells;
3) the assay is carried out according to following protocol:
i) the PBMCs are isolated using standard density centrifugation procedures and are suspended at $5\times10^6$ cells/ml in RPMI cell culture medium;
ii) the target cells are grown by standard tissue culture methods, harvested from the exponential growth phase with a viability higher than 90%, washed in RPMI cell culture medium, labeled with 100 micro-Curies of $^{51}Cr$, washed twice with cell culture medium, and resuspended in cell culture medium at a density of $10^5$ cells/ml;
iii) 100 microliters of the final target cell suspension above are transferred to each well of a 96-well microtiter plate;
iv) the immunoconjugate is serially-diluted from 4000 ng/ml to 0.04 ng/ml in cell culture medium and 50 microliters of the resulting immunoconjugate solutions are added to the target cells in the 96-well microtiter plate, testing in triplicate various immunoconjugate concentrations covering the whole concentration range above;
v) for the maximum release (MR) controls, 3 additional wells in the plate containing the labeled target cells, receive 50 microliters of a 2% (V/V) aqueous solution of non-ionic detergent (Nonidet, Sigma, St. Louis), instead of the immunoconjugate solution (point iv above);
vi) for the spontaneous release (SR) controls, 3 additional wells in the plate containing the labeled target cells, receive 50 microliters of RPMI cell culture medium instead of the immunoconjugate solution (point iv above);
vii) the 96-well microtiter plate is then centrifuged at 50×g for 1 minute and incubated for 1 hour at 4° C.;
viii) 50 microliters of the PBMC suspension (point i above) are added to each well to yield an effector:target cell ratio of 25:1 and the plates are placed in an incubator under 5% $CO_2$ atmosphere at 37° C. for 4 hours;
ix) the cell-free supernatant from each well is harvested and the experimentally released radioactivity (ER) is quantified using a gamma counter;
x) the percentage of specific lysis is calculated for each immunoconjugate concentration according to the formula (ER−MR)/(MR−SR)×100, where ER is the average radioactivity quantified (see point ix above) for that immunoconjugate concentration, MR is the average radioactivity quantified (see point ix above) for the MR controls (see point v above), and SR is the average radioactivity quantified (see point ix above) for the SR controls (see point vi above);
4) "increased ADCC" is defined as either an increase in the maximum percentage of specific lysis observed within the immunoconjugate concentration range tested above, and/or a reduction in the concentration of immunoconjugate required to achieve one half of the maximum percentage of specific lysis observed within the immunoconjugate concentration range tested above. The increase in ADCC is relative to the ADCC, measured with the above assay, mediated by the same immunoconjugate, produced by the same type of host cells, using the same standard production, purification, formulation and storage methods, which are known to those skilled in the art, but that has not been engineered.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, immunoconjugates of the invention are used to delay development of a disease or to slow the progression of a disease.

The term "package insert" is used to refer to instructions customarily included in commercial packages of therapeutic products, that contain information about the indications, usage, dosage, administration, combination therapy, contraindications and/or warnings concerning the use of such therapeutic products.

DETAILED DESCRIPTION OF THE EMBODIMENTS

In a first aspect the invention provides an immunoconjugate comprising a first antigen binding moiety, an Fc domain consisting of two subunits, and an effector moiety, wherein not more than one effector moiety is present. The absence of further effector moieties may reduce targeting of the immunoconjugate to sites where the respective effector moiety receptor is presented, thereby improving targeting to and accumulation at sites where the actual target antigen of the immunoconjugate, which is recognized by the antigen binding moiety, is presented. Furthermore, the absence of an avidity effect for the respective effector moiety receptor can reduce activation of effector moiety receptor-positive cells in peripheral blood upon intravenous administration of the immunoconjugate. Furthermore, the serum half-life of immunoconjugates comprising only a single effector moiety appears to be longer as compared to immunoconjugates comprising two or more effector moieties.

Immunoconjugate Formats

Figure 2A:
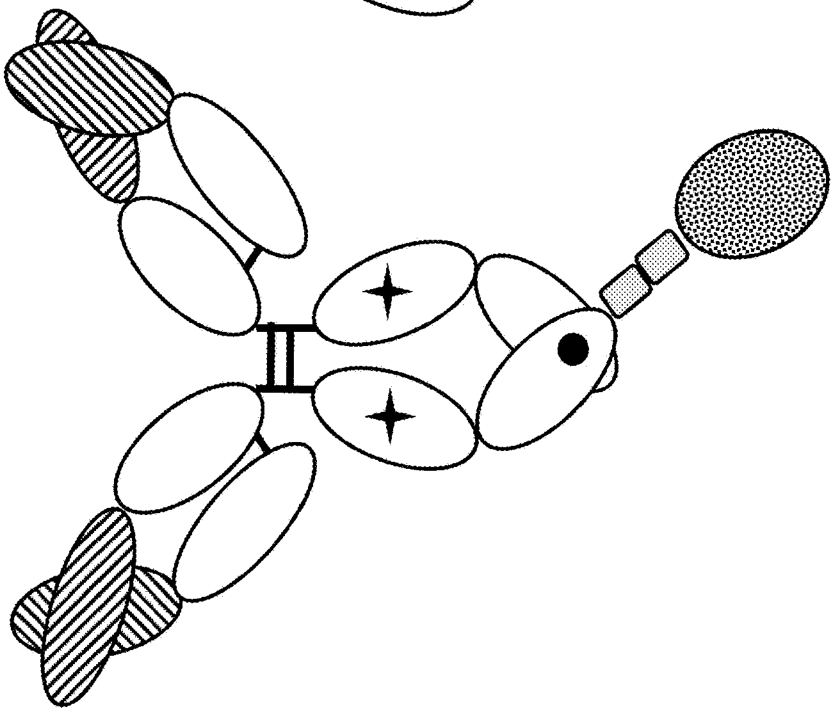
FIGS. 2A-C. Schematic representation of novel immunoconjugates according to the invention, comprising not more than one effector moiety (dotted). The effector moiety is fused, optionally via a linker peptide (grey boxes) to the carboxy-terminal (FIGURES A and B) or the amino-terminal amino acid (FIGURE C) of the Fc domain. The immunoconjugate comprises one (FIGURES B and C) or more (typically two, FIGURE A) antigen binding moieties, which may be Fab fragments comprising antibody heavy and light chain variable domains (hatched). The Fc domain may comprise a modification promoting heterodimerization of two non-identical polypeptide chains (black dot) and/or a modification altering Fc receptor binding and/or effector function (black star).
Figure 2B:
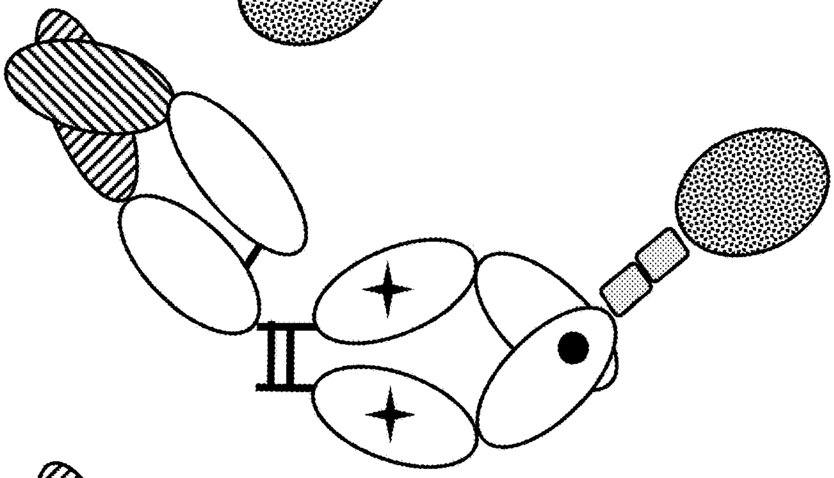
Figure 2C:
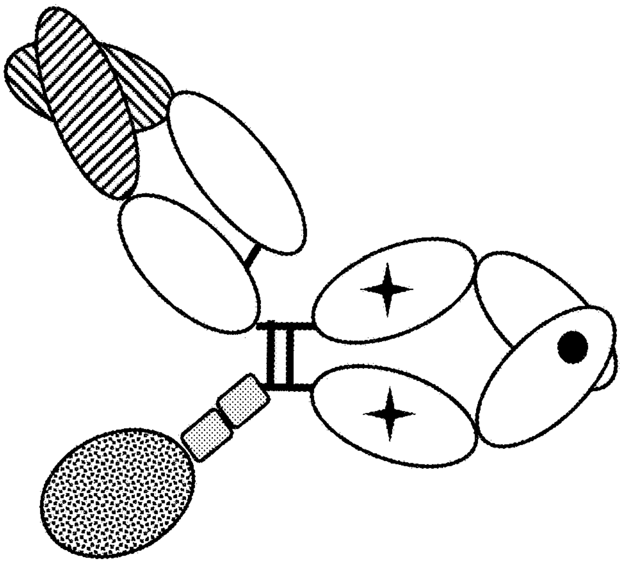
Figures 3A, 3B, 3C, 3D:
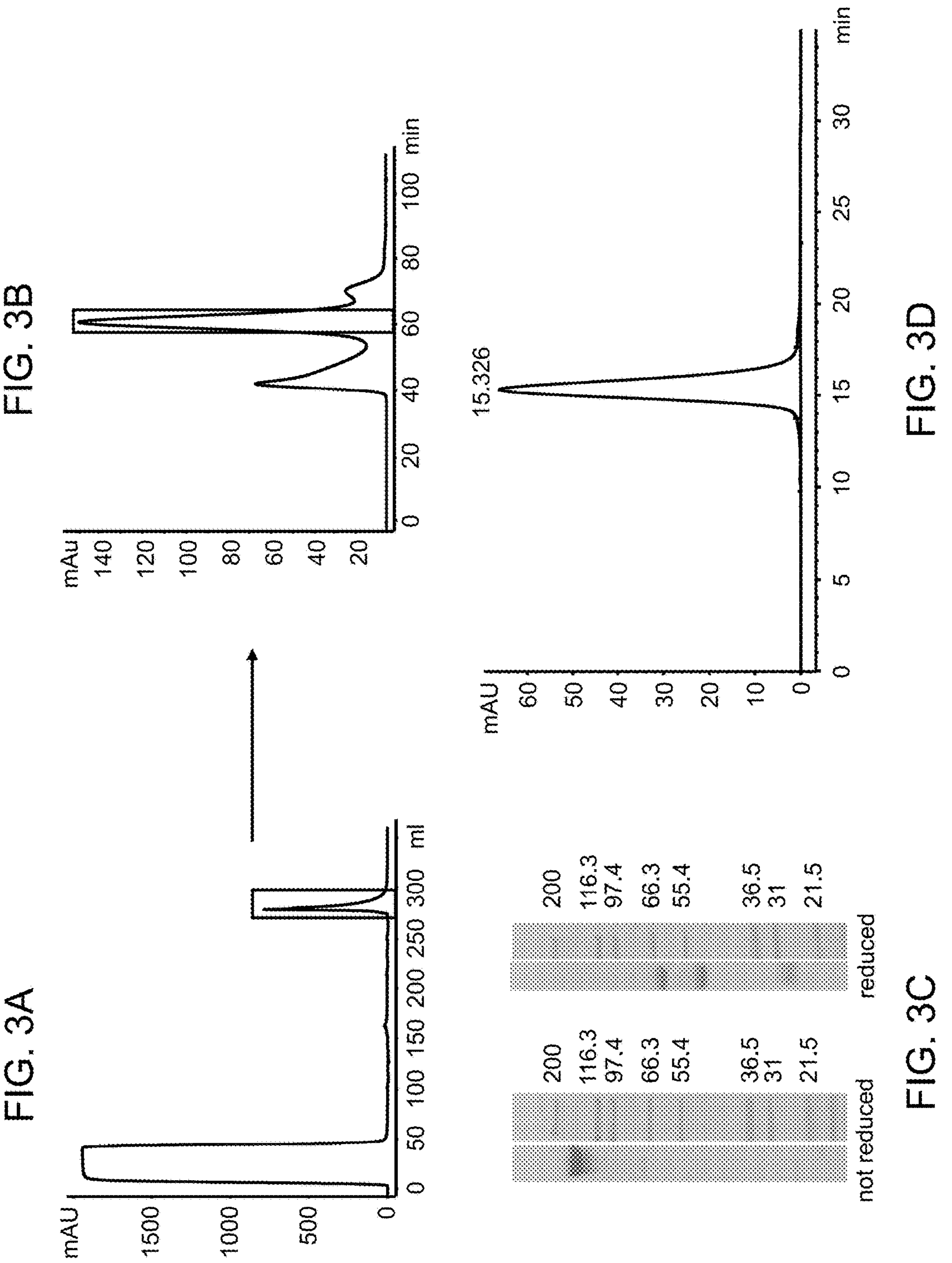
FIGS. 3A-D. Purification of FAP-targeted 4G8-based IgG-IL-2 quadruple mutant (qm) immunoconjugate.
Figures 4A, 4B, 4C, 4D:
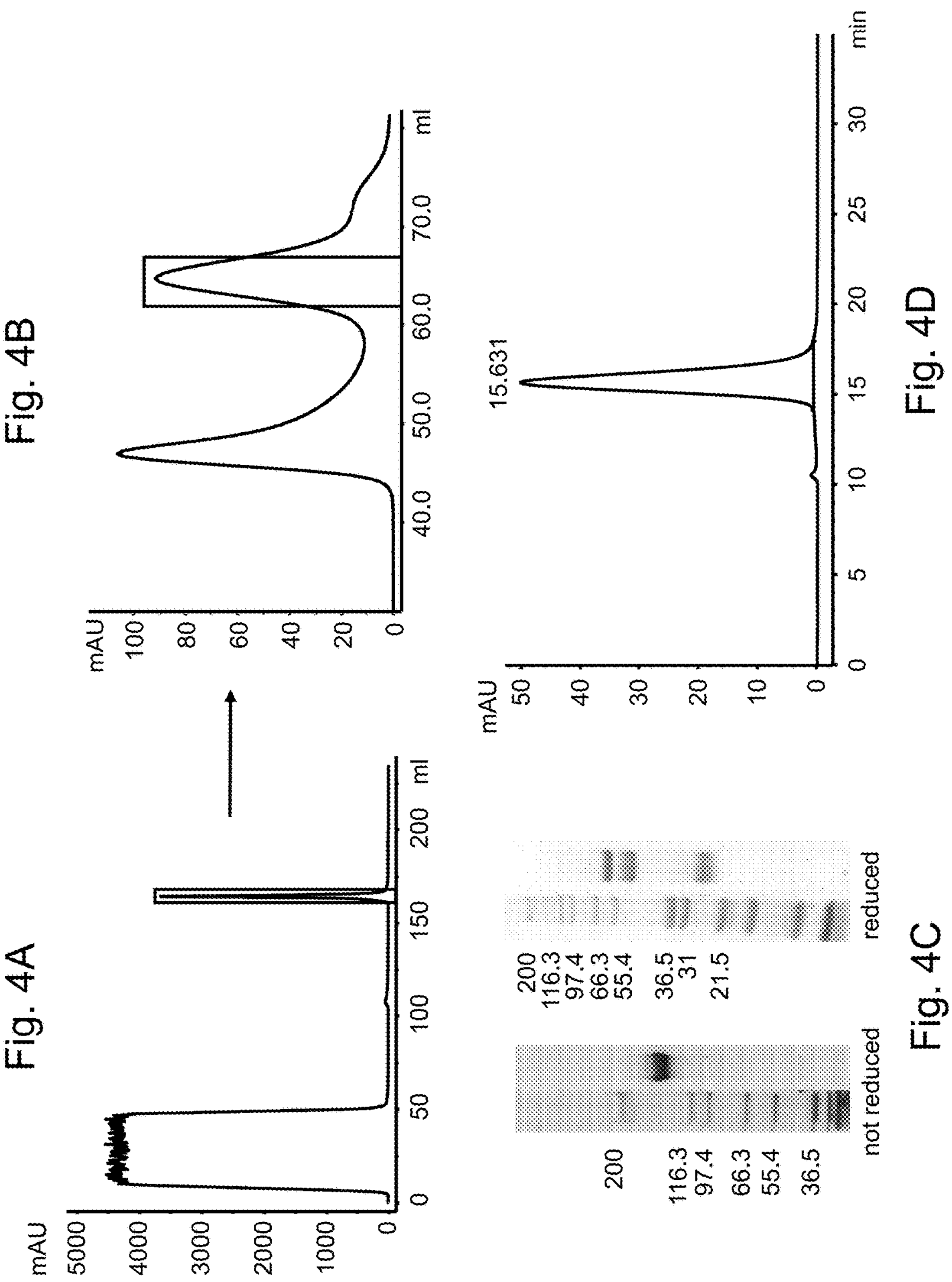
FIGS. 4A-D. Purification of FAP-targeted 28H1-based IgG-IL-2 qm immunoconjugate.
Figure 6A:
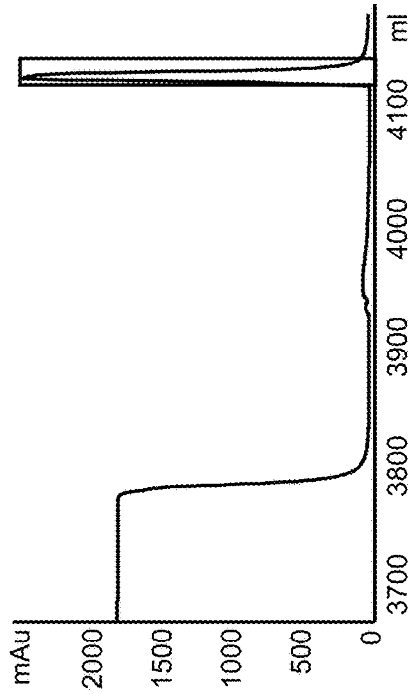
FIGS. 6A-D. Purification of FAP-targeted 4B9-based IgG-IL-2 qm immunoconjugate.
Figure 6B:
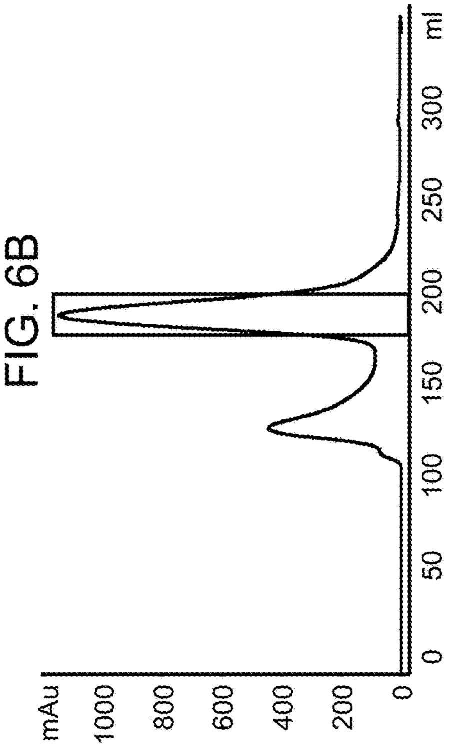
Figure 6C:
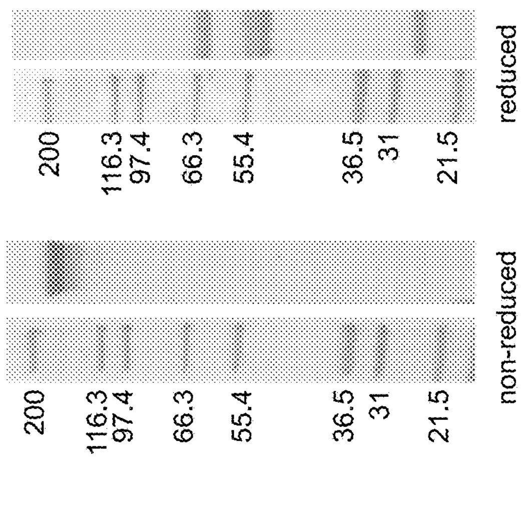
Figure 6D:
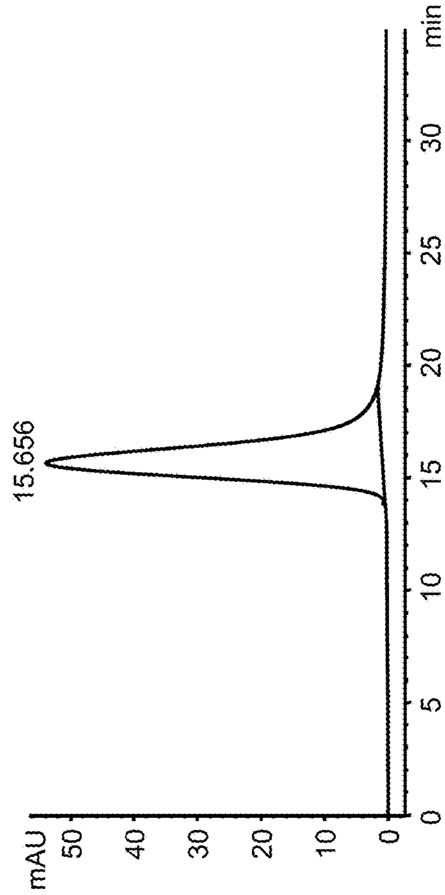
Figure 8A:
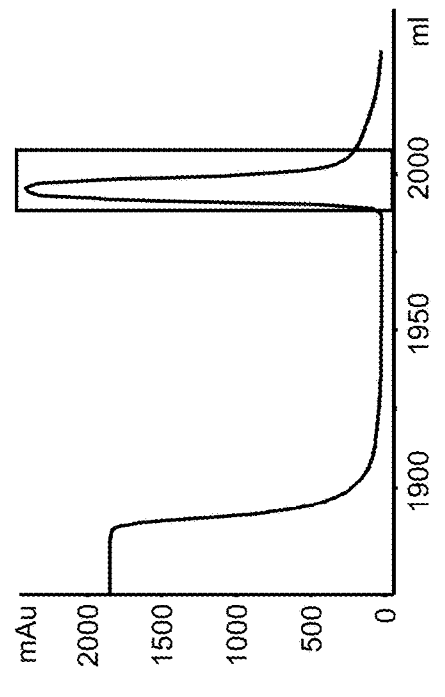
FIGS. 8A-D. Purification of TNC A2-targeted 2B10-based IgG-IL-2 qm immunoconjugate.
Figure 8B:
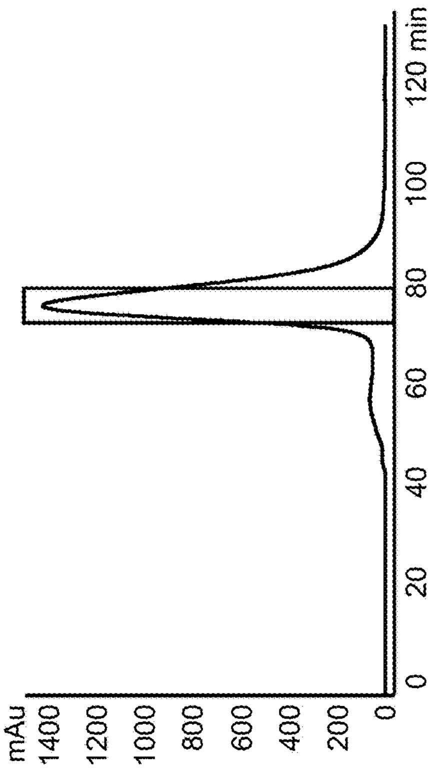
Figure 8C:
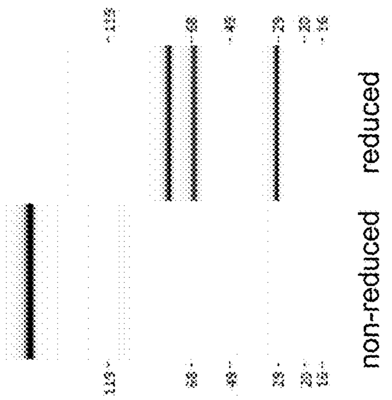
Figure 8D:
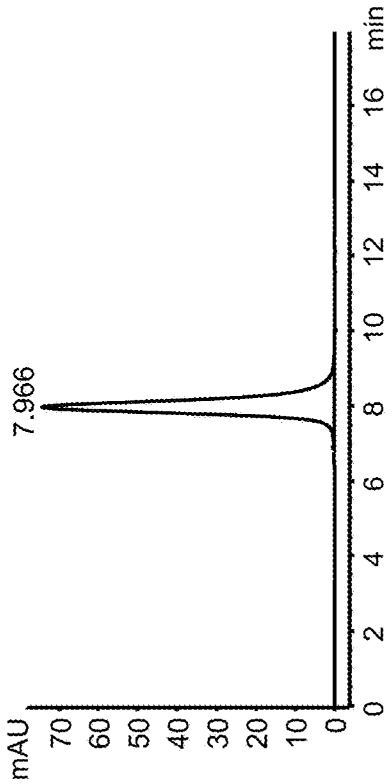
Figures 9A, 9B, 9C, 9D:
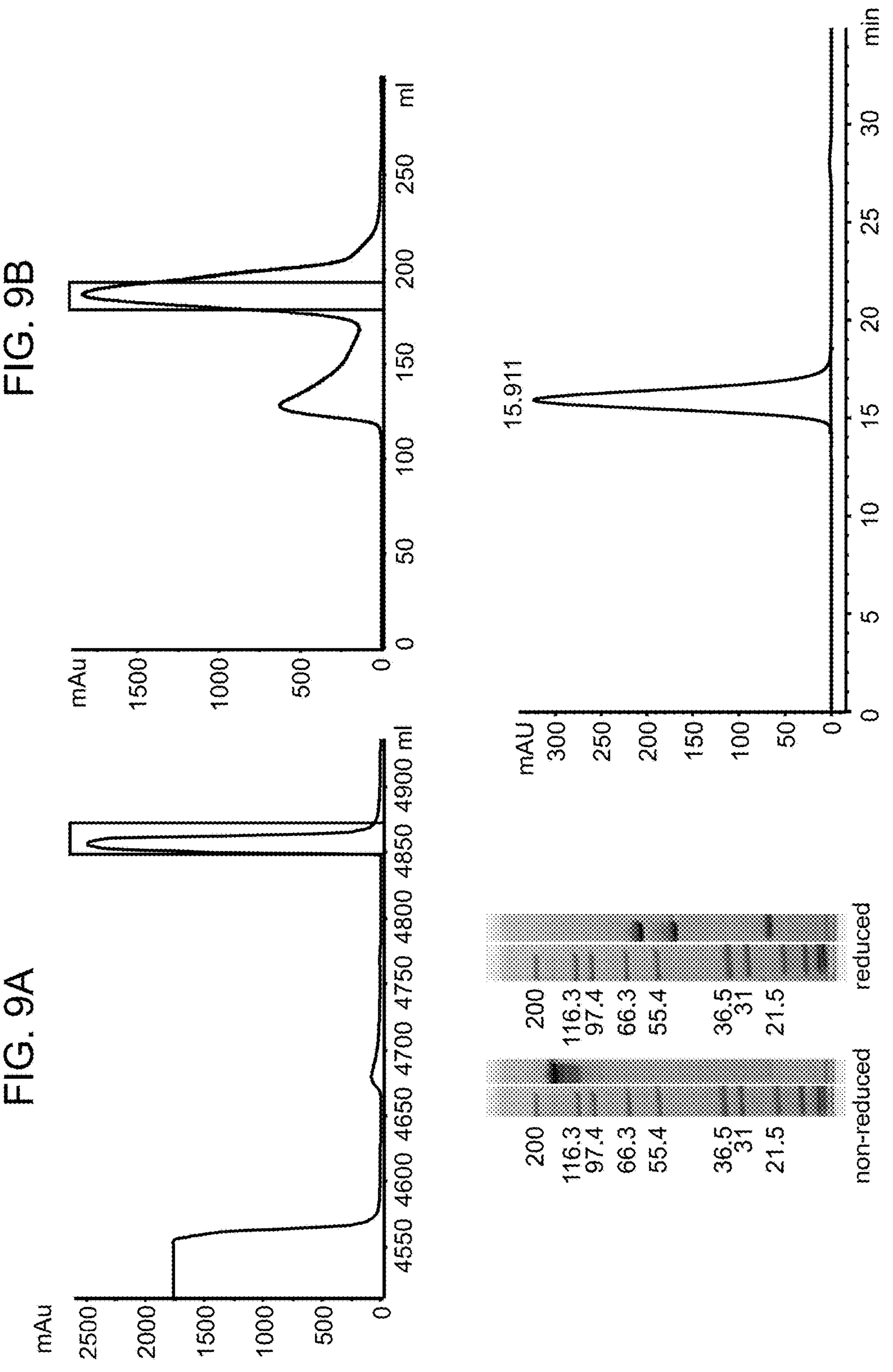
FIGS. 9A-D. Purification of untargeted DP47GS-based IgG-IL-2 qm immunoconjugate.

The components of the immunoconjugate can be fused to each other in a variety of configurations. Exemplary configurations are depicted in FIGS. 2A-C. In one embodiment the effector moiety is fused to the amino- or carboxy-terminal amino acid of one of the two subunits of the Fc domain. In one embodiment the effector moiety is fused to the carboxy-terminal amino acid of one of the two subunits of the Fc domain. The effector moiety may be fused to the Fc domain directly or through a linker peptide, comprising one or more amino acids, typically about 2-20 amino acids. Linker peptides are known in the art or are described herein. Suitable, non-immunogenic linker peptides include, for example, $(G_4S)_n$, $(SG_4)_n$ or $G_4(SG_4)_n$ linker peptides. "n" is generally a number between 1 and 10, typically between 2 and 4. Alternatively, where the effector moiety is linked to the N-terminus of an Fc domain subunit, it may be linked via an immunoglobulin hinge region or a portion thereof, with or without an additional linker peptide.

Similarly, the first antigen binding moiety can be fused to the amino- or carboxy-terminal amino acid of one of the two subunits of the Fc domain. In one embodiment the first antigen binding moiety is fused to the amino-terminal amino acid of one of the two subunits of the Fc domain.

The first antigen binding moiety may be fused to the Fc domain directly or through a linker peptide. In a particular embodiment the first antigen binding moiety is fused to the Fc domain through an immunoglobulin hinge region. In a specific embodiment, the immunoglobulin hinge region is a human $IgG_1$ hinge region.

In one embodiment the first antigen binding moiety comprises an antigen binding domain of an antibody, comprising an antibody heavy chain variable region and an antibody light chain variable region. In a particular embodiment the first antigen binding moiety is a Fab molecule. In one embodiment the Fab molecule is fused at its heavy or light chain carboxy-terminus to the amino-terminal amino acid of one of the two subunits of the Fc domain. In a particular embodiment the Fab molecule is fused at its heavy chain carboxy-terminus to the amino-terminal amino acid of one of the two subunits of the Fc domain. In a more particular embodiment the Fab molecule is fused to the Fc domain through an immunoglobulin hinge region. In a specific embodiment, the immunoglobulin hinge region is a human $IgG_1$ hinge region.

In one embodiment the immunoconjugate essentially consists of an antigen binding moiety, an Fc domain consisting of two subunits, an effector moiety, and optionally one or more linker peptides, wherein said antigen binding domain is a Fab molecule and is fused at its heavy chain carboxy-terminus to the amino-terminal amino acid of one of the two subunits of the Fc domain, and wherein said effector moiety is fused either (i) to the amino-terminal amino acid of the other one of the two subunits of the Fc domain, or (ii) to the carboxy-terminal amino acid of one of the two subunits of the Fc domain. In the latter case, the effector moiety and the first antigen binding moiety may both be fused to the same subunit of the Fc domain, or may each be fused to a different one of the two subunits of the Fc domain.

An immunoconjugate format with a single antigen binding moiety (for example as shown in FIGS. 2B and 2C) is useful, particularly in cases where internalization of the target antigen is to be expected following binding of a high affinity antigen binding moiety. In such cases, the presence of more than one antigen binding moiety per immunoconjugate may enhance internalization, thereby reducing availability of the target antigen.

In many other cases, however, it will be advantageous to have an immunoconjugate comprising two or more antigen binding moieties and a single effector moiety to optimize targeting to the target antigen versus the effector moiety receptor, and the pharmaceutical window of the immunoconjugate.

Thus, in a particular embodiment the immunoconjugate of the invention comprises a first and a second antigen binding moiety. In one embodiment each of said first and second antigen binding moieties is fused to the amino-terminal amino acid of one of the two subunits of the Fc domain.

The first and second antigen binding moieties may be fused to the Fc domain directly or through a linker peptide. In a particular embodiment each of said first and second antigen binding moieties is fused to a subunit of the Fc domain through an immunoglobulin hinge region. In a specific embodiment, the immunoglobulin hinge region is a human $IgG_1$ hinge region.

In one embodiment each of said first and second antigen binding moieties comprises an antigen binding domain of an antibody, comprising an antibody heavy chain variable region and an antibody light chain variable region. In a particular embodiment each of said first and second antigen binding moieties is a Fab molecule. In one embodiment each of said Fab molecules is fused at its heavy or light chain carboxy-terminus to the amino-terminal amino acid of one of the two subunits of the Fc domain. In a particular embodiment each of said Fab molecules is fused at its heavy chain carboxy-terminus to the amino-terminal amino acid of one of the two subunits of the Fc domain. In a more particular embodiment each of said Fab molecules is fused to a subunit of the Fc domain through an immunoglobulin hinge region. In a specific embodiment, the immunoglobulin hinge region is a human $IgG_1$ hinge region.

In one embodiment the first and the second antigen binding moiety and the Fc domain are part of an immunoglobulin molecule. In a particular embodiment the immunoglobulin molecule is an IgG class immunoglobulin. In an even more particular embodiment the immunoglobulin is an $IgG_1$ subclass immunoglobulin. In another particular embodiment the immunoglobulin is a human immunoglobulin. In other embodiments the immunoglobulin is a chimeric immunoglobulin or a humanized immunoglobulin. In one embodiment the effector moiety is fused to the carboxy-terminal amino acid of one of the immunoglobulin heavy chains. The effector moiety may be fused to the immunoglobulin heavy chain directly or through a linker peptide. In a particular embodiment the immunoconjugate essentially consists of an immunoglobulin molecule, an effector moiety fused to the carboxy-terminal amino acid of one of the immunoglobulin heavy chains, and optionally one or more linker peptides.

In one embodiment the immunoconjugate comprises a polypeptide wherein a Fab heavy chain shares a carboxy-terminal peptide bond with an Fc domain subunit and a polypeptide wherein an Fc domain subunit shares a carboxy-terminal peptide bond with an effector moiety polypeptide.

In another embodiment, the immunoconjugate comprises a polypeptide wherein a first Fab heavy chain shares a carboxy-terminal peptide bond with an Fc domain subunit, and a polypeptide wherein a second Fab heavy chain shares a carboxy-terminal peptide bond with an Fc domain subunit, which in turn shares a carboxy-terminal peptide bond with an effector moiety polypeptide. In a further embodiment the immunoconjugate comprises a polypeptide wherein a Fab heavy chain shares a carboxy-terminal peptide bond with an Fc domain subunit and a polypeptide wherein an effector moiety polypeptide shares a carboxy-terminal peptide bond with an Fc domain subunit. In some embodiments the immunoconjugate further comprises a Fab light chain polypeptide. In certain embodiments the polypeptides are covalently linked, e.g., by a disulfide bond.

According to any of the above embodiments, components of the immunoconjugate (e.g. effector moiety, antigen binding moiety, Fc domain) may be linked directly or through various linkers, particularly peptide linkers comprising one or more amino acids, typically about 2-20 amino acids, that are described herein or are known in the art. Suitable, non-immunogenic linker peptides include, for example, $(G4S)_n$, $(SG_4)_n$ or $G_4(SG_4)_n$ linker peptides, wherein n is generally a number between 1 and 10, typically between 2 and 4.

Fc Domain

The Fc domain of the immunoconjugate consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. In one embodiment the immunoconjugate of the invention comprises not more than one Fc domain.

In one embodiment according the invention the Fc domain of the immunoconjugate is an IgG Fc domain. In a particular embodiment the Fc domain is an $IgG_1$ Fc domain. In another embodiment, the Fc domain is an $IgG_4$ Fc domain. In a further particular embodiment the Fc domain is human. An exemplary sequence of a human $IgG_1$ Fc region is given in SEQ ID NO: 1.

The Fc domain confers to the immunoconjugate a greatly prolonged serum-half life as compared to immunoconjugate formats lacking an Fc domain. Particularly when the immunoconjugate comprises an effector moiety of rather weak activity (but e.g. reduced toxicity), a long half-life might be essential to achieve optimal efficacy in vivo. Moreover, the Fc domain can mediate effector functions, as will be further discussed below.

Fc Domain Modifications Promoting Heterodimerization

Immunoconjugates according to the invention comprise only one single effector moiety, fused to one of the two subunits of the Fc domain, thus they comprise two non-identical polypeptide chains. Recombinant co-expression of these polypeptides and subsequent dimerization leads to several possible combinations of the two polypeptides, out of which only heterodimers of the two non-identical polypeptides are useful according to the invention. To improve the yield and purity of immunoconjugates in recombinant production, it can thus be advantageous to introduce in the Fc domain of the immunoconjugate a modification which hinders the formation of homodimers of two identical polypeptides (i.e. two polypeptides comprising an effector moiety, or two polypeptides lacking an effector moiety) and/or promotes the formation of heterodimers of a polypeptide comprising an effector moiety and a polypeptide lacking an effector moiety.

Accordingly, in certain embodiments according to the invention the Fc domain of the immunoconjugate comprises a modification promoting heterodimerization of two non-identical polypeptide chains. The site of most extensive protein-protein interaction between the two polypeptide chains of a human IgG Fc domain is in the CH3 domain of the Fc domain. Thus, in one embodiment said modification is in the CH3 domain of the Fc domain.

In a specific embodiment said modification is a knob-into-hole modification, comprising a knob modification in one of the two subunits of the Fc domain and a hole modification in the other one of the two subunits of the Fc domain.

The knob-into-hole technology is described e.g. in U.S. Pat. No. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). The protuberance and cavity can be made by altering the nucleic acid encoding the polypeptides, e.g. by site-specific mutagenesis, or by peptide synthesis. In a specific embodiment a knob modification comprises the amino acid substitution T366W in one of the two subunits of the Fc domain, and the hole modification comprises the amino acid substitutions T366S, L368A and Y407V in the other one of the two subunits of the Fc domain. In a further specific embodiment, the subunit of the Fc domain comprising the knob modification additionally comprises the amino acid substitution S354C, and the subunit of the Fc domain comprising the hole modification additionally comprises the amino acid substitution Y349C. Introduction of these two cysteine residues results in formation of a disulfide bridge between the two subunits of the Fc region, further stabilizing the dimer (Carter, J Immunol Methods 248, 7-15 (2001)).

In an alternative embodiment a modification promoting heterodimerization of two non-identical polypeptide chains comprises a modification mediating electrostatic steering effects, e.g. as described in PCT publication WO 2009/089004. Generally, this method involves replacement of one or more amino acid residues at the interface of the two polypeptide chains by charged amino acid residues so that homodimer formation becomes electrostatically unfavorable but heterodimerization electrostatically favorable.

In a particular embodiment the effector moiety is fused to the amino- or carboxy-terminal amino acid of the subunit of the Fc domain comprising the knob modification. Without wishing to be bound by theory, fusion of the effector moiety to the knob-containing subunit of the Fc domain will further minimize the generation of homodimeric immunoconjugates comprising two effector moieties (steric clash of two knob-containing polypeptides).

Fc Domain Modifications Altering Fc Receptor Binding

In certain embodiments of the invention the Fc domain of the immunoconjugate is engineered to have altered binding affinity to an Fc receptor, specifically altered binding affinity to an Fcγ receptor, as compared to a non-engineered Fc domain.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. A suitable such binding assay is described herein. Alternatively, binding affinity of Fc domains or immunoconjugates comprising an Fc domain for Fc receptors may be evaluated using cell lines known to express particular Fc receptors, such as NK cells expressing FcγIIIa receptor.

In some embodiments the Fc domain of the immunoconjugate is engineered to have altered effector functions, particularly altered ADCC, as compared to a non-engineered Fc domain.

Effector function of an Fc domain, or an immunoconjugate comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some embodiments binding of the Fc domain to a complement component, specifically to C1q, is altered. Accordingly, in some embodiments wherein the Fc domain is engineered to have altered effector function, said altered effector function includes altered CDC. C1q binding assays may be carried out to determine whether the immunoconjugate is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

a) Decreased Fc Receptor Binding and/or Effector Function

The Fc domain confers to the immunoconjugate favorable pharmacokinetic properties, including a long serum half-life which contributes to good accumulation in the target tissue and a favorable tissue-blood distribution ratio. At the same time it may, however, lead to undesirable targeting of the immunoconjugate to cells expressing Fc receptors rather than to the preferred antigen-bearing cells. Moreover, the co-activation of Fc receptor signaling pathways may lead to cytokine release which, in combination with the effector moiety and the long half-life of the immunoconjugate, results in excessive activation of cytokine receptors and severe side effects upon systemic administration. In line with this, conventional IgG-IL-2 immunoconjugates have been described to be associated with infusion reactions (see e.g. King et al., J Clin Oncol 22, 4463-4473 (2004)).

Accordingly, in particular embodiments according to the invention the Fc domain of the immunoconjugate is engineered to have reduced binding affinity to an Fc receptor. In one such embodiment the Fc domain comprises one or more amino acid mutation that reduces the binding affinity of the Fc domain to an Fc receptor. Typically, the same one or more amino acid mutation is present in each of the two subunits of the Fc domain. In one embodiment said amino acid mutation reduces the binding affinity of the Fc domain to the Fc receptor by at least 2-fold, at least 5-fold, or at least 10-fold. In embodiments where there is more than one amino acid mutation that reduces the binding affinity of the Fc domain to the Fc receptor, the combination of these amino acid mutations may reduce the binding affinity of the Fc domain to the Fc receptor by at least 10-fold, at least 20-fold, or even at least 50-fold. In one embodiment the immunoconjugate comprising an engineered Fc domain exhibits less than 20%, particularly less than 10%, more particularly less than 5% of the binding affinity to an Fc receptor as compared to an immunoconjugate comprising a non-engineered Fc domain. In one embodiment the Fc receptor is an activating Fc receptor. In a specific embodiment the Fc receptor is an Fcγ receptor, more specifically an FcγRIIIa, FcγRI or FcγRIIa receptor. Preferably, binding to each of these receptors is reduced. In some embodiments binding affinity to a complement component, specifically binding affinity to C1q, is also reduced. In one embodiment binding affinity to neonatal Fc receptor (FcRn) is not reduced. Substantially similar binding to FcRn, i.e. preservation of the binding affinity of the Fc domain to said receptor, is achieved when the Fc domain (or the immunoconjugate comprising said Fc domain) exhibits greater than about 70% of the binding affinity of a non-engineered form of the Fc domain (or the immunoconjugate comprising said non-engineered form of the Fc domain) to FcRn. Fc domains, or immunoconjugates of the invention comprising said Fc domains, may exhibit greater than about 80% and even greater than about 90% of such affinity. In one embodiment the amino acid mutation is an amino acid substitution. In one embodiment the Fc domain comprises an amino acid substitution at position P329. In a more specific embodiment the amino acid substitution is P329A or P329G, particularly P329G. In one embodiment the Fc domain comprises a further amino acid substitution at a position selected from 5228, E233, L234, L235, N297 and P331. In a more specific embodiment the further amino acid substitution is S228P, E233P, L234A, L235A, L235E, N297A, N297D or P331 S. In a particular embodiment the Fc domain comprises amino acid substitutions at positions P329, L234 and L235. In a more particular embodiment the Fc domain comprises the amino acid mutations L234A, L235A and P329G (LALA P329G). This combination of amino acid substitutions almost completely abolishes Fcγ receptor binding of a human IgG Fc domain, as described in European patent application no. EP 11160251.2, incorporated herein by reference in its entirety. EP 11160251.2 also describes methods of preparing such mutant Fc domains and methods for determining its properties such as Fc receptor binding or effector functions.

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

In one embodiment the Fc domain is engineered to have decreased effector function, compared to a non-engineered Fc domain. The decreased effector function can include, but is not limited to, one or more of the following: decreased complement dependent cytotoxicity (CDC), decreased antibody-dependent cell-mediated cytotoxicity (ADCC), decreased antibody-dependent cellular phagocytosis (ADCP), decreased cytokine secretion, decreased immune complex-mediated antigen uptake by antigen-presenting cells, decreased binding to NK cells, decreased binding to macrophages, decreased binding to monocytes, decreased binding to polymorphonuclear cells, decreased direct signaling inducing apoptosis, decreased crosslinking of target-bound antibodies, decreased dendritic cell maturation, or decreased T cell priming.

In one embodiment the decreased effector function is one or more selected from the group of decreased CDC, decreased ADCC, decreased ADCP, and decreased cytokine secretion. In a particular embodiment the decreased effector function is decreased ADCC. In one embodiment the decreased ADCC is less than 20% of the ADCC induced by a non-engineered Fc domain (or an immunoconjugate comprising a non-engineered Fc domain).

In addition to the Fc domains described hereinabove and in European patent application no. EP 11160251.2, Fc domains with reduced Fc receptor binding and/or effector function also include those with substitution of one or more of Fc domain residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

$IgG_4$ antibodies exhibit reduced binding affinity to Fc receptors and reduced effector functions as compared to $IgG_1$ antibodies. Hence, in some embodiments the Fc domain of the T cell activating bispecific antigen binding molecules of the invention is an $IgG_4$ Fc domain, particularly a human $IgG_4$ Fc domain. In one embodiment the $IgG_4$ Fc domain comprises amino acid substitutions at position S228, specifically the amino acid substitution S228P. To further reduce its binding affinity to an Fc receptor and/or its effector function, in one embodiment the $IgG_4$ Fc domain comprises an amino acid substitution at position L235, specifically the amino acid substitution L235E. In another embodiment, the $IgG_4$ Fc domain comprises an amino acid substitution at position P329, specifically the amino acid substitution P329G. In a particular embodiment, the $IgG_4$ Fc domain comprises amino acid substitutions at positions S228, L235 and P329, specifically amino acid substitutions S228P, L235E and P329G. Such $IgG_4$ Fc domain mutants and their Fcγ receptor binding properties are described in European patent application no. EP 11160251.2, incorporated herein by reference in its entirety.

b) Increased Fc Receptor Binding and/or Effector Function

Conversely, there may be situations where it is desirable to maintain or even enhance Fc receptor binding and/or effector functions of immunoconjugates, for example when the immunoconjugate is targeted to a highly specific tumor antigen. Hence, in certain embodiments the Fc domain of the immunoconjugates of the invention is engineered to have increased binding affinity to an Fc receptor. Increased binding affinity may be an increase in the binding affinity of the Fc domain to the Fc receptor by at least 2-fold, at least 5-fold, or at least 10-fold. In one embodiment the Fc receptor is an activating Fc receptor. In a specific embodiment the Fc receptor is an Fcγ receptor. In one embodiment the Fc receptor is selected from the group of FcγRIIIa, FcγRI and FcγRIIa. In a particular embodiment the Fc receptor is FcγRIIIa.

In one such embodiment the Fc domain is engineered to have an altered oligosaccharide structure compared to a non-engineered Fc domain. In a particular such embodiment the Fc domain comprises an increased proportion of non-fucosylated oligosaccharides, compared to a non-engineered Fc domain. In a more specific embodiment, at least about 20%, about 25%, about 30%, about 35%, about 40%, about 45%, about 50%, about 55%, about 60%, about 65%, about 70%, about 75%, about 80%, about 85%, about 90%, about 95%, or about 100%, particularly at least about 50%, more particularly at least about 70%, of the N-linked oligosaccharides in the Fc domain of the immunoconjugate are non-fucosylated. The non-fucosylated oligosaccharides may be of the hybrid or complex type. In another specific embodiment the Fc domain comprises an increased proportion of bisected oligosaccharides, compared to a non-engineered Fc domain. In a more specific embodiment, at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, particularly at least about 50%, more particularly at least about 70%, of the N-linked oligosaccharides in the Fc domain of the immunoconjugate are bisected. The bisected oligosaccharides may be of the hybrid or complex type. In yet another specific embodiment the Fc domain comprises an increased proportion of bisected, non-fucosylated oligosaccharides, compared to a non-engineered Fc domain. In a more specific embodiment, at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, particularly at least about 15%, more particularly at least about 25%, at least about 35% or at least about 50%, of the N-linked oligosaccharides in the Fc domain of the immunoconjugate are bisected, non-fucosylated. The bisected, non-fucosylated oligosaccharides may be of the hybrid or complex type.

The oligosaccharide structures in the immunoconjugate Fc domain can be analysed by methods well known in the art, e.g. by MALDI TOF mass spectrometry as described in Umana et al., Nat Biotechnol 17, 176-180 (1999) or Ferrara et al., Biotechn Bioeng 93, 851-861 (2006). The percentage of non-fucosylated oligosaccharides is the amount of oligosaccharides lacking fucose residues, relative to all oligosaccharides attached to Asn 297 (e.g. complex, hybrid and high mannose structures) and identified in an N-glycosidase F treated sample by MALDI TOF MS. Asn 297 refers to the asparagine residue located at about position 297 in the Fc domain (EU numbering of Fc region residues); however, Asn297 may also be located about ±3 amino acids upstream or downstream of position 297, i.e., between positions 294 and 300, due to minor sequence variations in immunoglobulins. The percentage of bisected, or bisected non-fucosylated, oligosaccharides is determined analogously.

Modification of the glycosylation in the Fc domain of the immunoconjugate may result from production of the immunoconjugate in a host cell that has been manipulated to express altered levels of one or more polypeptides having glycosyltransferase activity.

In one embodiment the Fc domain of the immunoconjugate is engineered to have an altered oligosaccharide structure, as compared to a non-engineered Fc domain, by producing the immunoconjugate in a host cell having altered activity of one or more glycosyltransferase. Glycosyltransferases include for example β(1,4)-N-acetylglucosaminyltransferase III (GnTIII), β(1,4)-galactosyltransferase (GalT), β(1,2)-N-acetylglucosaminyltransferase I (GnTI), β(1,2)-N-acetylglucosaminyltransferase II (GnTII) and α(1,6)-fucosyltransferase. In a specific embodiment the Fc domain of the immunoconjugate is engineered to comprise an increased proportion of non-fucosylated oligosaccharides, as compared to a non-engineered Fc domain, by producing the immunoconjugate in a host cell having increased β(1,4)-N-acetylglucosaminyltransferase III (GnTIII) activity. In an even more specific embodiment the host cell additionally has increased α-mannosidase II (ManII) activity. The glycoengineering methodology that can be used for glycoengineering immunoconjugates of the present invention has been described in greater detail in Umana et al., Nat Biotechnol 17, 176-180 (1999); Ferrara et al., Biotechn Bioeng 93, 851-861 (2006); WO 99/54342 (U.S. Pat. No. 6,602,684; EP 1071700); WO 2004/065540 (U.S. Pat. Appl. Publ. No. 2004/0241817; EP 1587921), WO 03/011878 (U.S. Pat. Appl. Publ. No. 2003/0175884), the content of each of which is expressly incorporated herein by reference in its entirety.

Generally, any type of cultured cell line, including the cell lines discussed herein, can be used to generate cell lines for the production of immunoconjugates with altered glycosylation pattern. Particular cell lines include CHO cells, BHK cells, NS0 cells, SP2/0 cells, YO myeloma cells, P3X63 mouse myeloma cells, PER cells, PER.C6 cells or hybridoma cells, and other mammalian cells. In certain embodiments, the host cells have been manipulated to express increased levels of one or more polypeptides having β(1,4)-N-acetylglucosaminyltransferase III (GnTIII) activity. In certain embodiments the host cells have been further manipulated to express increased levels of one or more polypeptides having α-mannosidase II (ManII) activity. In a specific embodiment, the polypeptide having GnTIII activity is a fusion polypeptide comprising the catalytic domain of GnTIII and the Golgi localization domain of a heterologous Golgi resident polypeptide. Particularly, said Golgi localization domain is the Golgi localization domain of mannosidase II. Methods for generating such fusion polypeptides and using them to produce antibodies with increased effector functions are disclosed in Ferrara et al., Biotechn Bioeng 93, 851-861 (2006) and WO 2004/065540, the entire contents of which are expressly incorporated herein by reference.

The host cells which contain a coding sequence of an immunoconjugate of the invention and/or a coding sequence of a polypeptide having glycosyltransferase activity, and which express the biologically active gene products, may be identified e.g. by DNA-DNA or DNA-RNA hybridization, the presence or absence of "marker" gene functions, assessing the level of transcription as measured by the expression of the respective mRNA transcripts in the host cell, or detection of the gene product as measured by immunoassay or by its biological activity—methods which are well known in the art. GnTIII or Man II activity can be detected e.g. by employing a lectin which binds to biosynthesis products of GnTIII or ManII, respectively. An example for such a lectin is the $E_4$-PHA lectin which binds preferentially to oligosaccharides containing bisecting GlcNAc. Biosynthesis products (i.e. specific oligosaccharide structures) of polypeptides having GnTIII or ManII activity can also be detected by mass spectrometric analysis of oligosaccharides released from glycoproteins produced by cells expressing said polypeptides. Alternatively, a functional assay which measures the increased effector function and/or increased Fc receptor binding, mediated by immunoconjugates produced by the cells engineered with the polypeptide having GnTIII or ManII activity may be used.

In another embodiment the Fc domain is engineered to comprise an increased proportion of non-fucosylated oligosaccharides, as compared to a non-engineered Fc domain, by producing the immunoconjugate in a host cell having decreased α(1,6)-fucosyltransferase activity. A host cell having decreased α(1,6)-fucosyltransferase activity may be a cell in which the α(1,6)-fucosyltransferase gene has been disrupted or otherwise deactivated, e.g. knocked out (see Yamane-Ohnuki et al., Biotech Bioeng 87, 614 (2004); Kanda et al., Biotechnol Bioeng 94(4), 680-688 (2006); Niwa et al., J Immunol Methods 306, 151-160 (2006)).

Other examples of cell lines capable of producing defucosylated immunoconjugates include Lec13 CHO cells deficient in protein fucosylation (Ripka et al., Arch Biochem Biophys 249, 533-545 (1986); US Pat. Appl. No. US 2003/0157108; and WO 2004/056312, especially at Example 11). The immunoconjugates of the present invention can alternatively be glycoengineered to have reduced fucose residues in the Fc domain according to the techniques disclosed in EP 1 176 195 A1, WO 03/084570, WO 03/085119 and U.S. Pat. Appl. Pub. Nos. 2003/0115614, 2004/093621, 2004/110282, 2004/110704, 2004/132140, U.S. Pat. No. 6,946,292 (Kyowa), e.g. by reducing or abolishing the activity of a GDP-fucose transporter protein in the host cells used for immunoconjugate production.

Glycoengineered immunoconjugates of the invention may also be produced in expression systems that produce modified glycoproteins, such as those taught in WO 2003/056914 (GlycoFi, Inc.) or in WO 2004/057002 and WO 2004/024927 (Greenovation).

In one embodiment the Fc domain of the immunoconjugate is engineered to have increased effector function, compared to a non-engineered Fc domain. The increased effector function can include, but is not limited to, one or more of the following: increased complement dependent cytotoxicity (CDC), increased antibody-dependent cell-mediated cytotoxicity (ADCC), increased antibody-dependent cellular phagocytosis (ADCP), increased cytokine secretion, increased immune complex-mediated antigen uptake by antigen-presenting cells, increased binding to NK cells, increased binding to macrophages, increased binding to monocytes, increased binding to polymorphonuclear cells, increased direct signaling inducing apoptosis, increased crosslinking of target-bound antibodies, increased dendritic cell maturation, or increased T cell priming.

In one embodiment the increased effector function is one or more selected from the group of increased CDC, increased ADCC, increased ADCP, and increased cytokine secretion. In a particular embodiment the increased effector function is increased ADCC. In one embodiment ADCC induced by an engineered Fc domain (or an immunoconjugate comprising an engineered Fc domain) is a least 2-fold increased as compared to ADCC induced by a non-engineered Fc domain (or an immunoconjugate comprising a non-engineered Fc domain).

Effector Moieties

The effector moieties for use in the invention are generally polypeptides that influence cellular activity, for example, through signal transduction pathways. Accordingly, the effector moiety of the immunoconjugate useful in the invention can be associated with receptor-mediated signaling that transmits a signal from outside the cell membrane to modulate a response within the cell. For example, an effector moiety of the immunoconjugate can be a cytokine. In particular embodiments the effector moiety is human.

In certain embodiments the effector moiety is a single chain effector moiety. In a particular embodiment the effector moiety is a cytokine. Examples of useful cytokines include, but are not limited to, GM-CSF, IL-la, IL-1β, IL-2, IL-3, IL-4, IL-5, IL-6, IL-7, IL-8, IL-10, IL-12, IL-21, IFN-α, IFN-β, IFN-γ, MIP-1α, MIP-1β, TGF-β, TNF-α, and TNF-β. In one embodiment the effector moiety of the immunoconjugate is a cytokine selected from the group of GM-CSF, IL-2, IL-7, IL-8, IL-10, IL-12, IL-15, IL-21, IFN-α, IFN-γ, MIP-1α, MIP-1β and TGF-β. In one embodiment the effector moiety of the immunoconjugate is a cytokine selected from the group of IL-2, IL-7, IL-10, IL-12, IL-15, IFN-α, and IFN-γ. In certain embodiments the cytokine effector moiety is mutated to remove N- and/or O-glycosylation sites. Elimination of glycosylation increases homogeneity of the product obtainable in recombinant production.

In a particular embodiment the effector moiety of the immunoconjugate is IL-2. In a specific embodiment, the IL-2 effector moiety can elicit one or more of the cellular responses selected from the group consisting of: proliferation in an activated T lymphocyte cell, differentiation in an activated T lymphocyte cell, cytotoxic T cell (CTL) activity, proliferation in an activated B cell, differentiation in an activated B cell, proliferation in a natural killer (NK) cell, differentiation in a NK cell, cytokine secretion by an activated T cell or an NK cell, and NK/lymphocyte activated killer (LAK) antitumor cytotoxicity. In another particular embodiment the IL-2 effector moiety is a mutant IL-2 effector moiety having reduced binding affinity to the α-subunit of the IL-2 receptor. Together with the β- and γ-subunits (also known as CD122 and CD132, respectively), the α-subunit (also known as CD25) forms the heterotrimeric high-affinity IL-2 receptor, while the dimeric receptor consisting only of the β- and γ-subunits is termed the intermediate-affinity IL-2 receptor. As described in PCT patent application number PCT/EP2012/051991, which is incorporated herein by reference in its entirety, a mutant IL-2 polypeptide with reduced binding to the α-subunit of the IL-2 receptor has a reduced ability to induce IL-2 signaling in regulatory T cells, induces less activation-induced cell death (AICD) in T cells, and has a reduced toxicity profile in vivo, compared to a wild-type IL-2 polypeptide. The use of such an effector moiety with reduced toxicity is particularly advantageous in an immunoconjugate according to the invention, having a long serum half-life due to the presence of an Fc domain. In one embodiment, the mutant IL-2 effector moiety of the immunoconjugate according to the invention comprises at least one amino acid mutation that reduces or abolishes the affinity of the mutant IL-2 effector moiety to the α-subunit of the IL-2 receptor (CD25) but preserves the affinity of the mutant IL-2 effector moiety to the intermediate-affinity IL-2 receptor (consisting of the β- and γ-subunits of the IL-2 receptor), compared to the non-mutated IL-2 effector moiety. In one embodiment the one or more amino acid mutations are amino acid substitutions. In a specific embodiment, the mutant IL-2 effector moiety comprises one, two or three amino acid substitutions at one, two or three position(s) selected from the positions corresponding to residue 42, 45, and 72 of human IL-2. In a more specific embodiment, the mutant IL-2 effector moiety comprises three amino acid substitutions at the positions corresponding to residue 42, 45 and 72 of human IL-2. In an even more specific embodiment, the mutant IL-2 effector moiety is human IL-2 comprising the amino acid substitutions F42A, Y45A and L72G. In one embodiment the mutant IL-2 effector moiety additionally comprises an amino acid mutation at a position corresponding to position 3 of human IL-2, which eliminates the O-glycosylation site of IL-2. Particularly, said additional amino acid mutation is an amino acid substitution replacing a threonine residue by an alanine residue. A particular mutant IL-2 effector moiety useful in the invention comprises four amino acid substitutions at positions corresponding to residues 3, 42, 45 and 72 of human IL-2. Specific amino acid substitutions are T3A, F42A, Y45A and L72G. As demonstrated in PCT patent application number PCT/EP2012/051991 and in the appended Examples, said quadruple mutant IL-2 polypeptide (IL-2 qm) exhibits no detectable binding to CD25, reduced ability to induce apoptosis in T cells, reduced ability to induce IL-2 signaling in $T_{reg}$ cells, and a reduced toxicity profile in vivo. However, it retains ability to activate IL-2 signaling in effector cells, to induce proliferation of effector cells, and to generate IFN-γ as a secondary cytokine by NK cells.

The IL-2 or mutant IL-2 effector moiety according to any of the above embodiments may comprise additional mutations that provide further advantages such as increased expression or stability. For example, the cysteine at position 125 may be replaced with a neutral amino acid such as alanine, to avoid the formation of disulfide-bridged IL-2 dimers. Thus, in certain embodiments the IL-2 or mutant IL-2 effector moiety of the immunoconjugate according to the invention comprises an additional amino acid mutation at a position corresponding to residue 125 of human IL-2. In one embodiment said additional amino acid mutation is the amino acid substitution C125A.

In a specific embodiment the IL-2 effector moiety of the immunoconjugate comprises the polypeptide sequence of SEQ ID NO: 2. In another specific embodiment the IL-2 effector moiety of the immunoconjugate comprises the polypeptide sequence of SEQ ID NO: 3.

In another embodiment the effector moiety of the immunoconjugate is IL-12. In a specific embodiment said IL-12 effector moiety is a single chain IL-12 effector moiety. In an even more specific embodiment the single chain IL-12 effector moiety comprises the polypeptide sequence of SEQ ID NO: 4. In one embodiment, the IL-12 effector moiety can elicit one or more of the cellular responses selected from the group consisting of: proliferation in a NK cell, differentiation in a NK cell, proliferation in a T cell, and differentiation in a T cell.

In another embodiment the effector moiety of the immunoconjugate is IL-10. In a specific embodiment said IL-10 effector moiety is a single chain IL-10 effector moiety. In an even more specific embodiment the single chain IL-10 effector moiety comprises the polypeptide sequence of SEQ ID NO: 5. In another specific embodiment the IL-10 effector moiety is a monomeric IL-10 effector moiety. In a more specific embodiment the monomeric IL-10 effector moiety comprises the polypeptide sequence of SEQ ID NO: 6. In one embodiment, the IL-10 effector moiety can elicit one or more of the cellular responses selected from the group consisting of: inhibition of cytokine secretion, inhibition of antigen presentation by antigen presenting cells, reduction of oxygen radical release, and inhibition of T cell proliferation. An immunoconjugate according to the invention wherein the effector moiety is IL-10 is particularly useful for downregulation of inflammation, e.g. in the treatment of an inflammatory disorder.

In another embodiment the effector moiety of the immunoconjugate is IL-15. In a specific embodiment said IL-15 effector moiety is a mutant IL-15 effector moiety having reduced binding affinity to the α-subunit of the IL-15 receptor. Without wishing to be bound by theory, a mutant IL-15 polypeptide with reduced binding to to the α-subunit of the IL-15 receptor has a reduced ability to bind to fibroblasts throughout the body, resulting in improved pharmacokinetics and toxicity profile, compared to a wild-type IL-15 polypeptide. The use of an effector moiety with reduced toxicity, such as the described mutant IL-2 and mutant IL-15 effector moieties, is particularly advantageous in an immunoconjugate according to the invention, having a long serum half-life due to the presence of an Fc domain. In one embodiment the mutant IL-15 effector moiety of the immunoconjugate according to the invention comprises at least one amino acid mutation that reduces or abolishes the affinity of the mutant IL-15 effector moiety to the α-subunit of the IL-15 receptor but preserves the affinity of the mutant IL-15 effector moiety to the intermediate-affinity IL-15/IL-2 receptor (consisting of the β- and γ-subunits of the IL-15/IL-2 receptor), compared to the non-mutated IL-15 effector moiety. In one embodiment the amino acid mutation is an amino acid substitution. In a specific embodiment, the mutant IL-15 effector moiety comprises an amino acid substitution at the position corresponding to residue 53 of human IL-15. In a more specific embodiment, the mutant IL-15 effector moiety is human IL-15 comprising the amino acid substitution E53A. In one embodiment the mutant IL-15 effector moiety additionally comprises an amino acid mutation at a position corresponding to position 79 of human IL-15, which eliminates the N-glycosylation site of IL-15. Particularly, said additional amino acid mutation is an amino acid substitution replacing an asparagine residue by an alanine residue. In an even more specific embodiment the IL-15 effector moiety comprises the polypeptide sequence of SEQ ID NO: 7. In one embodiment, the IL-15 effector moiety can elicit one or more of the cellular responses selected from the group consisting of: proliferation in an activated T lymphocyte cell, differentiation in an activated T lymphocyte cell, cytotoxic T cell (CTL) activity, proliferation in an activated B cell, differentiation in an activated B cell, proliferation in a natural killer (NK) cell, differentiation in a NK cell, cytokine secretion by an activated T cell or an NK cell, and NK/lymphocyte activated killer (LAK) antitumor cytotoxicity.

Mutant cytokine molecules useful as effector moieties in the immunoconjugates can be prepared by deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing. Substitution or insertion may involve natural as well as non-natural amino acid residues. Amino acid modification includes well known methods of chemical modification such as the addition or removal of glycosylation sites or carbohydrate attachments, and the like.

In one embodiment, the effector moiety, particularly a single-chain effector moiety, of the immunoconjugate is GM-CSF. In a specific embodiment, the GM-CSF effector moiety can elicit proliferation and/or differentiation in a granulocyte, a monocyte or a dendritic cell. In one embodiment, the effector moiety, particularly a single-chain effector moiety, of the immunoconjugate is IFN-α. In a specific embodiment, the IFN-α effector moiety can elicit one or more of the cellular responses selected from the group consisting of: inhibiting viral replication in a virus-infected cell, and upregulating the expression of major histocompatibility complex I (MHC I). In another specific embodiment, the IFN-α effector moiety can inhibit proliferation in a tumor cell. In one embodiment the effector moiety, particularly a single-chain effector moiety, of the immunoconjugate is IFN-γ. In a specific embodiment, the IFN-γ effector moiety can elicit one or more of the cellular responses selected from the group of: increased macrophage activity, increased expression of MHC molecules, and increased NK cell activity. In one embodiment the effector moiety, particularly a single-chain effector moiety, of the immunoconjugate is IL-7. In a specific embodiment, the IL-7 effector moiety can elicit proliferation of T and/or B lymphocytes. In one embodiment, the effector moiety, particularly a single-chain effector moiety, of the immunoconjugate is IL-8. In a specific embodiment, the IL-8 effector moiety can elicit chemotaxis in neutrophils. In one embodiment, the effector moiety, particularly a single-chain effector moiety, of the immunoconjugate, is MIP-1α. In a specific embodiment, the MIP-1α effector moiety can elicit chemotaxis in monocytes and T lymphocyte cells. In one embodiment, the effector moiety, particularly a single-chain effector moiety, of the immunoconjugate is MIP-1β. In a specific embodiment, the MIP-1β effector moiety can elicit chemotaxis in monocytes and T lymphocyte cells. In one embodiment, the effector moiety, particularly a single-chain effector moiety, of the immunoconjugate is TGF-β. In a specific embodiment, the TGF-β effector moiety can elicit one or more of the cellular responses selected from the group consisting of: chemotaxis in monocytes, chemotaxis in macrophages, upregulation of IL-1 expression in activated macrophages, and upregulation of IgA expression in activated B cells.

In one embodiment, the immunoconjugate of the invention binds to an effector moiety receptor with a dissociation constant ($K_D$) that is at least about 1, 1.5, 2, 2.5, 3, 3.5, 4, 4.5, 5, 5.5, 6, 6.5, 7, 7.5, 8, 8.5, 9, 9.5 or 10 times greater than that for a control effector moiety. In another embodiment, the immunoconjugate binds to an effector moiety receptor with a $K_D$ that is at least 2, 3, 4, 5, 6, 7, 8, 9, or 10 times greater than that for a corresponding immunoconjugate molecule comprising two or more effector moieties. In another embodiment, the immunoconjugate binds to an effector moiety receptor with a dissociation constant $K_D$ that is about 10 times greater than that for a corresponding immunoconjugate molecule comprising two or more effector moieties.

Antigen Binding Moieties

The immunoconjugates of the invention comprise at least one antigen binding moiety. In particular embodiments, the immunoconjugates comprises two antigen binding moieties, i.e. a first and a second antigen binding moiety. In one embodiment the immunoconjugate comprises not more than two antigen binding moieties.

The antigen binding moiety of the immunoconjugate of the invention is generally a polypeptide molecule that binds to a specific antigenic determinant and is able to direct the entity to which it is attached (e.g. an effector moiety and an Fc domain) to a target site, for example to a specific type of tumor cell or tumor stroma that bears the antigenic determinant. The immunoconjugate can bind to antigenic determinants found, for example, on the surfaces of tumor cells, on the surfaces of virus-infected cells, on the surfaces of other diseased cells, free in blood serum, and/or in the extracellular matrix (ECM).

In certain embodiments the antigen binding moiety is directed to an antigen associated with a pathological condition, such as an antigen presented on a tumor cell or in a tumor cell environment, at a site of inflammation, or on a virus-infected cell.

Non-limiting examples of tumor antigens include MAGE, MART-1/Melan-A, gp100, Dipeptidyl peptidase IV (DPPIV), adenosine deaminase-binding protein (ADAbp), cyclophilin b, Colorectal associated antigen (CRC)-0017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21 ras, RCAS1, α-fetoprotein, E-cadherin, α-catenin, β-catenin and γ-catenin, p120ctn, gp100 Pmel117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, lmp-1, NA, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2.

Non-limiting examples of viral antigens include influenza virus hemagglutinin, Epstein-Barr virus LMP-1, hepatitis C virus E2 glycoprotein, HIV gp160, and HIV gp120.

Non-limiting examples of ECM antigens include syndecan, heparanase, integrins, osteopontin, link, cadherins, laminin, laminin type EGF, lectin, fibronectin, notch, tenascin, and matrixin.

The immunoconjugates of the invention can bind to the following specific non-limiting examples of cell surface antigens: FAP, Her2, EGFR, IGF-1R, CD22 (B-cell receptor), CD23 (low affinity IgE receptor), CD30 (cytokine receptor), CD33 (myeloid cell surface antigen), CD40 (tumor necrosis factor receptor), IL-6R (IL6 receptor), CD20, MCSP, and PDGFβR (β platelet-derived growth factor receptor). In particular embodiments the antigen is a human antigen.

In certain embodiments the antigen-binding moiety is directed to an antigen presented on a tumor cell or in a tumor cell environment. In other embodiments the antigen binding moiety is directed to an antigen presented at a site of inflammation. In a specific embodiment the antigen-binding moiety is directed to an antigen selected from the group of Fibroblast Activation Protein (FAP), the A1 domain of Tenascin-C (TNC A1), the A2 domain of Tenascin-C (TNC A2), the Extra Domain B of Fibronectin (EDB), Carcinoembryonic Antigen (CEA), and Melanoma-associated Chondroitin Sulfate Proteoglycan (MCSP).

In one embodiment, the immunoconjugate of the invention comprises two or more antigen binding moieties, wherein each of these antigen binding moieties specifically binds to the same antigenic determinant.

The antigen binding moiety can be any type of antibody or fragment thereof that retains specific binding to an antigenic determinant. Antibody fragments include, but are not limited to, $V_H$ fragments, $V_L$ fragments, Fab fragments, $F(ab)_2$ fragments, scFv fragments, $F_V$ fragments, minibodies, diabodies, triabodies, and tetrabodies (see e.g. Hudson and Souriau, Nature Med 9, 129-134 (2003)). In a particular embodiment the antigen binding moiety is a Fab molecule. In one embodiment said Fab molecule is human. In another embodiment said Fab molecule is humanized. In yet another embodiment said Fab molecule comprises human heavy and light chain constant regions.

In one embodiment the immunoconjugate comprises at least one, typically two or more antigen binding moieties that are specific for the Extra Domain B of fibronectin (EDB). In another embodiment the immunoconjugate comprises at least one, typically two or more antigen binding moieties that can compete with monoclonal antibody L19 for binding to an epitope of EDB. See, e.g., PCT publication WO 2007/128563 A1 (incorporated herein by reference in its entirety).

In yet another embodiment the immunoconjugate comprises a polypeptide sequence wherein a Fab heavy chain derived from the L19 monoclonal antibody shares a carboxy-terminal peptide bond with an Fc domain subunit comprising a knob modification, which in turn shares a carboxy-terminal peptide bond with an IL-2 polypeptide. In a more specific embodiment the immunoconjugate comprises the polypeptide sequence of SEQ ID NO: 215 or a variant thereof that retains functionality. In one embodiment the immunoconjugate comprises a polypeptide sequence wherein a Fab heavy chain derived from the L19 monoclonal antibody shares a carboxy-terminal peptide bond with an Fc domain subunit comprising a hole modification. In a more specific embodiment the immunoconjugate comprises the polypeptide sequence of SEQ ID NO: 213 or a variant thereof that retains functionality. In another embodiment the immunoconjugate comprises a Fab light chain derived from the L19 monoclonal antibody. In a more specific embodiment the immunoconjugate comprises the polypeptide sequence of SEQ ID NO: 217 or a variant thereof that retains functionality. In yet another embodiment the immunoconjugate comprises the polypeptide sequences of SEQ ID NO: 213, SEQ ID NO: 215 and SEQ ID NO: 217, or variants thereof that retain functionality. In another specific embodiment the polypeptides are covalently linked, e.g., by a disulfide bond. In some embodiments the Fc domain subunits each comprise the amino acid substitutions L234A, L235A, and P329G.

In a specific embodiment the immunoconjugate comprises a polypeptide sequence encoded by a polynucleotide sequence that is at least about 80%, 85%, 90%, 95%, 96%, 97%, 98%, or 99% identical to the sequence of SEQ ID NO: 216. In another specific embodiment the immunoconjugate comprises a polypeptide sequence encoded by the polynucleotide sequence of SEQ ID NO: 216. In another specific embodiment the immunoconjugate comprises a polypeptide sequence encoded by a polynucleotide sequence that is at least about 80%, 85%, 90%, 95%, 96%, 97%, 98%, or 99% identical to the sequence of SEQ ID NO: 214. In yet another specific embodiment the immunoconjugate comprises a polypeptide sequence encoded by the polynucleotide sequence of SEQ ID NO: 214. In another specific embodiment the immunoconjugate comprises a polypeptide sequence encoded by a polynucleotide sequence that is at least about 80%, 85%, 90%, 95%, 96%, 97%, 98%, or 99% identical to the sequence of SEQ ID NO: 218. In yet another specific embodiment the immunoconjugate comprises a polypeptide sequence encoded by the polynucleotide sequence of SEQ ID NO: 218.

In one embodiment the immunoconjugate of the invention comprises at least one, typically two or more antigen binding moieties that are specific for the A1 domain of Tenascin C (TNC-A1).

In another embodiment, the immunoconjugate comprises at least one, typically two or more antigen binding moieties that can compete with monoclonal antibody F16 for binding to an epitope of TNC-A1. See, e.g., PCT publication WO 2007/128563 A1 (incorporated herein by reference in its entirety). In one embodiment, the immunoconjugate comprises at least one, typically two or more antigen binding moieties that are specific for the A1 and/or the A4 domain of Tenascin C (TNC-A1 or TNC-A4 or TNC-A1/A4).

In a specific embodiment, the antigen binding moieties of the immunoconjugate comprise a heavy chain variable region sequence that is at least about 80%, 85%, 90%, 95%, 96%, 97%, 98%, 99% or 100% identical to either SEQ ID NO: 33 or SEQ ID NO: 35, or variants thereof that retain functionality. In another specific embodiment, the antigen binding moieties of the immunoconjugate comprise a light chain variable region sequence that is at least about 80%, 85%, 90%, 95%, 96%, 97%, 98%, 99% or 100% identical to either SEQ ID NO: 29 or SEQ ID NO: 31, or variants thereof that retain functionality. In a more specific embodiment, the antigen binding moieties of the immunoconjugate comprise a heavy chain variable region sequence that is at least about 80%, 85%, 90%, 95%, 96%, 97%, 98%, 99% or 100% identical to either SEQ ID NO: 33 or SEQ ID NO: 35 or variants thereof that retain functionality, and a light chain variable region sequence that is at least about 80%, 85%, 90%, 95%, 96%, 97%, 98%, 99% or 100% identical to either SEQ ID NO: 29 or SEQ ID NO: 31 or variants thereof that retain functionality. In another specific embodiment, the heavy chain variable region sequence of the antigen binding moieties of the immunoconjugate is encoded by a polynucleotide sequence that is at least about 80%, 85%, 90%, 95%, 96%, 97%, 98%, or 99% identical to either SEQ ID NO: 34 or SEQ ID NO: 36. In yet another specific embodiment, the heavy chain variable region sequence of the antigen binding moieties of the immunoconjugate is encoded by the polynucleotide sequence of either SEQ ID NO: 34 or SEQ ID NO: 36. In another specific embodiment, the light chain variable region sequence of the antigen binding moieties of the immunoconjugate is encoded by a polynucleotide sequence that is at least about 80%, 85%, 90%, 95%, 96%, 97%, 98%, or 99% identical to either SEQ ID NO: 30 or SEQ ID NO: 32. In yet another specific embodiment, the light chain variable region sequence of the antigen binding moieties of the immunoconjugate is encoded by the polynucleotide sequence of either SEQ ID NO: 30 or SEQ ID NO: 32.

In one embodiment, the immunoconjugate comprises a polypeptide sequence wherein a Fab heavy chain specific for the A1 domain of Tenascin C shares a carboxy-terminal peptide bond with an Fc domain subunit comprising a knob modification, which in turn shares a carboxy-terminal peptide bond with an IL-2 polypeptide. In another embodiment, the immunoconjugate comprises a polypeptide sequence wherein a Fab heavy chain specific for the A1 domain of Tenascin C shares a carboxy-terminal peptide bond with an Fc domain subunit comprising a hole modification. In a more specific embodiment the immunoconjugate comprises both of these polypeptide sequences. In another embodiment, the immunoconjugate further comprises a Fab light chain specific for the A1 domain of Tenascin C. In another specific embodiment, the polypeptides are covalently linked, e.g., by a disulfide bond. In some embodiments the Fc domain subunits each comprise the amino acid substitutions L234A, L235A, and P329G.

In a particular embodiment, the immunoconjugate comprises at least one, typically two or more antigen binding moieties that are specific for the A2 domain of Tenascin C (TNC-A2). In a specific embodiment, the antigen binding moieties of the immunoconjugate comprise a heavy chain variable region sequence that is at least about 80%, 85%, 90%, 95%, 96%, 97%, 98%, 99% or 100% identical to a sequence selected from the group of SEQ ID NO: 27, SEQ ID NO: 159, SEQ ID NO: 163, SEQ ID NO: 167, SEQ ID NO: 171, SEQ ID NO:175, SEQ ID NO: 179, SEQ ID NO: 183 and SEQ ID NO: 187, or variants thereof that retain functionality. In another specific embodiment, the antigen binding moieties of the immunoconjugate comprise a light chain variable region sequence that is at least about 80%, 85%, 90%, 95%, 96%, 97%, 98%, 99% or 100% identical to a sequence selected from the group of SEQ ID NO: 23, SEQ ID NO: 25; SEQ ID NO: 157, SEQ ID NO: 161, SEQ ID NO:165, SEQ ID NO: 169, SEQ ID NO: 173, SEQ ID NO: 177, SEQ ID NO: 181 and SEQ ID NO: 185, or variants thereof that retain functionality. In a more specific embodiment, the antigen binding moieties of the immunoconjugate comprise a heavy chain variable region sequence that is at least about 80%, 85%, 90%, 95%, 96%, 97%, 98%, 99% or 100% identical to a sequence selected from the group of SEQ ID NO: 27, SEQ ID NO: 159, SEQ ID NO: 163, SEQ ID NO: 167, SEQ ID NO: 171, SEQ ID NO:175, SEQ ID NO: 179, SEQ ID NO: 183 and SEQ ID NO: 187, or variants thereof that retain functionality, and a light chain variable region sequence that is at least about 80%, 85%, 90%, 95%, 96%, 97%, 98%, 99% or 100% identical to a sequence selected from the group of SEQ ID NO: 23, SEQ ID NO: 25; SEQ ID NO: 157, SEQ ID NO: 161, SEQ ID NO:165, SEQ ID NO: 169, SEQ ID NO: 173, SEQ ID NO: 177, SEQ ID NO: 181 and SEQ ID NO: 185, or variants thereof that retain functionality. In a particular embodiment, the antigen binding moieties of the immunoconjugate comprise the heavy chain variable region sequence of SEQ ID NO: 27 and the light chain variable region sequence of SEQ ID NO: 25.

In another specific embodiment, the heavy chain variable region sequence of the antigen binding moieties of the immunoconjugate is encoded by a polynucleotide sequence that is at least about 80%, 85%, 90%, 95%, 96%, 97%, 98%, or 99% identical to a sequence selected from the group of SEQ ID NO: 28, SEQ ID NO: 160, SEQ ID NO: 164, SEQ ID NO: 168, SEQ ID NO: 172, SEQ ID NO: 176, SEQ ID NO: 180, SEQ ID NO: 184 and SEQ ID NO: 188. In yet another specific embodiment, the heavy chain variable region sequence of the antigen binding moieties of the immunoconjugate is encoded by a polynucleotide sequence selected from the group of SEQ ID NO: 28, SEQ ID NO: 160, SEQ ID NO: 164, SEQ ID NO: 168, SEQ ID NO: 172, SEQ ID NO: 176, SEQ ID NO: 180, SEQ ID NO: 184 and SEQ ID NO: 188. In another specific embodiment, the light chain variable region sequence of the antigen binding moieties of the immunoconjugate is encoded by a polynucleotide sequence that is at least about 80%, 85%, 90%, 95%, 96%, 97%, 98%, or 99% identical to a sequence selected from the group of SEQ ID NO: 24, SEQ ID NO: 26, SEQ ID NO: 158, SEQ ID NO: 162, SEQ ID NO: 166, SEQ ID NO: 170, SEQ ID NO: 174, SEQ ID NO: 178, SEQ ID NO: 182 and SEQ ID NO: 186. In yet another specific embodiment, the light chain variable region sequence of the antigen binding moieties of the immunoconjugate is encoded by a polynucleotide sequence selected from the group of SEQ ID NO: 24, SEQ ID NO: 26, SEQ ID NO: 158, SEQ ID NO: 162, SEQ ID NO: 166, SEQ ID NO: 170, SEQ ID NO: 174, SEQ ID NO: 178, SEQ ID NO: 182 and SEQ ID NO: 186.

In yet another embodiment, the immunoconjugate comprises a polypeptide sequence wherein a Fab heavy chain specific for the A2 domain of Tenascin C shares a carboxy-terminal peptide bond with an Fc domain subunit comprising a hole modification, which in turn shares a carboxy-terminal peptide bond with an IL-10 polypeptide. In a more specific embodiment, the immunoconjugate comprises the polypeptide sequence of SEQ ID NO: 235 or SEQ ID NO: 237, or a variant thereof that retains functionality. In one embodiment the immunoconjugate comprises a polypeptide sequence wherein a Fab heavy chain specific for the A2 domain of Tenascin C shares a carboxy-terminal peptide bond with an Fc domain subunit comprising a knob modification. In a more specific embodiment, the immunoconjugate comprises the polypeptide sequence of SEQ ID NO: 233 or a variant thereof that retains functionality. In another embodiment, the immunoconjugate comprises a Fab light chain specific for the A2 domain of Tenascin C. In a more specific embodiment, the immunoconjugate comprises the polypeptide sequence of SEQ ID NO: 239 or a variant thereof that retains functionality. In another embodiment, the immunoconjugate comprises the polypeptide sequences of SEQ ID NO: 233, SEQ ID NO: 235 and SEQ ID NO: 239 or variants thereof that retain functionality. In yet another embodiment, the immunoconjugate comprises the polypeptide sequences of SEQ ID NO: 233, SEQ ID NO: 237 and SEQ ID NO: 239 or variants thereof that retain functionality. In another specific embodiment, the polypeptides are covalently linked, e.g., by a disulfide bond. In some embodiments the Fc domain subunits each comprise the amino acid substitutions L234A, L235A, and P329G.

In a specific embodiment, the immunoconjugate comprises a polypeptide sequence encoded by a polynucleotide sequence that is at least about 80%, 85%, 90%, 95%, 96%, 97%, 98%, or 99% identical to the sequence of SEQ ID NO: 236 or SEQ ID NO: 238. In another specific embodiment, the immunoconjugate comprises a polypeptide sequence encoded by the polynucleotide sequence of SEQ ID NO: 236 or SEQ ID NO: 238. In another specific embodiment, the immunoconjugate comprises a polypeptide sequence encoded by a polynucleotide sequence that is at least about 80%, 85%, 90%, 95%, 96%, 97%, 98%, or 99% identical to the sequence of SEQ ID NO: 234. In yet another specific embodiment, the immunoconjugate comprises a polypeptide sequence encoded by the polynucleotide sequence of SEQ ID NO: 234. In another specific embodiment, the immunoconjugate comprises a polypeptide sequence encoded by a polynucleotide sequence that is at least about 80%, 85%, 90%, 95%, 96%, 97%, 98%, or 99% identical to the sequence of SEQ ID NO: 240. In yet another specific embodiment, the immunoconjugate comprises a polypeptide sequence encoded by the polynucleotide sequence of SEQ ID NO: 240.

In yet another embodiment, the immunoconjugate comprises a polypeptide sequence wherein a Fab heavy chain specific for the A2 domain of Tenascin C shares a carboxy-terminal peptide bond with an Fc domain subunit comprising a knob modification, which in turn shares a carboxy-terminal peptide bond with an IL-2 polypeptide. In a more specific embodiment, the immunoconjugate comprises the polypeptide sequence of SEQ ID NO: 285, or a variant thereof that retains functionality. In one embodiment the immunoconjugate comprises a polypeptide sequence wherein a Fab heavy chain specific for the A2 domain of Tenascin C shares a carboxy-terminal peptide bond with an Fc domain subunit comprising a hole modification. In a more specific embodiment, the immunoconjugate comprises the polypeptide sequence of SEQ ID NO: 287, or a variant thereof that retains functionality. In another embodiment, the immunoconjugate comprises a Fab light chain specific for the A2 domain of Tenascin C. In a more specific embodiment, the immunoconjugate comprises the polypeptide sequence of SEQ ID NO: 239 or a variant thereof that retains functionality. In another embodiment, the immunoconjugate comprises the polypeptide sequences of SEQ ID NO: 285, SEQ ID NO: 287 and SEQ ID NO: 239 or variants thereof that retain functionality. In another specific embodiment, the polypeptides are covalently linked, e.g., by a disulfide bond. In some embodiments the Fc domain subunits each comprise the amino acid substitutions L234A, L235A, and P329G.

In a specific embodiment, the immunoconjugate comprises a polypeptide sequence encoded by a polynucleotide sequence that is at least about 80%, 85%, 90%, 95%, 96%, 97%, 98%, or 99% identical to the sequence of SEQ ID NO: 286. In another specific embodiment, the immunoconjugate comprises a polypeptide sequence encoded by the polynucleotide sequence of SEQ ID NO: 286. In another specific embodiment, the immunoconjugate comprises a polypeptide sequence encoded by a polynucleotide sequence that is at least about 80%, 85%, 90%, 95%, 96%, 97%, 98%, or 99% identical to the sequence of SEQ ID NO: 288. In yet another specific embodiment, the immunoconjugate comprises a polypeptide sequence encoded by the polynucleotide sequence of SEQ ID NO: 288. In another specific embodiment, the immunoconjugate comprises a polypeptide sequence encoded by a polynucleotide sequence that is at least about 80%, 85%, 90%, 95%, 96%, 97%, 98%, or 99% identical to the sequence of SEQ ID NO: 240. In yet another specific embodiment, the immunoconjugate comprises a polypeptide sequence encoded by the polynucleotide sequence of SEQ ID NO: 240.

In a particular embodiment, the immunoconjugate comprises at least one, typically two or more antigen binding moieties that are specific for the Fibroblast Activated Protein (FAP). In a specific embodiment, the antigen binding moieties of the immunoconjugate comprise a heavy chain variable region sequence that is at least about 80%, 85%, 90%, 95%, 96%, 97%, 98%, 99% or 100% identical to a sequence selected from the group consisting of SEQ ID NO: 41, SEQ ID NO: 45, SEQ ID NO: 47, SEQ ID NO: 51, SEQ ID NO: 55, SEQ ID NO: 59, SEQ ID NO: 63, SEQ ID NO: 67, SEQ ID NO: 71, SEQ ID NO: 75, SEQ ID NO: 79, SEQ ID NO: 83, SEQ ID NO: 87, SEQ ID NO: 91, SEQ ID NO: 95, SEQ ID NO: 99, SEQ ID NO: 103, SEQ ID NO: 107, SEQ ID NO: 111, SEQ ID NO: 115, SEQ ID NO: 119, SEQ ID NO: 123, SEQ ID NO: 127, SEQ ID NO: 131, SEQ ID NO: 135, SEQ ID NO: 139, SEQ ID NO: 143, SEQ ID NO: 147, SEQ ID NO: 151 and SEQ ID NO: 155, or variants thereof that retain functionality. In another specific embodiment, the antigen binding moieties of the immunoconjugate comprise a light chain variable region sequence that is at least about 80%, 85%, 90%, 95%, 96%, 97%, 98%, 99% or 100% identical to a sequence selected from the group consisting of: SEQ ID NO: 37, SEQ ID NO: 39, SEQ ID NO: 43, SEQ ID NO: 49, SEQ ID NO: 53, SEQ ID NO: 57, SEQ ID NO: 61, SEQ ID NO: 65, SEQ ID NO: 69, SEQ ID NO: 73, SEQ ID NO: 77, SEQ ID NO: 81, SEQ ID NO: 85, SEQ ID NO: 89, SEQ ID NO: 93, SEQ ID NO: 97, SEQ ID NO: 101, SEQ ID NO: 105, SEQ ID NO: 109, SEQ ID NO: 113, SEQ ID NO: 117, SEQ ID NO: 121, SEQ ID NO: 125, SEQ ID NO: 129, SEQ ID NO: 133, SEQ ID NO: 137, SEQ ID NO: 141, SEQ ID NO: 145, SEQ ID NO: 149 and SEQ ID NO: 153, or variants thereof that retain functionality. In a more specific embodiment, the antigen binding moieties of the immunoconjugate comprise a heavy chain variable region sequence that is at least about 80%, 85%, 90%, 95%, 96%, 97%, 98%, 99% or 100% identical to a sequence selected from the group consisting of SEQ ID NO: 41, SEQ ID NO: 45, SEQ ID NO: 47, SEQ ID NO: 51, SEQ ID NO: 55, SEQ ID NO: 59, SEQ ID NO: 63, SEQ ID NO: 67, SEQ ID NO: 71, SEQ ID NO: 75, SEQ ID NO: 79, SEQ ID NO: 83, SEQ ID NO: 87, SEQ ID NO: 91, SEQ ID NO: 95, SEQ ID NO: 99, SEQ ID NO: 103, SEQ ID NO: 107, SEQ ID NO: 111, SEQ ID NO: 115, SEQ ID NO: 119, SEQ ID NO: 123, SEQ ID NO: 127, SEQ ID NO: 131, SEQ ID NO: 135, SEQ ID NO: 139, SEQ ID NO: 143, SEQ ID NO: 147, SEQ ID NO: 151 and SEQ ID NO: 155, or variants thereof that retain functionality, and a light chain variable region sequence that is at least about 80%, 85%, 90%, 95%, 96%, 97%, 98%, 99% or 100% identical to a sequence selected from the group consisting of: SEQ ID NO: 37, SEQ ID NO: 39, SEQ ID NO: 43, SEQ ID NO: 49, SEQ ID NO: 53, SEQ ID NO: 57, SEQ ID NO: 61, SEQ ID NO: 65, SEQ ID NO: 69, SEQ ID NO: 73, SEQ ID NO: 77, SEQ ID NO: 81, SEQ ID NO: 85, SEQ ID NO: 89, SEQ ID NO: 93, SEQ ID NO: 97, SEQ ID NO: 101, SEQ ID NO: 105, SEQ ID NO: 109, SEQ ID NO: 113, SEQ ID NO: 117, SEQ ID NO: 121, SEQ ID NO: 125, SEQ ID NO: 129, SEQ ID NO: 133, SEQ ID NO: 137, SEQ ID NO: 141, SEQ ID NO: 145, SEQ ID NO: 149 and SEQ ID NO: 153, or variants thereof that retain functionality. In a particular embodiment, the antigen binding moieties of the immunoconjugate comprise the heavy chain variable region sequence of SEQ ID NO: 111 and the light chain variable region sequence of SEQ ID NO: 109. In a further particular embodiment, the antigen binding moieties of the immunoconjugate comprise the heavy chain variable region sequence of SEQ ID NO: 143 and the light chain variable region sequence of SEQ ID NO: 141. In yet another particular embodiment, the antigen binding moieties of the immunoconjugate comprise the heavy chain variable region sequence of SEQ ID NO: 51 and the light chain variable region sequence of SEQ ID NO: 49.

In another specific embodiment, the heavy chain variable region sequence of the antigen binding moieties of the immunoconjugate is encoded by a polynucleotide sequence that is at least about 80%, 85%, 90%, 95%, 96%, 97%, 98%, or 99% identical to a sequence selected from the group consisting of: SEQ ID NO: 42, SEQ ID NO: 46, SEQ ID NO: 48, SEQ ID NO: 52, SEQ ID NO: 56, SEQ ID NO: 60, SEQ ID NO: 64, SEQ ID NO: 68, SEQ ID NO: 72, SEQ ID NO: 76, SEQ ID NO: 80, SEQ ID NO: 84, SEQ ID NO: 88, SEQ ID NO: 92, SEQ ID NO: 96, SEQ ID NO: 100, SEQ ID NO: 104, SEQ ID NO: 108, SEQ ID NO: 112, SEQ ID NO: 116, SEQ ID NO: 120, SEQ ID NO: 124, SEQ ID NO: 128, SEQ ID NO: 132, SEQ ID NO: 136, SEQ ID NO: 140, SEQ ID NO: 144, SEQ ID NO: 148, SEQ ID NO: 152, and SEQ ID NO: 156. In yet another specific embodiment, the heavy chain variable region sequence of the antigen binding moieties of the immunoconjugate is encoded by a polynucleotide sequence selected from the group consisting of: SEQ ID NO: 42, SEQ ID NO: 46, SEQ ID NO: 48, SEQ ID NO: 52, SEQ ID NO: 56, SEQ ID NO: 60, SEQ ID NO: 64, SEQ ID NO: 68, SEQ ID NO: 72, SEQ ID NO: 76, SEQ ID NO: 80, SEQ ID NO: 84, SEQ ID NO: 88, SEQ ID NO: 92, SEQ ID NO: 96, SEQ ID NO: 100, SEQ ID NO: 104, SEQ ID NO: 108, SEQ ID NO: 112, SEQ ID NO: 116, SEQ ID NO: 120, SEQ ID NO: 124, SEQ ID NO: 128, SEQ ID NO: 132, SEQ ID NO: 136, SEQ ID NO: 140, SEQ ID NO: 144, SEQ ID NO: 148, SEQ ID NO: 152, and SEQ ID NO: 156. In another specific embodiment, the light chain variable region sequence of the antigen binding moieties of the immunoconjugate is encoded by a polynucleotide sequence that is at least about 80%, 85%, 90%, 95%, 96%, 97%, 98%, or 99% identical to sequence selected from the group consisting of: SEQ ID NO: 38, SEQ ID NO: 40, SEQ ID NO: 44, SEQ ID NO: 50, SEQ ID NO: 54, SEQ ID NO: 58, SEQ ID NO: 62, SEQ ID NO: 66, SEQ ID NO: 70, SEQ ID NO: 74, SEQ ID NO: 78, SEQ ID NO: 82, SEQ ID NO: 86, SEQ ID NO: 90, SEQ ID NO: 94, SEQ ID NO: 98, SEQ ID NO: 102, SEQ ID NO: 106, SEQ ID NO: 110, SEQ ID NO: 114, SEQ ID NO: 118, SEQ ID NO: 122, SEQ ID NO: 126, SEQ ID NO: 130, SEQ ID NO: 134, SEQ ID NO: 138, SEQ ID NO: 142, SEQ ID NO: 146, SEQ ID NO: 150, and SEQ ID NO: 154. In yet another specific embodiment, the light chain variable region sequence of the antigen binding moieties of the immunoconjugate is encoded by a polynucleotide sequence selected from the group consisting of: SEQ ID NO: 38, SEQ ID NO: 40, SEQ ID NO: 44, SEQ ID NO: 50, SEQ ID NO: 54, SEQ ID NO: 58, SEQ ID NO: 62, SEQ ID NO: 66, SEQ ID NO: 70, SEQ ID NO: 74, SEQ ID NO: 78, SEQ ID NO: 82, SEQ ID NO: 86, SEQ ID NO: 90, SEQ ID NO: 94, SEQ ID NO: 98, SEQ ID NO: 102, SEQ ID NO: 106, SEQ ID NO: 110, SEQ ID NO: 114, SEQ ID NO: 118, SEQ ID NO: 122, SEQ ID NO: 126, SEQ ID NO: 130, SEQ ID NO: 134, SEQ ID NO: 138, SEQ ID NO: 142, SEQ ID NO: 146, SEQ ID NO: 150, and SEQ ID NO: 154.

In one embodiment, the immunoconjugate comprises a polypeptide sequence wherein a Fab heavy chain specific for FAP shares a carboxy-terminal peptide bond with an Fc domain subunit comprising a knob modification, which in turn shares a carboxy-terminal peptide bond with an IL-2 polypeptide. In a more specific embodiment, the immunoconjugate comprises a polypeptide sequence selected from the group of SEQ ID NO: 195, SEQ ID NO: 197, SEQ ID NO: 203, SEQ ID NO: 209, SEQ ID NO: 269, SEQ ID NO: 271 and SEQ ID NO: 273, or variants thereof that retain functionality. In one embodiment, the immunoconjugate comprises a polypeptide sequence wherein a Fab heavy chain specific for FAP shares a carboxy-terminal peptide bond with an Fc domain subunit comprising a knob modification, which in turn shares a carboxy-terminal peptide bond with an IL-15 polypeptide. In a more specific embodiment, the immunoconjugate comprises the polypeptide sequence of SEQ ID NO: 199, or a variant thereof that retains functionality. In one embodiment the immunoconjugate comprises a polypeptide sequence wherein a Fab heavy chain specific for FAP shares a carboxy-terminal peptide bond with an Fc domain subunit comprising a hole modification. In a more specific embodiment, the immunoconjugate comprises a polypeptide sequence selected from the group of SEQ ID NO: 193, SEQ ID NO: 201 and SEQ ID NO: 207, or variants thereof that retain functionality. In another embodiment, the immunoconjugate comprises a Fab light chain specific for FAP. In a more specific embodiment, the immunoconjugate comprises the polypeptide sequence of SEQ ID NO: 205 or SEQ ID NO: 211, or a variant thereof that retains functionality. In another embodiment, the immunoconjugate comprises the polypeptide sequence of SEQ ID NO: 205, the polypeptide sequence of SEQ ID NO: 193, and a polypeptide sequence selected from the group of SEQ ID NO: 195, SEQ ID NO: 197, SEQ ID NO: 199 and SEQ ID NO: 269, or variants thereof that retain functionality. In yet another embodiment, the immunoconjugate comprises the polypeptide sequences of SEQ ID NO: 201, SEQ ID NO: 203 and SEQ ID NO: 205, or variants thereof that retain functionality. In yet another embodiment, the immunoconjugate comprises the polypeptide sequences of SEQ ID NO: 207, SEQ ID NO: 209 and SEQ ID NO: 211, or variants thereof that retain functionality. In yet another embodiment, the immunoconjugate comprises the polypeptide sequences of SEQ ID NO: 205, SEQ ID NO: 193 and SEQ ID NO: 269, or variants thereof that retain functionality. In yet another embodiment, the immunoconjugate comprises the polypeptide sequences of SEQ ID NO: 211, SEQ ID NO: 207 and SEQ ID NO: 271, or variants thereof that retain functionality. In yet another embodiment, the immunoconjugate comprises the polypeptide sequences of SEQ ID NO: 211, SEQ ID NO: 207 and SEQ ID NO: 273, or variants thereof that retain functionality. In another specific embodiment, the polypeptides are covalently linked, e.g., by a disulfide bond. In some embodiments the Fc domain subunits each comprise the amino acid substitutions L234A, L235A, and P329G.

In yet another embodiment, the immunoconjugate comprises a polypeptide sequence wherein a Fab heavy chain specific for FAP shares a carboxy-terminal peptide bond with an Fc domain subunit comprising a hole modification, which in turn shares a carboxy-terminal peptide bond with an IL-10 polypeptide. In a more specific embodiment, the immunoconjugate comprises the polypeptide sequence of SEQ ID NO: 243 or SEQ ID NO: 245, or a variant thereof that retains functionality. In one embodiment the immunoconjugate comprises a polypeptide sequence wherein a Fab heavy chain specific for FAP shares a carboxy-terminal peptide bond with an Fc domain subunit comprising a knob modification. In a more specific embodiment, the immunoconjugate comprises the polypeptide sequence of SEQ ID NO: 241 or a variant thereof that retains functionality. In another embodiment, the immunoconjugate comprises a Fab light chain specific for FAP. In a more specific embodiment, the immunoconjugate comprises the polypeptide sequence of SEQ ID NO: 205 or a variant thereof that retains functionality. In another embodiment, the immunoconjugate comprises the polypeptide sequences of SEQ ID NO: 205, SEQ ID NO: 241 and SEQ ID NO: 243, or variants thereof that retain functionality. In yet another embodiment, the immunoconjugate comprises the polypeptide sequences of SEQ ID NO: 205, SEQ ID NO: 241 and SEQ ID NO: 245, or variants thereof that retain functionality. In another specific embodiment, the polypeptides are covalently linked, e.g., by a disulfide bond. In some embodiments the Fc domain subunits each comprise the amino acid substitutions L234A, L235A, and P329G.

In a specific embodiment, the immunoconjugate comprises a polypeptide sequence encoded by a polynucleotide sequence that is at least about 80%, 85%, 90%, 95%, 96%, 97%, 98%, or 99% identical to a sequence selected from the group of SEQ ID NO: 196, SEQ ID NO: 198, SEQ ID NO: 200, SEQ ID NO: 204, SEQ ID NO: 210, SEQ ID NO: 244, SEQ ID NO: 246, SEQ ID NO: 270, SEQ ID NO: 272 and SEQ ID NO: 274. In another specific embodiment, the immunoconjugate comprises a polypeptide sequence encoded by a polynucleotide sequence selected from the group of SEQ ID NO: 196, SEQ ID NO: 198, SEQ ID NO: 200, SEQ ID NO: 204, SEQ ID NO: 210, SEQ ID NO: 244, SEQ ID NO: 246, SEQ ID NO: 270, SEQ ID NO: 272 and SEQ ID NO: 274. In another specific embodiment, the immunoconjugate comprises a polypeptide sequence encoded by a polynucleotide sequence that is at least about 80%, 85%, 90%, 95%, 96%, 97%, 98%, or 99% identical to a sequence selected from the group of SEQ ID NO: 194, SEQ ID NO: 202, SEQ ID NO: 208 and SEQ ID NO: 242. In yet another specific embodiment, the immunoconjugate comprises a polypeptide sequence encoded by a polynucleotide sequence selected from the group of SEQ ID NO: 194, SEQ ID NO: 202, SEQ ID NO: 208 and SEQ ID NO: 242. In another specific embodiment, the immunoconjugate comprises a polypeptide sequence encoded by a polynucleotide sequence that is at least about 80%, 85%, 90%, 95%, 96%, 97%, 98%, or 99% identical to the sequence of SEQ ID NO: 206 or SEQ ID NO: 212. In yet another specific embodiment, the immunoconjugate comprises a polypeptide sequence encoded by the polynucleotide sequence of SEQ ID NO: 206 or SEQ ID NO: 212.

In one embodiment, the immunoconjugate comprises at least one, typically two or more antigen binding moieties that are specific for the Carcinoembryonic Antigen (CEA). In a specific embodiment, the antigen binding moieties of the immunoconjugate comprise a heavy chain variable region sequence that is at least about 80%, 85%, 90%, 95%, 96%, 97%, 98%, 99% or 100% identical to the sequence of SEQ ID NO: 191 or SEQ ID NO: 295, or a variant thereof that retains functionality. In another specific embodiment, the antigen binding moieties of the immunoconjugate comprise a light chain variable region sequence that is at least about 80%, 85%, 90%, 95%, 96%, 97%, 98%, 99% or 100% identical to the sequence of SEQ ID NO: 189 or SEQ ID NO: 293, or a variant thereof that retains functionality. In a more specific embodiment, the antigen binding moieties of the immunoconjugate comprise a heavy chain variable region sequence that is at least about 80%, 85%, 90%, 95%, 96%, 97%, 98%, 99% or 100% identical to the sequence of SEQ ID NO: 191, or a variant thereof that retains functionality, and a light chain variable region sequence that is at least about 80%, 85%, 90%, 95%, 96%, 97%, 98%, 99% or 100% identical to the sequence of SEQ ID NO: 189, or a variant thereof that retains functionality. In another specific embodiment, the antigen binding moieties of the immunoconjugate comprise a heavy chain variable region sequence that is at least about 80%, 85%, 90%, 95%, 96%, 97%, 98%, 99% or 100% identical to the sequence of SEQ ID NO: 295, or a variant thereof that retains functionality, and a light chain variable region sequence that is at least about 80%, 85%, 90%, 95%, 96%, 97%, 98%, 99% or 100% identical to the sequence of SEQ ID NO: 293, or a variant thereof that retains functionality.

In another specific embodiment, the heavy chain variable region sequence of the antigen binding moieties of the immunoconjugate is encoded by a polynucleotide sequence that is at least about 80%, 85%, 90%, 95%, 96%, 97%, 98%, or 99% identical to the sequence of SEQ ID NO: 192 or SEQ ID NO: 296. In yet another specific embodiment, the heavy chain variable region sequence of the antigen binding moieties of the immunoconjugate is encoded by the polynucleotide sequence of SEQ ID NO: 192 or SEQ ID NO: 296. In another specific embodiment, the light chain variable region sequence of the antigen binding moieties of the immunoconjugate is encoded by a polynucleotide sequence that is at least about 80%, 85%, 90%, 95%, 96%, 97%, 98%, or 99% identical to the sequence of SEQ ID NO: 190 or SEQ ID NO: 294. In yet another specific embodiment, the light chain variable region sequence of the antigen binding moieties of the immunoconjugate is encoded by the polynucleotide sequence of SEQ ID NO: 190 or SEQ ID NO: 294.

In one embodiment, the immunoconjugate comprises a polypeptide sequence wherein a Fab heavy chain specific for CEA shares a carboxy-terminal peptide bond with an Fc domain subunit comprising a knob modification, which in turn shares a carboxy-terminal peptide bond with an IL-2 polypeptide. In a more specific embodiment, the immunoconjugate comprises a polypeptide sequence selected from the group consisting of SEQ ID NO: 229, SEQ ID NO: 275, SEQ ID NO: 277 and SEQ ID NO: 279, or a variant thereof that retains functionality. In one embodiment the immunoconjugate comprises a polypeptide sequence wherein a Fab heavy chain specific for CEA shares a carboxy-terminal peptide bond with an Fc domain subunit comprising a hole modification. In a more specific embodiment, the immunoconjugate comprises the polypeptide sequence of SEQ ID NO: 227 or SEQ ID NO: 281, or a variant thereof that retains functionality. In another embodiment, the immunoconjugate comprises a Fab light chain specific for CEA. In a more specific embodiment, the immunoconjugate comprises the polypeptide sequence of SEQ ID NO: 231 or SEQ ID NO: 283, or a variant thereof that retains functionality. In another embodiment, the immunoconjugate comprises the polypeptide sequences of SEQ ID NO: 227, SEQ ID NO: 229 and SEQ ID NO: 231, or variants thereof that retain functionality. In another embodiment, the immunoconjugate comprises the polypeptide sequences of SEQ ID NO: 275, SEQ ID NO: 281 and SEQ ID NO: 283, or variants thereof that retain functionality. In another embodiment, the immunoconjugate comprises the polypeptide sequences of SEQ ID NO: 277, SEQ ID NO: 281 and SEQ ID NO: 283, or variants thereof that retain functionality. In another embodiment, the immunoconjugate comprises the polypeptide sequences of SEQ ID NO: 279, SEQ ID NO: 281 and SEQ ID NO: 283, or variants thereof that retain functionality. In another specific embodiment, the polypeptides are covalently linked, e.g., by a disulfide bond. In some embodiments the Fc domain polypeptide chains comprise the amino acid substitutions L234A, L235A, and P329G.

In a specific embodiment, the immunoconjugate comprises a polypeptide sequence encoded by a polynucleotide sequence that is at least about 80%, 85%, 90%, 95%, 96%, 97%, 98%, or 99% identical to a sequence selected from the group consisting of SEQ ID NO: 230, SEQ ID NO: 276, SEQ ID NO: 278 and SEQ ID NO: 280. In another specific embodiment, the immunoconjugate comprises a polypeptide sequence encoded by the polynucleotide sequence selected from the group consisting of SEQ ID NO: 230, SEQ ID NO: 276, SEQ ID NO: 278 and SEQ ID NO: 280. In another specific embodiment, the immunoconjugate comprises a polypeptide sequence encoded by a polynucleotide sequence that is at least about 80%, 85%, 90%, 95%, 96%, 97%, 98%, or 99% identical to the sequence of SEQ ID NO: 228 or SEQ ID NO: 282. In yet another specific embodiment, the immunoconjugate comprises a polypeptide sequence encoded by the polynucleotide sequence of SEQ ID NO: 228 or SEQ ID NO: 282. In another specific embodiment, the immunoconjugate comprises a polypeptide sequence encoded by a polynucleotide sequence that is at least about 80%, 85%, 90%, 95%, 96%, 97%, 98%, or 99% identical to the sequence of SEQ ID NO: 232 or SEQ ID NO: 284. In yet another specific embodiment, the immunoconjugate comprises a polypeptide sequence encoded by the polynucleotide sequence of SEQ ID NO: 232 or SEQ ID NO: 284.

In some embodiments the immunoconjugate comprises a polypeptide sequence wherein an effector moiety polypeptide shares a carboxy-terminal peptide bond with an Fc domain subunit comprising a knob modification. In a more specific embodiment, the immunoconjugate comprises a polypeptide sequence selected from the group of SEQ ID NO: 247, SEQ ID NO: 249 and SEQ ID NO: 251, or a variant thereof that retains functionality. In one such embodiment the immunoconjugate further comprises a polypeptide sequence wherein a Fab heavy chain specific for FAP shares a carboxy-terminal peptide bond with an Fc domain subunit comprising a hole modification. In a more specific embodiment, the immunoconjugate further comprises a polypeptide sequence selected from the group of SEQ ID NO: 193, SEQ ID NO: 201 and SEQ ID NO: 207, or a variant thereof that retains functionality. In another such embodiment the immunoconjugate further comprises a polypeptide sequence wherein a Fab heavy chain specific for EDB, TNC A1, TNC A2 or CEA shares a carboxy-terminal peptide bond with an Fc domain subunit comprising a hole modification. In some embodiments the Fc domain subunits each comprise the amino acid substitutions L234A, L235A, and P329G. According to any of the above embodiments the immunoconjugate may further comprise a Fab light chain specific for the corresponding antigen.

Immunoconjugates of the invention include those that have sequences that are at least about 80%, 85%, 90%, 95%, 96%, 97%, 98%, 99%, or 100% identical to the sequences set forth in SEQ ID NOs 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 293, 295, 193, 195, 197, 199, 201, 203, 205, 207, 209, 211, 213, 215, 217, 227, 229, 231, 233, 235, 237, 239, 241, 243, 245, 247, 249, 251, 269, 271, 273, 275, 277, 279, 281, 283, 285 and 287, including functional fragments or variants thereof. The invention also encompasses immunoconjugates comprising these sequences with conservative amino acid substitutions.

Polynucleotides

The invention further provides isolated polynucleotides encoding an immunoconjugate as described herein or a fragment thereof.

Polynucleotides of the invention include those that are at least about 80%, 85%, 90%, 95%, 96%, 97%, 98%, 99%, or 100% identical to the sequences set forth in SEQ ID NOs 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 294, 296, 194, 196, 198, 200, 202, 204, 206, 208, 210, 212, 214, 216, 218, 228, 230, 232, 234, 236, 238, 240, 242, 244, 246, 248, 250, 252, 270, 272, 274, 276, 278, 280, 282, 284, 286 and 288, including functional fragments or variants thereof.

The polynucleotides encoding immunoconjugates of the invention may be expressed as a single polynucleotide that encodes the entire immunoconjugate or as multiple (e.g., two or more) polynucleotides that are co-expressed. Polypeptides encoded by polynucleotides that are co-expressed may associate through, e.g., disulfide bonds or other means to form a functional immunoconjugate. For example, the light chain portion of an antigen binding moiety may be encoded by a separate polynucleotide from the portion of the immunoconjugate comprising the heavy chain portion of the antigen binding moiety, an Fc domain subunit and optionally the effector moiety. When co-expressed, the heavy chain polypeptides will associate with the light chain polypeptides to form the antigen binding moiety. In another example, the portion of the immunoconjugate comprising the heavy chain portion of a first antigen binding moiety, one of the two Fc domain subunits and the effector moiety could be encoded by a separate polynucleotide from the portion of the immunoconjugate comprising the heavy chain portion of a second antigen binding moiety and the other of the two Fc domain subunits. When co-expressed, the Fc domain subunits will associate to form the Fc domain.

In one embodiment, an isolated polynucleotide of the invention encodes a fragment of an immunoconjugate comprising a first antigen binding moiety, an Fc domain consisting of two subunits, and a single effector moiety, wherein the antigen binding moiety is an antigen binding domain comprising a heavy chain variable region and a light chain variable region, particularly a Fab molecule. In one embodiment, an isolated polynucleotide of the invention encodes the heavy chain of the first antigen binding moiety, a subunit of the Fc domain, and the effector moiety. In another embodiment, an isolated polynucleotide of the invention encodes the heavy chain of the first antigen binding moiety and a subunit of the Fc domain. In yet another embodiment, an isolated polynucleotide of the invention encodes a subunit of the Fc domain and the effector moiety. In a more specific embodiment the isolated polynucleotide encodes a polypeptide wherein a Fab heavy chain shares a carboxy-terminal peptide bond with an Fc domain subunit.

In another specific embodiment the isolated polynucleotide encodes a polypeptide wherein an Fc domain subunit shares a carboxy-terminal peptide bond with an effector moiety polypeptide. In yet another specific embodiment, the isolated polynucleotide encodes a polypeptide wherein a Fab heavy chain shares a carboxy-terminal peptide bond with an Fc domain subunit, which in turn shares a carboxy-terminal peptide bond with an effector moiety polypeptide. In yet another specific embodiment the isolated polynucleotide encodes a polypeptide wherein an effector moiety polypeptide shares a carboxy-terminal peptide bond with an Fc domain subunit.

In another embodiment, the present invention is directed to an isolated polynucleotide encoding an immunoconjugate or fragment thereof, wherein the polynucleotide comprises a sequence that encodes a variable region sequence as shown in SEQ ID NO 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 293 or 295. In another embodiment, the present invention is directed to an isolated polynucleotide encoding an immunoconjugate or fragment thereof, wherein the polynucleotide comprises a sequence that encodes a polypeptide sequence as shown in SEQ ID NO 193, 195, 197, 199, 201, 203, 205, 207, 209, 211, 213, 215, 217, 227, 229, 231, 233, 235, 237, 239, 241, 243, 245, 247, 249, 251, 269, 271, 273, 275, 277, 279, 281, 283, 285 or 287. In another embodiment, the invention is further directed to an isolated polynucleotide encoding an immunoconjugate or fragment thereof, wherein the polynucleotide comprises a sequence that is at least about 80%, 85%, 90%, 95%, 96%, 97%, 98%, or 99% identical to a nucleotide sequence shown SEQ ID NO 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 294, 296, 194, 196, 198, 200, 202, 204, 206, 208, 210, 212, 214, 216, 218, 228, 230, 232, 234, 236, 238, 240, 242, 244, 246, 248, 250, 252, 270, 272, 274, 276, 278, 280, 282, 284, 286 or 288. In another embodiment, the invention is directed to an isolated polynucleotide encoding an immunoconjugate or fragment thereof, wherein the polynucleotide comprises a nucleic acid sequence shown in SEQ ID NO 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 294, 296, 194, 196, 198, 200, 202, 204, 206, 208, 210, 212, 214, 216, 218, 228, 230, 232, 234, 236, 238, 240, 242, 244, 246, 248, 250, 252, 270, 272, 274, 276, 278, 280, 282, 284, 286 or 288. In another embodiment, the invention is directed to an isolated polynucleotide encoding an immunoconjugate or fragment thereof, wherein the polynucleotide comprises a sequence that encodes a variable region sequence that is at least about 80%, 85%, 90%, 95%, 96%, 97%, 98%, or 99% identical to an amino acid sequence of SEQ ID NO 23, 25, 27, 29, 31, 33, 35, 37, 39, 41, 43, 45, 47, 49, 51,53, 55, 57, 59, 61,63, 65, 67, 69, 71,73, 75, 77, 79, 81,83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 293 or 295. In another embodiment, the invention is directed to an isolated polynucleotide encoding an immunoconjugate or fragment thereof, wherein the polynucleotide comprises a sequence that encodes a polypeptide sequence that is at least 80%, 85%, 90%, 95%, 96%, 97%, 98%, or 99% identical to an amino acid sequence of SEQ ID NO 193, 195, 197, 199, 201, 203, 205, 207, 209, 211, 213, 215, 217, 227, 229, 231, 233, 235, 237, 239, 241, 243, 245, 247, 249, 251, 269, 271, 273, 275, 277, 279, 281, 283, 285 or 287. The invention encompasses an isolated polynucleotide encoding an immunoconjugate or fragment thereof, wherein the polynucleotide comprises a sequence that encodes the variable region sequences of SEQ ID NO 23, 25, 27, 29, 31, 33, 35, 37, 39, 41, 43, 45, 47, 49, 51,53, 55, 57, 59, 61,63, 65, 67, 69, 71,73, 75, 77, 79, 81,83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 293 or 295 with conservative amino acid substitutions. The invention also encompasses an isolated polynucleotide encoding an immunoconjugate of the invention or fragment thereof, wherein the polynucleotide comprises a sequence that encodes the polypeptide sequences of SEQ ID NO 193, 195, 197, 199, 201, 203, 205, 207, 209, 211, 213, 215, 217, 227, 229, 231, 233, 235, 237, 239, 241, 243, 245, 247, 249, 251, 269, 271, 273, 275, 277, 279, 281, 283, 285 or 287 with conservative amino acid substitutions.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Untargeted Conjugates

The invention provides not only immunoconjugates targeted to a specific antigen (e.g. a tumor antigen) but also untargeted conjugates comprising one or more Fab molecules which do not specifically bind to any antigen, particularly not bind to any human antigen. The absence of specific binding of these conjugates to any antigen (i.e. the absence of any binding that can be discriminated from non-specific interaction) can be measured e.g. by ELISA or surface plasmon resonance as described herein. Such conjugates are particularly useful e.g. for enhancing the serum half life of the effector moiety they comprise, as compared to the serum half-life of the unconjugated effector moiety, where targeting to a particular tissue is not desired.

Specifically, the invention provides a conjugate comprising a first Fab molecule which does not specifically bind any antigen, an Fc domain consisting of two subunits, and an effector moiety, wherein not more than one effector moiety is present. More specifically, the invention provides a conjugate comprising a first Fab molecule comprising the heavy chain variable region sequence of SEQ ID NO: 299 and the light chain variable region sequence of SEQ ID NO: 297, an Fc domain consisting of two subunits, and an effector moiety, wherein not more than one effector moiety is present. Like the immunoconjugates of the invention, the conjugates can have a variety of configurations, as described above under "Immunoconjugate Formats" (the antigen binding moiety of the immunoconjugate being replaced by a Fab molecule which does not specifically bind to any antigen, such as a Fab molecule comprising the heavy chain variable region sequence of SEQ ID NO: 299 and the light chain variable region sequence of SEQ ID NO: 297). Likewise, the features of the Fc domain as well as the effector moiety as described above under "Fc domain" and "Effector moieties" for the immunoconjugates of the invention equally apply, alone or in combination, to the untargeted conjugates of the invention.

In a particular embodiment, the conjugate comprises (i) an immunoglobulin molecule, comprising a first and a second Fab molecule which do not specifically bind any antigen and an Fc domain, and (ii) an effector moiety, wherein not more than one effector moiety is present and wherein the immunoglobulin molecule is a human IgG1 subclass immunoglobulin; the Fc domain comprises a knob modification in one and a hole modification in the other one of its two subunits, and the amino acid substitutions L234A, L235A and P329G in each of its subunits; and the effector moiety is an IL-2 molecule fused to the carboxy-terminal amino acid of one of the immunoglobulin heavy chains, optionally through a linker peptide. In a specific embodiment, the conjugate comprises the heavy chain variable region sequence of SEQ ID NO: 299 and the light chain variable region sequence of SEQ ID NO: 297.

In certain embodiments, the conjugate comprises (i) an immunoglobulin molecule, comprising the heavy chain variable region sequence of SEQ ID NO: 299 and the light chain variable region sequence of SEQ ID NO: 297, and (ii) an effector moiety, wherein not more than one effector moiety is present. In one such embodiment the immunoglobulin molecule is a human IgG1 subclass immunoglobulin. In one such embodiment the Fc domain comprises a knob modification in one and a hole modification in the other one of its two subunits. In a specific such embodiment, the Fc domain comprises the amino acid substitutions L234A, L235A and P329G in each of its subunits. In yet another such embodiment, the effector moiety is an IL-2 molecule fused to the carboxy-terminal amino acid of one of the immunoglobulin heavy chains, optionally through a linker peptide.

In one embodiment the conjugate comprises a polypeptide sequence wherein a Fab heavy chain which does not specifically bind to any antigen shares a carboxy-terminal peptide bond with an Fc domain subunit comprising a knob modification, which in turn shares a carboxy-terminal peptide bond with an IL-2 polypeptide. In a more specific embodiment, the conjugate comprises a polypeptide sequence selected from the group of SEQ ID NO: 221, SEQ ID NO: 223, SEQ ID NO: 289 and SEQ ID NO: 291, or a variant thereof that retains functionality. In one embodiment the conjugate comprises a polypeptide sequence wherein a Fab heavy chain which does not specifically bind to any antigen shares a carboxy-terminal peptide bond with an Fc domain subunit comprising a hole modification. In a more specific embodiment, the conjugate comprises the polypeptide sequence of SEQ ID NO: 219, or a variant thereof that retains functionality. In another embodiment, the conjugate comprises a Fab light chain which does not specifically bind any antigen. In a more specific embodiment, the conjugate comprises the polypeptide sequence of SEQ ID NO: 225, or a variant thereof that retains functionality. In another embodiment, the conjugate comprises the polypeptide sequences of SEQ ID NO: 219, SEQ ID NO: 221 and SEQ ID NO: 225, or variants thereof that retain functionality. In another embodiment, the conjugate comprises the polypeptide sequences of SEQ ID NO: 219, SEQ ID NO: 223 and SEQ ID NO: 225, or variants thereof that retain functionality. In another embodiment, the conjugate comprises the polypeptide sequences of SEQ ID NO: 219, SEQ ID NO: 289 and SEQ ID NO: 225, or variants thereof that retain functionality. In another embodiment, the conjugate comprises the polypeptide sequences of SEQ ID NO: 219, SEQ ID NO: 291 and SEQ ID NO: 225, or variants thereof that retain functionality. In another specific embodiment, the polypeptides are covalently linked, e.g., by a disulfide bond. In some embodiments the Fc domain polypeptide chains comprise the amino acid substitutions L234A, L235A, and P329G.

In a specific embodiment, the conjugate comprises a polypeptide sequence encoded by a polynucleotide sequence that is at least about 80%, 85%, 90%, 95%, 96%, 97%, 98%, or 99% identical to a sequence selected from the group consisting of SEQ ID NO: 298, SEQ ID NO: 300, SEQ ID NO: 220, SEQ ID NO: 222, SEQ ID NO: 224, SEQ ID NO: 226, SEQ ID NO: 290 and SEQ ID NO: 292. In another specific embodiment, the immunoconjugate comprises a polypeptide sequence encoded by the polynucleotide sequence selected from the group consisting of SEQ ID NO: 298, SEQ ID NO: 300, SEQ ID NO: 220, SEQ ID NO: 222, SEQ ID NO: 224, SEQ ID NO: 226, SEQ ID NO: 290 and SEQ ID NO: 292.

The invention also provides an isolated polynucleotide encoding the conjugate of the invention of a fragment thereof. In a specific embodiment, the isolated polynucleotide comprises a sequence that is at least about 80%, 85%, 90%, 95%, 96%, 97%, 98%, 99% or 100% identical to the a sequence selected from the group of SEQ ID NO: 298, SEQ ID NO: 300, SEQ ID NO: 220, SEQ ID NO: 222, SEQ ID NO: 224, SEQ ID NO: 226, SEQ ID NO: 290 and SEQ ID NO: 292. The invention further provides an expression vector comprising the isolated polynucleotide, and a host cell comprising the isolated polynucleotide or the expression vector of the invention. In another aspect is provided a method of producing the conjugate of the invention, comprising the steps of a) culturing the host cell of the invention under conditions suitable for the expression of the conjugate and b) recovering the conjugate. The invention also encompasses a conjugate produced by the method of the invention. The disclosure provided herein in relating to methods of producing the immunoconjugates of the invention (see e.g. under "Recombinant Methods") can equally be applied to the conjugates of the invention.

The invention further provides a pharmaceutical composition comprising the conjugate of the invention and a pharmaceutically acceptable carrier. The disclosure provided herein in relating to pharmaceutical compositions of the immunoconjugates of the invention (see e.g. under "Compositions, Formulations, and Routes of Administration") can equally be applied to the conjugates of the invention. Furthermore, the conjugate can be employed in the methods of use described herein for the immunoconjugates of the invention. The disclosure provided herein in relating to methods of using the immunoconjugates of the invention in the treatment of disease (see e.g. under "Therapeutic Methods and Compositions", "Other Agents and Treatments" and "Articles of manufacture") can equally be applied to the conjugates of the invention.

Recombinant Methods

Immunoconjugates of the invention may be obtained, for example, by solid-state peptide synthesis (e.g. Merrifield solid phase synthesis) or recombinant production. For recombinant production one or more polynucleotide encoding the immunoconjugate (fragment), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of an immunoconjugate (fragment) along with appropriate transcriptional/translational control signals. These methods include in vitro recombinant DNA techniques, synthetic techniques and in vivo recombination/genetic recombination. See, for example, the techniques described in Maniatis et al., Molecular Cloning: a Laboratory Manual, Cold Spring Harbor Laboratory, N.Y. (1989); and Ausubel et al., Current Protocols in Molecular Biology, Greene Publishing Associates and Wiley Interscience, N.Y (1989). The expression vector can be part of a plasmid, virus, or may be a nucleic acid fragment. The expression vector includes an expression cassette into which the polynucleotide encoding the immunoconjugate (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the immunoconjugate (fragment) of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the immunoconjugate is desired, DNA encoding a signal sequence may be placed upstream of the nucleic acid encoding an immunoconjugates of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase. Exemplary amino acid and corresponding polynucleotide sequences of secretory signal peptides are shown in SEQ ID NOs 8-16.

DNA encoding a short protein sequence that could be used to facilitate later purification (e.g. a histidine tag) or assist in labeling the immunoconjugate may be included within or at the ends of the immunoconjugate (fragment) encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g. has been transformed or transfected with) a vector comprising a polynucleotide that encodes (part of) an immunoconjugate of the invention. As used herein, the term "host cell" refers to any kind of cellular system which can be engineered to generate the immunoconjugates of the invention or fragments thereof. Host cells suitable for replicating and for supporting expression of immunoconjugates are well known in the art. Such cells may be transfected or transduced as appropriate with the particular expression vector and large quantities of vector containing cells can be grown for seeding large scale fermenters to obtain sufficient quantities of the immunoconjugate for clinical applications. Suitable host cells include prokaryotic microorganisms, such as *E. coli*, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr⁻ CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B.K.C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell). Standard technologies are known in the art to express foreign genes in these systems. Cells expressing a polypeptide comprising either the heavy or the light chain of an antigen binding domain such as an antibody, may be engineered so as to also express the other of the antibody chains such that the expressed product is an antibody that has both a heavy and a light chain.

In one embodiment, a method of producing an immunoconjugate according to the invention is provided, wherein the method comprises culturing a host cell comprising a polynucleotide encoding the immunoconjugate, as provided herein, under conditions suitable for expression of the immunoconjugate, and recovering the immunoconjugate from the host cell (or host cell culture medium).

The components of the immunoconjugate are genetically fused to each other. Immunoconjugates can be designed such that its components are fused directly to each other or indirectly through a linker sequence. The composition and length of the linker may be determined in accordance with methods well known in the art and may be tested for efficacy. Examples of linker sequences between the effector moiety and the Fc domain are found in the sequences shown in SEQ ID NO 195, 197, 199, 203, 209, 215, 229, 235, 237, 243, 245, 247, 249, 251, 269, 271, 273, 275, 277, 279 and 285. Additional sequences may also be included to incorporate a cleavage site to separate the individual components of the fusion if desired, for example an endopeptidase recognition sequence.

In certain embodiments the one or more antigen binding moieties of the immunoconjugate comprise at least an antibody variable region capable of binding an antigenic determinant. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty). Antigen binding moieties and methods for producing the same are also described in detail in PCT publication WO 2011/020783, the entire content of which is incorporated herein by reference.

Any animal species of antibody, antibody fragment, antigen binding domain or variable region can be used in the immunoconjugates of the invention. Non-limiting antibodies, antibody fragments, antigen binding domains or variable regions useful in the present invention can be of murine, primate, or human origin. If the immunoconjugate is intended for human use, a chimeric form of antibody may be used wherein the constant regions of the antibody are from a human. A humanized or fully human form of the antibody can also be prepared in accordance with methods well known in the art (see e.g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, N.J., 2001); and McCafferty et al., Nature 348, 552-554; Clackson et al., Nature 352, 624-628 (1991)). Phage typically display antibody fragments, either as single-chain Fv (scFv) fragments or as Fab fragments. A detailed description of the preparation of antigen binding moieties for immunoconjugates by phage display can be found in the Examples appended to PCT publication WO 2011/020783.

In certain embodiments, the antigen binding moieties useful in the present invention are engineered to have enhanced binding affinity according to, for example, the methods disclosed in PCT publication WO 2011/020783 (see Examples relating to affinity maturation) or U.S. Pat. Appl. Publ. No. 2004/0132066, the entire contents of which are hereby incorporated by reference. The ability of the immunoconjugate of the invention to bind to a specific antigenic determinant can be measured either through an enzyme-linked immunosorbent assay (ELISA) or other techniques familiar to one of skill in the art, e.g. surface plasmon resonance technique (analyzed on a BIACORE T100 system) (Liljeblad, et al., Glyco J 17, 323-329 (2000)), and traditional binding assays (Heeley, Endocr Res 28, 217-229 (2002)). Competition assays may be used to identify an antibody, antibody fragment, antigen binding domain or variable domain that competes with a reference antibody for binding to a particular antigen, e.g. an antibody that competes with the L19 antibody for binding to the Extra Domain B of fibronectin (EDB). In certain embodiments, such a competing antibody binds to the same epitope (e.g. a linear or a conformational epitope) that is bound by the reference antibody. Detailed exemplary methods for mapping an epitope to which an antibody binds are provided in Morris (1996) "Epitope Mapping Protocols," in Methods in Molecular Biology vol. 66 (Humana Press, Totowa, N.J.). In an exemplary competition assay, immobilized antigen (e.g. EDB) is incubated in a solution comprising a first labeled antibody that binds to the antigen (e.g. L19 antibody) and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen. See Harlow and Lane (1988) Antibodies: A Laboratory Manual ch. 14 (Cold Spring Harbor Laboratory, Cold Spring Harbor, N.Y.).

Immunoconjugates prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the immunoconjugate binds. For example, for affinity chromatography purification of immunoconjugates of the invention, a matrix with protein A or protein G may be used. Sequential Protein A or G affinity chromatography and size exclusion chromatography can be used to isolate an immunoconjugate essentially as described in the Examples. The purity of the immunoconjugate can be determined by any of a variety of well known analytical methods including gel electrophoresis, high pressure liquid chromatography, and the like. For example, the heavy chain fusion proteins expressed as described in the Examples were shown to be intact and properly assembled as demonstrated by reducing SDS-PAGE (see e.g. FIGS. 4A-D). Three bands were resolved at approximately Mr 25,000, Mr 50,000 and Mr 60,000, corresponding to the predicted molecular weights of the immunoglobulin light chain, heavy chain and heavy chain/effector moiety fusion protein.

Assays

Immunoconjugates provided herein may be identified, screened for, or characterized for their physical/chemical properties and/or biological activities by various assays known in the art.

Affinity Assays

The affinity of the immunoconjugate for an effector moiety receptor (e.g. IL-10R or various forms of IL-2R), an Fc receptor, or a target antigen, can be determined in accordance with the methods set forth in the Examples by surface plasmon resonance (SPR), using standard instrumentation such as a BIAcore instrument (GE Healthcare), and receptors or target proteins such as may be obtained by recombinant expression. Alternatively, binding of immunoconjugates for different receptors or target antigens may be evaluated using cell lines expressing the particular receptor or target antigen, for example by flow cytometry (FACS). A specific illustrative and exemplary embodiment for measuring binding affinity is described in the following and in the Examples below.

According to one embodiment, $K_D$ is measured by surface plasmon resonance using a BIACORE® T100 machine (GE Healthcare) at 25° C. with ligand (e.g. effector moiety receptor, Fc receptor or target antigen) immobilized on CMS chips. Briefly, carboxymethylated dextran biosensor chips (CMS, GE Healthcare) are activated with N-ethyl-N'-(3-dimethylaminopropyl)-carbodiimide hydrochloride (EDC) and N-hydroxysuccinimide (NHS) according to the supplier's instructions. Recombinant ligand is diluted with 10 mM sodium acetate, pH 5.5, to 0.5-30 μg/ml before injection at a flow rate of 10 μl/minute to achieve approximately 100-5000 response units (RU) of coupled protein. Following the injection of the ligand, 1 M ethanolamine is injected to block unreacted groups. For kinetics measurements, three- to five-fold serial dilutions of immunoconjugate (range between ~0.01 nM to 300 nM) are injected in HBS-EP+(GE Healthcare, 10 mM HEPES, 150 mM NaCl, 3 mM EDTA, 0.05% Surfactant P20, pH 7.4) at 25° C. at a flow rate of approximately 30-50 μl/min. Association rates ($k_{on}$) and dissociation rates (kw) are calculated using a simple one-to-one Langmuir binding model (BIACORE® T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999).

Activity Assays

Biological activity of the immunoconjugates of the invention can be measured by various assays as described in the Examples. Biological activities may for example include the induction of proliferation of effector moiety receptor-bearing cells, the induction of signaling in effector moiety receptor-bearing cells, the induction of cytokine secretion by effector moiety receptor-bearing cells, and the induction of tumor regression and/or the improvement of survival.

Compositions, Formulations, and Routes of Administration

In a further aspect, the invention provides pharmaceutical compositions comprising any of the immunoconjugates provided herein, e.g., for use in any of the below therapeutic methods. In one embodiment, a pharmaceutical composition comprises any of the immunoconjugates provided herein and a pharmaceutically acceptable carrier. In another embodiment, a pharmaceutical composition comprises any of the immunoconjugates provided herein and at least one additional therapeutic agent, e.g., as described below.

Further provided is a method of producing an immunoconjugate of the invention in a form suitable for administration in vivo, the method comprising (a) obtaining an immunoconjugate according to the invention, and (b) formulating the immunoconjugate with at least one pharmaceutically acceptable carrier, whereby a preparation of immunoconjugate is formulated for administration in vivo.

Pharmaceutical compositions of the present invention comprise a therapeutically effective amount of one or more immunoconjugate dissolved or dispersed in a pharmaceutically acceptable carrier. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one immunoconjugate and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countries. Preferred compositions are lyophilized formulations or aqueous solutions. As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The composition may comprise different types of carriers depending on whether it is to be administered in solid, liquid or aerosol form, and whether it need to be sterile for such routes of administration as injection. Immunoconjugates of the present invention (and any additional therapeutic agent)

can be administered intravenously, intradermally, intraarterially, intraperitoneally, intralesionally, intracranially, intraarticularly, intraprostatically, intrasplenically, intrarenally, intrapleurally, intratracheally, intranasally, intravitreally, intravaginally, intrarectally, intratumorally, intramuscularly, intraperitoneally, subcutaneously, subconjunctivally, intravesicularlly, mucosally, intrapericardially, intraumbilically, intraocularally, orally, topically, locally, by inhalation (e.g. aerosol inhalation), injection, infusion, continuous infusion, localized perfusion bathing target cells directly, via a catheter, via a lavage, in cremes, in lipid compositions (e.g. liposomes), or by other method or any combination of the forgoing as would be known to one of ordinary skill in the art (see, for example, Remington's Pharmaceutical Sciences, 18th Ed. Mack Printing Company, 1990, incorporated herein by reference). Parenteral administration, in particular intravenous injection, is most commonly used for administering polypeptide molecules such as the immunoconjugates of the invention.

Parenteral compositions include those designed for administration by injection, e.g. subcutaneous, intradermal, intralesional, intravenous, intraarterial intramuscular, intrathecal or intraperitoneal injection. For injection, the immunoconjugates of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the immunoconjugates may be in powder form for constitution with a suitable vehicle, e.g., sterile pyrogen-free water, before use. Sterile injectable solutions are prepared by incorporating the immunoconjugates of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

In addition to the compositions described previously, the immunoconjugates may also be formulated as a depot preparation. Such long acting formulations may be administered by implantation (for example subcutaneously or intramuscularly) or by intramuscular injection. Thus, for example, the immunoconjugates may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the immunoconjugates of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The immunoconjugates may be formulated into a composition in a free acid or base, neutral or salt form. Pharmaceutically acceptable salts are salts that substantially retain the biological activity of the free acid or base. These include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

Therapeutic Methods and Compositions

Any of the immunoconjugates provided herein may be used in therapeutic methods. Immunoconjugates of the invention can be used as immunotherapeutic agents, for example in the treatment of cancers.

For use in therapeutic methods, immunoconjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, immunoconjugates of the invention for use as a medicament are provided. In further aspects, immunoconjugates of the invention for use in treating a disease are provided. In certain embodiments, immunoconjugates of the invention for use in a method of treatment are provided. In one embodiment, the invention provides an immunoconjugate as described herein for use in the treatment of a disease in an individual in need thereof. In certain embodiments, the invention provides an immunoconjugate for use in a method of treating an individual having a disease comprising administering to the individual a therapeutically effective amount of the immunoconjugate. In certain embodiments the disease to be treated is a proliferative disorder. In a particular embodiment the disease is cancer. In other embodiments the disease to be treated is an inflammatory disorder. In certain embodiments the method further comprises administering to the individual a therapeutically effective amount of at least one additional therapeutic agent, e.g., an anti-cancer agent if the disease to be treated is cancer. An "individual" according to any of the above embodiments is a mammal, preferably a human.

In a further aspect, the invention provides for the use of an immunconjugate of the invention in the manufacture or preparation of a medicament for the treatment of a disease in an individual in need thereof. In one embodiment, the medicament is for use in a method of treating a disease comprising administering to an individual having the disease a therapeutically effective amount of the medicament. In certain embodiments the disease to be treated is a proliferative disorder. In a particular embodiment the disease is cancer. In other embodiments the disease to be treated is an inflammatory disorder. In one embodiment, the method further comprises administering to the individual a therapeutically effective amount of at least one additional therapeutic agent, e.g., an anti-cancer agent if the disease to be treated is cancer. An "individual" according to any of the above embodiments may be a mammal, preferably a human.

In a further aspect, the invention provides a method for treating a disease in an individual, comprising administering to said individual a therapeutically effective amount of an immunoconjugate of the invention. In one embodiment a composition is administered to said individual, comprising immunoconjugate of the invention in a pharmaceutically acceptable form.

In certain embodiments the disease to be treated is a proliferative disorder. In a particular embodiment the disease is cancer. In other embodiments the disease to be treated is an inflammatory disorder. In certain embodiments the method further comprises administering to the individual a therapeutically effective amount of at least one additional therapeutic agent, e.g., an anti-cancer agent if the disease to be treated is cancer. An "individual" according to any of the above embodiments may be a mammal, preferably a human.

In certain embodiments the disease to be treated is a proliferative disorder, particularly cancer. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using an immunoconjugate of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. In some embodiments, particularly where the effector moiety of the immunoconjugate is IL-10, the disease to be treated is an inflammatory disorder. Non-limiting examples of inflammatory disorders include rheumatoid arthritis, psoriasis or Crohn's disease. A skilled artisan readily recognizes that in many cases the immunoconjugates may not provide a cure but may only provide partial benefit. In some embodiments, a physiological change having some benefit is also considered therapeutically beneficial. Thus, in some embodiments, an amount of immunoconjugate that provides a physiological change is considered an "effective amount" or a "therapeutically effective amount". The subject, patient, or individual in need of treatment is typically a mammal, more specifically a human.

The immunoconjugates of the invention are also useful as diagnostic reagents. The binding of an immunoconjugate to an antigenic determinant can be readily detected by using a secondary antibody specific for the effector moiety. In one embodiment, the secondary antibody and the immunoconjugate facilitate the detection of binding of the immunoconjugate to an antigenic determinant located on a cell or tissue surface.

In some embodiments, an effective amount of an immunoconjugate of the invention is administered to a cell. In other embodiments, a therapeutically effective amount of an immunoconjugates of the invention is administered to an individual for the treatment of disease. For the prevention or treatment of disease, the appropriate dosage of an immunoconjugate of the invention (when used alone or in combination with one or more other additional therapeutic agents) will depend on the type of disease to be treated, the route of administration, the body weight of the patient, the type of immunoconjugate, the severity and course of the disease, whether the immunoconjugate is administered for preventive or therapeutic purposes, previous or concurrent therapeutic interventions, the patient's clinical history and response to the immunoconjugate, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The immunoconjugate is suitably administered to the patient at one time or over a series of treatments. Depending on the type and severity of the disease, about 1 μg/kg to 15 mg/kg (e.g. 0.1 mg/kg-10 mg/kg) of immunoconjugate can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the immunoconjugate would be in the range from about 0.005 mg/kg to about 10 mg/kg. In other non-limiting examples, a dose may also comprise from about 1 microgram/kg body weight, about 5 microgram/kg body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg body weight to about 500 milligram/kg body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the immunoconjugate). An initial higher loading dose, followed by one or more lower doses may be administered. However, other dosage regimens may be useful. The progress of this therapy is easily monitored by conventional techniques and assays.

The immunoconjugates of the invention will generally be used in an amount effective to achieve the intended purpose. For use to treat or prevent a disease condition, the immunoconjugates of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the immunoconjugates which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the immunoconjugates may not be related to plasma concentration. One having skill in the art will be able to optimize therapeutically effective local dosages without undue experimentation.

A therapeutically effective dose of the immunoconjugates described herein will generally provide therapeutic benefit without causing substantial toxicity. Toxicity and therapeutic efficacy of an immunoconjugate can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Immunoconjugates that exhibit large therapeutic indices are preferred. In one embodiment, the immunoconjugate according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with immunoconjugates of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The immunoconjugates of the invention may be administered in combination with one or more other agents in therapy. For instance, an immunoconjugate of the invention may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is an immunomodulatory agent, a cytostatic agent, an inhibitor of cell adhesion, a cytotoxic agent, an activator of cell apoptosis, or an agent that increases the sensitivity of cells to apoptotic inducers. In a particular embodiment, the additional therapeutic agent is an anti-cancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent.

Such other agents are suitably present in combination in amounts that are effective for the purpose intended. The effective amount of such other agents depends on the amount of immunoconjugate used, the type of disorder or treatment, and other factors discussed above. The immunoconjugates are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the immunoconjugate of the invention can occur prior to, simultaneously, and/or following, administration of the additional therapeutic agent and/or adjuvant. Immunoconjugates of the invention can also be used in combination with radiation therapy.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an immunoconjugate of the invention. The label or package insert indicates that the composition is used for treating the condition of choice. Moreover, the article of manufacture may comprise (a) a first container with a composition contained therein, wherein the composition comprises an immunoconjugate of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

The following are examples of methods and compositions of the invention. It is understood that various other embodiments may be practiced, given the general description provided above.

Example 1

General Methods

Recombinant DNA Techniques

Standard methods were used to manipulate DNA as described in Sambrook et al., Molecular cloning: A laboratory manual; Cold Spring Harbor Laboratory Press, Cold Spring Harbor, N.Y., 1989. The molecular biological reagents were used according to the manufacturer's instructions. General information regarding the nucleotide sequences of human immunoglobulins light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments where required were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells. SEQ ID NOs 8-16 give exemplary leader peptides and polynucleotide sequences encoding them.

Preparation of IL-2R βγ Subunit-Fc Fusions and IL-2R α Subunit Fc Fusion

To study IL-2 receptor binding affinity, a tool was generated that allowed for the expression of a heterodimeric IL-2 receptor; the β-subunit of the IL-2 receptor was fused to an Fc molecule that was engineered to heterodimerize (Fc(hole)) (see SEQ ID NOs 17 and 18) using the "knobs-into-holes" technology (Merchant et al., Nat Biotech. 16, 677-681 (1998)). The γ-subunit of the IL-2 receptor was then fused to the Fc(knob) variant (see SEQ ID NOs 19 and 20), which heterodimerized with Fc(hole). This heterodimeric Fc-fusion protein was then used as a substrate for analyzing the IL-2/IL-2 receptor interaction. The IL-2R α-subunit was expressed as monomeric chain with an AcTev cleavage site and an Avi His tag (SEQ ID NOs 21 and 22). The respective IL-2R subunits were transiently expressed in HEK EBNA 293 with serum for the IL-2R βγ subunit construct and without serum for the α-subunit construct. The IL-2R βγ subunit construct was purified on protein A (GE Healthcare), followed by size exclusion chromatography (GE Healthcare, Superdex 200). The IL-2R α-subunit was purified via His tag on a NiNTA column (Qiagen) followed by size exclusion chromatography (GE Healthcare, Superdex 75). Amino acid and corresponding nucleotide sequences of various receptor constructs are given in SEQ ID NOs 17-22 and 255-268.

Preparation of Immunconjugates

Details about the generation and affinity maturation of antigen binding moieties directed to FAP can be found in the Examples appended to PCT patent application publication no. WO 2012/020006, which is incorporated herein by reference in its entirety. As described therein, various antigen binding domains directed to FAP have been generated by phage display, including the ones designated 4G8, 28H1 and 4B9 used in the following examples. Clone 28H1 is an affinity matured antibody based on parental clone 4G8, while clone 4B9 is an affinity matured antibody based on parental clone 3F2. The antigen binding domain designated 2B10 used herein is directed to the A2 domain of Tenascin C (TNC A2). Details about this and other antigen binding moieties directed against TNC A2 can be found in PCT patent application publication no. WO 2012/020038, which is incorporated herein by reference in its entirety. The antigen binding domain designated L19, directed against the Extra Domain B (EDB) of fibronectin is derived from the L19 antibody described in PCT publication WO 2007/128563. The antigen binding domains designated CH1A1A and CH1A1A 98/99 2F1 used herein are directed to CEA, and are described in more detail in PCT patent application no. PCT/EP2012/053390, which is incorporated herein by reference in its entirety.

The IL-2 quadruple mutant (qm) used as effector moiety in some of the following examples is described in detail in PCT patent application no. PCT/EP2012/051991, which is incorporated herein by reference in its entirety. Briefly, IL-2 qm is characterized by the following mutations:

1. T3A—knockout of predicted O-glycosylation site
2. F42A—knockout of IL-2/IL-2R α interaction
3. Y45A—knockout of IL-2/IL-2R α interaction
4. L72G—knockout of IL-2/IL-2R α interaction
5. C125A—mutation to avoid disulfide-bridged IL-2 dimers The T3A mutation was chosen to eliminate the O-glycosylation site and obtain a protein product with higher homogeneity and purity when the IL-2 qm polypeptide or an immunoconjugate comprising it is expressed in eukaryotic cells such as CHO or HEK293 cells. The three mutations F42A, Y45A and L72G were chosen to interfere with the binding to CD25, the α-subunit of the IL-2 receptor. Reduced or abolished CD25 binding results in reduced activation-induced cell death (AICD), lack of preferential activation of regulatory T cells, as well as reduced toxicity (as described in EP 11153964.9).

The DNA sequences were generated by gene synthesis and/or classical molecular biology techniques and subcloned into mammalian expression vectors under the control of an MPSV promoter and upstream of a synthetic polyA site, each vector carrying an EBV OriP sequence.

Immunoconjugates as applied in the examples below were produced by co-transfecting exponentially growing HEK293-EBNA cells with the mammalian expression vectors using calcium phosphate-transfection. Alternatively, HEK293 cells growing in suspension were transfected by polyethylenimine (PEI) with the respective expression vectors. Alternatively, stably transfected CHO cell pools or CHO cell clones were used for production in serum-free media. Subsequently, the IgG-cytokine fusion proteins were purified from the supernatant. Briefly, IgG-cytokine fusion proteins were purified by one affinity step with protein A (HiTrap ProtA, GE Healthcare) equilibrated in 20 mM sodium phosphate, 20 mM sodium citrate pH 7.5. After loading of the supernatant, the column was first washed with 20 mM sodium phosphate, 20 mM sodium citrate, pH 7.5 and subsequently washed with 13.3 mM sodium phosphate, 20 mM sodium citrate, 500 mM sodium chloride, pH 5.45. The IgG-cytokine fusion protein was eluted with 20 mM sodium citrate, 100 mM sodium chloride, 100 mM glycine, pH 3. Fractions were neutralized and pooled and purified by size exclusion chromatography (HiLoad 16/60 Superdex 200, GE Healthcare) in final formulation buffer: 25 mM potassium phosphate, 125 mM sodium chloride, 100 mM glycine pH 6.7. Exemplary detailed purification procedures and results are given for selected constructs below. The protein concentration of purified protein samples was determined by measuring the optical density (OD) at 280 nm, using the molar extinction coefficient calculated on the basis of the amino acid sequence. Purity and molecular weight of immunoconjugates were analyzed by SDS-PAGE in the presence and absence of a reducing agent (5 mM 1,4-dithiotreitol) and stained with Coomassie blue (SimpleBlue™ SafeStain, Invitrogen). The NuPAGE® Pre-Cast gel system (Invitrogen) was used according to the manufacturer's instructions (4-20% Tris-glycine gels or 3-12% Bis-Tris). The aggregate content of immunoconjugate samples was analyzed using a Superdex 200 10/300GL analytical size-exclusion column (GE Healthcare) in 2 mM MOPS, 150 mM NaCl, 0.02% $NaN_3$, pH 7.3 running buffer at 25° C. The integrity of the amino acid backbone of reduced antibody light and heavy chains can be verified by Nano-Electrospray Q-TOF mass spectrometry after removal of N-glycans by enzymatic treatment with Peptide-N Glycosidase F (Roche Molecular Biochemicals). The oligosaccharides attached to the Fc domain of the immunoconjugates are analysed by MALDI TOF-MS as described below. Oligosaccharides are enzymatically released from the immunoconjugates by PNGaseF digestion. The resulting digest solution containing the released oligosaccharides is either prepared directly for MALDI TOF-MS analysis or is further digested with EndoH glycosidase prior to sample preparation for MALDI TOF-MS analysis.

Example 2

FAP-targeted IgG-IL-2 qm fusion proteins were generated based on the FAP-antibodies 4G8, 28H1 and 4B9, wherein one single IL-2 quadruple mutant (qm) was fused to the C-terminus of one heterodimeric heavy chain as shown in FIG. 2A. Targeting to the tumor stroma where FAP is selectively expressed is achieved via the bivalent antibody Fab region (avidity effect). Heterodimerization resulting in the presence of a single IL-2 quadruple mutant is achieved by application of the knob-into-hole technology. In order to minimize the generation of homodimeric IgG-cytokine fusions the cytokine was fused to the C-terminus (with deletion of the C-terminal Lys residue) of the knob-containing IgG heavy chain via a $(G_4S)_3$ or $G_4$-$(SG_4)_2$ linker. The antibody-cytokine fusion has IgG-like properties. To reduce FcγR binding/effector function and prevent FcR co-activation, P329G L234A L235A (LALA) mutations were introduced in the Fc domain. The sequences of these immunoconjugates are given SEQ ID NOs 193, 269 and 205 (28H1 with $(G_4S)_3$ linker), SEQ ID NOs 193, 195 and 205 (28H1 with $G_4$-$(SG_4)_2$ linker), SEQ ID NOs 201, 203 and 205 (4G8 with $G_4$-$(SG_4)_2$ linker), SEQ ID NOs 207, 209 and 211 (4B9 with $G_4$-$(SG_4)_2$ linker), SEQ ID NOs 207, 271 and 211 (4B9 with $(G_4S)_3$ linker).

In addition, a CEA-targeted IgG-IL-2 qm fusion protein based on the anti-CEA antibody CH1A1A 98/99 2F1, a control DP47GS non-targeted IgG-IL-2 qm fusion protein wherein the IgG does not bind to a specified target, as well as a tumor stroma specific 2B10-based IgG-IL-2 qm fusion protein targeted against the A2 domain of tenascin-C were generated. The sequences of these immunoconjugates are given in SEQ ID NOs 275, 281 and 283 (CH1A1A 98/99 2F1 with $G_4$-$(SG_4)_2$ linker), SEQ ID NOs 277, 281 and 283 (CH1A1A 98/99 2F1 with $(G_4S)_3$ linker), SEQ ID NOs 219, 221 and 225 (DP47GS with $G_4$-$(SG_4)_2$ linker), SEQ ID NOs 219, 289 and 225 (DP47GS with $(G_4S)_3$ linker), SEQ ID NOs 285, 287 and 239 (2B10 with $(G_4S)_3$ linker). The constructs were generated by transient expression in HEK293 EBNA cells and purified as described above. FIGS. 3A-D to FIGS. 9A-D show exemplary chromatograms and elution profiles of the purification (A, B) as well as the analytical SDS-PAGE and size exclusion chromatographies of the final purified constructs (C, D). Transient expression yields were 42 mg/L for the 4G8-based, 20 mg/L for the 28H1-based, 10 mg/L for the 4B9-based, 5.3 mg/L for the CH1A1A 98/99 2F1-based, 36.7 mg/L for the 2B10-based and 13.8 mg/L for the DP47GS-based IgG-IL-2 qm immunoconjugate.

In addition a 28H1-based FAP-targeted IgG-IL-15 immunoconjugate is being generated, the sequences of which are given in SEQ ID NOs 193, 199 and 205. In the IL-15 polypeptide sequence the glutamic acid residue at position 53 is replaced by alanine to reduce binding to the α-subunit of the IL-15 receptor, and the asparagine residue at position 79 is replaced by alanine to abolish glycosylation. The IgG-IL-15 fusion protein is generated by transient expression and purified as described above.

FAP Binding Affinity

The FAP binding activity of the IgG-IL-2 qm immunoconjugates based on 4G8 and 28H1 anti-FAP antibodies were determined by surface plasmon resonance (SPR) on a Biacore machine in comparison to the corresponding unmodified IgG antibodies. Briefly, an anti-His antibody (Penta-His, Qiagen 34660) was immobilized on CM5 chips to capture 10 nM His-tagged human FAP (20 s). Temperature was 25° C. and HBS-EP was used as buffer. Analyte concentration was 50 nM down to 0.05 nM at a flow rate of 50 μl/min (association: 300 s, dissociation: 900 s, regeneration: 60 s with 10 mM glycine pH 2). Fitting was performed based on a 1:1 binding model, RI=0, Rmax=local (because of capture format). The following table gives the estimated apperent bivalent affinities (pM avidity) as determined by SPR fitted with 1:1 binding RI=0, Rmax=local.

| | Hu FAP |
|---|---|
| 4G8 IgG-IL-2 qm | 100 pM |
| 4G8 IgG | 50 pM |
| 28H1 IgG-IL-2 qm | 175 pM |
| 28H1 IgG | 200 pM |

The data show that within the error of the method affinity for human FAP is retained for the 28H1-based immunoconjugate or only slightly decreased for the 4G8-based immunoconjugate as compared to the corresponding unmodified antibodies.

Similarly, the affinity ($K_D$) of 4B9 IgG-IL-2 qm (16 pM), CH1A1A 98/99 2F1 IgG-IL-2 qm (400 pM), CH1A1A 98/99 2F1 IgG-IL-2 wt (see Example 4; 470 pM) and 2B10 IgG-IL-2 qm (150 pM, vs. 300 pM for unconjugated 2B10 IgG) to human FAP, CEA and TNC A2, respectively, were determined by SPR at 25° C. Cross-reactivity of the 4B9 and 2B10 antibodies to human, murine and cynomolgus FAP or TNC A2, respectively, was also confirmed.

Subsequently, the affinity of the 4G8- and 28H1-based IgG-IL-2 qm immunoconjugates to the IL-2R βγ heterodimer and the IL-2R α-subunit were determined by surface plasmon resonance (SPR) in direct comparison to the Fab-IL-2 qm-Fab immunoconjugate format described in PCT patent application no. PCT/EP2012/051991. Briefly, the ligands—either the human IL-2R α-subunit or the human IL-2R βγ heterodimer—were immobilized on a CM5 chip. Subsequently, the 4G8- and 28H1-based IgG-IL-2 qm immunoconjugates or the 4G8- and 28H1-based Fab-IL-2 qm-Fab immunoconjugates for comparison were applied to the chip as analytes at 25° C. in HBS-EP buffer in concentrations ranging from 300 nM down to 1.2 nM (1:3 dil.). Flow rate was 30 μl/min and the following conditions were applied for association: 180 s, dissociation: 300 s, and regeneration: 2×30 s with 3 M $MgCl_2$ for IL-2R βγ heterodimer, 10 s with 50 mM NaOH for IL-2R α-subunit. 1:1 binding was applied for fitting (1:1 binding RI≠0, Rmax=local for IL-2R βγ, apparent $K_D$, 1:1 binding RI=0, Rmax=local for IL-2R α). The respective $K_D$ values are given in the table below.

| Apparent $K_D$ [nM] | Hu IL-2R βγ | Hu IL-2R α |
|---|---|---|
| 4G8 IgG-IL-2 qm | 5.9 | No binding |
| 4G8 Fab-IL-2 qm-Fab | 10.4 | No binding |
| 28H1 IgG-IL-2 qm | 6.2 | No binding |
| 28H1 Fab-IL-2 qm-Fab | 11.4 | No binding |

The data show that the 4G8- and 28H1-based IgG-IL-2 qm immunoconjugates bind with at least as good affinity as the Fab-IL-2 qm-Fab immunoconjugates to the IL-2R βγ heterodimer, whereas they do not bind to the IL-2R α-subunit due to the introduction of the mutations interfering with CD25 binding. Compared to the respective Fab-IL-2 qm-Fab immunoconjugates the affinity of the IgG-IL-2 qm fusion proteins appears to be slightly enhanced within the error of the method.

Similarly, the affinity of further constructs (4B9, DP47GS, 2B10, CH1A1A 98/99 2F1) comprising either IL-2 wt (see Example 4) or IL-2 qm to the IL-2R βγ heterodimer and the IL-2R α-subunit was determined by SPR at 25° C. For all constructs the apparent $K_D$ for the human IL-2R βγ heterodimer was between 6 and 12 nM (irrespective of whether the construct comprises IL-2 wt or IL-2 qm), whereas only the constructs comprising IL-2 wt bind to the IL-2R α-subunit at all ($K_D$ for human IL-2R α around 20 nM).

Biological Activity Assays with IgG-Cytokine Immunoconjugates

The biological activity of FAP-targeted 4G8-based IgG-IL-2 qm fusions was investigated in several cellular assays in comparison to commercially available IL-2 (Proleukin, Novartis/Chiron) and/or the Fab-IL-2-Fab immunoconjugates described in EP 11153964.9.

Binding to FAP Expressing Cells

Binding of FAP-targeted 4G8-based IgG-IL-2 qm immunoconjugate to human FAP expressed on stably transfected HEK293 cells was measured by FACS. Briefly, 250 000 cells per well were incubated with the indicated concentration of the immunoconjugate in a round-bottom 96-well plate, incubated for 30 min at 4° C., and washed once with PBS/0.1% BSA. Bound immunoconjugate was detected after incubation for 30 min at 4° C. with FITC-conjugated AffiniPure F(ab')2 Fragment goat anti-human F(ab')2 Specific (Jackson Immuno Research Lab #109-096-097, working solution: 1:20 diluted in PBS/0.1% BSA, freshly prepared) using a FACS CantoII (Software FACS Diva). The results are shown in FIG. 10. The data show that the IgG-IL-2 qm immunoconjugate binds to FAP-expressing cells with an EC50 value of 0.9 nM, comparable to that of the corresponding 4G8-based Fab-IL-2 qm-Fab construct (0.7 nM).

IFN-γ Release by NK Cells (in Solution)

Subsequently, FAP-targeted 4G8-based IgG-IL-2 qm immunoconjugate was studied for the induction of IFN-γ release by NK92 cells as induced by activation of IL-2R βγ signaling. Briefly, IL-2 starved NK92 cells (100 000 cells/well in 96-U-well plate) were incubated with different concentrations of IL-2 immunoconjugate, comprising quadruple mutant IL-2, for 24 h in NK medium (MEM alpha from Invitrogen (#22561-021) supplemented with 10% FCS, 10% horse serum, 0.1 mM 2-mercaptoethanol, 0.2 mM inositol and 0.02 mM folic acid). Supernatants were harvested and the IFN-γ release was analysed using the anti-human IFN-γ ELISA Kit II from Becton Dickinson (#550612). Proleukin (Novartis) and 28H1-based Fab-IL-2 qm-Fab served as positive control for IL-2-mediated activation of the cells. FIG. 11 shows that the FAP-targeted 4G8-based IgG-IL-2 qm immunoconjugate is equally efficacious in inducing IFN-γ release as the affinity matured 28H1-based Fab-IL-2 qm-Fab immunoconjugate.

STAT5 Phosphorylation Assay

In a last set of experiments we studied the effects of the FAP-targeted 4G8-based IgG-IL-2 qm immunoconjugate on the induction of STAT5 phosphorylation compared to the 28H1 based Fab-IL-2-Fab and Fab-IL-2 qm-Fab immunoconjugates as well as Proleukin on human NK cells, $CD4^+$ T cells, $CD8^+$ T cells and $T_{reg}$ cells from human PBMCs. Briefly, blood from healthy volunteers was taken in heparin-containing syringes and PBMCs were isolated. PBMCs were treated with the indicated immunoconjuagtes at the indicated concentrations or with Proleukin (Novartis) as control. After 20 min incubation at 37° C., PBMCs were fixed with pre-warmed Cytofix buffer (Becton Dickinson #554655) for 10 min at 37° C., followed by permeabilization with Phosflow Perm Buffer III (Becton Dickinson #558050) for 30 min at 4° C. Cells were washed twice with PBS containing 0.1% BSA before FACS staining was performed using mixtures of flow cytometry antibodies for detection of different cell populations and phosphorylation of STAT5. Samples were analysed using a FACSCantoII with HTS from Becton Dickinson. NK cells were defined as $CD3^-CD56^+$, CD8 positive T cells were defined as $CD3^+CD8^+$, CD4 positive T cells were defined as $CD4^+CD25^-CD127^+$ and $T_{reg}$ cells were defined as $CD4^+CD25^+FoxP3^+$. For NK cells and $CD8^+$ T cells that show no or very low CD25 expression (meaning that IL-2R signaling is mediated primarily via the IL-2R βγ heterodimer) the results show that the 4G8-based IgG-IL-2 qm immunoconjugate was <10-fold less potent in inducing STAT5 phosphorylation than Proleukin, but slightly more potent than 28H1-based Fab-IL-2-Fab and Fab-IL-2 qm-Fab immunoconjugates. On $CD4^+$ T cells, that show a rapid up-regulation of CD25 upon stimulation, the 4G8-based IgG-IL-2 qm immunoconjugate was less potent than the 28H1 Fab-IL-2-Fab immunoconjugate, but slightly more potent than the 28H1 Fab-IL-2 qm-Fab immunoconjugate, and still showed induction of IL-2R signaling at saturating concentrations comparable to Proleukin and 28H1 Fab-IL-2-Fab. This is in contrast to $T_{reg}$ cells where the potency of the 4G8-based IgG-IL-2 qm immunoconjugate was significantly reduced compared to the Fab-IL-2-Fab immunoconjugate due to the high CD25 expression on $T_{reg}$ cells and the low binding affinity of the 4G8-based IgG-IL-2 qm immunoconjugate to CD25. As a consequence of the abolishment of CD25 binding in the 4G8-based IgG-IL-2 qm immunoconjugatee, IL-2 signaling in $T_{reg}$ cells is only activated via the IL-2R heterodimer at concentrations where IL-2R signaling is activated on CD25-negative effector cells through the IL-2R βγ heterodimer. Taken together the 4G8-based IgG-IL-2 qm immunoconjugate described here is able to activate IL-2R signaling through the IL-2R βγ heterodimer, but does not result in a preferential stimulation of $T_{reg}$ cells over other effector cells. The results of these experiments are shown in FIGS. 12A-D.

Binding of 2B10 IgG-IL-2 qm to TNC A2 Expressing Cells

Binding of TNC A2-targeted 2B10-based IgG-IL-2 qm immunoconjugate to human TNC A2 expressed on U87MG cells was measured by FACS. Briefly, 200 000 cells per well were incubated with the indicated concentration of the immunoconjugate in a round-bottom 96-well plate, incubated for 30 min at 4° C., and washed twice with PBS/0.1% BSA. Bound immunoconjugate was detected after incubation for 30 min at 4° C. with FITC-conjugated AffiniPure F(ab')2 Fragment goat anti-human IgG Fcγ Specific (Jackson Immuno Research Lab #109-096-098, working solution: 1:20 diluted in PBS/0.1% BSA, freshly prepared) using a FACS CantoII (Software FACS Diva). The results are shown in FIG. 13. The data show that the 2B10 IgG-IL-2 qm immunoconjugate binds to TNC A2-expressing U87MG cells equally well as the corresponding unconjugated IgG.

Induction of NK92 Cell Proliferation by IgG-IL-2 Immunoconjugates

2B10 IgG-IL-2 qm, CH1A1A 98/99 2F1 IgG-IL-2 qm, CH1A1A 98/99 2F1 IgG-IL-2 wt, 4B9 IgG-IL-2 qm and 4B9 IgG-IL-2 wt immunoconjugates were tested for their ability to induce proliferation of NK92 cells. For proliferation assays, NK92 cells were starved in IL-2-free medium for 2 hours, 10000 cells/well seeded into a flat-bottom 96-well plate and then incubated for 3 days in a humidified incubator at 37° C., 5% $CO_2$ in the presence of the IL-2 immunoconjugates ( ). After 3 days, the ATP content of the cell lysates was measured using the CellTiter-Glo Luminescent Cell Viability Assay from Promega (#G7571/2/3). The percentage of growth was calculated setting a Proleukin (Novartis) concentration of 1.1 mg/ml to 100% proliferation and untreated cells without IL-2 stimulus to 0% proliferation. The results are shown in FIGS. 14 and 15. The data show that all constructs were able to induce NK92 cell proliferation, with the CH1A1A-based constructs being more active than the 2B10 IgG-IL-2 qm immunoconjugate, and the constructs comprising IL-2 wt being more active than the corresponding constructs with IL-2 qm.

Example 3

In general, the P329G LALA mutations that almost completely abolish FcγR interaction of human $IgG_1$ antibodies (see European patent application no. EP 11160251.2, incorporated herein by reference in its entirety) are introduced in order to reduce FcγR binding/effector function and thus prevent excessive cytokine release when the respective cytokine receptors are co-activated with FcγR signaling. In specific cases, for example when the antibody is targeting a highly tumor specific antigen, Fc effector functions may be retained by using an unmodified IgG Fc domain or may be even further enhanced via glycoengineering of the IgG Fc domain.

As an example thereof, we generated a CEA-targeted IgG-IL-2 qm immunoconjugate where one single IL-2 quadruple mutant was fused to the C-terminus of one heterodimeric heavy chain via a $(SG_4)_3$-linker based on the anti-CEA antibody clone CH1A1A. In this immunoconjugate the P329G LALA mutation was not included (see sequences of SEQ ID NOs 227, 229 and 231). The immunoconjugate was expressed and purified as human wildtype IgG- or glycoengineered IgG-IL-2 qm fusion protein as described below.

Preparation of (Glycoengineered) IgG-IL-2 qm Immunoconjugate

CEA-targeted CH1A1A-based IgG-IL-2 qm immunoconjugate was produced by co-transfecting HEK293-EBNA cells with the mammalian antibody expression vectors. Exponentially growing HEK293-EBNA cells were transfected by the calcium phosphate method. Alternatively, HEK293 cells growing in suspension are transfected by polyethylenimine. For the production of unmodified non-glycoengineered IgG-IL-2 qm immunoconjugate, the cells were transfected only with antibody heavy and light chain expression vectors in a 1:1 ratio (wherein the antibody heavy chain vector is a 1:1 mixture of two vectors: a vector for the heavy chain with the effector moiety, and a vector for the heavy chain without effector moiety).

For the production of the glycoengineered CEA-targeted IgG-IL-2 qm immunoconjugate, the cells were co-transfected with two additional plasmids, one for expression of a GnTIII fusion polypeptide (a GnT-III expression vector), and one for mannosidase II expression (a Golgi mannosidase II expression vector) at a ratio of 4:4:1:1, respectively. Cells were grown as adherent monolayer cultures in T flasks using DMEM culture medium supplemented with 10% FCS, and were transfected when they are between 50 and 80% confluent. For the transfection of a T150 flask, 15 million cells were seeded 24 hours before transfection in 25 ml DMEM culture medium supplemented with FCS (at 10% v/v final), and cells were placed at 37° C. in an incubator with a 5% $CO_2$ atmosphere overnight. For each T150 flask to be transfected, a solution of DNA, $CaCl_2$ and water was prepared by mixing 94 μg total plasmid vector DNA divided equally between the light and heavy chain expression vectors, water to a final volume of 469 μl, and 469 μl of a 1M $CaCl_2$ solution. To this solution, 938 μl of a 50 mM HEPES, 280 mM NaCl, 1.5 mM $Na_2HPO_4$ solution at pH 7.05 were added, mixed immediately for 10 sec and left to stand at room temperature for 20 sec. The suspension was diluted with 10 ml of DMEM supplemented with 2% FCS, and added to the T150 flask in place of the existing medium. Then additional 13 ml of transfection medium were added. The cells were incubated at 37° C., 5% $CO_2$ for about 17 to 20 hours, before the medium was replaced with 25 ml DMEM, 10% FCS. The conditioned culture medium was harvested approximately 7 days after the media exchange by centrifugation for 15 min at 210×g. The solution was sterile filtered (0.22 μm filter) and sodium azide in a final concentration of 0.01% w/v was added, and kept at 4° C.

The secreted wildtype or glycoengineered CEA IgG-IL-2 qm immunoconjugates were purified from cell culture supernatants by affinity chromatography using Protein A affinity chromatography, followed by a size exclusion chromatographic step on a HiLoad Superdex 200 column (GE Healthcare) as described above. Protein concentration, purity, molecular weight, aggregate content and integrity were analysed as described above.

Oligosaccharide Structure Analysis of (Glycoengineered) IgG-IL-2 qm Immunoconjugates For determination of the relative ratios of fucose-containing and non-fucosylated oligosaccharide structures, released glycans of purified immunoconjugate material are analyzed by MALDI TOF mass spectrometry. The immunoconjugate sample (about 50 μg) is incubated overnight at 37° C. with 5 mU N-glycosidase F (QAbio; PNGaseF: E-PNG01) in 2 mM Tris, pH 7.0, in order to release the oligosaccharide from the protein backbone. For deamination of glycans acetic acid to a final concentration of 150 mM is added and incubated for 1 h at 37° C. For analysis by MALDI TOF mass spectrometry, 2 μL of the sample are mixed on the MALDI target with 2 μL DHB matrix solution (2, 5-dihydroxybenzoic acid [Bruker Daltonics #201346] dissolved in 50% ethanol/5 mM NaCl at 4 mg/ml) and analysed with MALDI TOF Mass Spectrometer Autoflex II instrument (Bruker Daltonics). Routinely, 50-300 shots are recorded and summed up to a single experiment. The spectra obtained are evaluated by the flex analysis software (Bruker Daltonics) and masses are determined for the each of the peaks detected. Subsequently, the peaks are assigned to fucose-containing or non-fucosylated carbohydrate structures by comparing the masses calculated and the masses theoretically expected for the respective structures (e.g. complex, hybrid and oligo- or high-mannose, respectively, with and without fucose).

For determination of the ratio of hybrid structures, the antibody samples are digested with N-glycosidase F and Endo-glycosidase H [QAbio; EndoH: E-EH02] concomitantly. N-glycosidase F releases all N-linked glycan structures (complex, hybrid and oligo- and high mannose structures) from the protein backbone and the Endo-glycosidase H cleaves all the hybrid type glycans additionally between the two N-acetylglucosamine (GlcNAc) residues at the reducing end of the glycan. This digest is subsequently treated and analysed by MALDI TOF mass spectrometry in the same way as described above for the N-glycosidase F digested sample. By comparing the pattern from the N-glycosidase F digest and the combined N-glycosidase F/Endo H digest, the degree of reduction of the signals of a specific carbohydrate structure is used to estimate the relative content of hybrid structures. The relative amount of each carbohydrate structure is calculated from the ratio of the peak height of an individual structure and the sum of the peak heights of all oligosaccharides detected. The amount of fucose is the percentage of fucose-containing structures related to all carbohydrate structures identified in the N-glycosidase F treated sample (e.g. complex, hybrid and oligo- and high-mannose structures). The degree of non-fucosylation is the percentage of structures lacking fucose relative to all carbohydrates identified in the N-glycosidase F treated sample (e.g. complex, hybrid and oligo- and high-mannose structures).

Antibody-Dependent Cell-Mediated Cytotoxicity Assay

The wildtype and glycoengineered CEA-targeted CH1A1A IgG-IL-2 qm immunoconjugates were compared in ADCC assays for their potential to mediate antibody mediated cellular cytotoxicity. Briefly, CEA-overexpressing A549 human tumor cells as target cells were collected, washed and resuspended in culture medium, stained with freshly prepared Calcein AM (Molecular Probes) at 37° C. for 30 min, washed three times, counted and diluted to 300 000 cells/ml. This suspension was transferred to a round-bottom 96-well plate (30000 cells/well), the respective immunoconjugate dilution was added and incubated for 10 min to allow the binding of the tested immunoconjugate to the cells prior to contact with effector cells. Effector to target ratio was 25 to 1 for freshly isolated PBMCs. Co-incubation was performed for 4 hours. Two different read-out systems were used: the release of lactate dehydrogenase (LDH) into supernatant after disintegration of the attacked cells, and the retention of Calcein in the remaining living cells. LDH from co-culture supernatant was collected and analyzed with a LDH detection Kit (Roche Applied Science). Substrate conversion by the LDH enzyme was measured with an ELISA absorbance reader (SoftMaxPro software, reference wavelengths: 490 nm versus 650 nm). Residual Calcein in living cells was analyzed in a fluorescence reader (Wallac VICTOR3 1420 Multilabel COUNTER (Perkin Elmer)) after removing the rest of supernatant from pelletized cells, one washing step in PBS prior to lysis, and fixation of the cells by borate buffer (50 mM borate, 0.1% Triton).

FIG. 16 shows the result based on LDH detection. A similar result was obtained based on the calcein retention (not shown). Both the constructs were able to mediate ADCC, the glycoengineered construct being similarly active as the corresponding glycoengineered unconjugated IgG. As expected, the non-glycoengineered construct showed reduced activity as compared to the glycoengineered construct.

Example 4

FAP-targeted 28H1- or 4B9-based, CEA-targeted CH1A1A 98/99 2F1-based and non-targeted DP47GS-based IgG-IL-2 immunoconjugates were generated wherein one single wildtype IL-2 polypeptide is fused to the C-terminus of one heterodimeric heavy chain. Heterodimerization resulting in an immunoconjugate with a single IL-2 moiety was achieved by application of the knob-into-hole technology. In order to minimize the generation of homodimeric IgG-IL-2 fusions proteins the cytokine was fused to the knob-containing heavy chain (with deletion of the C-terminal Lys residue) via a $G_4$-$(SG_4)_2$ or a $(G_4S)_3$ linker. The sequences of these immunoconjugates are given in SEQ ID NOs 193, 197 and 205 (28H1 with $G_4$-$(SG_4)_2$ linker) SEQ ID NOs 207, 273 and 211 (4B9 with $(G_4S)_3$ linker), SEQ ID NOs 277, 279 and 283 (CH1A1A 98/99 2F1 with $(G_4S)_3$ linker), SEQ ID NOs 219, 223 and 225 (DP47GS with $G_4$-$(SG_4)_2$ linker), SEQ ID NOs 219, 293 and 225 (DP47GS with $(G_4S)_3$ linker). The antibody-cytokine fusion has IgG-like properties. To reduce FcγR binding/effector function and prevent FcR co-activation, P329G LALA mutations were introduced in the Fc domain. Both constructs were purified according to the methods described above. Final purification was done by size exclusion chromatography (HiLoad 26/60 Superdex 200, GE Healthcare) in the final formulation buffer 20 mM histidine, 140 mM sodium chloride pH 6. FIGS. 17A-D to FIGS. 20A-D show the respective chromatograms and elution profiles of the purification (A, B) as well as the analytical SDS-PAGE and size exclusion chromatographies of the final purified constructs (C, D). Yield was 15.6 mg/L for the untargeted DP47GS IgG-IL-2 immunoconjugate, 26.7 mg/ml for the 28H1 IgG-IL-2 immunoconjugate, 4.6 mg/L for the CH1A1A 98/99 2F1 IgG-IL-2 immunoconjugate and 11 mg/L for the 4B9 IgG-IL-2 immunoconjugate.

Subsequently, their binding properties to FAP, respectively lack of binding, as well as binding to IL-2R βγ and IL-2R α chain were determined by SPR as described above (see Example 2). Cellular activity on immune effector cell populations and in vivo pharmacodynamic effects were also studied.

Example 5

FAP-targeted 4G8-based as well as TNC A2-targeted 2B10-based IgG-IL-10 immunoconjugates were constructed by fusing two different IL-10 cytokine formats to the C-terminus of the heavy chain of the heterodimeric IgG comprising a hole modification: either a single-chain IL-10 wherein a $(G_4S)_4$ 20-mer linker was inserted between two IL-10 molecules, or an engineered monomeric IL-10 (Josephson et al., J Biol Chem 275, 13552-7 (2000)). Both molecules were fused via a $(G_4S)_3$ 15-mer linker to the C-terminus of the heavy chain comprising a hole modification, with deletion of the C-terminal Lys residue. Heterodimerization resulting in only one heavy chain carrying an IL-10 moiety was achieved by application of the knob-into-hole technology. The IgG-cytokine fusion has IgG-like properties. To reduce FcγR binding/effector function and prevent FcR co-activation, P329G LALA mutations were introduced in the Fc domain of the immunoconjugate. The sequences of the respective constructs are given in SEQ ID NOs 233, 235 and 239 (2B10 with scIL-10), SEQ ID NOs 233, 237 and 239 (2B10 with monomeric IL-10 "IL-10M1"), SEQ ID NOs 241, 243 and 205 (4G8 with scIL-10), SEQ ID NOs 241, 245 and 205 (4G8 with IL-10M1). All these immunoconjugates were purified according to the methods described above. Subsequently, their binding properties to FAP or TNC A2, respectively, as well as their affinities to human IL-10R1 were determined by SPR using the ProteOn XPR36 biosensor. Briefly, the targets FAP or TNC A2 as well as human IL-10R1 were immobilized in vertical orientation on the sensorchip surface (FAP by standard amine coupling, TNC A2 and human IL-10R1 (both biotinylated via a C-terminal avi-tag) by neutravidin-capture). Subsequently, the IgG-IL-10 immunoconjugates were injected in six different concentrations, including a zero-concentration, as analytes in horizontal orientation.

After double-referencing, the sensorgrams were fit to a 1:1 interaction model to determine kinetic rate constants and affinities. The results from analytical SDS PAGE analysis and SPR-based affinity determinations to target antigens as well as IL-10 receptor are shown in FIGS. 21A-C and 22A-C. The data show that the immunoconjugates bind to TNC A2 or FAP with $K_D$ values of 52 or 26 pM, respectively, while $K_D$ values for IL-10 receptor are 520 and 815 pM.

Example 6

According to the methods described above, IgG-cytokine fusion proteins were generated and expressed consisting of one single 28H1-based or 4B9-based Fab region directed to FAP fused to the N-terminus of an Fc domain subunit comprising a hole modification, while the second Fab region of the IgG heavy chain with the knob modification was replaced by a cytokine moiety via a $(G_4S)_n$ linker (n=1). See FIG. 2C for a schematic representation of this immunoconjugate format (also referred to as "1+1" format). Cytokine moieties used were the IL-2 quadruple mutant described above and in PCT patent application no. PCT/EP2012/051991 (see SEQ ID NO: 3), IL-7 and IFN-α. Corresponding sequences of the fusion polypeptides comprising the cytokine moiety, fused to the N-terminus of an Fc domain subunit comprising a knob modification via a linker peptide, are given in SEQ ID NOs 247 (comprising quadruple mutant IL-2), 249 (comprising IL-7), and 251 (comprising IFN-α). In these constructs, targeting of the immunoconjugate is achieved via the high affinity monovalent Fab region. This format may be recommended in cases where internalization of the antigen may be reduced using a monovalent binder. The immunoconjugates were produced, purified and analysed as described above. For constructs comprising IL-2 qm or IL-7, protein A affinity chromatography and size exclusion chromatography were combined in a single run. 20 mM histidine, 140 mM NaCl pH 6.0 was used as size exclusion chromatography and final formulation buffer. FIGS. 23A-C to 26A-D show the elution profiles and chromatograms of the purifications as well as the analytical SDS-PAGE and size exclusion chromatograms of the final purified constructs. The yields were 11 mg/L for the 4B9 “1+1” IgG-IL-2 qm, 43 mg/L for the 28H1 “1+1” IgG-IL-2 qm, 20.5 mg/L for the 4B9 “1+1” IgG-IL-7 and 10.5 mg/L for the 4B9 “1+1” IgG-IFN-α constructs.

The ability of “1+1” constructs comprising IL-2 qm to induce NK cell proliferation, compared to IgG-IL-2 qm immunoconjugates, was tested. NK-92 cells were starved for 2 h before seeding 10000 cells/well into 96-well-black-flat-clear bottom plates. The immunoconjugates were titrated onto the seeded NK-92 cells. After 72 h the ATP content was measured to determine the number of viable cells using the “CellTiter-Glo Luminescent Cell Viability Assay” Kit (Promega) according to the manufacturer’s instructions. FIG. 27 shows that the “1+1” constructs are able to induce proliferation of NK-92 cells, being slightly less active than the corresponding IgG-IL-2 qm constructs.

The 4B9-based “1+1” constructs comprising IL-2 qm or IL-7 were tested for their ability to induce T cell proliferation, compared to IgG-IL-2 immunoconjugates. Peripheral blood mononuclear cells (PBMC) were prepared using Histopaque-1077 (Sigma Diagnostics Inc., St. Louis, Mo., USA). In brief, blood from buffy coats was diluted 5:1 with calcium- and magnesium-free PBS, and layered on Histopaque-1077. The gradient was centrifuged at 450×g for 30 min at room temperature (RT) without breaks. The interphase containing the PBMCs was collected and washed three times with PBS (350×g followed by 300×g for 10 min at RT). PBMCs were pre-stimulated with 1 μg/ml PHA-M (Sigma Aldrich #L8902) overnight, before they were labeled with 100 nM CFSE (carboxyfluorescein succinimidyl ester) for 15 min at 37° C. Cells were washed with 20 ml medium before recovering the labeled PBMCs for 30 min at 37° C. The cells were washed, counted, and 100000 cells were seeded into 96-well-U-bottom plates. The immunoconjugates were titrated onto the seeded cells for an incubation time of 6 days. Thereafter, cells were washed, stained for appropriate cell surface markers, and analyzed by FACS using a BD FACSCantoII. CD4 T cells were defined as $CD3^+/CD8^-$, and CD8 T cells as $CD3^+/CD8^+$.

FIGS. 28A-B show that the “1+1” constructs comprising either IL-2 qm or IL-7 are able to induce proliferation of PHA-activated CD4 (FIG. 28A) and CD8 T cells (FIG. 28B). As for NK cells, the “1+1” construct comprising IL-2 qm is slightly less active than an IgG-IL-2 qm construct.

The 4B9-based “1+1” construct comprising IFN-α was tested for its ability to inhibit Daudi cell proliferation, in comparison to Roferon A (Roche). Briefly, Daudi cells were labeled with 100 nM CFSE and seeded into a 96-well U-bottom plate (50'000 cells/well). The molecules were added at the indicated concentrations, followed by incubation for 3 days at 37° C. Proliferation was measured by analyzing the CFSE dilution, excluding dead cells from analysis by use of life/dead stain.

FIG. 29 shows that the construct was able to inhibit proliferation of Daudi cells, at least as potently as Roferon A.

Example 7

A single dose pharmacokinetics (PK) study was performed in tumor-free immunocompetent 129 mice for FAP-targeted IgG-IL2 immunoconjugates comprising either wild type or quadruple mutant IL-2, and untargeted IgG-IL-2 immunoconjugates comprising either wild type or quadruple mutant IL-2.

Female 129 mice (Harlan, United Kingdom), aged 8-9 weeks at the start of the experiment, were maintained under specific-pathogen-free conditions with daily cycles of 12 h light/12 h darkness according to committed guidelines (GV-Solas; Felasa; TierschG). The experimental study protocol was reviewed and approved by local government (P 2008016). After arrival, animals were maintained for one week to get accustomed to the new environment and for observation. Continuous health monitoring was carried out on a regular basis.

Mice were injected i.v. once with FAP-targeted 28H1 IgG-IL2 wt (2.5 mg/kg) or 28H1 IgG-IL2 qm (5 mg/kg), or untargeted DP47GS IgG-IL2 wt (5 mg/kg) or DP47GS IgG-IL2 qm (5 mg/kg). All mice were injected i.v. with 200 μl of the appropriate solution. To obtain the proper amount of immunoconjugate per 200 the stock solutions were diluted with PBS as necessary.

Mice were bled at 1, 8, 24, 48, 72, 96 h; and every 2 days thereafter for 3 weeks. Sera were extracted and stored at −20° C. until ELISA analysis. Immunoconjugate concentrations in serum were determined using an ELISA for quantification of the IL-2-immunoconjugate antibody (Roche-Penzberg). Absorption was measured using a measuring wavelength of 405 nm and a reference wavelength of 492 nm (VersaMax tunable microplate reader, Molecular Devices).

FIGS. 30A-B show the pharmacokinetics of these IL-2 immunoconjugates. Both the FAP-targeted (FIG. 30A) and untargeted (FIG. 30B) IgG-IL2 qm constructs have a longer serum half-life (approx. 30 h) than the corresponding IgG-IL-2 wt constructs (approx. 15 h). Of note, although the experimental conditions are not directly comparable, the serum half-life of the IL-2 immunoconjugates of the invention appears to be longer than the serum half-life of art-known “2+2” IgG-IL-2 immunoconjugates (see FIG. 1) as reported e.g. in Gillies et al., Clin Cancer Res 8, 210-216 (2002).

| Compound | Dose | Formulation buffer | Concentration (mg/mL) |
|---|---|---|---|
| 28H1-IgG-IL2 wt | 2.5 mg/kg | 20 mM Histidine, 140 mM NaCl, pH 6.0 | 3.84 (= stock solution) |
| 28H1-IgG-IL2 qm | 5 mg/kg | 20 mM Histidine, 140 mM NaCl, pH 6.0 | 2.42 (= stock solution) |
| DP47GS-IgG-IL2wt | 5 mg/kg | 20 mM Histidine, 140 mM NaCl, pH 6.0 | 3.74 (= stock solution) |
| DP47GS-IgG-IL2QM | 5 mg/kg | 20 mM Histidine, 140 mM NaCl, pH 6.0 | 5.87 (= stock solution) |

Example 8

A biodistribution study was performed to assess tumor targeting of the immunoconjugates of the invention. FAP-targeted 28H1-based IgG-IL-2 qm was compared to FAP-targeted unconjugated 28H1 IgG and 4B9 IgG, and untargeted DP47GS IgG. Furthermore, a SPECT/CT imaging study was performed with 4B9 IgG-IL-2 qm, compared to DP47GS IgG-IL-2 qm, 4B9 IgG and DP47GS IgG.

DTPA Conjugation and $^{111}$In Labeling

Solutions of 28H1 IgG-IL-2 qm, 28H1 $IgG_1$, 4B9 IgG-IL-2 qm, 4B9 $IgG_1$ and DP47 $IgG_1$ were dialysed against phosphate buffered saline (PBS, 15 mM). Two mg of the constructs (5 mg/ml) were conjugated with isothiocyanato-benzyl-diethylenetriaminepentaacetic acid (ITC-DTPA, Macrocyclis, Dallas, Tex.) in 0.1 M $NaHCO_3$, pH 8.2, under strict metal-free conditions, by incubation with a 5-fold molar excess of ITC-DTPA for one hour at room temperature (RT). Unconjugated ITC-DTPA was removed by dialysis against 0.1 M 2-(N-morpholino)ethanesulfonic acid (MES) buffer, pH 5.5.

The purified conjugates were radiolabeled by incubation with $^{111}$In (Covidien BV, Petten, The Netherlands) in 0.1 M MES buffer, pH 5.5 containing 0.05% bovine serum albumin (BSA) and 0.05% Tween-80, at RT, under strict metal-free conditions for 30 min. After radiolabeling ethylenediaminetetraacetic acid (EDTA) was added to a final concentration of 5 mM to chelate the unbound $^{111}$In. The $^{111}$In labeled products were purified by gelfiltration on disposable G25M columns (PD10, Amersham Biosciences, Uppsala, Sweden). Radiochemical purity of purified $^{111}$In labeled constructs were determined by instant thin-layer chromatography (ITLC) on TEC Control chromatography strips (Biodex, Shirley, N.Y.), using 0.1 M citrate buffer, pH 6.0, as the mobile phase. The specific activity of the $^{111}$In-labeled preparations was 0.6-4.6 MBq/μg.

Lindmo Assay

The immunoreactive fraction of $^{111}$In labeled antibody preparations was determined as described previously (Lindmo et al. (1984) J Immunol Methods 72, 77-89). Briefly, a serial dilution series of human embryonic kidney (HEK) cells transfected with fibroblast activation protein (FAP) cDNA (HEK-FAP cells) were incubated with 200 Bq of the $^{111}$In-labeled construct at 37° C. for 1 hour. A duplicate of the lowest cell concentration was incubated in the presence of an excess of non-labeled construct to correct for non-specific binding. After incubation, the cells were washed, spun down and cell associated radioactivity was determined in the cell pellet in a gamma-counter (Wallac Wizzard 3" 1480 automatic γ-counter, Pharmacia LKB). The immunoreactive fraction of the preparations ranged between 75-94%.

Animals

Female BALB/c nude mice (8-9 weeks, +/−20 g) were purchased from Janvier and housed in the Central Animal Facility of the Radboud University Nijmegen Medical Centre under standard conditions with 5 animals in individually ventilated cages with ad lib. access to food and water. After one week acclimatization the animals were inoculated s.c. with $10\times10^6$ HEK-FAP cells in matrigel (1:3) in the left flank and optionally with $5\times10^6$ HEK-293 cells in matrigel (1:3) in the right flank. Xenograft growth was monitored by caliper measurement (volume=(4/3·π)·(½·length)·(½·width)·(½·height). When xenografts reached a volume of 100 $mm^3$, mice were injected i.v. with the $^{111}$In-labeled constructs.

Biodistribution (28H1 IgG-IL-2 qm, 28H1 $IgG_1$, 4B9 $IgG_1$ and DP47GS $IgG_1$)

$^{111}$In-labeled constructs (5 MBq, 150 μg, 200 μl) were injected i.v. via the tail vein. Twenty-four hours after injection the animals were euthanized by suffocation in $CO_2/O_2$ atmosphere. Blood, muscle, xenograft, lung, spleen, pancreas, kidney, stomach (empty), duodenum (empty) and liver were collected, weighed and radioactivity was determined in a gamma-counter (Wallac Wizard). Standards of the injected dose (1%) were counted simultaneously and tissue uptake was calculated as % of the injected dose per gram tissue (% ID/g).

SPECT-CT Analysis (4B9 IgG-IL-2 qm, 4B9 $IgG_1$, DP47GS IgG-IL-2 qm and DP47GS $IgG_1$)

$^{111}$In-labeled 4B9-IgG-IL-2 qm, 4B9-$IgG_1$, DP47GS-IgG-IL-2 qm and DP47GS-IgG, were injected i.v. (20 MBq, 50, 150, 300 μg, 200 μl). At 4, 24, 72 and 144 hours after injection the animals were anesthetized with isoflurane/$O_2$ and scanned for 30 to 60 min in a U-SPECT II microSPECT/CT camera (MILabs, Utrecht, The Netherlands) equipped with a 1.0 mm mouse collimator. Computed tomography (CT) was performed directly after SPECT. Both SPECT (voxel size of 0.4 mm) and CT scans were reconstructed with MILabs software and SPECT and CT scans were co-registered to determine exact location of radio-signal. 3D images were created using Siemens Inveon Research Workplace software.

FIG. 31 shows that there is no significant difference between tissue distribution and tumor targeting of 28H1 and 4B9 IgG1 and 28H1 IgG-IL-2 qm at 24 hours (hence the cytokine does not significantly alter the tissue distribution and tumor targeting properties of the immunoconjugates), and that tumor-to-blood ratios for the FAP-targeted constructs are significantly greater than for the non-targeted DP47GS control IgG.

These results were confirmed in SPECT/CT imaging for the 4B9 IgG-IL-2 qm immunconjugate (data not shown). 4B9 IgG-IL-2 qm localized in the FAP-positive HEK-FAP but not in the FAP-negative HEK-293 control tumors, while the untargeted DP47GS immunoconjugate did not localize in either tumor. Unlike with the unconjugated IgGs, a weak uptake of 4B9 IgG-IL-2 qm was observed also in the spleen.

Example 9

Figure 1:
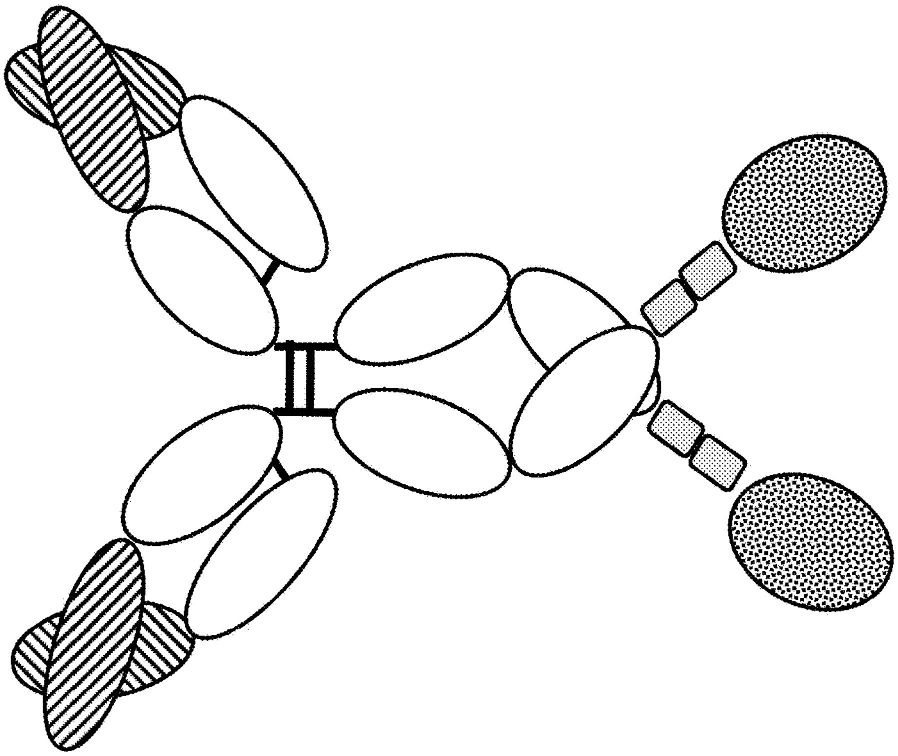
FIG. 1. Schematic representation of typical immunoglobulin-cytokine immunoconjugate as known in the art, with a cytokine (dotted) fused to the C-terminus of each of the two immunoglobulin heavy chains.

Binding of 28H1-based IgG-IL-2 qm and a 28H1-based IgG-(IL-2 $qm)_2$ (i.e. a "2+2" format immunoconjugate as depicted in FIG. 1; sequences are shown in SEQ ID NOs 253 and 205) to NK 92 cells was compared. 200000 NK92 cells per well were seeded in a 96-well plate. The immunoconjugates were titrated onto the NK92 cells and incubated for 30 min at 4° C. to allow binding. The cells were washed twice with PBS containing 0.1% BSA to remove unbound constructs. For detection of the immunoconjugates a FITC-labeled anti-human Fc-specific antibody was added for 30 min at 4° C. The cells were again washed twice with PBS containing 0.1% BSA and analyzed by FACS using a BD FACSCantoII.

As illustrated in FIG. 32, the "2+2" immunoconjugate shows better binding to NK 92 cells than the corresponding "2+1" construct.

Example 10

Induction of Human PBMC Proliferation by IL-2 Immunoconjugates

Peripheral blood mononuclear cells (PBMC) were prepared using Histopaque-1077 (Sigma Diagnostics Inc., St. Louis, Mo., USA). In brief, venous blood from healthy volunteers was drawn into heparinized syringes. The blood was diluted 2:1 with calcium- and magnesium-free PBS, and layered on Histopaque-1077. The gradient was centrifuged at 450×g for 30 min at room temperature (RT) without breaks. The interphase containing the PBMCs was collected and washed three times with PBS (350×g followed by 300×g for 10 min at RT).

Subsequently, PBMCs were labeled with 40 nM CFSE (carboxyfluorescein succinimidyl ester) for 15 min at 37° C. Cells were washed with 20 ml medium before recovering the labeled PBMCs for 30 min at 37° C. The cells were washed, counted, and 100000 cells were seeded into 96-well-U-bottom plates. Pre-diluted Proleukin (commercially available wild-type IL-2) or IL2-immunoconjugates were titrated onto the seeded cells which were incubated for the indicated time points. After 4-6 days, cells were washed, stained for appropriate cell surface markers, and analyzed by FACS using a BD FACSCantoII. NK cells were defined as CD37CD56$^+$, CD4 T cells as CD3$^+$/CD8$^-$, and CD8 T cells as CD3$^+$/CD8$^+$.

FIGS. 33A-C show proliferation of NK cells after incubation with different FAP-targeted 28H1 IL-2 immunoconjugates for 4 (FIG. 33A), 5 (FIG. 33B) or 6 (FIG. 33C) days. All tested constructs induced NK cell proliferation in a concentration-dependent manner. Proleukin was more efficacious than the immunoconjugates at lower concentrations, this difference no longer existed at higher concentrations, however. At earlier time points (day 4), the IgG-IL2 constructs appeared slightly more potent than the Fab-IL2-Fab constructs. At later time points (day 6), all constructs had comparable efficacy, with the Fab-IL2 qm-Fab construct being least potent at the low concentrations.

FIGS. 34A-C show proliferation of CD4 T-cells after incubation with different FAP-targeted 28H1 IL-2 immunoconjugates for 4 (FIG. 34A), 5 (FIG. 34B) or 6 (FIG. 34C) days. All tested constructs induced CD4 T cell proliferation in a concentration-dependent manner. Proleukin had a higher activity than the immunoconjugates, and the immunoconjugates comprising wild-type IL-2 were slightly more potent than the ones comprising quadruple mutant IL-2. As for the NK cells, the Fab-IL2 qm-Fab construct had the lowest activity. Most likely the proliferating CD4 T cells are partly regulatory T cells, at least for the wild-type IL-2 constructs.

FIGS. 35A-C show proliferation of CD8 T-cells after incubation with different FAP-targeted 28H1 IL-2 immunoconjugates for 4 (FIG. 35A), 5 (FIG. 35B) or 6 (FIG. 35C) days. All tested constructs induced CD8 T cell proliferation in a concentration-dependent manner. Proleukin had a higher activity than the immunoconjugates, and the immunoconjugates comprising wild-type IL-2 were slightly more potent than the ones comprising quadruple mutant IL-2. As for the NK and CD4 T cells, the Fab-IL2 qm-Fab construct had the lowest activity.

Example 11

Proliferation and Activation Induced Cell Death of IL-2 Activated PBMCs

Freshly isolated PBMCs from healthy donors were pre-activated overnight with PHA-M at 1 μg/ml in RPMI1640 with 10% FCS and 1% Glutamine. After pre-activation PBMCs were harvested, labeled with 40 nM CFSE in PBS, and seeded in 96-well plates at 100 000 cells/well. Pre-activated PBMCs were stimulated with different concentrations of IL-2 immunoconjugates (4B9 IgG-IL-2 wt, 4B9 IgG-IL-2 qm, 4B9 Fab-IL-2 wt-Fab, and 4B9 Fab-IL-2 qm-Fab). After six days of IL-2 treatment PBMCs were treated with 0.5 μg/ml activating anti-Fas antibody overnight. Proliferation of CD4 (CD3$^+$CD8$^-$) and CD8 (CD3$^+$CD8$^+$) T cells was analyzed after six days by CFSE dilution. The percentage of living T cells after anti-Fas treatment was determined by gating on CD3$^+$ Annexin V negative living cells.

As shown in FIGS. 36A-B, all constructs induced proliferation of pre-activated T cells. At low concentrations the constructs comprising wild-type IL-2 wt were more active than the IL-2 qm-comprising constructs. IgG-IL-2 wt, Fab-IL-2 wt-Fab and Proleukin had similar activity. Fab-IL-2 qm-Fab was slightly less active than IgG-IL-2 qm. The constructs comprising wild-type IL-2 were more active on CD4 T cells than on CD8 T cells, most probably because of the activation of regulatory T cells. The constructs comprising quadruple mutant IL-2 were similarly active on CD8 and CD4 T cells.

As shown in FIG. 37, T cells stimulated with high concentrations of wild-type IL-2 are more sensitive to anti-Fas induced apoptosis than T cells treated with quadruple mutant IL-2.

Example 12

The untargeted DP47GS construct (see SEQ ID NO: 299 and 297 for VH and VL sequences, respectively) was further characterized. As described above, conjugates of DP47GS IgG with wild-type or quadruple mutant IL-2 were made. These constructs showed similar binding to IL-2R and induction of immune cell (e.g. NK cell, CD8$^+$ cell and CD4$^+$ cell) proliferation in vitro as corresponding targeted constructs (data not shown). In contrast to immunoconjugates targeting a tumor antigen, however, they did not accumulate in tumor tissue (see Example 8).

A further pharmacokinetic study (in addition to the one shown in Example 7) was performed with the untargeted DP47GS IgG-IL-2 constructs comprising either wild-type or quadruple mutant IL-2. Male C57BL/6J mice (n=6 per group) were injected i.v. with 0.3, 1, 3 or 10 mg/kg DP47GS IgG-IL-2 wt or DP47GS IgG-IL-2 qm construct. The injection volume was 1 ml for all mice. Blood samples were taken at 2, 4, 8, 24, 48, 72, 96 and 168 hours after injection (from 3 mice at each time point) and stored at −20° C. until analysis. The constructs were quantified in the serum samples by ELISA, using anti-Fab antibodies for capturing and detection of the constructs. All samples and calibration standards were diluted 1:25 in mouse serum (obtained from Bioreclamation) prior to the analysis. Briefly, streptavidin-coated 96 well plates (Roche) were washed three times for 10 sec with PBS/0.05% Tween 20, before incubation with 100 μl/well (0.5 μg/ml) biotinylated anti-human Fab antibody (M-1.7.10; Roche Diagnostics) for 1 hour at room temperature. After washing the plate again three times with PBS/0.05% Tween 20, 50 μl/well of the serum samples or calibration standards and 50 μl/well PBS/0.5% BSA were added to give a final sample dilution of 1:50. Samples were incubated for 1 hour at room temperature, followed by washing the plate again three times with PBS/0.05% Tween 20. Next, the plate was incubated with 100 μl/well (0.5 μg/ml) digoxigenin-labeled anti-human Fab antibody (M-1.19.31; Roche Diagnostics) for 1 hour at room temperature, washed, incubated with 100 μl/well anti-digoxigenin POD (Roche Diagnostics Cat#11633716001) for 1 hour at room temperature, and washed again. Finally, 100 μl/well TMB peroxidase substrate (Roche Diagnostics Cat#11484281001) was added for about 5 minutes, before the substrate reaction was stopped with 50 μl/well 2N HCl. The plate was read within 2 minutes after stopping the reaction at 450 nm with a reference wavelength of 650 nm.

The result of this study is shown in FIGS. 38A-B. Both constructs showed long serum half life, with the construct comprising quadruple mutant IL-2 (FIG. 38B) being even longer lived than the one comprising wild-type IL-2 (FIG. 38A).

In addition, the lack of binding of DP47GS IgG to various proteins as well as human cells (PBMCs) was confirmed.

The binding specificity (or lack of such) of the DP47GS antibody was assessed in an ELISA-based test system with a panel of different unrelated antigens. The test was performed on 384 well MaxiSorp™ microtiter plates (Thermo Scientific Nunc, Cat#460372). After each incubation step the plates were washed three times with PBS/0.05% Tween-20. First, the different antigens, diluted in PBS, were coated on plates overnight at 6° C. The test concentrations and detailed information for the used antigens are listed in the table below.

| Antigen | Source | Supplier | Cat# | Test concentration [μg/ml] |
|---|---|---|---|---|
| Histons | calf thymus | Roche Diagnostics | 10223565601 | 2 |
| BSA Fraction V | bovine | Roche Diagnostics | 10735108001 | 2 |
| Insulin | human | Roche Diagnostics | 11376497001 | 2 |
| Cardiolipin | bovine | Sigma-Aldrich | C1649 | 2 |
| Heparin | porcine | Sigma-Aldrich | H9902 | 2 |
| CD40 (hFc) | human | Sino Biological | 1077-H03H | 1 |
| Parathyroid hormone aa 1-34 (PTH) (biotinylated) | human | AnaSpec | 20690 | 0.5 |
| dsDNA | calf thymus | Sigma-Aldrich | D4522 | 0.16 |
| Hemocyanin | keyhole limpet | Sigma-Aldrich | H7017 | 0.22 |
| Actin beta 2 | human | Cytoskeleton | APHL99 | 0.67 |
| Streptavidin | *Streptomyces avidinii* | Roche Diagnostics | 11721674001 | 1 |
| Gelatin | bovine | Roche Diagnostics | 11111965001 | 2% blocking buffer |
| *E. coli* lysate | *E. coli* | inhouse | — | diluted 1:600 |

Thereafter, the wells were blocked with 2% gelatin in water for 1 hour at room temperature (RT). The DP47GS antibody (1 μg/ml in PBS) was incubated with the panel of captured antigens for 1.5 hours at RT. Bound antibody was detected using anti-human IgG antibody-HRP conjugate (GE Healthcare, Cat#9330V; diluted 1:1000 in PBS with 0.2% Tween-20 and 0.5% gelatin). After 1 hour incubation the plates were washed 6 times with PBS/0.05% Tween-20 and developed with freshly prepared BM blue POD substrate solution (BM blue: 3,3'-5,5'-tetramethylbenzidine, Roche Diagnostics, Cat#11484281001) for 30 minutes at RT. Absorbance was measured at 370 nm. The blank value was defined without addition of antibody. An inhouse human $IgG_1$ antibody which exhibits unspecific binding to almost all of the captured antigens served as positive control.

The result of this experiment is shown in FIG. 39. The DP47GS antibody showed no binding to any of the captured antigens. The detected signals were in the range of the control samples without antibody.

Finally, the binding of the DP47GS antibody to human PBMCs was assessed. Since in the course of a typical immune response the combination of cell surface-presented proteins changes dramatically, binding was tested on PBMCs directly after isolation from healthy adults as well as after in vitro activation with two different stimuli.

Human PBMCs were isolated by Ficoll density gradient centrifugation from buffy coats or from heparinized fresh blood from healthy volunteers using Histopaque 1077 (Sigma-Aldrich, Germany). PBMCs were either directly subjected to binding assays (fresh PBMCs) or cultured and stimulated further. PBMCs were cultured at a cell density of $2\times10^6$ cells/ml in T cell medium consisting of RPMI 1640 (Gibco) supplemented with 10% (v/v) heat-inactivated FBS (PAA Laboratories), 1 mM sodium pyruvate (Sigma-Aldrich), 1% (v/v) L-alanyl-L-gluthamine (Biochrom) and 10 nM β-mercaptoethanol (Sigma-Aldrich) at 37° C. For in vitro stimulation, Proleukin (200 U/ml, Novartis) and phytohaemagglutinin (PHA-L; 2 μg/mL, Sigma-Aldrich) were added during six days of cultivation (PHA-L activated PBMC). For in vitro re-stimulation, 6-well cell culture plates were coated with mouse anti-human CD3 (clone KT3, 1 μg/ml) and mouse anti-human CD28 antibodies (clone 28.2, 2 μg/ml, both from eBioscience) and PHA-L activated PBMC were added for additional 24 hours (re-stimulated PBMC). Binding of DP47GS antibody (with or without the L234A L235A (LALA) P329G mutation in the Fc domain) to cell surface proteins was monitored for a five-fold serial dilution series (highest concentration 200 nM) using a goat anti-human IgG Fc-specific secondary antibody conjugated to fluorescein isothiocyanate (FITC) (Jackson Laboratories) and flow cytometric analysis. All assays were performed at 4° C. to prevent internalization of surface proteins. Incubation of primary and secondary antibody was for 2 hours and for 1 hour, respectively. To allow simultaneous typing of leukocytes, combinations of fluorochrome-labeled mouse anti-human CD14, CD15, CD4, CD19 (all Biolegend), NKp46, CD3, CD56, CD8 (all BD Pharmingen) were added to the secondary antibody. Propidium iodide (1 μg/ml) was added directly before measurement on a FACSCantoII device running FACS Diva software (both BD Bioscience) to exclude permeable dead cells. Propidium iodide negative living cells were gated for T cells ($CD14^-CD3^+CD4^+$/$CD8^+$), B cells ($CD14^-CD19^+$), NK Cells ($CD14^-NKp46^+$/$CD56^+$) or monocytes/neutrophils ($CD3^-CD56^-CD14^+$/$CD15^+$). The median FITC fluorescence of the various leukocyte types was determined as indicator for bound primary antibody and blotted against the primary antibody concentration using Prism4 (GraphPad Software).

As shown in FIGS. 40A-L, the DP47GS IgG antibody without Fc mutation showed binding only to Fcγ receptor bearing cells, e.g. NK cells and monocytes/neutrophils. No binding of DP47GS (LALA P329G) was detected on human PBMCs, regardless of their activation status. The LALA P329G mutation in the Fc domain completely abolished binding also to Fcγ receptor bearing cells.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. An immunoconjugate comprising a mutant interleukin-2 (IL-2) polypeptide and an antigen binding moiety, wherein said mutant IL-2 polypeptide is a mutant of a human IL-2 polypeptide comprising the amino acid sequence of SEQ ID NO: 2 and comprises three amino acid substitutions at positions corresponding to positions 42, 45, and 72 of SEQ ID NO: 2, wherein said three amino acid substitutions are F42A, Y45A and L72G; and wherein said antigen binding moiety is an IgG1 subclass immunoglobulin molecule specific for Carcinoembryonic Antigen (CEA), comprising a heavy chain variable region comprising, according to the Kabat numbering system, (i) the heavy chain CDR1, (ii) heavy chain CDR2 and (iii) heavy chain CDR3 of the heavy chain variable region sequence of SEQ ID NO: 191, and a light chain variable region comprising, according to the Kabat numbering system, (i) the light chain CDR1, (ii) light chain CDR2, and (iii) light chain CDR3 of the light chain variable region of SEQ ID NO: 189.

2. A pharmaceutical composition comprising the immunoconjugate of claim 1 and a pharmaceutically acceptable carrier.

3. The immunoconjugate of claim 1, wherein said mutant IL-2 polypeptide further comprises one or more of the amino acid substitutions at positions corresponding to positions 3 or 125 of SEQ ID NO: 2, wherein said one or more of the amino acid substitutions are T3A or C125A.

4. The immunoconjugate of claim 1, wherein said mutant IL-2 polypeptide comprises the sequence of SEQ ID NO: 3.

5. The immunoconjugate of claim 4, wherein said mutant IL-2 polypeptide is joined at its amino-terminal amino acid to the carboxy-terminal amino acid of one of the immunoglobulin heavy chains.

6. The immunoconjugate of claim 5, wherein the immunoconjugate comprises not more than one mutant IL-2 polypeptide.

7. The immunoconjugate of claim 6, wherein the $IgG_1$ subclass immunoglobulin molecule comprises in the Fc domain a modification promoting heterodimerization of two non-identical immunoglobulin heavy chains.

8. The immunoconjugate of claim 7, wherein the modification is a knob-into-hole modification, comprising a knob modification in one of the immunoglobulin heavy chains and a hole modification in the other one of the immunoglobulin heavy chains.

9. The immunoconjugate of claim 8, wherein the knob modification comprises the amino acid substitution T366W in one of the two immunoglobulin heavy chains, and the hole modification comprises the amino acid substitutions T366S, L368A and Y407V in the other one of the two immunoglobulin heavy chains, according to the EU numbering of Kabat.

10. The immunoconjugate of claim 9, wherein the immunoglobulin heavy chain comprising the knob modification further comprises the amino acid substitution S354C, and the immunoglobulin heavy chain comprising the hole modification further comprises the amino acid substitution Y349C, according to the EU numbering of Kabat.

11. The immunoconjugate of claim 4, wherein the $IgG_1$ molecule comprises in its Fc domain one or more amino acid mutations that reduce the binding affinity of the immunoconjugate to an FcγRIIIa, FcγRI or FcγRIIa receptor.

12. The immunoconjugate of claim 11, wherein the $IgG_1$ molecule comprises the amino acid mutations L234A, L235A and P329G, according to the EU numbering of Kabat.

13. The immunoconjugate of claim 4, wherein the heavy chain variable region comprises a sequence that is at least about 90%, 95%, 96%, 97%, 98%, 99% or 100% identical to SEQ ID NO: 191, and the light chain variable region comprises a sequence that is at least about 90%, 95%, 96%, 97%, 98%, 99% or 100% identical to SEQ ID NO: 189.

14. The immunoconjugate of claim 1, wherein said mutant IL-2 polypeptide is joined at its amino-terminal amino acid to the carboxy-terminal amino acid of one of the heavy chains of said immunoglobulin molecule.

15. The immunoconjugate of claim 14, wherein the immunoconjugate comprises not more than one mutant IL-2 polypeptide.

16. The immunoconjugate of claim 1, wherein the $IgG_1$ subclass immunoglobulin molecule comprises in the Fc domain a modification promoting heterodimerization of two non-identical immunoglobulin heavy chains.

17. The immunoconjugate of claim 16, wherein the modification is a knob-into-hole modification, comprising a knob modification in one of the immunoglobulin heavy chains and a hole modification in the other one of the immunoglobulin heavy chains.

18. The immunoconjugate of claim 17, wherein the knob modification comprises the amino acid substitution T366W in one of the two immunoglobulin heavy chains, and the hole modification comprises the amino acid substitutions T366S, L368A and Y407V in the other one of the two immunoglobulin heavy chains, according to the EU numbering of Kabat.

19. The immunoconjugate of claim 18, wherein the immunoglobulin heavy chain comprising the knob modification further comprises the amino acid substitution S354C, and the immunoglobulin heavy chain comprising the hole modification further comprises the amino acid substitution Y349C, according to the EU numbering of Kabat.

20. The immunoconjugate of claim 1, wherein the $IgG_1$ molecule comprises in its Fc domain one or more amino acid mutations that reduce the binding affinity of the immunoconjugate to an FcγRIIIa, FcγRI or FcγRIIa receptor.

21. The immunoconjugate of claim 20, wherein the $IgG_1$ molecule comprises the amino acid mutations L234A, L235A and P329G, according to the EU numbering of Kabat.

22. The immunoconjugate of claim 1, wherein the heavy chain variable region comprises a sequence that is at least about 90%, 95%, 96%, 97%, 98%, 99% or 100% identical to SEQ ID NO: 191, and the light chain variable region comprises a sequence that is at least about 90%, 95%, 96%, 97%, 98%, 99% or 100% identical to SEQ ID NO: 189.

23. The immunoconjugate of claim 1, comprising a polypeptide sequence that is at least about 90%, 95%, 96%, 97%, 98% or 99% identical to SEQ ID NO: 277, a polypeptide sequence that is at least about 90%, 95%, 96%, 97%, 98% or 99% identical to SEQ ID NO: 281, and a polypeptide sequence that is at least about 90%, 95%, 96%, 97%, 98% or 99% identical to SEQ ID NO: 283.

* * * * *